US008933018B2

(12) United States Patent
Glinka et al.

(10) Patent No.: US 8,933,018 B2
(45) Date of Patent: Jan. 13, 2015

(54) BORON CONTAINING POLYBASIC BACTERIAL EFFLUX PUMP INHIBITORS AND THERAPEUTIC USES THEREOF

(75) Inventors: Tomasz Glinka, Cupertino, CA (US); Robert Higuchi, Solana Beach, CA (US); Scott Hecker, Del Mar, CA (US); Brian Eastman, San Diego, CA (US); Olga Rodny, Mill Valley, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/983,747

(22) PCT Filed: Feb. 6, 2012

(86) PCT No.: PCT/US2012/024023
§ 371 (c)(1),
(2), (4) Date: Aug. 5, 2013

(87) PCT Pub. No.: WO2012/109164
PCT Pub. Date: Aug. 16, 2012

(65) Prior Publication Data
US 2013/0316943 A1    Nov. 28, 2013

Related U.S. Application Data

(60) Provisional application No. 61/477,129, filed on Apr. 19, 2011, provisional application No. 61/440,311, filed on Feb. 7, 2011.

(51) Int. Cl.
*A61K 38/00*    (2006.01)
*A61P 31/04*    (2006.01)
*C07K 5/06*    (2006.01)
*C07F 5/02*    (2006.01)
*A61K 38/05*    (2006.01)

(52) U.S. Cl.
CPC ............ *C07K 5/06191* (2013.01); *C07F 5/025* (2013.01); *A61K 38/05* (2013.01)
USPC .......................................................... 514/2.4

(58) Field of Classification Search
CPC ..... A61K 38/05; C07F 5/025; C07K 5/06191
See application file for complete search history.

(56) References Cited

U.S. PATENT DOCUMENTS

2008/0076741 A1    3/2008    Glinka et al.

OTHER PUBLICATIONS

Barrett, J.F., 'MC-207110 Daiichi Seiyaku/Microcide Pharmaceuticals', Current Opinion in Investigational Drugs, Pharma Press Ltd., 2001, 2(2), 212-215.
International Search Report dated May 21, 2012 received in International Application No. PCT/US2012/024023.
Poole, K., 'Efflux-mediated resistance to fluoroquinolones in gram-negative bacteria', Antimicrobial Agents and Chemotherapy, 2000, 44(9), 2233-2241.
Afonso, A. et al., "Solid-phase Synthesis of Biaryl Cyclic Peptides by Borylation and Microwave-assisted Intramolecular Suzuki-Miyaura Reaction", Tetrahedron (2011) 67:2238-2245.
European Search Report dated Jul. 7, 2014 for corresponding Application No. EP 12745348.8, filed Sep. 5, 2013.

*Primary Examiner* — Thomas S Heard
(74) *Attorney, Agent, or Firm* — Knobbe Martens Olson & Bear LLP

(57) ABSTRACT

Disclosed herein are polybasic bacterial efflux pump inhibitors containing boronic acid functionality and their methods of synthesis, methods of use, and pharmaceutical compositions. Some embodiments include methods of treating or preventing a bacterial infection by co-administering to a subject infected with bacteria or at risk of infection with bacteria the efflux pump inhibitor with another anti-bacterial agent.

29 Claims, No Drawings

BORON CONTAINING POLYBASIC BACTERIAL EFFLUX PUMP INHIBITORS AND THERAPEUTIC USES THEREOF

RELATED APPLICATIONS

This application is the U.S. National Phase of PCT Application No. PCT/US2012/024023 entitled "BORON CONTAINING POLYBASIC BACTERIAL EFFLUX PUMP INHIBITORS AND THERAPEUTIC USES THEREOF" filed Feb. 6, 2012, and published in English on Aug. 16, 2012 as WO 2012/109164 which claims the benefit of U.S. Provisional Application No. 61/440,311, filed Feb. 7, 2011 and U.S. Provisional Application No. 61/477,129, filed Apr. 19, 2011, all of which are incorporated herein by reference in their entireties.

BACKGROUND OF THE INVENTION

1. Field of the Invention

This invention relates to the fields of chemistry and medicine. More specifically, it relates to Efflux Pump Inhibitor (EPI) compounds to be co-administered with antimicrobial agents for the treatment of infections caused by bacterial pathogens. Some embodiments include novel compounds useful as efflux pump inhibitors, compositions and devices including such efflux pump inhibitors, and therapeutic use of such compounds.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target. There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics that would otherwise inhibit or kill the bacterial cells. Some bacteria utilize both mechanisms, combining a low permeability of the cell wall (including membranes) with an active efflux of antibiotics.

Some efflux pumps selectively extrude specific antibiotics. Examples of such pumps include the Tet or CmlA transporters, which can extrude tetracycline or chloramphenicol, respectively. Other efflux pumps, so-called multi-drug resistance (MDR) pumps, extrude a variety of structurally diverse compounds. In the latter case, a single efflux system may confer resistance to multiple antibiotics with different modes of action. In this respect, bacterial MDR pumps are similar to mammalian MDR transporters. In fact, one such pump, P-glycoprotein, the first discovered MDR pump, confers multiple drug resistance on cancer cells and is considered to be one of the major reasons tumors are resistance to anti-cancer therapy. A typical example of bacterial MDR pump is MexAB-OprM from *Pseudomonas aeruginosa*. This pump has been shown to affect the susceptibility of the organism to almost all antibiotic classes including fluoroquinolones, β-lactams, macrolides, phenicols, tetracyclines, and oxazolidinones.

It is clear that in many cases, a dramatic effect on the susceptibility of problematic pathogens would be greatly enhanced if efflux-mediated resistance were to be nullified. Two approaches to combat the adverse effects of efflux on the efficacy of antimicrobial agents can be envisioned: identification of derivatives of known antibiotics that are not effluxed and development of therapeutic agents that inhibit transport activity of efflux pumps and could be used in combination with existing antibiotics to increase their potency.

There are several examples when the first approach has been successfully reduced to practice. These examples include new fluoroquinolones, which are not affected by multidrug resistance pumps in *Staphylococcus aureus* or *Streptococcus pneumoniae* or new tetracycline and macrolide derivatives, which are not recognized by the corresponding antibiotic-specific pumps. However, this approach appears to be much less successful in the case of multidrug resistance pumps from gram-negative bacteria. In gram-negative bacteria, particular restrictions are imposed on the structure of successful drugs: they must be amphiphilic in order to cross both membranes. It is this very property that makes antibiotics good substrates of multi-drug resistance efflux pumps from gram-negative bacteria. In the case of these bacteria, the efflux pump inhibitory approach becomes the major strategy in improving the clinical effectiveness of existing antibacterial therapy.

Thus, there is need for new efflux pump inhibitors for use in treating bacterial infections, particularly infections that are resistant or susceptible to developing resistance.

SUMMARY OF THE INVENTION

Some embodiments disclosed herein include polybasic bacterial efflux pump inhibitors containing boronic acid functionality. Other embodiments disclosed herein include pharmaceutical compositions and methods of treatment using these compounds.

One embodiment disclosed herein includes a compound having the structure of formula I:

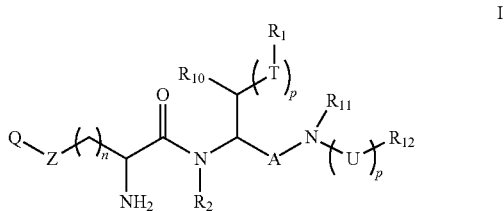

or a pharmaceutically acceptable salt thereof where;
$R_1$ is selected from the group consisting of $C_1$-$C_6$ alkyl, $C_3$-$C_7$ carbocyclyl, heterocyclyl, aryl and heteroaryl, each optionally substituted with one or more substituents independently selected from the group consisting of a halogen, $C_1$-$C_4$ alkyl optionally substituted with one or more halogen, $C_3$-$C_7$ carbocyclyl, —$OR_2$, —$SR_2$, —$SO_2R_2$, —$SO_2NHR_2$, —$N(R_2)_2$, —CN, and —$CO_2C_1$-$C_4$ alkyl;

each $R_2$ is independently selected from the group consisting of H and $C_1$-$C_6$ alkyl optionally substituted with one or more halogen;

A is —C(O)— or $CH_2$;

Z is selected from the group consisting of —$CH_2$—, —C(O)—, —S(O)$_2$—, —C(O)O—, —C(O)S—, —C(O)NH— and S(O)$_2$NH—;

Q is selected from the group consisting of —$NR_3R_4$, —$CHR_3R_4$,

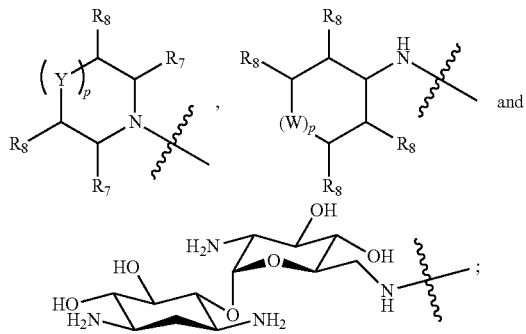

$R_3$ is selected from the group consisting of —$CH_2$[CH($R_5$)]$_p$CH($R_6$)$NH_2$, —CH(CH$R_6$$NH_2$)$_2$ and —$CH_2$C(OH)(CH$_2$$NH_2$)$_2$;

$R_4$ is selected from the group consisting of H and —$CH_2$[CH($R_5$)]$_p$CH($R_6$)$NH_2$;

each $R_5$ is independently selected from the group consisting of H, —OH, -halogen, and $C_1$-$C_4$ alkyl substituted with one or more —OH or halogen;

each $R_6$ is independently selected from the group consisting of H and $C_1$-$C_4$ alkyl substituted with one or more —OH or halogen;

each $R_7$ is independently selected from the group consisting of H and $C_1$-$C_4$ alkyl substituted with one or more —OH or $NH_2$;

optionally, two $R_7$ can be linked by —(CH$_2$)$_m$— to form a bicyclic ring, where m is an integer of 1 to 3;

each $R_8$ is independently selected from the group consisting of H, —$NH_2$, —$CH_2NH_2$, —OH and —$CH_2OH$;

Y is selected from the group consisting of $CHR_9$, O, S, $SO_2$ and $NR_2$;

W is $CHR_8$;

$R_9$ is selected from the group consisting of H, —$NH_2$, —OH and $C_1$-$C_4$ alkyl substituted with one or more —OH or $NH_2$;

T is selected from the group consisting of $CH_2$, O, S and $NR_2$;

$R_{10}$ is selected from the group consisting of H and OH, with the limitation that when $R_{10}$ is OH, T is $CH_2$;

$R_{11}$ is selected from the group consisting of H and $C_1$-$C_6$ alkyl, wherein when $R_{11}$ is $C_1$-$C_6$ alkyl, it is optionally linked to $R_{12}$ to form a ring;

U is selected from the group consisting of $C_1$-$C_4$ alkyl, C=O, spirocyclic $C_3$-$C_7$ carbocyclyl, and 3-7 membered spirocyclic heterocyclyl;

$R_{12}$ is —(X)$_p$—V—B(OH)O$R_{13}$);

X is $CH_2$;

V is selected from the group consisting of $C_3$-$C_7$ carbocyclyl, heterocyclyl, aryl and heteroaryl, each optionally substituted with one or more $C_1$-$C_4$ alkyl optionally substituted with one or more halogen, halogen, $C_1$-$C_4$ alkoxy optionally substituted with one or more halogen, and —CN;

$R_{13}$ is selected from the group consisting of H; —(CR$_{19}$R$_{20}$)$_p$-spirocyclic $C_3$-$C_7$ carbocyclyl-(CR$_{21}$R$_{22}$)$_p$—; —(CR$_{19}$R$_{20}$)$_p$-three- to seven-membered spirocyclic heterocyclyl-(CR$_{21}$R$_{22}$)$_p$— optionally substituted with $C_{1-6}$ alkyl; and $C_1$-$C_4$ alkyl optionally substituted with one or more halogen, $C_1$-$C_4$ alkyl optionally substituted with one or more halogen, $C_1$-$C_4$ alkoxy optionally substituted with one or more halogen, and oxo; wherein when $R_{13}$ is optionally substituted $C_1$-$C_4$ alkyl, —(CR$_{19}$R$_{20}$)$_p$-spirocyclic $C_3$-$C_7$ carbocyclyl-(CR$_{21}$R$_{22}$)$_p$—, or —(CR$_{19}$R$_{20}$)$_p$-three- to seven-membered spirocyclic heterocyclyl —(CR$_{21}$R$_{22}$)$_p$— optionally substituted with $C_{1-6}$ alkyl, it is linked to X or V to form a ring;

or optionally, $R_{13}$ is a bond linked directly to X to form a ring;

$R_{19}$ and $R_{20}$ are independently selected from the group consisting of H, halogen, $C_1$-$C_4$ alkyl optionally substituted with one or more halogen, and $C_1$-$C_4$ alkoxy optionally substituted with one or more halogen;

$R_{21}$ and $R_{22}$ are independently selected from the group consisting of H, halogen, $C_1$-$C_4$ alkyl optionally substituted with one or more halogen, and $C_1$-$C_4$ alkoxy optionally substituted with one or more halogen, or together they are oxo;

n is equal to 1, 2 or 3; and each p is independently equal to 0 or 1.

In some embodiments of formula I, $R_{12}$ is selected from the group consisting of:

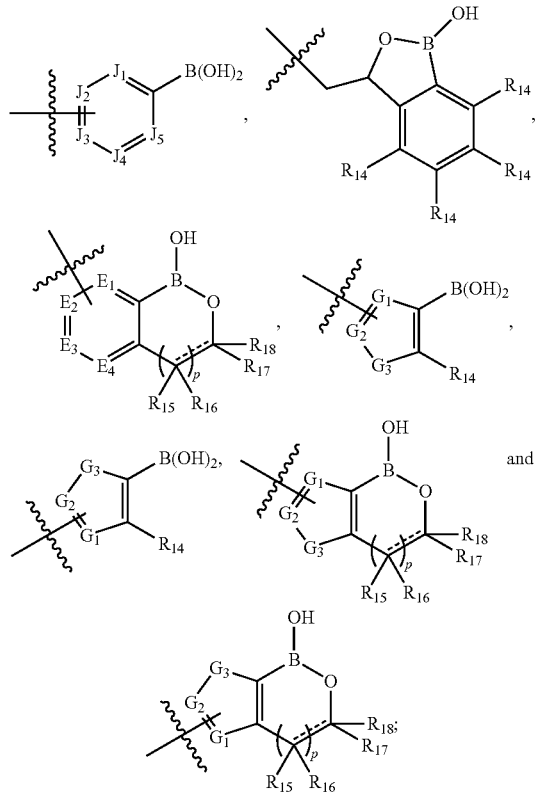

one $J_1$, $J_2$, $J_3$, $J_4$, and $J_5$ is

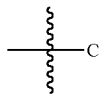

and is the attachment point to the rest of the molecule and the remaining $J_1$, $J_2$, $J_3$, $J_4$, and $J_5$ is independently selected from the group consisting of $CR_{14}$ and N;

one of $E_1$, $E_2$, $E_3$ and $E_4$ is

and is the attachment point to the rest of the molecule and the remaining $E_1$, $E_2$, $E_3$ and $E_4$ are independently selected from the group consisting of C $R_{14}$ and N;

$G_1$ and $G_2$ are independently selected from the group consisting of N and

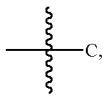

which is the attachment point to the rest of the molecule;

$G_3$ is the group consisting of O, —S and $NR_2$;

each $R_{14}$ is independently selected from the group consisting of H, $C_1$-$C_4$ alkyl, halogen, $C_1$-$C_4$ alkoxy, —$CF_3$, —$OCF_3$ and —CN;

$R_{15}$ and $R_{16}$ are independently selected from the group consisting of H, halogen, $C_1$-$C_4$ alkyl optionally substituted with one or more halogen, and $C_1$-$C_4$ alkoxy optionally substituted with one or more halogen, or together they are oxo, or together they form a spirocyclic $C_3$-$C_7$ carbocyclyl or a three- to seven-membered heterocyclyl containing one or two heteroatoms selected from O, S or $NR_2$;

$R_{17}$ and $R_{18}$ are independently selected from the group consisting of H, halogen, $C_1$-$C_4$ alkyl optionally substituted with one or more halogen, and $C_1$-$C_4$ alkoxy optionally substituted with one or more halogen, or together they form a spirocyclic $C_3$-$C_7$ carbocyclyl or a three- to seven-membered spirocyclic heterocyclyl containing one or two heteroatoms selected from O, S or $NR_2$; and bonds indicated by a dashed and solid line are selected from a single bond and a double bond, where when the bond is a double bond, $R_{16}$ and $R_{17}$ are absent.

Other embodiments disclosed herein include methods of inhibiting a bacterial efflux pump by administering to a subject infected with bacteria a compound according to formula I.

Another embodiment disclosed herein includes a method of treating or preventing a bacterial infection by co-administering to a subject infected with bacteria or at risk of infection with bacteria, a compound according to formula I and another anti-bacterial agent.

Another embodiment disclosed herein includes a pharmaceutical composition that has a compound according to formula I and a pharmaceutically acceptable carrier, diluent, or excipient.

In some embodiments, the bacterial infection includes an infection caused by bacteria selected from one or more of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*.

In particular embodiments, the bacteria is selected from one or more of *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainjluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, and *Bacteroides splanchnicus*.

It is to be understood that both the foregoing general description and the following detailed description are exemplary and explanatory only and are not restrictive of the invention as claimed.

DETAILED DESCRIPTION

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Compositions and methods for inhibiting intrinsic drug resistance and/or preventing acquired drug resistance in microbes would be of tremendous benefit. Certain embodiments provide such compositions and methods.

Some embodiments relate to a method for treating a microbial infection whose causative microbe employs an efflux pump resistance mechanism, including contacting the microbial cell with an efflux pump inhibitor in combination with an antimicrobial agent. The efflux pump inhibitors of preferred embodiments can include polybasic structures, as disclosed herein.

Some embodiments include a method for prophylactic treatment of a mammal. In this method, an efflux pump inhibitor is administered to a mammal at risk of a microbial infection, e.g., a bacterial infection. In some embodiments, an antimicrobial agent is administered in combination with or co-administered with the efflux pump inhibitor. Such administration can reduce the likelihood that the mammal will develop a microbial infection.

Some embodiments also feature a method of enhancing the antimicrobial activity of an antimicrobial agent against a microbe, in which such a microbe is contacted with an efflux pump inhibitor, and an antibacterial agent.

In some embodiments, pharmaceutical compositions are provided that are effective for treatment of an infection of an animal, e.g., a mammal, by a microbe, such as a bacterium or a fungus. The composition includes a pharmaceutically acceptable carrier and an efflux pump inhibitor as described herein. Some embodiments provide antimicrobial formulations that include an antimicrobial agent, an efflux pump inhibitor, and a carrier. In some embodiments, the antimicrobial agent is an antibacterial agent.

Some embodiments of the present invention include compounds of formula (I) and pharmaceutically acceptable salts thereof:

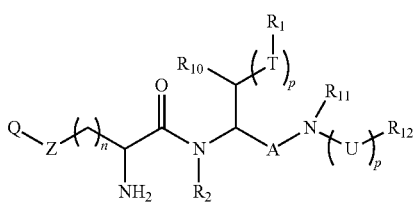

I

In some embodiments, $R_1$ is selected from the group consisting of $C_1$-$C_6$ alkyl, $C_3$-$C_7$ carbocyclyl, heterocyclyl, aryl and heteroaryl, each optionally substituted with one or more substituents independently selected from the group consisting of a halogen, $C_1$-$C_4$ alkyl optionally substituted with one or more halogen, $C_3$-$C_7$ carbocyclyl, —$OR_2$, —$SR_2$, —$SO_2R_2$, —$SO_2NHR_2$, —$N(R_2)_2$, —CN, and —$CO_2C_1$-$C_4$ alkyl.

In some embodiments, each $R_2$ is independently selected from the group consisting of H and $C_1$-$C_6$ alkyl optionally substituted with one or more halogen.

In some embodiments, Z is selected from the group consisting of —$CH_2$—, —C(O)—, —S(O)$_2$—, —C(O)O—, —C(O)S—, —C(O)NH— and S(O)$_2$NH—;

In some embodiments, Q is selected from the group consisting of —$NR_3R_4$, —$CHR_3R_4$,

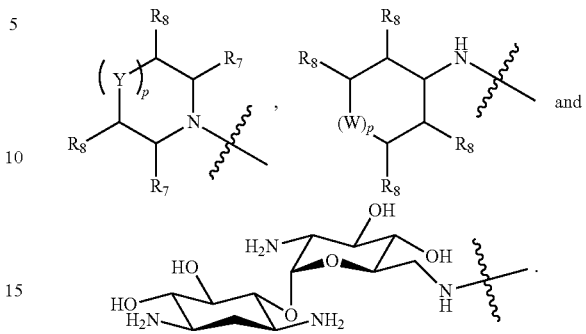

In some embodiments, $R_3$ is selected from the group consisting of —$CH_2[CH(R_5)]_pCH(R_6)NH_2$, —$CH(CHR_6NH_2)_2$ and —$CH_2C(OH)(CH_2NH_2)_2$.

In some embodiments, $R_4$ is selected from the group consisting of H and —$CH_2[CH(R_5)]_pCH(R_6)NH_2$.

In some embodiments, each $R_5$ is independently selected from the group consisting of H, —OH, halogen, and $C_1$-$C_4$ alkyl substituted with one or more —OH or halogen.

In some embodiments, each $R_6$ is independently selected from the group consisting of H and $C_1$-$C_4$ alkyl substituted with one or more —OH or halogen.

In some embodiments, each $R_7$ is independently selected from the group consisting of H and $C_1$-$C_4$ alkyl substituted with one or more —OH or $NH_2$.

In some embodiments, two $R_7$ can be linked by —$(CH_2)_m$— to form a bicyclic ring, where m is an integer of 1 to 3.

In some embodiments, each $R_8$ is independently selected from the group consisting of H, —$NH_2$, —$CH_2NH_2$, —OH and —$CH_2OH$.

In some embodiments, Y is selected from the group consisting of $CHR_9$, O, S, $SO_2$ and $NR_2$.

In some embodiments, W is $CHR_8$.

In some embodiments, $R_9$ is selected from the group consisting of H, —$NH_2$, —OH and $C_1$-$C_4$ alkyl substituted with one or more —OH or $NH_2$.

In some embodiments, T is selected from the group consisting of $CH_2$, O, S and $NR_2$.

In some embodiments, $R_{10}$ is selected from the group consisting of H and OH, with the limitation that when $R_{10}$ is OH, T is $CH_2$.

In some embodiments, $R_{11}$ is selected from the group consisting of H and $C_1$-$C_6$ alkyl. In some embodiments, when $R_{11}$ is $C_1$-$C_6$ alkyl, it is optionally linked to $R_{12}$ to form a ring.

In some embodiments, U is selected from the group consisting of $C_1$-$C_4$ alkyl, C=O, spirocyclic $C_3$-$C_7$ carbocyclyl, and 3-7 membered spirocyclic heterocyclyl.

In some embodiments, $R_{12}$ is —$(X)_p$—V—B(OH)(OR$_{13}$).

In some embodiments, X is $CH_2$.

In some embodiments, V is selected from the group consisting of $C_3$-$C_7$ carbocyclyl, heterocyclyl, aryl and heteroaryl, each optionally substituted with one or more $C_1$-$C_4$ alkyl optionally substituted with one or more halogen, halogen, $C_1$-$C_4$ alkoxy optionally substituted with one or more halogen, or —CN.

In some embodiments, $R_{13}$ is selected from the group consisting of H; —$(CR_{19}R_{20})_p$-spirocyclic $C_3$-$C_7$ carbocyclyl-$(CR_{21}R_{22})_p$—; —$(CR_{19}R_{20})_p$-three- to seven-membered spirocyclic heterocyclyl-$(CR_{21}R_{22})_p$— optionally substituted with $C_{1-6}$ alkyl; and $C_1$-$C_4$ alkyl optionally substituted with one or more halogen, $C_1$-$C_4$ alkyl optionally substituted with one or more halogen, $C_1$-$C_4$ alkoxy optionally substituted with one or more halogen, and oxo; wherein when $R_{13}$ is optionally substituted $C_1$-$C_4$ alkyl, —$(CR_{19}R_{20})_p$-spirocyclic $C_3$-$C_7$ carbocyclyl-$(CR_{21}R_{22})_p$—, or —$(CR_{19}R_{20})_p$-three- to seven-membered spirocyclic heterocyclyl —$(CR_{21}R_{22})_p$— optionally substituted with $C_{1-6}$ alkyl, it is linked to X or V to form a ring.

In some embodiments, $R_{13}$ is a bond linked directly to X to form a ring.

In some embodiments, $R_{19}$ and $R_{20}$ are independently selected from the group consisting of H, halogen, $C_1$-$C_4$ alkyl optionally substituted with one or more halogen, and $C_1$-$C_4$ alkoxy optionally substituted with one or more halogen.

In some embodiments, $R_{21}$ and $R_{22}$ are independently selected from the group consisting of H, halogen, $C_1$-$C_4$ alkyl optionally substituted with one or more halogen, and $C_1$-$C_4$ alkoxy optionally substituted with one or more halogen, or together they are oxo.

In some embodiments, n is equal to 1, 2 or 3.

In some embodiments, each p is independently equal to 0 or 1.

In some embodiments of formula I, $R_{12}$ is

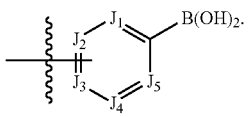

In some embodiments of formula I, $R_{12}$ is

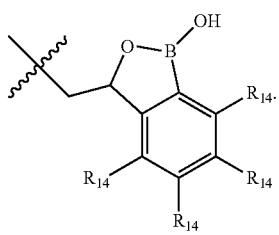

In some embodiments of formula I, $R_{12}$ is

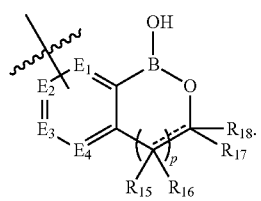

In some embodiments of formula I, $R_{12}$ is

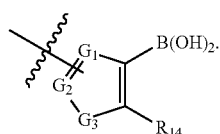

In some embodiments of formula I, $R_{12}$ is

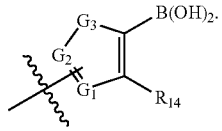

In some embodiments of formula I, $R_{12}$ is

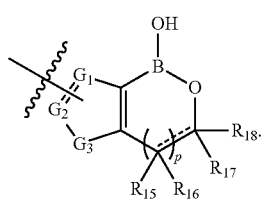

In some embodiments of formula I, $R_{12}$ is

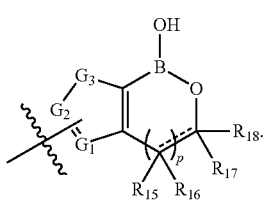

In some embodiments, one $J_1$, $J_2$, $J_3$, $J_4$, and $J_5$ is

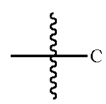

and is the attachment point to the rest of the molecule and the remaining $J_1$, $J_2$, $J_3$, $J_4$, and $J_5$ is independently selected from the group consisting of $CR_{14}$ and N.

In some embodiments, one of $E_1$, $E_2$, $E_3$ and $E_4$ is

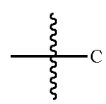

and is the attachment point to the rest of the molecule and the remaining $E_1$, $E_2$, $E_3$ and $E_4$ are independently selected from the group consisting of $CR_{14}$ and N.

In some embodiments, $G_1$ and $G_2$ are independently selected from the group consisting of N and

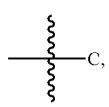

which is the attachment point to the rest of the molecule.

In some embodiments, $G_3$ is selected from the group consisting of O, —S and $NR_2$.

In some embodiments, each $R_{14}$ is independently selected from the group consisting of H, $C_1$-$C_4$ alkyl, halogen, $C_1$-$C_4$ alkoxy, —$CF_3$, —$OCF_3$ and —CN.

In some embodiments, $R_{15}$ and $R_{16}$ are independently selected from the group consisting of H, halogen, and $C_1$-$C_4$ alkyl optionally substituted with one or more halogen, or together they are oxo, or together they form a spirocyclic $C_3$-$C_7$ carbocyclyl.

In some embodiments, $R_{17}$ and $R_{18}$ are independently selected from the group consisting of H, halogen, $C_1$-$C_4$ alkyl, and $C_1$-$C_4$ alkoxy, or together they form a spirocyclic $C_3$-$C_7$ carbocyclyl or a three- to seven-membered spirocyclic heterocyclyl containing one or two heteroatoms selected from O, S or $NR_2$;

In some embodiments, bonds indicated by a dashed and solid line are selected from a single bond and a double bond, where when the bond is a double bond, $R_{16}$ and $R_{17}$ are absent.

In more specific embodiments of formula I, $R_{12}$ is selected from the group consisting of:

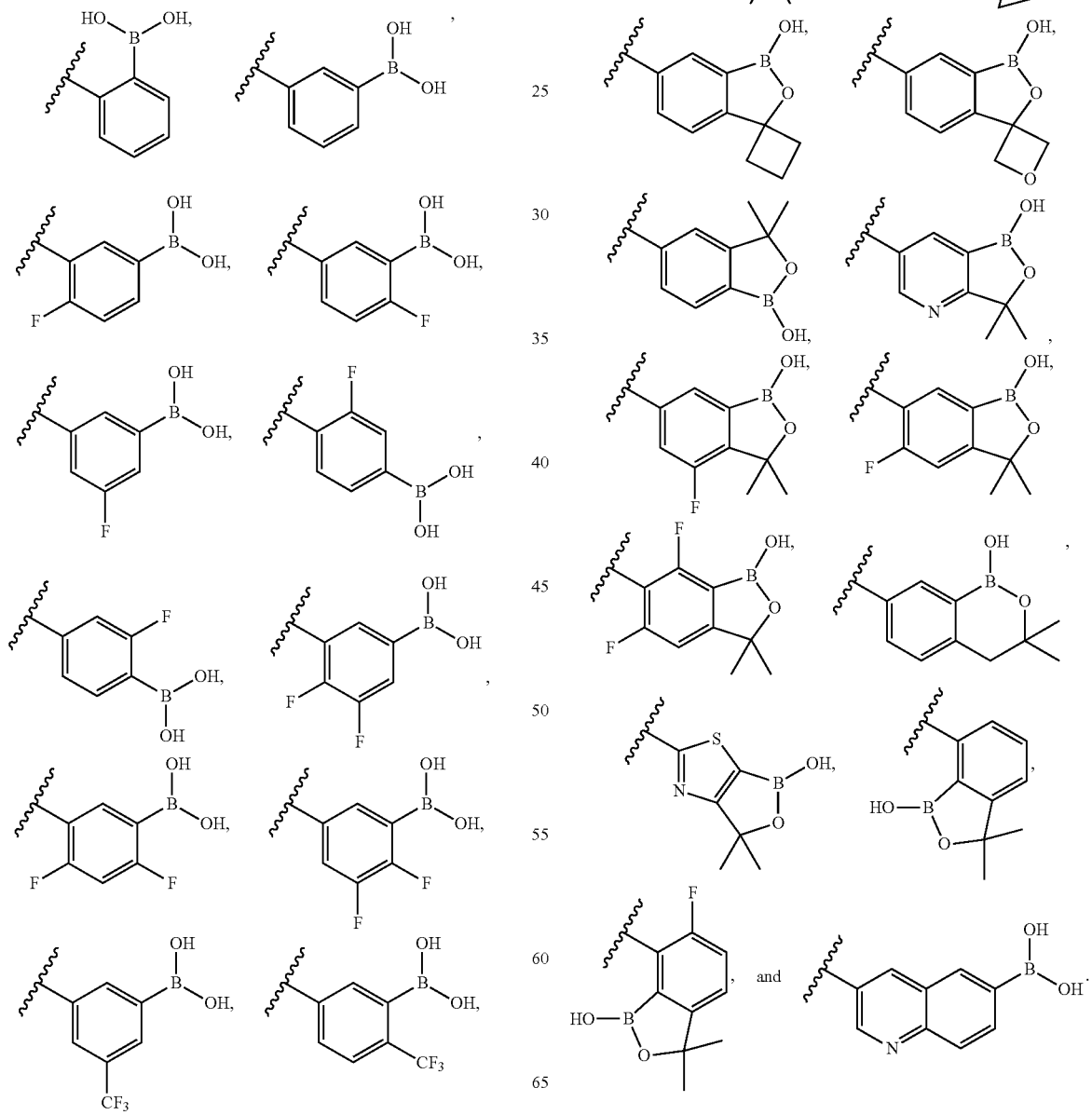

In more specific embodiments of formula I, U is selected from the group consisting of —CH₂—, —C(CH₃)₂, C=O,

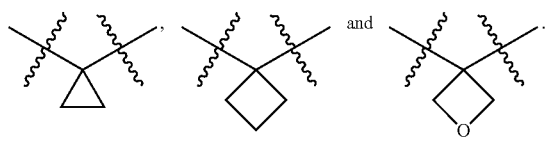 [SMILES: *C1(*)CC1 ; *C1(*)CCC1 ; *C1(*)COC1]

In more specific embodiments of formula I, V is selected from the group consisting of C₃-C₇ carbocyclyl, heterocyclyl, aryl and heteroaryl, each optionally substituted with one or more C₁-C₄ alkyl, halogen, C₁-C₄ alkoxy, —CF₃, —OCF₃ or —CN.

In more specific embodiments of formula I,

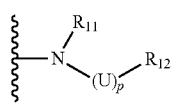

is selected from the group consisting of:

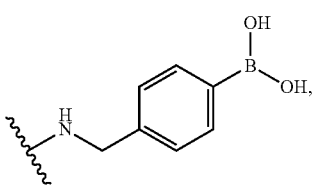

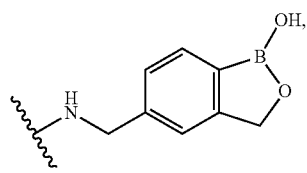

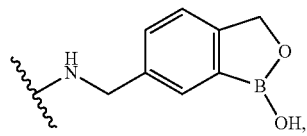

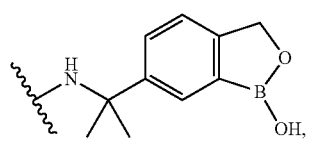

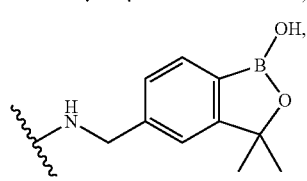

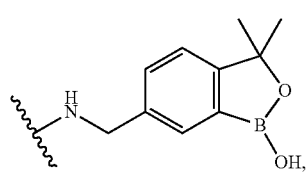

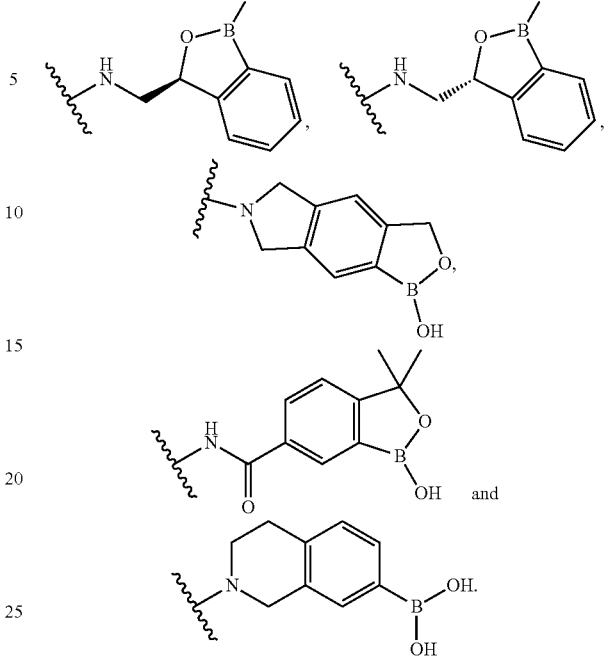

In more specific embodiments of formula I, $R_1$ is substituted or unsubstituted carbocyclyl or substituted or unsubstituted aryl. In some embodiments, $R_1$ is carbocyclyl or aryl optionally substituted with one or more halogen, C₁-C₄ alkyl, —CF₃, and —OCF₃.

In more specific embodiments of formula I, $R_1$ is selected from the group consisting of:

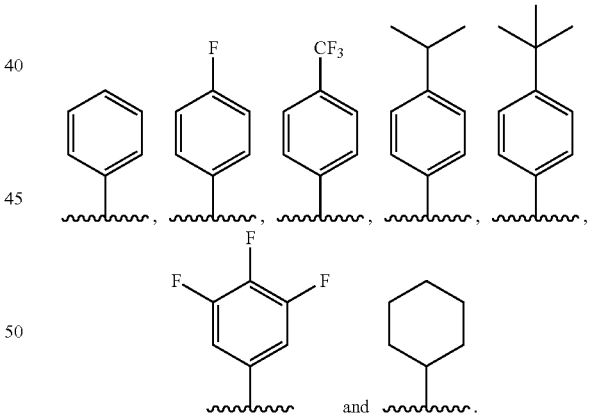

In more specific embodiments of formula I, $R_1$ is substituted or unsubstituted carbocyclyl or substituted or unsubstituted aryl, T is CH₂ or O and p of $(T)_p$ is 1.

In more specific embodiments of formula I, $R_1$ is substituted or unsubstituted carbocyclyl or substituted or unsubstituted aryl and p of $(T)_p$ is 0.

In more specific embodiments of formula I, Z is —CH₂— and n is 2.

In more specific embodiments of formula I, Z is —C(O)— and n is 1.

In more specific embodiments of formula I, Z is —C(O)— and n is 2.

In more specific embodiments of formula I, Q is selected from the group consisting of:

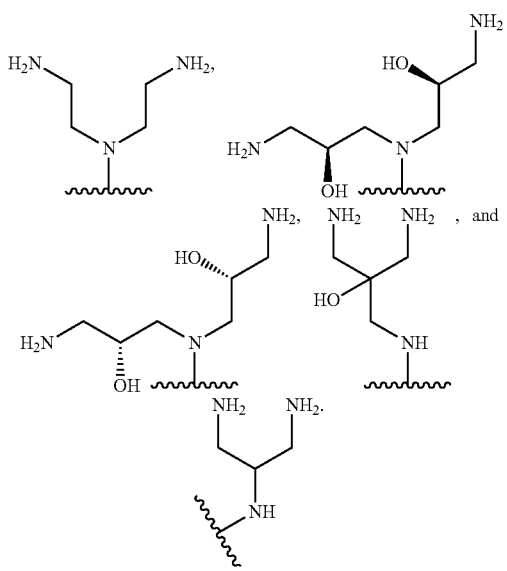

In other more specific embodiments of formula I, Q is selected from the group consisting of:

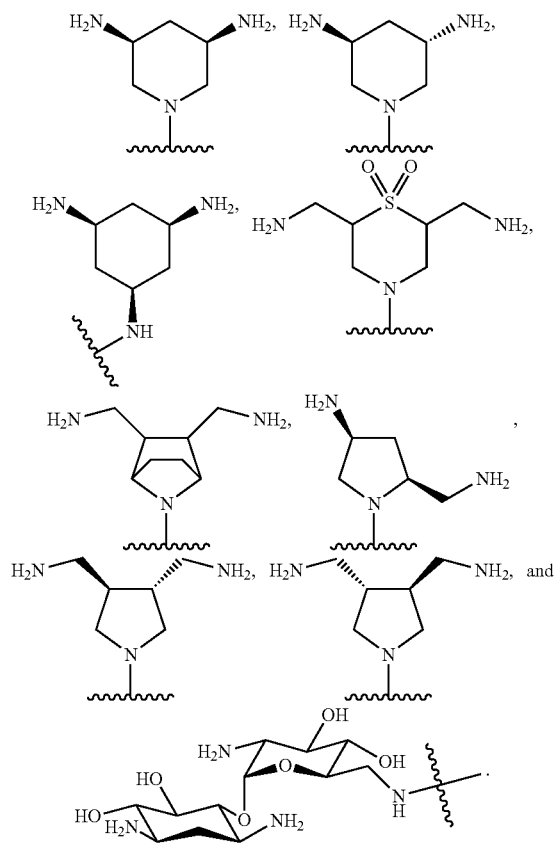

In some embodiments of formula I:

$R_1$ is selected from the group consisting of $C_1$-$C_6$ alkyl, $C_3$-$C_7$ carbocyclyl, heterocyclyl, aryl and heteroaryl, each optionally substituted with one or more substituents independently selected from the group consisting of a halogen, $C_1$-$C_4$ alkyl, $C_3$-$C_7$ cycloalkyl, —$OR_2$, —$SR_2$, —$SO_2R_2$, —$SO_2NHR_2$, —$CF_3$, —$OCF_3$, —$N(R_2)_2$, —CN, and —$CO_2C_1$-$C_4$ alkyl;

each $R_2$ is independently selected from the group consisting of H and $C_1$-$C_6$ alkyl;

A is —C(O)—;

Z is selected from the group consisting of —$CH_2$—, —C(O)—, —$S(O)_2$—, —C(O)NH— and —$S(O)_2NH$—;

Q is selected from the group consisting of —$NR_3R_4$,

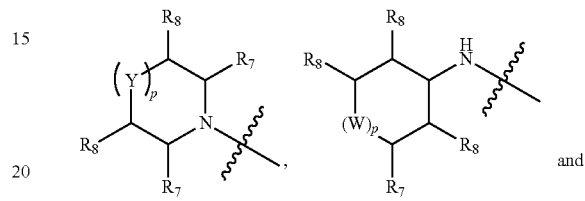

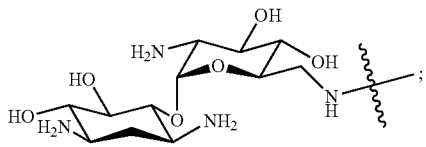

each $R_5$ is independently selected from the group consisting of H, —OH, —$CH_2OH$, halogen, and —$CH_2F$;

each $R_6$ is independently selected from the group consisting of H, —$CH_2OH$, and —$CH_2F$;

each $R_7$ is independently selected from the group consisting of H—$CH_2NH_2$ and —$CH_2OH$, or optionally, two $R_7$ can be linked by —$(CH_2)_m$— to form a bicyclic ring, wherein m is an integer of 1 to 3;

$R_9$ is selected from the group consisting of H, —$NH_2$, —$CH_2NH_2$, —OH and —$CH_2OH$;

U is selected from the group consisting of —$CH_2$—, —$C(CH_3)_2$, and

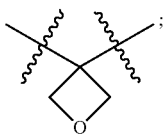 [SMILES: *C1(*)COC1]

V is selected from the group consisting of $C_3$-$C_7$ carbocyclyl, heterocyclyl, aryl and heteroaryl, each optionally substituted with one or more $C_1$-$C_4$ alkyl, halogen, $C_1$-$C_4$ alkoxy, —$CF_3$, —$OCF_3$ or —CN;

$R_{13}$ is selected from the group consisting of H; —$(CH_2)_p$-spirocyclic $C_3$-$C_7$ carbocyclyl-$(CH_2)_p$—; —$(CH_2)_p$-three- to seven-membered spirocyclic heterocyclyl-$(CH_2)_p$— optionally substituted with $C_{1-6}$ alkyl; and $C_1$-$C_4$ alkyl optionally substituted with one or more halogen, $C_1$-$C_4$ alkyl, $C_1$-$C_4$ alkoxy, and oxo;

or optionally, $R_{13}$ is a bond linked directly to X to form a ring; and n is equal to 1 or 2;

provided that when Y is O, S, $SO_2$, or $NR_2$, $R_8$ is not $NH_2$ or OH.

Some embodiments of formula I have the structure:

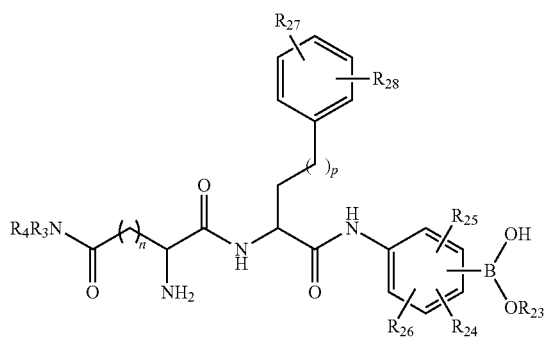

wherein:

$R_{23}$ is selected from the group consisting of H, spirocyclic $C_3$-$C_7$ carbocyclyl linked to the phenyl ring to which the boron is attached, three- to seven-membered spirocyclic heterocyclyl linked to the phenyl ring to which the boron is attached, and $C_1$-$C_4$ alkyl linked to the phenyl ring to which the boron is attached;

$R_{24}$, $R_{25}$, and $R_{26}$ are each independently selected from the group consisting of absent, hydrogen, $C_1$-$C_4$ alkyl optionally substituted with one or more halogen, halogen, $C_1$-$C_4$ alkoxy optionally substituted with one or more halogen, and —CN; and $R_{27}$ and $R_{28}$ are each independently selected from the group consisting of hydrogen, halogen, $C_1$-$C_4$ alkyl optionally substituted with one or more halogen, $C_3$-$C_7$ carbocyclyl, —$OR_2$, —$SR_2$, —$SO_2R_2$, —$SO_2NHR_2$, —$N(R_2)_2$, —CN, and —$CO_2C_1$-$C_4$ alkyl.

In some embodiments, all possible stereoisomers of the shown structures are contemplated. Compounds of any absolute and relative configurations at the stereocenters as well as mixtures of enantiomers and diastereoisomers of any given structure are also contemplated.

Synthetic Methods

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

Compounds of formula (I) of the present invention where Z is —C(O)— can be prepared as depicted in Scheme 1. Compounds where Z is —$CH_2$—, —$S(O)_2$—, —C(O)O—, —C(O)S—, —C(O)NH— and $S(O)_2NH$— may be prepared by related bond-forming reactions well known to those skilled in the art of organic chemistry.

Scheme 1

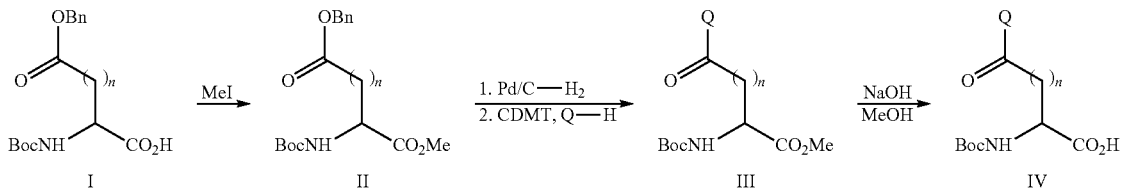

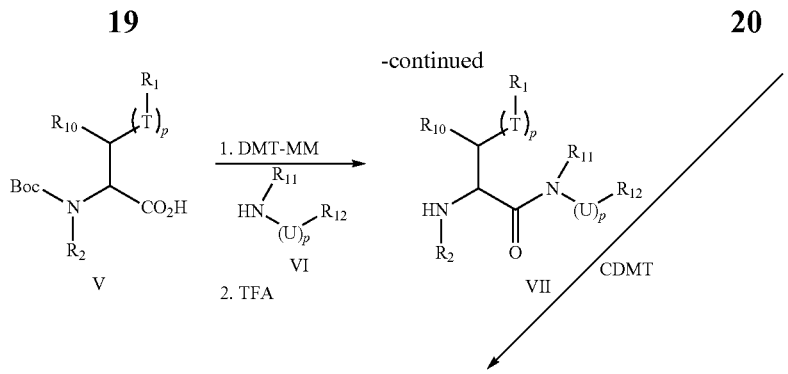

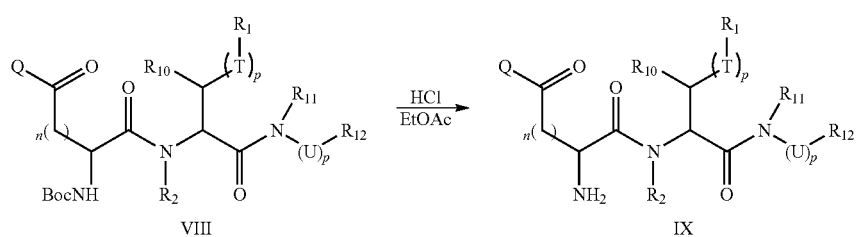

Scheme 1 describes a [2+2] method for preparation of EPI derivatives (IX). The first half is prepared by methylating a Boc protected amino acid containing a benzyl ester (I) with MeI to form methyl ester II. The benzyl group on II is removed by hydrogenation followed by standard CDMT coupling conditions to attach amine Q-H to give methyl ester III. Typically other amino groups present in Q-H are protected, e.g. by a t-butyloxycarbonyl (Boc) or benzyloxycarbonyl (Cbz) group. The methyl ester is cleaved with NaOH to yield acid IV. The second half is prepared by reacting Boc protected amino acid V with amine VI under standard DMT-MM coupling conditions following by TFA mediated Boc deprotection to give amine VII. Acid IV and amine VII are coupled using standard CDMT conditions followed by Boc deprotection to yield the EPI derivatives (IX).

Compounds of formula (I) of the present invention where Z is —C(O)— can be prepared by the alternative method depicted in Scheme 2. Compounds where Z is —CH$_2$—, —S(O)$_2$—, —C(O)O—, —C(O)S—, —C(O)NH— and S(O)$_2$NH— may be prepared by related bond-forming reactions well known to those skilled in the art of organic chemistry.

Scheme 2 describes a [3+1] method for preparation of EPI derivatives (IX). The first half is prepared by reacting amine VII with Boc protected amino acid I under standard TBTU coupling conditions. The benzyl group on XI is removed by hydrogenation followed by standard CDMT coupling conditions to attach amine Q-H. Typically other amino groups present in Q-H are protected, e.g. by a t-butyloxycarbonyl (Boc) group. Acid mediated Boc deprotection produces the final EPI derivatives (IX).

DEFINITIONS

Terms and substituents are given their ordinary meaning unless defined otherwise, and may be defined when introduced and retain their definitions throughout unless otherwise specified, and retain their definitions whether alone or as part of another group unless otherwise specified.

Scheme 2

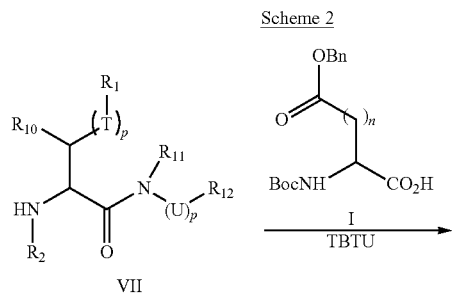

As used herein, "alkyl" means a branched, or straight chain chemical group containing only carbon and hydrogen, such as methyl, isopropyl, isobutyl, sec-butyl and pentyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary, with a protecting group. Alkyl groups can be saturated or unsaturated (e.g., containing —C═C— or —C≡C— subunits), at one or several positions. Typically, alkyl groups will include 1 to 9 carbon atoms, preferably 1 to 6, and more preferably 1 to 4 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyls may include a "spirocyclic carbocyclyl", which refers to a diradical carbocyclyl attached to the rest of the molecule through two attachment points from the same ring atom. Examples of spirocyclic carbocyclyl includes

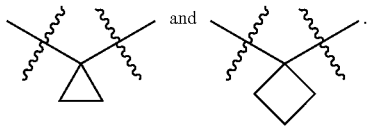 [SMILES: *C1(*)CC1 ; *C1(*)CCC1]

Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, in some embodiments, with a protecting group. Typically, carbocyclyl groups will include 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, carbocyclyl-CON—, aryl-CON—, heteroaryl-CON— or heterocyclyl-CON group where the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. A preferred aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, carbocyclyl, haloalkyl, alkoxy, aryl, nitro, halo, mercapto, and other substituents. Examples of heteroaryl include thienyl, pyridyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, quinolinyl, quinazolinyl, triazinyl, thiazolyl and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, carbocyclyl, hydroxy, alkoxy, cyano, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO—, aryl-CO—, heteroaryl-CO— or heterocyclyl-CO— group where the alkyl, carbocyclyl, aryl or heterocyclyl group is as herein described. Preferred acyls contain a lower alkyl. Exemplary alkyl acyl groups include acetyl, propanoyl, 2-methylpropanoyl, t-butylacetyl, butanoyl and palmitoyl.

As used herein, "halo or halide" is a chloro, bromo, fluoro or iodo atom radical. Chloro and fluoro are preferred halides. The term "halo" also contemplates terms sometimes referred to as "halogen", or "halide".

As used herein, "heterocyclyl" means a cyclic ring system including at least one heteroatom in the ring system backbone. Heterocyclyls may include multiple fused rings. Heterocyclyls may have any degree of saturation provided that at least one ring in the ring system is not aromatic. Heterocyclyls may include a "spirocyclic heterocyclyl", which refers to a diradical heterocyclyl attached to the rest of the molecule through two attachment points from the same ring atom. An examples of a spirocyclic heterocyclyl includes

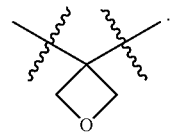 [SMILES: *C1(*)COC1]

Heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and where when the heterocycle is five membered, preferably it has one or two heteroatoms selected from O, N, or S.

As used herein, "substituted amino" means an amino radical which is substituted by one or two alkyl, carbocyclyl, aryl, heteroaryl or heterocyclyl groups, where the alkyl, carbocyclyl, aryl, heteroaryl or heterocyclyl are defined as above.

As used herein, "substituted hydroxyl" means RO— group where R is an alkyl, carbocyclyl, aryl, heteroaryl or a heterocyclyl group, where the alkyl, carbocyclyl, aryl, heteroaryl or heterocyclyl are defined as above.

As used herein, "substituted thiol" means RS— group where R is an alkyl, carbocyclyl, aryl, heteroaryl or a heterocyclyl group, where the alkyl, carbocyclyl, aryl, heteroaryl or heterocyclyl are defined as above.

As used herein, "sulfonyl" means an alkylSO$_2$, arylSO$_2$, heteroarylSO$_2$, carbocyclylSO$_2$, or heterocyclyl-SO$_2$ group where the alkyl, carbocyclyl, aryl, heteroaryl or heterocyclyl are defined as above.

As used herein, "sulfonamido" means an alkyl-S(O)$_2$NH—, aryl-S(O)$_2$NH—, heteroaryl-S(O)$_2$NH—, carbocyclyl-S(O)$_2$NH— or heterocyclyl-S(O)$_2$NH— group where the alkyl, carbocyclyl, aryl, heteroaryl or heterocyclyl group is as herein described.

As used herein, "ureido" means an alkyl-NHCONH—, aryl-NHCONH—, heteroaryl-NHCONH—, carbocyclyl-NHCONH— or heterocyclyl-NHCONH— group where the alkyl, carbocyclyl, aryl, heteroaryl or heterocyclyl group is as herein described.

As used herein, "guanidino" means an alkyl-NHC(=NR')NH—, aryl-NHC(=NR')NH—, heteroaryl-NHC(=NR')NH—, carbocyclyl-NHC(=NR')NH— or heterocyclyl-NHC(=NR')NH— group where R is an H, substituted or unsubstituted hydroxyl, CN, alkyl, carbocyclyl, aryl, heteroaryl or a heterocyclyl group, where the alkyl, carbocyclyl, aryl, heteroaryl or heterocyclyl group is as herein described.

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring as allowed by the definitions of the constituent groups. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members.

As used herein, when two groups are indicated as being taken "together" to form a ring, the ring formed is a carbocyclyl, heterocyclyl, aryl, or heteroaryl ring as specifically recited. Such rings are not limited by the definitions of the two groups taken individually.

The skilled artisan will recognize that some structures described herein may be resonance forms or tautomers of compounds that may be fairly represented by other chemical structures, even when thermodynamically disfavored; the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes humans, cattle, horses, dogs, and cats, but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant an amount of a compound (e.g., an efflux pump inhibitor, or amounts individually of an efflux pump inhibitor and an antimicrobial agent) that have a therapeutic effect (e.g., inhibition to some extent of the normal metabolism of microbial cells causing or contributing to a microbial infection). The doses of efflux pump inhibitor and antimicrobial agent, which are useful in combination as a treatment, are therapeutically effective amounts. Thus, as used herein, a therapeutically effective amount includes those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective to prevent a microbial infection.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for therapeutic purposes. The term "prevent," "preventing," or "prophylactic treatment" refers to use in a patient who is not yet infected, but who is susceptible to, or otherwise at risk of, a particular infection, whereby the treatment reduces the likelihood that the patient will develop an infection. The term "therapeutic treatment" refers to administering treatment to a patient already suffering from an infection.

The term "administration" or "administering" refers to a method of giving a dosage of an antimicrobial pharmaceutical composition to a vertebrate or invertebrate, including a mammal, a bird, a fish, or an amphibian, where the method is, e.g., intrarespiratory, topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "efflux pump" refers to a protein assembly that exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump, which spans the outer membrane.

The term "multidrug resistance pump" refers to an efflux pump that is not highly specific to a particular antibiotic. The term thus includes broad substrate pumps (efflux a number of compounds with varying structural characteristics). An "efflux pump inhibitor" ("EPI") is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity.

A "diagnostic" as used herein is a compound, method, system, or device that assists in the identification and characterization of a health or disease state.

The term "comprising" as used herein is synonymous with "including," "containing," or "characterized by," and is inclusive or open-ended and does not exclude additional, unrecited elements or method steps.

Administration and Pharmaceutical Compositions

Some embodiments include pharmaceutical compositions including: (a) a safe and therapeutically effective amount of the efflux pump inhibitor, or its corresponding enantiomer, diastereoisomer or tautomer, or pharmaceutically acceptable salt; and (b) a pharmaceutically acceptable carrier, diluent, or excipient.

The efflux pump inhibitors are administered at a therapeutically effective dosage, e.g., a dosage sufficient to provide treatment for the disease states previously described. While human dosage levels have yet to be optimized for the compounds of the preferred embodiments, generally, a daily dose for most of the inhibitors described herein is from about 0.05 mg/kg or less to about 100 mg/kg or more of body weight, preferably from about 0.10 mg/kg to 10.0 mg/kg of body weight, and most preferably from about 0.15 mg/kg to 1.0 mg/kg of body weight. Thus, for administration to a 70 kg person, the dosage range would be about 3.5 mg per day or less to about 7000 mg per day or more, preferably from about 7.0 mg per day to 700.0 mg per day, and most preferably from about 10.0 mg per day to 100.0 mg per day. The amount of active compound administered will, of course, be dependent on the subject and disease state being treated, the severity of the affliction, the manner and schedule of administration and the judgment of the prescribing physician; for example, a likely dose range for oral administration can be from about 70 mg per day to 700 mg per day, whereas for intravenous administration a likely dose range can be from about 700 mg per day to 7000 mg per day, the active agents being selected for longer or shorter plasma half-lives, respectively. Screening techniques described herein for the compounds of preferred embodiments can be used with other efflux pump inhibitors described herein to establish the efficacy of those inhibitors in comparison to reference compounds, and the dosage of the inhibitor can thus be adjusted to achieve an equipotent dose to the dosages of reference compound.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in *Remington's The Science and Practice of Pharmacy*, 21$^{st}$ Ed., Lippincott Williams & Wilkins (2005), incorporated by reference in its entirety.

In addition to the selected compound useful as described above, the compositions of the present invention contain a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to 7.0-8.0. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parental administration include propylene glycol, ethyl oleate, pyrrolidone, ethanol, and sesame oil.

In addition, the compounds can be co-administered with, and the pharmaceutical compositions can include, other medicinal agents, pharmaceutical agents, adjuvants, and the like. Suitable additional active agents include, for example, antimicrobial agents as described above. When used, other active agents may be administered before, concurrently, or after administration of an efflux pump inhibitor of the preferred embodiments. In some embodiments, an efflux pump inhibitor is co-administered with one or more other antimicrobial agents. By "co-administer" it is meant that the efflux pump inhibitors are administered to a patient such that the present compounds as well as the co-administered compound may be found in the patient's bloodstream at the same time, regardless of when the compounds are actually administered, including simultaneously. In one advantageous embodiment, the pharmacokinetics of the efflux pump inhibitors and the co-administered antimicrobial agent are substantially the same.

Thus, in the preferred embodiments, an efflux pump inhibitor compound as set forth herein can be administered through a first route of administration, and the antimicrobial agent can be administered through a second route. Thus, for example, an efflux pump inhibitor can be administered via a pulmonary route, e.g., through a nebulizer, atomizer, mister, aerosol, dry powder inhaler, or other suitable device or technique, and the antimicrobial can be administered via the same or a different route, e.g., orally, parenterally, intramuscularly, intraperitoneally, intratracheally, intravenously, subcutaneously, transdermally, or as a rectal or vaginal suppository. The blood levels of drugs are affected by the route of administration. Thus, in one preferred embodiment, when the efflux pump inhibitor is administered by a first route, and the antibiotic or antimicrobial through a second route, the dosages or dosage forms are adjusted, as appropriate, to match the pharmacokinetic profiles of each drug. This may also be done when both drugs are administered by the same route. In either event, conventional techniques, including controlled release formulations, timing of administration, use of pumps and depots, and/or use of biodegradable or bioerodible carriers can be used to match the pharmacokinetic of the two active moieties.

The compositions of this invention are preferably provided in unit dosage form. As used herein, a "unit dosage form" is a composition of this invention containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. Unit dosage forms in which the two active ingredients (inhibitor and antimicrobial) are physically separated are also contemplated; e.g., capsules with granules of each drug; two-layer tablets; two-compartment gel caps, etc. The skilled artisan will recognize that the formulation does not specifically contemplate the entire course of therapy and such decisions are left for those skilled in the art of treatment rather than formulation.

The compositions useful as described above may be in any of a variety of forms, suitable (for example) for oral, nasal, rectal, topical (including transdermal), ocular, intracerebral, intracranial, intrathecal, intra-arterial, intravenous, intramuscular, or other parental route of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. These include solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, 4$^{th}$ Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. These oral forms include a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically include conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically include one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically include one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Efflux pump inhibitors (EPIs) as described herein, including any of the compounds generically or specifically described herein, can also be administered to the respiratory tract as an aerosol. For the purposes of delivery to the respiratory tract, any of the inhaler designs known in the art may be used. In some embodiments, a metered dose inhaler (MDI) is used. A typical MDI for use with the EPIs described herein includes the EPI compound suspended or dissolved in a pressurized liquid propellant, with or without other excipients. When the MDI inhaler is activated, a metered amount of the propellant is released and rapidly evaporates due to the sudden reduction in pressure. The process causes an aerosol cloud of drug particles to be released that can be inhaled by the patient.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Methods of Treatment

Some embodiments include a method of inhibiting a bacterial efflux pump including administering to a subject infected with bacteria, a compound according to any of the structures described above. Other embodiments include a method of treating or preventing a bacterial infection including administering to a subject infected with bacteria or subject to infection with bacteria, a compound according to any of the structures described above in combination with another anti-bacterial agent.

Microbial Species

The microbial species to be inhibited through the use of efflux pump inhibitors, such as the above-described EPIs, can be from bacterial groups or species, such as one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In particular embodiments, the bacteria is selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

A particularly appropriate example of a microbe appropriate for the use of an efflux pump inhibitor of the preferred embodiments is a pathogenic bacterial species, *Pseudomonas aeruginosa,* which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor of preferred embodiments, the antibacterial agent, which would otherwise be maintained at a very low intracellular concentration by the export process, can accumulate to a concentration, which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

Antimicrobial Agents

In particular embodiments various antibacterial agents can be used in combination with the efflux pump inhibitors described herein. These include quinolones, tetracyclines, glycopeptides, aminoglycosides, β-lactams, rifamycins, macrolides/ketolides, oxazolidinones, coumermycins, and chloramphenicol. In particular embodiments, an antibiotic of the above classes can be, for example, one of the following.

β-Lactam Antibiotics

Beta-lactam antibiotics include, but are not limited to, imipenem, meropenem, biapenem, doripenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, ceftobiprole, ceftaroline, FK-312, S-1090, CP-0467, BK-218, FK-037, DQ-2556, FK-518, cefozopran, ME1228, KP-736, CP-6232, Ro 09-1227, OPC-20000, and LY206763

Macrolides

Macrolides include, but are not limited to, azithromycin, clarithromycin, erythromycin, oleandomycin, rokitamycin, rosaramicin, roxithromycin, and troleandomycin.

Ketolides

Ketolides include, but are not limited to, telithromycin and cethrimycin.

Quinolones

Quinolones include, but are not limited to, amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, moxifloxacin; gemifloxacin; garenofloxacin; prulifloxacin, finafloxacin, delafloxacin, PD131628, PD138312, PD140248, Q-35, AM-1155, NM394, T-3761, rufloxacin, OPC-17116, DU-6859a (see, e.g., Sato, K. et al., 1992, Antimicrob Agents Chemother. 37:1491-98), and DV-7751a (see, e.g., Tanaka, M. et al., 1992, Antimicrob. Agents Chemother. 37:2212-18).

Tetracyclines, Glycylcyclines and Oxazolidinones

Tetracyclines, glycylcyclines, and oxazolidinones include, but are not limited to, chlortetracycline, demeclocycline, doxycycline, lymecycline, methacycline, minocycline, oxytetracycline, tetracycline, tigecycline, PTK 0796, linezolide, eperozolid and torezolide.

Aminoglycosides

Aminoglycosides include, but are not limited to amikacin, arbekacin, butirosin, dibekacin, fortimicins, gentamicin, kanamycin, neomycin, netilmicin, ribostamycin, sisomicin, spectinomycin, streptomycin, and tobramycin.

Lincosamides

Lincosamides include, but are not limited to, clindamycin and lincomycin.

Efflux pumps export substrate molecules from the cytoplasm and/or periplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. While the endogenous substrates of efflux pumps are not yet identified, there are some indications that efflux pumps may be important for bacterial virulence. Thus, also disclosed herein are compositions that include such efflux pump inhibitors and methods for treating microbial infections using those compositions.

In some embodiments, a method is provided for treating a microbial infection in an animal, specifically including in a mammal, by treating an animal suffering from such an infection with an antimicrobial agent and an efflux pump inhibitor, which increase the susceptibility of the microbe for that antimicrobial agent. Such efflux pump inhibitors can be selected from any of the compounds generically or specifically described herein. In this way a microbe involved in the infection can be treated using the antimicrobial agent in smaller quantities, or can be treated with an antimicrobial agent, which is not therapeutically effective when used in the absence of the efflux pump inhibitor. Thus, this method of treatment is especially appropriate for the treatment of infections involving microbial strains that are difficult to treat using an antimicrobial agent alone due to a need for high dosage levels (which can cause undesirable side effects), or due to lack of any clinically effective antimicrobial agents. However, it is also appropriate for treating infections involving microbes that are susceptible to particular antimicrobial agents as a way to reduce the dosage of those particular agents. This can reduce the risk of side effects. It is also appropriate for treating infections involving microbes that are susceptible to particular antimicrobial agents as a way of reducing the frequency of selection of resistant microbes. In particular embodiments the microbe is a bacterium, which may, for example, be from any of the groups or species indicated above.

In some embodiments, a method is provided for prophylactic treatment of a mammal. In this method, an antimicrobial agent and an efflux pump inhibitor is administered to a mammal at risk of a microbial infection, e.g., a bacterial infection. The efflux pump inhibitor can be selected from any of the compounds generically or specifically described herein.

In some embodiments, a method is provided for enhancing the antimicrobial activity of an antimicrobial agent against a microbe, in which such a microbe is contacted with an efflux pump inhibitor, and an antibacterial agent. The efflux pump inhibitor can be selected from any of the compounds generically or specifically described herein. Thus, this method makes an antimicrobial agent more effective against a cell, which expresses an efflux pump when the cell is treated with the combination of an antimicrobial agent and an efflux pump inhibitor. In particular embodiments the microbe is a bacterium or a fungus, such as any of those indicated above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In other embodiments, a method is provided for suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, in the presence of a concentration of antibacterial agent below the MIC of the bacterium. The efflux pump inhibitor can be selected from any of the compounds generically or specifically described herein. This method is useful, for example, to prevent or cure contamination of a cell culture by a bacterium possessing an efflux pump. However, it applies to any situation where such growth suppression is desirable.

In some embodiments, any of the compounds generically or specifically described herein may be administered as an efflux pump inhibitor either alone or, more preferably, in conjunction with another therapeutic agent. In some embodiments, any of the compounds generically or specifically described herein may be administered as an efflux pump inhibitor in conjunction with any of the antibacterial agents specifically or generically described herein, as well as with any other antibacterial agent useful against the species of bacterium to be treated, when such bacteria do not utilize an efflux pump resistance mechanism. In some embodiments, the antibacterial agents are administered at their usual recommended dosages. In other embodiments, the antibacterial agents are administered at reduced dosages, as determined by a physician. For all conventional antibacterials on the market, and many in clinical development, dosage ranges and preferred routes of administration are well established, and those dosages and routes can be used in conjunction with the efflux pump inhibitors of the preferred embodiments. Reduced dosages of the antibacterials are contemplated due to the increased efficacy of the antibacterial when combined with an efflux pump inhibitor.

Potential efflux pump inhibitor compounds can be tested for their ability to inhibit multi-drug resistance efflux pumps of various microbes using the methods described herein as well as those known in the art. For example, treatment of *P. aeruginosa* with a test compound allows obtaining one or more of the following biological effects:

1) *P. aeruginosa* strains will become susceptible to antibiotics that could not be used for treatment of pseudomonad infections, or become more susceptible to antibiotics, which do inhibit pseudomonal growth.
2) *P. aeruginosa* strains will become more susceptible to antibiotics currently used for treatment of pseudomonad infections.
3) Inhibition of the pump will result in a decreased frequency of resistance development to antibiotic, which is a substrate of the pump.

Obtaining even one of these effects provides a potential therapeutic treatment for infections by this bacterium. Also, similar pumps are found in other microorganisms. Some or all of the above effects can also be obtained with those microbes, and they are therefore also appropriate targets for detecting or using efflux pump inhibitors.

The following examples will further describe the present invention, and are used for the purposes of illustration only, and should not be considered as limiting.

EXAMPLES

General Procedures $^1$H nuclear magnetic resonance spectra (NMR) were measured in the indicated solvents on either a Bruker NMR spectrometer (Avance™ DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; brs, broad singlet; d, doublet; brd, broad doublet; t, triplet; q, quartet; dd, doublet of doublets; td, triplet of doublets; m, multiplet; ABq, AB quartet.

The following abbreviations have the indicated meanings:
Ac$_2$O=acetic anhydride
'BDMSCl=tert-butyldimethylsilyl chloride
BID=twice (two times) a day
Boc$_2$O=di-tert-butyl dicarbonate
B(OMe)$_3$=trimethyl borate
nBuLi=n-butyl lithium
Bu$_4$NCN=tetrabutylammonium cyanide
Bzl-OH=benzyl alcohol
CBz-OSu=N-(benzyloxycarbonyloxy)succinimide
CDMT=2-chloro-4,6-dimethoxy-1,3,5-triazine
CFU=colony-forming unit
CoCl$_3$=cobalt (III) chloride
CsCO$_3$=cesium carbonate
DCM=dichloromethane
DIBAL-H=diisobutylaluminium hydride
DBU=1,8-diazabicyclo[5.4.0]undec-7-ene
DEAD=diethyl azodicarboxylate
DIPEA=diisopropylethylamine
DMAP=4-dimethylaminopyridine
DMF=N,N-dimethylforamide
DMSO=dimethylsulfoxide
DMT-MM=4-(4,6-dimethoxy-1,3,5-triazin-2-yl)-4-methylmorpholinium chloride
DPPA=diphenylphosphoryl azide
ESIMS=electron spray mass spectrometry
EtOAc=ethyl acetate
EtOH=ethanol
EtONa=sodium ethoxide
HATU=2-(7-aza-1H-benzotriazole-1-yl)-1,1,3,3-tetramethyluronium hexafluorophosphate
HOAc=acetic acid
K$_2$CO$_3$=potassium carbonate
KHSO$_4$=potassium bisulfate
KOAc=potassium acetate
MeCN=acetonitrile
MeMgBr=methylmagnesium bromide
MeOH=methanol
MeONa=sodium methoxide
Me$_3$P=trimethyl phosphine
MgSO$_4$=magnesium sulfate
MsCl=mesyl chloride or methanesulfonyl chloride
NaBH$_4$=sodium borohydride
NaHCO$_3$=sodium bicarbonate
NaIO$_4$=sodium periodate
Na$_2$S$_2$O$_3$=sodium thiosulfate
NBS=N-bromosuccinimide
NH$_4$Cl=ammonium chloride
NMM=N-methylmorpholine
NMR=nuclear magnetic resonance
pd(dppf)Cl$_2$=1,1'-bis(diphenylphosphino)ferrocene] dichloropalladium(II)
Pd/C=palladium on carbon
Pd(OH)$_2$=palladium hydroxide
POCl$_3$=phosphorus oxychloride
PtO$_2$=Adams' catalyst or platinum dioxide
rt=room temperature
RuO$_2$=ruthenium oxide
TBTU=(2-(1H-benzotriazole-1-yl)-1,1,3,3-tetramethyluronium tetrafluoroborate)
TEA=triethylamine
TFA=trifluoroacetic acid
THF=tetrahydrofuran
TMSCN=trimethylsilyl cyanide
TrCl=triphenylmethyl chloride or trityl chloride
pTsOH=para-toluenesulfonic acid

Compound Examples

Preparation of intermediate (XVI) is depicted below in Scheme 3.

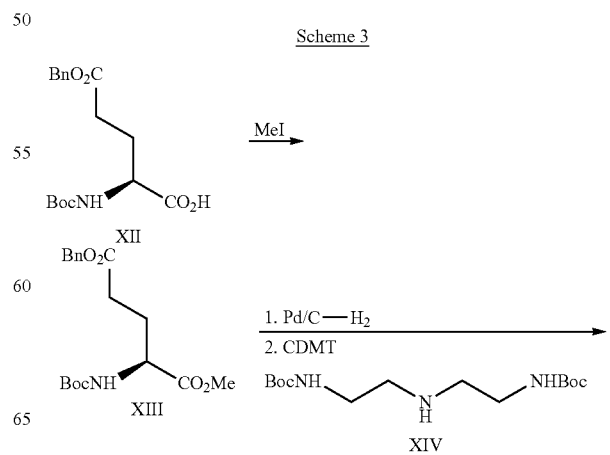

Scheme 3

-continued

XV

XVI

Step 1

Methyl iodide (1.01 mL, 16.3 mmol) was added dropwise to a solution of (2S)-5-(benzyloxy)-2-{[(tert-butoxy)carbonyl]amino}-5-oxopentanoic acid XII (5.00 g, 14.82 mmol) and $K_2CO_3$ (2.25 g, 16.3 mmol) in DMF (25 mL) at room temperature The reaction mixture was stirred about 3 h at room temperature before adding additional methyl iodide (1.01 mL, 16.3 mmol). EtOAc was then added to the reaction and washed 3×10% $Na_2S_2O_3$ and dried over $MgSO_4$. The solvent was removed under reduced pressure and the crude product was purified on a silica gel column (100:1 and then 50:1 $CHCl_3$/MeOH) to give 5-benzyl 1-methyl (2S)-2-{[(tert-butoxy)carbonyl]amino}pentanedioate XIII (4.20 g, 12.23 mmol, 82% yield). ESIMS found for $C_{18}H_{25}NO_6$ m/z 352 (M+H).

Step 2

To a solution of 5-benzyl 1-methyl (2S)-2-{[(tert-butoxy)carbonyl]amino}pentanedioate XIII (4.2 g, 12.23 mmol) in EtOH/water (40 mL/6 mL) under argon was added 10% Pd/C catalyst (catalytic amount). The mixture was stirred under an atmosphere of hydrogen for 6 h at room temperature. The mixture was then filtered through Celite and evaporated to dryness to afford the free acid (3.0 g, 11.48 mmol, 32% yield). ESIMS found for $C_{32}H_{61}N_7O_{10}$ m/z 262 (M+H).

Step 3

To a solution of CDMT (2.22 g, 12.62 mmol) in DCM (40 mL) and cooled to 0° C. was added N-methylmorpholine (1.38 mL, 12.63 mmol). The mixture was stirred for 10 min before adding (4S)-4-{[(tert-butoxy)carbonyl]amino}-5-methoxy-5-oxopentanoic acid (3.0 g, 11.48 mmol). The solution was stirred for 60 min at 0° C. The tert-butyl N-{2-[(2-{[(tert-butoxy)carbonyl]amino}ethyl)amino]ethyl}carbamate XIV was then added and the mixture stirred at room temperature overnight. The solution was washed with 1 M aq. $K_2CO_3$, 1 M aq. HCl, brine and dried over anhydrous $MgSO_4$. The crude product was crystallized from DCM/hexane to give methyl (2S)-4-[bis(2-{[(tert-butoxy)carbonyl]amino}ethyl)carbamoyl]-2-{[(tert-butoxy)carbonyl]amino}butanoate (XV) (4.91 g, 8.98 mmol, 72% yield). $^1H$ NMR (DMSO-$d_6$) δ ppm 1.35-1.47 (m, 27H), 1.80-1.91 (m, 1H), 2.19-2.32 (m, 1H), 2.33-2.42 (m, 1H), 2.46-2.57 (m, 1H), 3.11-3.38 (m, 6H), 3.40-3.53 (m, 1H), 3.54-3.62 (m, 1H), 3.73 (s, 3H), 4.26-4.38 (m, 1H), 4.99-5.09 (brs, 1H), 5.31-5.46 (m, 2H); ESIMS found for $C_{25}H_{46}N_4O_9$ m/z 547 (M+H).

Step 4

To the solution of the ester (XV) (290 mg, 0.51 mmol) in MeOH (10 mL) was added 4 M NaOH dropwise until pH=13. The mixture was stirred overnight at room temperature before evaporating the MeOH under reduced pressure. The residue was mixed with water and washed with ether. After acidifying to pH~3 with 2 M HCl, the product was extracted with DCM, dried over $MgSO_4$ and concentrated under vacuum to give (S)-5-(bis(2-(tert-butoxycarbonylamino)ethyl)amino)-2-(tert-butoxycarbonylamino)-5-oxopentanoic acid (XVI) (250 mg, 0.45 mmol, 88% yield). ESIMS found for $C_{24}H_{44}N_4O_9$ m/z 533 (M+H).

Preparation of intermediate (XXIV) is depicted below in Scheme 4.

Scheme 4

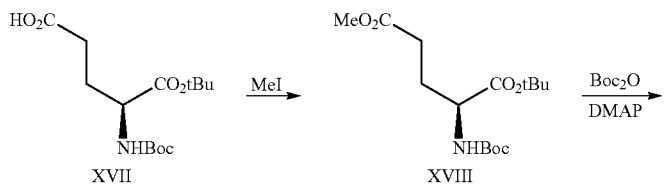

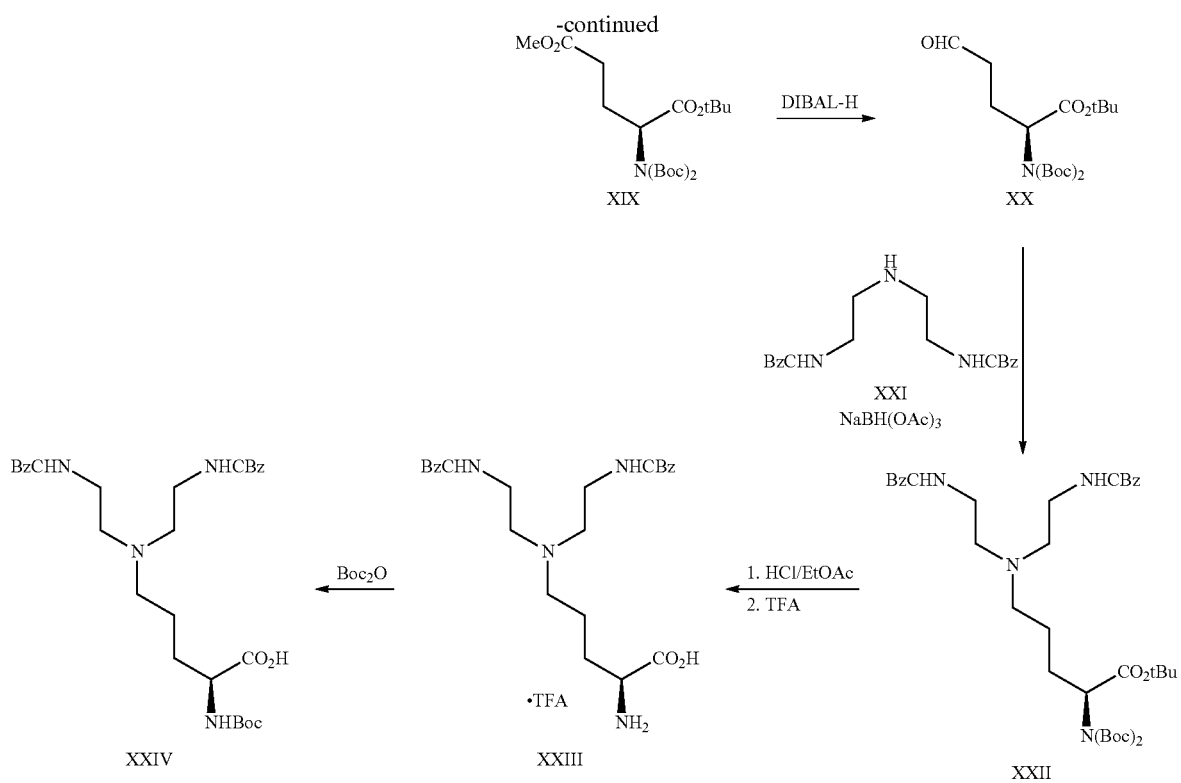

Step 1

To a solution of Boc-glutamic acid tert-butyl ester XVII (50 g, 164.8 mmol) and $K_2CO_3$ (34.2 g, 247.2 mmol) in DMF (250 mL) was added MeI (10.8 ml, 173.1 mmol) dropwise. The reaction mixture was stirred at room temperature for 2 h before adding EtOAc. The organic extract was washed 10% $Na_2S_2O_3$ (3×) and dried over $MgSO_4$. The solvent was removed under reduced pressure and the crude product was crystallized from hexane to give the product XVIII as a white solid (50.7 g, 159.8 mmol, 95% yield). $^1$H NMR (CDCl$_3$) δ ppm 1.44 (s, 9H), 1.46 (s, 9H), 1.86-1.96 (m, 11H), 2.08-2.20 (m, 1H), 2.32-2.46 (m, 2H), 3.46 (m, 2H), 3.68 (s, 3H), 4.17-4.21 (m, 1H); ESIMS found for $C_{15}H_{27}NO_6$ m/z 318 (M+H).

Step 2

To a solution of 1-tert-butyl 5-methyl (2S)-2-{[(tert-butoxy)carbonyl]amino}pentanedioate XVIII (50.7 g, 159.8 mmol), TEA (26.6 mL, 191.7 mmol) and DMAP (19.5 g, 159.8 mmol) in MeCN (480 mL) was added Boc$_2$O (69.7 g, 319.5 mmol). The reaction mixture was stirred at room temperature overnight before adding additional TEA (11.1 mL, 79.0 mmol), DMAP (9.8 g, 79.9 mmol) and Boc$_2$O (34.8 g, 159.8 mmol) and stirring for another 2 days. The solvent was removed under reduced pressure and residue was purified on a silica gel column (1:100→1:50→1:30 EtOAc:hexane) to give pure product XIX as colorless oil. (50.0 g, 119.8 mmol, 75% yield). $^1$H NMR (CDCl$_3$) δ ppm 1.44 (s, 9H), 1.49 (s, 18H), 2.15 (ddd, J=3 Hz, J=8 Hz, J=19 Hz, 1H), 2.33-2.46 (m, 3H), 3.66 (s, 3H), 4.75 (m, 1H); ESIMS found for $C_{20}H_{35}NO_8$ m/z 857 (2M+23).

Step 3

To a solution of 1-tert-butyl 5-methyl (2S)-2-{bis[(tert-butoxy)carbonyl]amino}pentanedioate XIX (50.0 g, 119.8 mmol) in dry ethyl ether (120 mL) at −78° C. under Ar was added a solution of DIBAL-H in THF (65.0 mL, 65.0 mmol). The reaction mixture was stirred 1.5-2.5 hours at −78° C. The mixture was treated with MeOH (240 mL) and allowed to warm to room temperature. The suspension was filtered through Celite and washed with MeOH. The solvent was removed under reduced pressure and the residue was purified on a silica gel column (1:20 EtOAc:hexane) to give pure product XX as a colorless oil. (37.1 g, 95.8 mmol, 80% yield). $^1$H NMR (CDCl$_3$) δ ppm 1.44 (s, 9H), 1.47 (s, 18H), 2.07-2.15 (m, 1H), 2.37-2.56 (m, 3H), 4.70 (dd, J=5 Hz, J=10 Hz, 1H), 9.73 (s, 1H); ESIMS found for $C_{19}H_{33}NO_7$ m/z 410 (M+23).

Step 4

To a solution of benzyl N-{2-[(2-{[(benzyloxy)carbonyl]amino}ethyl)amino]ethyl}carbamate XXI (13.34 g, 35.92 mmol) in dry DCM (100 mL) was added acetic acid (9.34 mL, 163.25 mmol). The mixture was cooled with water/ice bath before adding tert-butyl (2S)-2-{bis[(tert-butoxy)carbonyl]amino}-5-oxopentanoate XX. The reaction mixture was stirred for 1 h at 0° C. and then sodium triacetoxyborohydride (10.37 g, 48.98 mmol) was added in portions. The reaction mixture was stirred at room temperature overnight. The reaction was washed with water, 1 M HCl, brine and dried over MgSO$_4$. The solvent was removed under reduced pressure and product was purified on a silica gel column (1:15→1:10→1:10→1:1 EtOAc:hexane→100% EtOAc) to give the protected amino acid XXII as yellow oil (15.12 g, 20.35 mmol, 57% yield). $^1$H NMR (CDCl$_3$) δ ppm 1.44 (s, 9H), 1.50 (s, 18H), 1.70-1.98 (m, 4H), 2.00-2.16 (m, 2H), 3.15 (brs, 4H), 3.56 (brs, 4H), 4.55-4.67 (m, 1H), 5.08 (s, 4H), 6.36 (brs, 2H), 7.32 (brs, 10H); ESIMS found for $C_{39}H_{58}N_4O_{10}$ m/z 743 (M+H).

Step 5

To a solution of tert-butyl (2S)-5-[bis(2-{[(benzyloxy)carbonyl]amino}ethyl)amino]-2-{bis[(tert-butoxy)carbonyl]amino}pentanoate XXII (3.00 g, 4.04 mmol) in EtOAc (20 mL) was added HCl (3.5 M solution in EtOAc, 20 mL). The reaction mixture was stirred for 30 min at room temperature before adding ethyl ether (about 50 mL). The precipitate was filtered and washed with ether to give tert-butyl (2S)-5-[bis(2-{[(benzyloxy)carbonyl]amino}ethyl)amino]-2-aminopentanoic acid as a white crystalline solid (1.82 g, 3.14 mmol, 78% yield).

Step 6

A solution of tert-butyl (2S)-5-[bis(2-{[(benzyloxy)carbonyl]amino}ethyl)amino]-2-aminopentanoic acid (1.82 g, 3.14 mmol) in TFA (20 mL) was stirred overnight. The TFA was removed under reduced pressure to give (2S)-2-amino-5-[bis(2-{[(benzyloxy)carbonyl]amino}ethyl)amino]pentanoic acid, trifluoroacetic acid salt (XXIII) as a light brown foam (1.70 g, 2.83 mmol, 90% yield). ESIMS found for $C_{25}H_{34}N_4O_6$ m/z 487 (M+H).

Step 7

To a solution of (2S)-2-amino-5-[bis(2-{[(benzyloxy)carbonyl]amino}ethyl)amino]pentanoic acid XXIII (1.70 g, 2.83 mmol) in water (20 mL) was added $K_2CO_3$ followed by a solution of $Boc_2O$ (0.80 g, 3.68 mmol) in acetone (15 mL). The reaction mixture was stirred for 1 h with additional portions of $K_2CO_3$ being added to maintain the pH of 10. The mixture was stirred overnight and then the acetone was evaporated under reduced pressure and alkalized to pH=12. The aqueous residue was washed with diethyl ether (2×) and acidified with 6 N HCl to pH=2. The aqueous phase was washed with DCM (4×) and the combined DCM extracts were washed with brine and dried over $MgSO_4$. The solvent was removed under reduced pressure and product was purified on a silica gel column (100:1→50:1→30:1→20:1 EtOAc:MeOH) to give (2S)-5-[bis(2-{[(benzyloxy)carbonyl]amino}ethyl)amino]-2-{[(tert-butoxy)carbonyl]amino}pentanoic acid XXIV (1.35 g, 3.30 mmol, 81% yield). $^1$H NMR (CDCl$_3$) δ ppm 1.41 (s, 9H), 1.83 (brs, 4H), 3.25 (brs, 6H), 3.55 (brs, 4H), 4.23 (brs, 1H), 5.07 (s, 4H), 5.72 (brs, 1H), 6.10 (brs, 1H), 6.68 (brs, 1H), 7.32 (brs, 10H); ESIMS found for $C_{30}H_{42}N_4O_8$ m/z 587 (M+H).

Preparation of intermediate (XXIX) is depicted below in Scheme 5.

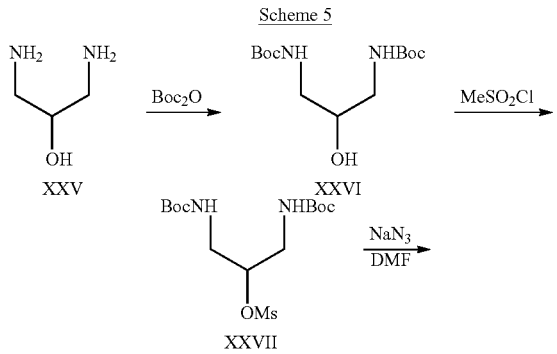

Scheme 5

Step 1

To a solution of 1,3-diamine-2-hydroxypropane (XXV) (10 g, 110 mmol) in 5% $NaHCO_3$ (pH~9) was added a solution of $Boc_2O$ (97 g, 440 mmol) in acetone (200 mL). The reaction mixture was stirred overnight. The acetone was evaporated under vacuum and aqueous residue was washed 5×EtOAc. The organic layer was washed with brine and dried over $MgSO_4$. The solvent was removed under reduced pressure to give crude product. The product was purified on a silica gel column (1:200→1:150→1:120→100:1→80:1→50:1 MeOH:DCM) to give the pure tert-butyl N-(3-{[(tert-butoxy)carbonyl]amino}-2-hydroxypropyl)carbamate XXVI as white solid (20.10 g, 69.3 mmol, 62% yield). ESIMS found for $C_{13}H_{26}N_2O_5$ m/z 291 (M+H).

Step 2

To a solution of tert-butyl N-(3-{[(tert-butoxy)carbonyl]amino}-2-hydroxypropyl)carbamate XXVI (1.83 g, 6.3 mmol) in DCM was added TEA (1.38 mL, 10 mmol) was added. The mixture was cooled to 10° C. before adding mesyl chloride (0.77 mL, 10 mmol) dropwise. The reaction mixture was stirred for 30 min and then the solvent was removed under reduced pressure. The residue was dissolved in DCM, washed 1 M HCl (3×), 5% aq. $NaHCO_3$ and dried over $MgSO_4$. The solvent was again removed under vacuum to give tert-butyl N-(3-{[(tert-butoxy)carbonyl]amino}-2-(methanesulfonyloxy)propyl)carbamate XXVII (2.31 g, 6.3 mmol, 99% yield). ESIMS found for $C_{14}H_{28}N_2O_7S$ m/z 369 (M+H).

Step 3

To a solution of tert-butyl N-(3-{[(tert-butoxy)carbonyl]amino}-2-(methanesulfonyloxy)propyl)carbamate XXVII (2.31 g, 6.6 mmol) in DMF was added $NaN_3$. The mixture was heated overnight at 60° C., diluted with DCM and washed with 10% $Na_2S_2O_3$ (5×), 5% $NaHCO_3$, brine and dried over $MgSO_4$. The solvent was evaporated under vacuum to give crude product (1.75 g). The product was purified on a silica gel column (1:10 EtOAc:hexane) to give the pure tert-butyl N-(2-azido-3-{[(tert-butoxy)carbonyl]amino}propyl)carbamate XXVIII as white crystals (1.33 g, 4.2 mmol, 67% yield). $^1$H NMR (CDCl$_3$) δ ppm 1.47 (s, 18H), 3.07-3.26 (m, 2H), 3.27-3.53 (m, 2H), 3.59-3.75 (m, 1H), 5.06 (brs, 2H); ESIMS found for $C_{13}H_{25}N_5O_4$ m/z 316 (M+H).

Step 4

To a solution of the azide XXVIII (1.33 g, 4.22 mmol) in a mixture of ethanol/water (9:1) was added a catalytic amount of Pd/C. The mixture was stirred under hydrogen overnight. The mixture was filtered through a pad of Celite and the filtrate was concentrated to dryness under vacuum to give tert-butyl N-(2-amino-3-{[(tert-butoxy)carbonyl]amino}propyl)carbamate XIX (0.85 g, 2.94 mmol, 70% yield). ¹H NMR (CDCl₃) δ ppm 1.46 (s, 18H), 2.88-3.00 (m, 1H), 3.00-3.27 (m, 4H), 5.12 (brs, 2H); ESIMS found for C₁₃H₂₇N₃O₄ m/z 290 (M+H).

Preparation of intermediate (XXXV) is depicted below in Scheme 6.

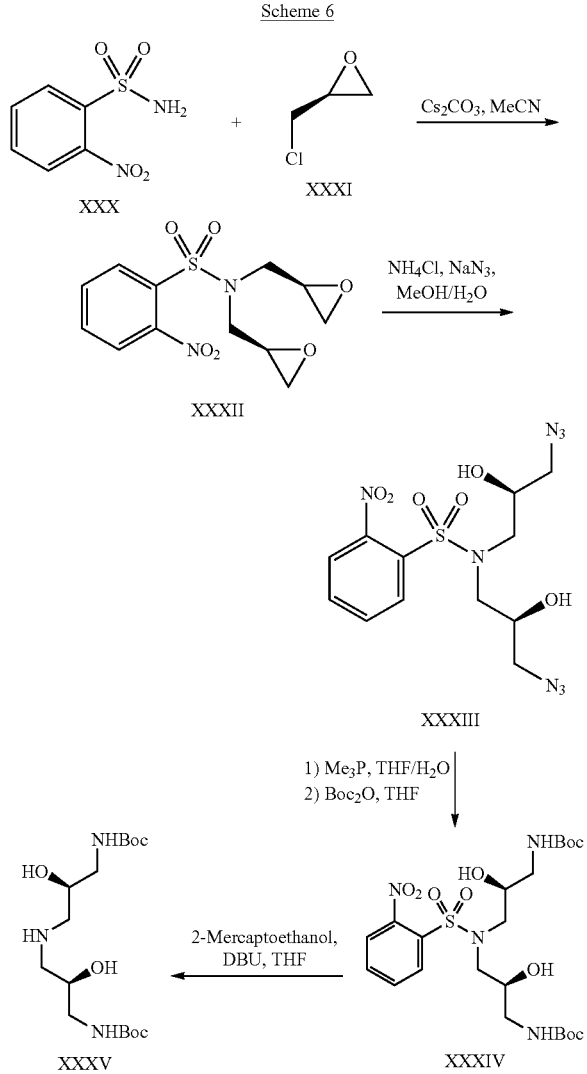

Step 1

To a solution of 2-nitrobenzenesulfonamide (XXX) (1 g, 4.95 mmol) in acetonitrile (1.5 mL) was added cesium carbonate (3.56 g, 10.93 mmol) followed by (R)-(−)-epichlorohydrin (XXXI) (1.6 mL, 20.4 mmol). This reaction mixture was refluxed for 16 hours. 100 mL of water was added to the cooled solution followed by extraction with EtOAc (3×75 mL) The organic layer was dried over sodium sulfate, the solvent removed under vacuum and the residue purified by automated silica gel chromatography using hexanes/EtOAc 0→100% to give 2-nitro-N,N-bis((R)-oxiran-2-ylmethyl) benzenesulfonamide (XXXII) (0.48 g, 1.5 mmol, 32% yield). ¹H NMR (DMSO-d₆) δ ppm 8.08 (d, J=7.8, 1H), 8.00 (d, J=7.8, 1H), 7.91 (t, J=7.6, 1H), 7.84 (t, J=7.6, 1H), 3.64 (ABq, J=4.0, 15.4, 2H), 3.38 (dd, J=3.6, 6.2, 2H), 3.12-3.08 (m, 2H), 2.75 (t, J=4.3, 2H), 2.59 (dd, J=2.6, 4.9, 2H), 2.50 (p, J=1.72, 2H). ESIMS found for C₁₂H₁₄N₂O₆S m/z 314.9 (M+H).

Step 2

2-Nitro-N,N-bis((R)-oxiran-2-ylmethyl)benzenesulfonamide (XXXII) (100 mg, 0.32 mmol) was added to a mixture of MeOH/water (8:1) (1 mL), followed by ammonium chloride (37.4 mg, 0.70 mmol) and sodium azide (103.4 mg, 1.59 mmol). This mixture was stirred at room temperature for 24 hours, diluted with DCM (100 mL) and dried over Na₂SO₄ before the solvent was removed under vacuum. The residue was purified by automated silica gel chromatography using a gradient of 0 to 100% hexanes/EtOAc to produce N,N-bis ((S)-3-azido-2-hydroxypropyl)-2-nitrobenzenesulfonamide (XXXIII) (87.2 mg, 0.22 mmol, 68% yield). ¹H NMR (DMSO-d₆) δ ppm 8.07 (d, J=7.9, 1H), 7.98 (d, J=7.9, 1H), 7.88 (t, J=7.7, 1H), 7.84 (t, J=7.7, 1H), 5.52 (d, J=5.5, 2H, D₂O exchange), 3.92-3.88 (m, 2H), 3.43-3.32 (m, 4H), 3.28-3.24 (m, 2H), 3.19-3.15 (m, 2H). ESIMS found for C₁₂H₁₆N₈O₆S m/z 423.0 (M+Na).

Step 3

N,N-bis((S)-3-azido-2-hydroxypropyl)-2-nitrobenzenesulfonamide (XXXIII) (265 mg, 0.76 mmol) was added to a mixture of THF/Water (6:1) (7.6 mL) followed by trimethylphosphine (236 µl, 2.28 mmol). This reaction mixture was stirred for 2 hours at which time the solvent was removed and the residue dissolved in THF (5 mL). Boc₂O (350 mg, 1.6 mmol) was added and the reaction mixture was stirred for 20 hours. The solvent was removed under vacuum and the residue was purified by automated silica gel chromatography using hexanes/EtOAc 0 to 100% to produce tert-butyl (2S, 2'S)-3,3'-(2-nitrophenylsulfonylazanediyl)bis(2-hydroxypropane-3,1-diyl)dicarbamate (XXXIV) (295 mg, 0.54 mmol, 71% yield). ¹H NMR (DMSO-d₆) δ ppm 8.05 (d, J=7.9, 1H), 7.97 (d, J=7.9, 1H), 7.85 (t, J=7.7, 1H), 7.81 (t, J=7.7, 1H), 6.71 (t, J=5.7, 2H), 5.11 (d, J=5.3, 2H), 3.69-3.64 (m, 2H), 3.39-3.27 (m, 4H), 2.94-2.82 (m, 4H), 1.35 (s, 18H). ESIMS found for C₂₂H₃₆N₄O₁₀S m/z 571.0 (M+Na).

Step 4 tert-Butyl (2S,2'S)-3,3'-(2-nitrophenyl sulfonylazanediyl) bis(2-hydroxypropane-3,1-diyl)dicarbamate (290 mg, 0.53 mmol) was added to THF (5.3 mL) followed by 2-mercaptoethanol (372 µl, 5.29 mmol) and DBU (395 µl, 2.64 mmol), this mixture was stirred for 30 minutes at room temperature. The solvent was removed under vacuum and the residue was purified by automated silica gel chromatography using 0-20% DCM/MeOH with 1% ammonium hydroxide as the modifier. To produce tert-butyl (2R,2'R)-3,3'-azanediylbis(2-hydroxypropane-3,1-diyl)dicarbamate (XXXV) (36.3 mg, 0.10 mmol, 18.9% yield). ¹H NMR (DMSO-d₆) δ ppm 6.70 (br s, 2H), 4.77 (br s, 2H), 3.56-3.52 (m, 2H), 2.95-2.92 (m, 4H), 2.51-2.49 (m, 4H), 1.37 (s, 18H). ESIMS found for C₁₆H₃₃N₃O₆ m/z 364.1 (M+H).

Preparation of intermediate (XXXVIII) is depicted below in Scheme 7.

Scheme 7

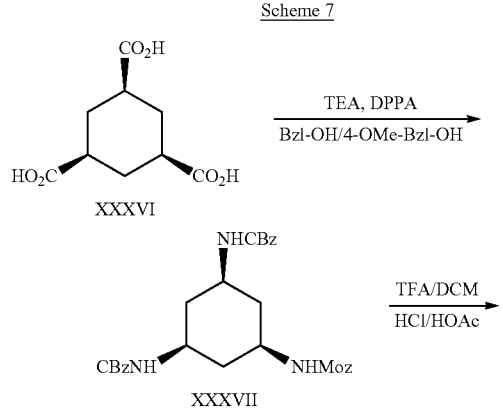

Step 1

(1α,3α,5α)-1,3,5-Cyclohexane tricarboxylic acid (XXXVI) (12 g, 55.5 mmol) was dissolved in benzene (250 mL). Et$_3$N (23.1 mL, 166.5 mmol) was added following by DPPA (36 mL, 166.5 mmol) and the mixture was stirred at room temperature for 30 min and then refluxed for 30 min. Benzyl alcohol (14.22 mL, 137.4 mmol) was mixed with (4-methoxyphenyl)methanol (5.71 mL, 45.8 mmol) and added in one portion. The mixture was heated at 60° C. overnight and refluxed for 4 h. The reaction was cooled to room temperature and solid was precipitated, filtered off, washed with cold benzene (100 mL) and dried to give 16.8 g of XXXVII as a white solid (impure-3×NHCbz was observed). Crude product was used in Step 2. ESIMS found for C$_{31}$H$_{35}$N$_3$O$_7$ m/z 584.6 (M+Na) and 554.5 (M+Na) (by-product).

Step 2

Crude XXXVII (16.8 g) was stirred in TFA/DCM (10/90 mL) for 30 min at room temperature before evaporating to dryness. 4.3 M HCl/HOAc (100 mL) was added, stirred 1 h at room temperature and evaporated. To the residue was added Et$_2$O causing a precipitate to form, the solid was filtered off, washed with Et$_2$O and dried to give 12 g of impure XXXVIII (3×NHCbz was still observed). The solid was suspended in DCM and the by-product was filtered off and washed with DCM. The filtrate was evaporated to dryness to give benzyl (1R,3S,5R)-5-aminocyclohexane-1,3-diyldicarbamate (XXXVIII) as a yellow solid (8.5 g, 21.4 mmol, 38.5% yield after 2 steps). ESIMS found for C$_{22}$H$_{27}$N$_3$O$_4$ m/z 398.4 (M+H).

Preparation of intermediate (XLIV) is depicted below in Scheme 8.

Scheme 8

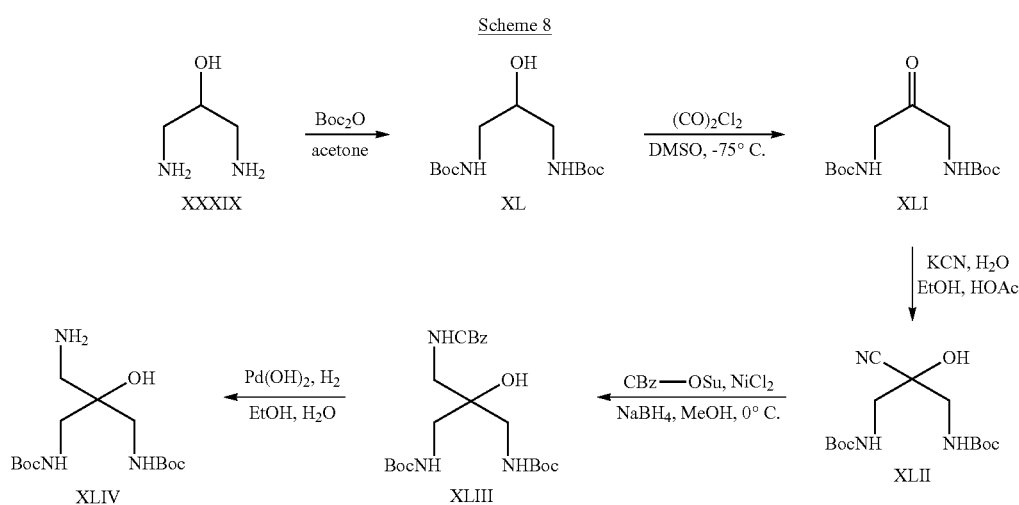

-continued

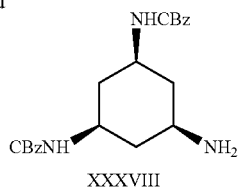

XXXVIII

Step 1

1,3-diamino-2-propanol (XXXIX) (1.6 g, 17.75 mmol) was dissolved in water (3 ml/mmol, 53 mL) and then aq. 5% NaHCO$_3$ was added until pH was ~9, followed by acetone. The mixture was cooled to 0° C. before adding a solution of Boc$_2$O (7.74 g, 35.5 mmol) in acetone (2 mL/mmol, 35.5 ml) slowly dropwise over 2 h. The reaction mixture was allowed to warm to room temperature and stirred overnight. The acetone was evaporated under vacuum and the aqueous residue was washed with Et$_2$O (×3). The organic layers were combined and dried over anhydrous MgSO$_4$. The solvent was removed under reduced pressure to give the crude product as a dark yellow oil. The crude product was crystallized from Et$_2$O/hexane to give tert-butyl 2-hydroxypropane-1,3-diyldicarbamate (XL) (3.71 g, 12.78 mmol, 72% yield). $^1$H NMR (CDCl$_3$) δ ppm 1.40 (s, 18H), 3.06-3.27 (m, 4H), 3.61-3.67 (m, 1H), 4.00 (brs, 1H), 5.16-5.4 (m, 2H). ESIMS found for C$_{13}$H$_{26}$N$_2$O$_5$ m/z 313.6 (M+Na).

Step 2

Oxalyl chloride (1.67 mL, 19.17 mmol) was dissolved in DCM (1.2 mL/mmol, 23 mL), cooled to −75° C. before a solution of anhydrous DMSO (2.7 mL, 38.34 mmol) in DCM 0.5 mL/mmol, 19.2 mL) was added dropwise under argon. The mixture was stirred at −75° C. for 20 min. To this mixture was added a solution of tert-butyl 2-hydroxypropane-1,3-diyldicarbamate (XL) (3.71 g, 12.78 mmol) in DCM (0.95 mL/mmol, 12.1 mL) dropwise and the mixture was stirred at −75° C. for 30 minutes. TEA (8.89 mL, 63.9 mmol) was then added. The cooling bath was removed and the reaction mixture was stirred for 1 h at room temperature under an argon atmosphere. The reaction mixture was diluted with DCM and washed with water (×2), 1 M HCl (×3), brine and dried over anhydrous $MgSO_4$. The solvent was removed in vacuo to give tert-butyl 2-oxopropane-1,3-diyldicarbamate (XLI) as a white solid (2.9 g, 10.05 mmol, 78.8% yield). $^1$H NMR ($CDCl_3$) δ ppm 1.43 (s, 18H), 4.04 (d, J=5.05 Hz, 4H), 5.17 (brs, 2H). ESIMS found for $C_{13}H_{24}N_2O_5$ m/z 311.5 (M+Na).

Step 3

KCN (0.98 g, 15.07 mmol) was dissolved in water (6 mL, 0.6 mL/mmol), cooled to 0° C. before adding tert-butyl 2-oxopropane-1,3-diyldicarbamate (XLI) (2.9 g, 10.05 mmol) in EtOH (20.1 mL, 2 mL/mmol) dropwise. HOAc (0.69 mL, 12.06 mmol) in EtOH (10 mL, 1 mL/mmol) was then added dropwise. The reaction mixture was stirred over the weekend at room temperature during which time a solid formed. The reaction mixture was diluted with water and solid was filtered off to give tert-butyl 2-cyano-2-hydroxypropane-1,3-diyldicarbamate (XLII) as a white solid (2.8 g, 8.88 mmol, 89% yield). ESIMS found for $C_{14}H_{25}N_3O_5$ m/z 338.6 (M+Na).

Step 4 tert-Butyl 2-cyano-2-hydroxypropane-1,3-diyldicarbamate (XLII) (2.8 g, 8.88 mmol) was dissolved in MeOH (45 mL, 5 mL/mmol) and cooled to −10° C. CBz-OSu (4.4 g, 17.76 mmol) and $NiCl_2×6H_2O$ (0.21 g, 0.88 mmol) were then added. To this mixture was added $NaBH_4$ (0.33 g, 8.88 mmol) in portions. The reaction mixture after addition of first small portion of $NaBH_4$ became black. After 40 min additional $NaBH_4$ (0.33 g, 8.88 mmol) was added. The reaction mixture was stirred for another 1 h at 0° C. The solvent was evaporated to dryness and the crude product was purified on a silica gel column using EtOAc:hexane 1:10 to give [2-({[(benzyloxy)carbonyl]amino}methyl)-1,3-bis({[(tert-butoxy)carbonyl]amino}) propan-2-yl]-$\lambda^1$-oxidanyl (XLIII) (1.62 g, 3.57 mmol, 40%). ESIMS found for $C_{22}H_{35}N_3O_7$ m/z 476.6 (M+Na).

Step 5

To a solution of [2-({[(benzyloxy)carbonyl]amino}methyl)-1,3-bis({[(tert-butoxy)carbonyl]amino}) propan-2-yl]-$\lambda^1$-oxidanyl (XLIII) (1.62 g, 3.57 mmol) in EtOH/water (70 mL/7 mL) was added a catalytic amount of $Pd(OH)_2$/C under argon. The mixture was stirred under an atmosphere of hydrogen at room temperature overnight. The mixture was then filtered through a pad of Celite and evaporated to dryness to give tert-butyl 2-(aminomethyl)-2-hydroxypropane-1,3-diyldicarbamate (XLIV) (1.08 g, 3.38 mmol, 94% yield). $^1$H NMR ($CDCl_3$) δ ppm 1.46 (s, 18H), 2.84 (dd, J=4.81 Hz, J=4.81 Hz, 2H), 2.98 (brs, 3H), 3.32 (dd, J=8.24 Hz, J=8.24 Hz, 2H), 5.52-5.58 (m, 2H); ESIMS found for $C_{14}H_{29}N_3O_5$ m/z 342.4 (M+Na).

Preparation of intermediate (LV) is depicted below in Scheme 9.

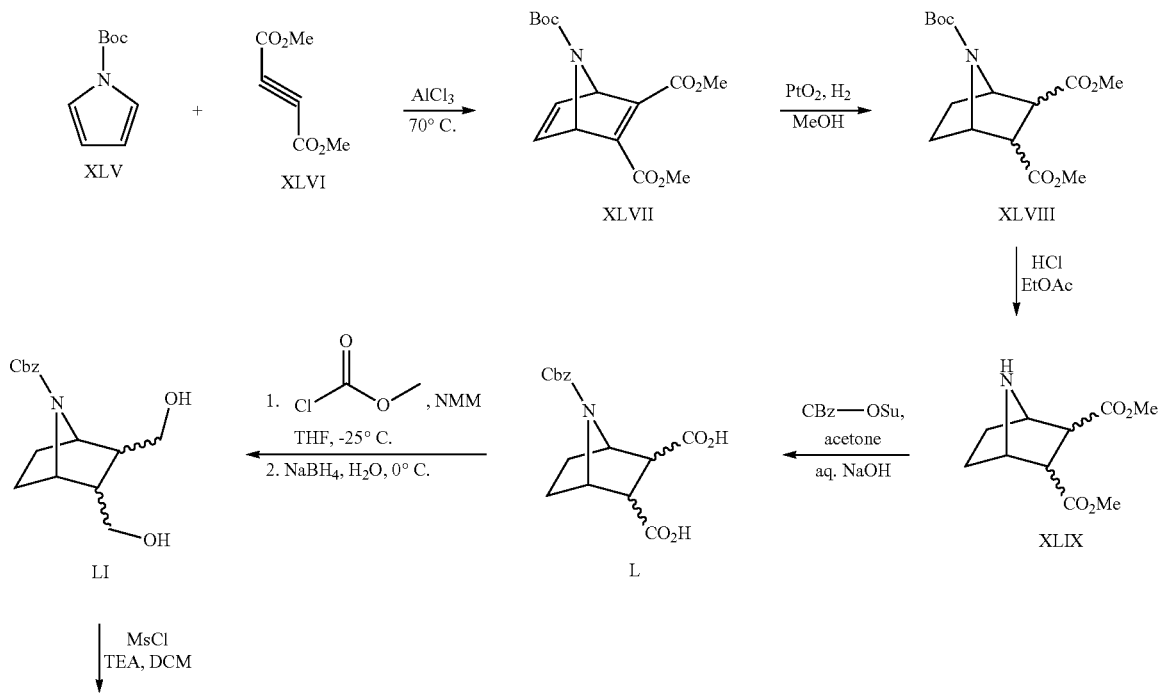

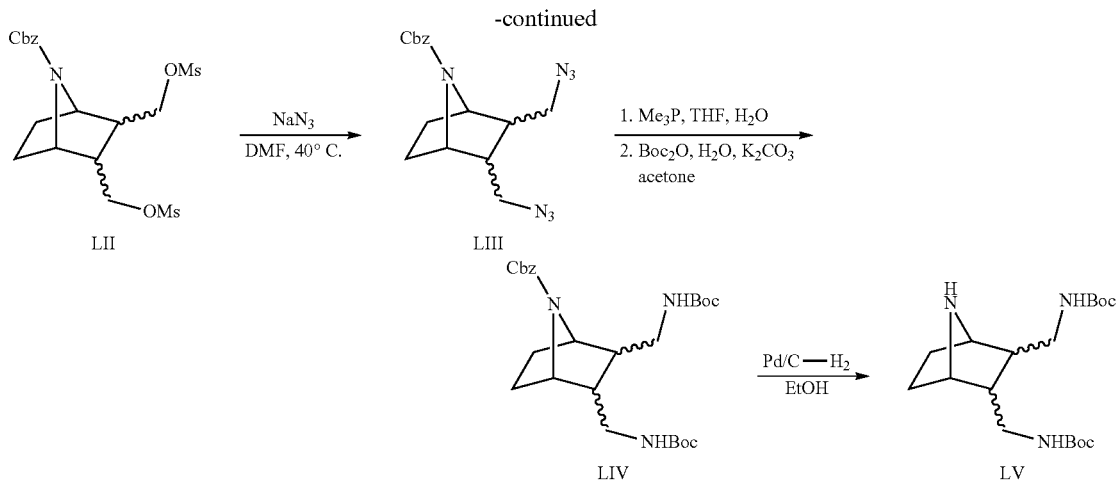

Step 1

A mixture of tert-butyl 1H-pyrrole-1-carboxylate (XLV) (3.50 g 20.93 mmol), dimethyl but-2-ynedioate (XLVI) (2.57 mL, 20.93 mmol) and $AlCl_3$ (28 mg, 0.21 mmol) were stirred for 3 days at 70° C. The crude product was purified by silica gel chromatography using 100% DCM then DCM/MeOH 1000/1→500/1 to give (1R,4S)-7-tert-butyl 2,3-dimethyl 7-azabicyclo[2.2.1]hepta-2,5-diene-2,3,7-tricarboxylate (XLVII) as a yellow oil (3.41 g, 11.04 mmol, 53% yield). $^1$H NMR (CDCl$_3$) δ ppm 1.40 (s, 9H), 3.80 (s, 6H), 5.44 (s, 2H), 7.13 (d, J=13 Hz, 2H); ESIMS found for $C_{15}H_{19}NO_6$ m/z 332 (M+Na).

Step 2

(1R,4S)-7-tert-butyl 2,3-dimethyl 7-azabicyclo[2.2.1]hepta-2,5-diene-2,3,7-tricarboxylate (XLVII) (3.41 g, 11.04 mmol) was dissolved in MeOH (50 mL) under an argon atmosphere. Adams' catalyst was added and the reaction was flushed with hydrogen. The mixture was stirred under hydrogen overnight at room temperature. The catalyst was filtered off and the solvent was removed in vacuo to give a yellow oil. The oily residue was crystallized from hot heptane to give (1R,4S)-7-tert-butyl 2,3-dimethyl 7-azabicyclo[2.2.1]heptane-2,3,7-tricarboxylate (XLVIII) as a white solid (3.28 g, 10.49 mmol, 95% yield). $^1$H NMR (CDCl$_3$) (two isomers in a 3/1 ratio) δ ppm [1.40 (s, $2^{nd}$ isomer), 1.44 (s, $2^{nd}$ isomer), 9H], 1.60-2.00 (m, 4H), [3.66 (s, $1^{st}$ isomer), 3.71 (s, $2^{nd}$ isomer), 6H], [4.37 (brs, $1^{st}$ isomer), 4.51 (brs, $2^{nd}$ isomer), 2H]; ESIMS found for $C_{15}H_{23}NO_6$ m/z 336 (M+Na).

Step 3

(1R,4S)-7-tert-butyl 2,3-dimethyl 7-azabicyclo[2.2.1]heptane-2,3,7-tricarboxylate (XLVIII) (3.28 g, 10.49 mmol) was dissolved in EtOAc (20 mL) and treated with 1M HCl/EtOAc (20 mL) and stirred for 15 minutes at room temperature. The solvent was removed under vacuum and the oily residue was triturated with $Et_2O$ to give (1R,4S)-dimethyl 7-azabicyclo[2.2.1]heptane-2,3-dicarboxylate (LXIX) as a light pink solid (2.46 g, 9.86 mmol, 94% yield). $^1$H NMR (DMSO-d$_6$) (two isomers in a 4/1 ratio) δ ppm [1.41-1.53 (m, $2^{nd}$ isomer), 1.77-1.83 (m, $1^{st}$ isomer), 2H], [1.63-1.72 (m, $2^{nd}$ isomer), 1.93-2.02 (m, $1^{st}$ isomer), 2H], [3.16 (d. J=6 Hz, $2^{nd}$ isomer), 3.38 (brs, $1^{st}$ isomer), 2H], [3.57 (s, $1^{st}$ isomer), 3.62 (s, $2^{nd}$ isomer), 6H], [4.34 (brs, $1^{st}$ isomer), 4.40 (d, J=4 Hz, $2^{nd}$ isomer), 2H], [9.68 (brs, $1^{st}$ isomer), 9.92 (brs, $2^{nd}$ isomer, 2H]. ESIMS found for $C_{10}H_{15}NO_4$ m/z 214 (M+H).

Step 4

(1R,4S)-dimethyl 7-azabicyclo[2.2.1]heptane-2,3-dicarboxylate (LXIX) (2.46 g, 9.86 mmol) was suspended in water (50 mL) and aq. 1 M NaOH was added to adjust the suspension to pH 12. To this mixture was added a solution of CBz-OSu (2.70 g, 10.84 mmol) in acetone (50 mL) and the reaction mixture was stirred overnight at room temperature. An additional portion of aqueous 4 M NaOH was added to adjust the mixture to pH 14, and the mixture was stirred for another 4 hours at room temperature. The acetone was removed under vacuum and aqueous residue was washed with $Et_2O$ (×2). The aqueous layer was acidified to pH 3 using 6 M HCl and extracted with EtOAc (×3). The combined organic layers were dried over $MgSO_4$, filtered and evaporated under vacuum. The crude product was purified by silica gel chromatography using 100% DCM then DCM/MeOH 200/1→100/1 to give (1R,4S)-7-(benzyloxycarbonyl)-7-azabicyclo[2.2.1]heptane-2,3-dicarboxylic acid (L) as a white foam (2.33 g, 7.30 mmol, 74% yield). $^1$H NMR (CDCl$_3$) δ ppm 1.57 (brs, 2H), 1.75 (brs, 1H), 1.87 (brs, 1H), 3.03 (brs, 1H), 3.60 (brs, 1H), 4.67 (brs, 2H), 5.08 (brs, 2H), 7.03 (brs, 5H), 8.60 (brs, 2H); ESIMS found for $C_{16}H_{17}NO_6$ m/z 342 (M+Na).

Step 5

To a solution of (1R,4S)-7-(benzyloxycarbonyl)-7-azabicyclo[2.2.1]heptane-2,3-dicarboxylic acid (L) (2.33 g, 7.30 mmol) in THF (50 mL) was added N-methylmorpholine (2.00 mL, 18.25 mmol). The mixture was cooled to −25° C. before adding methyl chloroformate (1.41 mL, 18.25 mmol) dropwise. The mixture was stirred at −25° C. for 20 minutes and the solid was removed by filtration. The solution was carefully added to a solution of NaBH$_4$ (1.65 g, 43.80 mmol) in water (100 mL) at 0° C. The mixture was stirred for 1 hour at room temperature. The acetone was removed under vacuum and the aqueous phase was extracted with EtOAc (×3). The combined organic phases were washed with 1 M NaOH, dried over MgSO$_4$ and concentrated under vacuum to give (1R,4S)-benzyl 2,3-bis(hydroxymethyl)-7-azabicyclo[2.2.1]heptane-7-carboxylate (LI) as a colorless oil (1.85 g, 6.35 mmol, 87% yield). $^1$H NMR (CDCl$_3$) δ ppm 1.40 (brs, 1H), 1.54 (brs, 1H), 1.63 (brs, 2H), 1.81 (brs, 1H), 1.98 (brs, 1H), 3.50-3.56 (m, 1H), 3.58-3.67 (m, 2H), 3.69-3.78 (m, 1H), 4.10 (brs, 2H), 5.09 (brs, 2H), 7.34 (brs, 5H); ESIMS found for C$_{16}$H$_{21}$NO$_4$ m/z 292 (M+H).

Step 6

To a solution of (1R,4S)-benzyl 2,3-bis(hydroxymethyl)-7-azabicyclo[2.2.1]heptane-7-carboxylate (LI) (1.85 g, 6.35 mmol) and Et$_3$N (2.65 mL, 19.05 mmol) in DCM (70 mL) at −30° C. was added a solution of MsCl (1.47 mL, 19.05 mmol) in DCM (15 mL) dropwise. The reaction mixture was stirred for 15 min at −10° C. then for 1.5 h at 0° C. The reaction mixture was dilluted with DCM, washed with 1 M HCl, 1 M K$_2$CO$_3$, brine and then dried over MgSO$_4$. The solvent was removed under vacuum to give (1R,4S)-benzyl 2,3-bis((methylsulfonyloxy)methyl)-7-azabicyclo[2.2.1]heptane-7-carboxylate (LII) as a very thick, light yellow oil (2.70 g, 6.03 mmol, 95% yield). $^1$H NMR (CDCl$_3$) δ ppm 1.74 (brs, 4H), 1.88 (brs, 1H), 2.16 (brs, 1H), 2.97 (brs, 2H), 3.03 (brs, 3H), 3.97-4.09 (m, 1H), 4.10-4.18 (m, 1H), 4.22 (brs, 1H), 4.26-4.34 (m, 1H), 4.40 (brs, 1H), 5.11 (brs, 2H), 7.35 (brs, 5H); ESIMS found for C$_{18}$H$_{25}$NO$_8$S$_2$ m/z 448 (M+H).

Step 7

To a solution of (1R,4S)-benzyl 2,3-bis((methylsulfonyloxy)methyl)-7-azabicyclo[2.2.1]heptane-7-carboxylate (LII) (2.70 g, 6.03 mmol) in dry DMF (50 mL) was added NaN$_3$ (1.96 g, 30.15 mmol) and reaction mixture was stirred overnight at 40° C. An additional portion of NaN$_3$ (390 mg, 6.03 mmol) was added and the reaction was stirred for another 4 days at 50° C. The mixture was diluted with EtOAc and washed with aq. Na$_2$S$_2$O$_7$ (×2). The organic layer was dried over MgSO$_4$, filtered and the solvent removed under vacuum to give (1R,4S)-benzyl 2,3-bis(azidomethyl)-7-azabicyclo[2.2.1]heptane-7-carboxylate (LIII) as a yellow oil (1.77 g, 5.2 mmol, 86% yield).

Step 8

To a solution of (1R,4S)-benzyl 2,3-bis(azidomethyl)-7-azabicyclo[2.2.1]heptane-7-carboxylate (LIII) (1.77 g, 5.2 mmol) in THF/H$_2$O (40 mL/5 mL) was added a 1 M solution of Me$_3$P in THF (31.2 mL, 31.2 mmol). The solution was stirred overnight at room temperature. The THF was removed under vacuum. The remaining aqueous solution was further diluted with water (20 mL) and the solution was adjusted to pH 12 with 1 M K$_2$CO$_3$. A solution of Boc$_2$O (3.40 g, 15.6 mmol) in acetone (50 mL) was added and the solution was stirred overnight at room temperature. The acetone was removed under vacuum and the aqueous residue was extracted with EtOAc (×3). The combined organic fractions were washed with brine, dried over MgSO$_4$ filtered, and evaporated under vacuum. The crude product was purified by silica gel chromatography using 100% DCM to produce (1R, 4S)-benzyl 2,3-bis((tert-butoxycarbonylamino)methyl)-7-azabicyclo[2.2.1]heptane-7-carboxylate (LIV) as a colorless oil (1.90 g, 3.88 mmol). $^1$H NMR (CDCl$_3$) δ ppm 1.43 (s, 18H), 1.55-1.92 (m, 6H), 2.95 (brs, 2H), 3.14 (brs, 2H), 4.05 (brs, 1H), 4.26 (brs, 1H), 5.09 (brs, 2H), 7.34 (brs, 5H); ESIMS found for C$_{26}$H$_{39}$N$_3$O$_6$ m/z 512 (M+Na).

Step 9

To a solution of (1R,4S)-benzyl 2,3-bis((tert-butoxycarbonylamino)methyl)-7-azabicyclo[2.2.1]heptane-7-carboxylate (LIV) (1.90 g, 3.88 mmol) in EtOH under an argon atmosphere was added palladium on carbon, and the reaction was flushed with hydrogen. The mixture was stirred under hydrogen for 3 days at room temperature and then for another 12 h at 45° C. The catalyst was filtered through Celite and the ethanol was removed under vacuum to give tert-butyl (1R,4S)-7-azabicyclo[2.2.1]heptane-2,3-diylbis(methylene)dicarbamate (LV) as a colourless oil (1.30 g, 3.65 mmol, 94% yield). $^1$H NMR (CDCl$_3$) δ ppm 1.43 (s, 18H), 1.53-1.88 (m, 4H), 2.40 (brs, 2H), 2.98-3.20 (m, 4H), 3.39-3.46 (m, 1H), 3.57-3.65 (m, 1H), 4.67 (brs, 1H); ESIMS found for C$_{18}$H$_{33}$N$_3$O$_4$ m/z 356 (M+H).

Preparation of intermediate (LIX) is depicted below in Scheme 10.

Scheme 10

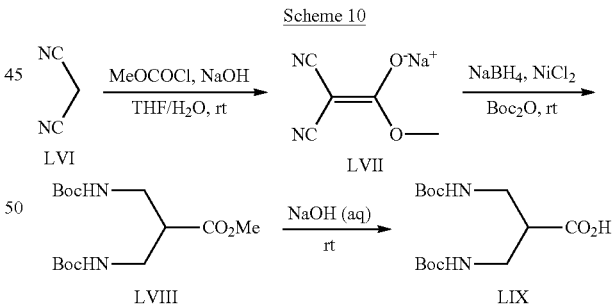

Preparation of intermediate (LXVI) is depicted below in Scheme 11.

Scheme 11

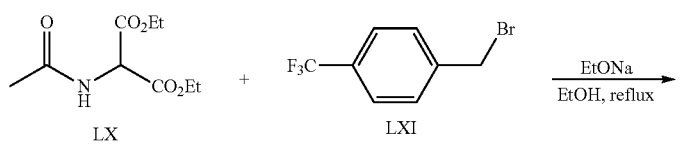

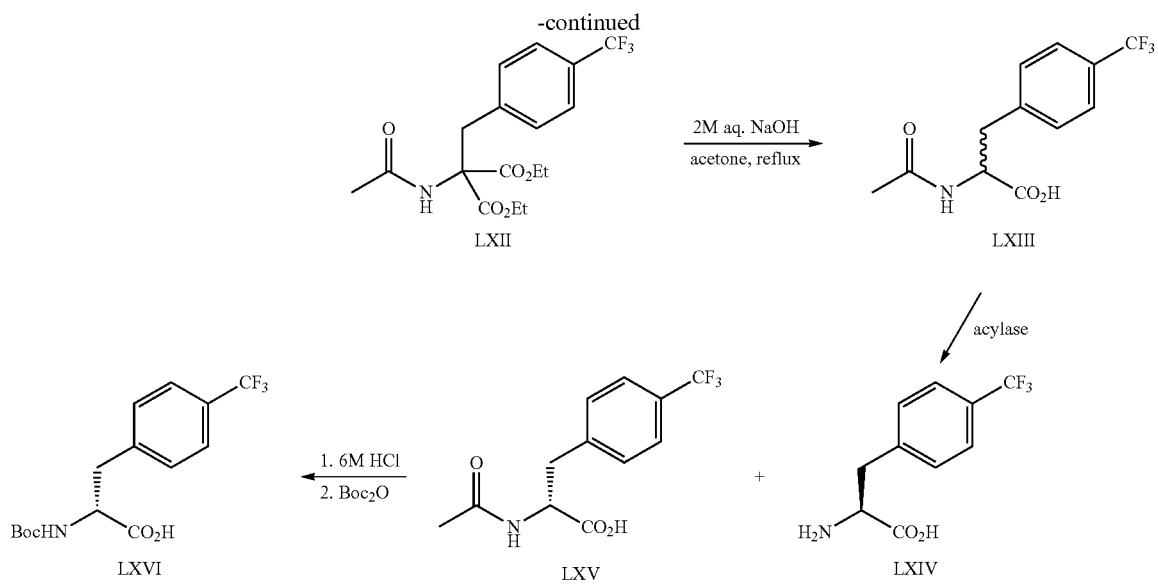

Step 1

To a solution of sodium metal (2.9 g; 0.125 mol) in absolute ethanol (500 mL) was added diethyl acetamidomalonate (LX) (27.2 g, 0.125 mol) followed by 4-(trifluoromethyl) benzyl bromide (LXI) (29.9 g, 0.125 mol). The reaction mixture was stirred at reflux overnight, during which time substantial amount of sodium bromide precipitated. The reaction mixture was concentrated to ca. 30% of its initial volume under reduced pressure and poured into cold water (400 mL). The precipitate was filtered and washed with water (3×250 mL), hexanes (3×150 mL) and then air dried to yield diethyl 2-acetamido-2-(4-(trifluoromethyl)benzyl)malonate (LXII) as a white solid used directly for the next step.

Step 2

To a solution of diethyl 2-acetamido-2-(4-(trifluoromethyl)benzyl)malonate (LXII) (theoretical 0.125 mole) in acetone (400 mL) was added aq. 2 M NaOH (400 mL). The mixture was refluxed overnight before the solvent was removed under reduced pressure. The residue was taken up in water, washed with hexane (3×), acidified to pH=1 and filtered to produce 2-acetamido-3-(4-(trifluoromethyl)phenyl) propanoic acid (LXIII) as a white solid (25.8 g, 93.7 mmol, 75% yield after two steps).

Step 3

A solution of 2-acetamido-3-(4-(trifluoromethyl)phenyl) propanoic acid (LXIII) (30 g, 109 mol) in 1 M NaOH (50 mL) and water (1 L) was adjusted to pH 7.6-7.8 before adding $CoCl_2$ (300 mg, 2.3 mmol) and Acylase I (3 g) (from *Aspergilus melleus*). The reaction was stirred at room temperature under argon for 2 days at which time Marfey's test was performed and additional enzyme (1 g) was added and the reaction was stirred for an additional day. The mixture was acidified with 2 M HCl to pH 1 and extracted with EtOAc (3×) (the aqueous phase containing the L-enantiomer (LXIV) was saved). The combined organic extracts were washed with 2 M HCl (3×), brine (3×) and dried over $MgSO_4$. The solvent was removed under reduced pressure and the residue was recrystallized from EtOAc/hexane, affording (R)-2-acetamido-3-(4-(trifluoromethyl)phenyl)propanoic acid (LXV) (10.2 g, 37 mmol, 68% yield).

Step 4

(R)-2-acetamido-3-(4-(trifluoromethyl)phenyl)propanoic acid (LXV) was refluxed in 6 M aqueous HCl (100 mL) overnight. When the removal of the acetyl group was complete (as judged by disappearance of starting material by LC/MS), the solution was adjusted to pH 9.5 with 4 M NaOH (300 mL) and a solution of $Boc_2O$ (8.7 g, 40 mmol) in acetone (200 mL) was added in portions. The mixture was stirred at room temperature overnight. The solution was washed with $Et_2O$, acidified with 2 N aqueous HCl to pH ~2 and extracted with EtOAc. The organic layer was washed with brine and dried over MgSO4. The solvent was removed in vacuo to give (R)-2-(tert-butoxycarbonylamino)-3-(4-(trifluoromethyl) phenyl) propanoic acid (LXVI) (10 g, 30 mmol, 81% yield).

Preparation of intermediate (LXXI) is depicted below in Scheme 12.

Scheme 12

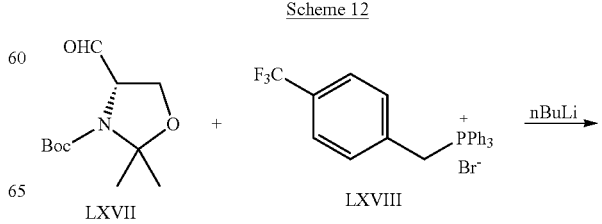

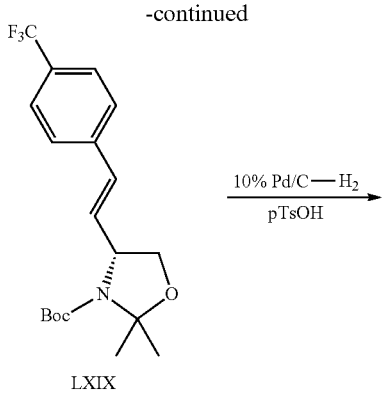

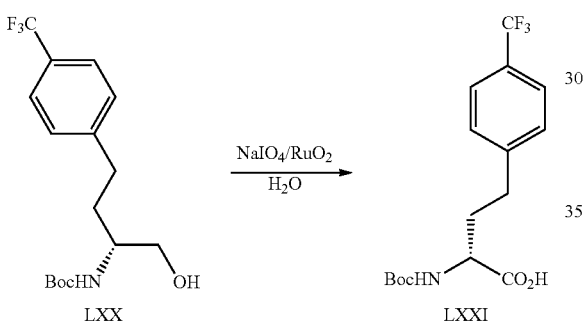

Step 1

To a solution of triphenyl(4-(trifluoromethyl)benzyl)phosphonium bromide (LXVIII) (80.2 g; 0.16 mol) in THF (640 mL) under argon and cooled to −78° C. was added n-BuLi (100 mL; 0.56 mol; as 2.5 M solution in hexanes). After 10 minutes the reaction mixture was warmed to −40° C. until the precipitate disappeared. The mixture was cooled to −78° C. again and a solution of Garner's aldehyde LXVII (36.7 g; 0.16 mol) (obtained from L-serine) in THF (50 mL) was added dropwise over 25 minutes. The reaction was warmed to room temperature and stirred overnight before quenching with MeOH (250 mL) for an additional 30 minutes. The solvent was removed under reduced pressure and the residue was then purified on a silica gel column (20:1 hexane:EtOAc) to give (R, Z-E)-tert-butyl-2,2-dimethyl-4-(4-trifluoromethylstyryl) oxazolidine-3-carboxylate (LXIX) as a light-yellow oil (47.3 g, 0.128 mol, 80% yield). ESIMS found for $C_{19}H_{24}F_3NO_3$ m/z 372.4 (M+H).

Step 2

To a solution of (R,Z-E)-tert-butyl-2,2-dimethyl-4-(4-trifluoromethylstyryl) oxazolidine-3-carboxylate (LXIX) (47.2 g; 0.127 mol) in MeOH (500 mL) was added 10% Pd/C (4 g) and para-toluenesulfonic acid monohydrate (0.24 g; 1.27 mmol). The suspension was stirred under hydrogen at room temperature overnight. The mixture was filtered through Celite and concentrated under reduced pressure to produce (R)-tert-butyl 1-hydroxy-4-(4-(trifluoromethyl)phenyl)butan-2-ylcarbamate (LXX) as a white solid (41.7 g, 125.1 mmol, 98% yield). ESIMS found for $C_{16}H_{22}F_3NO_3$ m/z 334.3 (M+H).

Step 3

To a solution of (R)-tert-butyl 1-hydroxy-4-(4-(trifluoromethyl)phenyl)butan-2-ylcarbamate (LXX) (41.3 g; 0.124 mol) in 60% aqueous acetone was added solid sodium (meta) periodate (266 g; 1.24 mol) followed by ruthenium(II) oxide hydrate (1.65 g; 12.4 mmol). The greenish suspension was stirred for 3 h before adding propan-2-ol (500 mL) and stirring for an additional 30 min. The resulting suspension was filtered through Celite, and the filtrate was concentrated under vacuum to give a brown foam. To the brown foam was added 1 N HCl to pH 1 which was followed by extraction with EtOAc. The organic layer was washed with brine and dried with $MgSO_4$. The crude residue was then purified on a silica gel column (10:1 hexane:EtOAc) to obtain (2R)-2-[(tert-butoxycarbonyl)amino]-4-[4-(trifluoromethyl)phenyl]butanoic acid (LXXI) (18 g; 51.8 mmol, 42% yield). $^1$H NMR (CDCl$_3$) δ ppm 1.46 (brs, 9H), 1.93-2.30 (m, 2H), 2.68-2.87 (m, 2H), 4.12-4.47 (m, 1H), 5.04-5.23 (m, 1H), 7.30 (d, J=8, 2H), 7.55 (d, J=8, 2H); ESIMS found for $C_{16}H_{20}F_3NO_4$ m/z 348.3 (M+H).

Preparation of intermediate (LXXX) is depicted below in Scheme 13.

Scheme 13

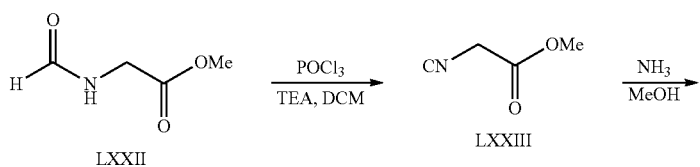

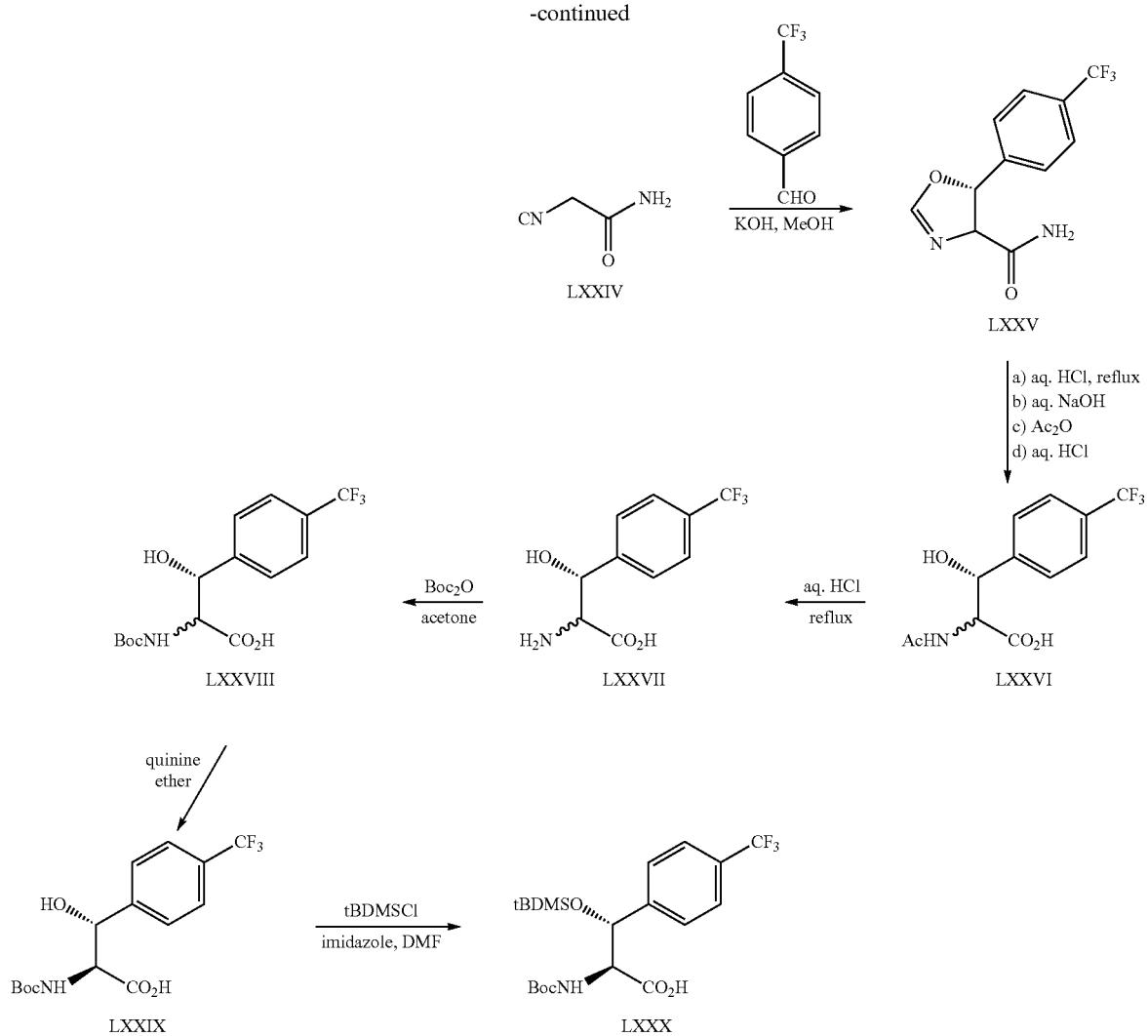

Step 1

To a solution of N-formylglycine methyl ester (LXXII) (27.5 g, 235 mmol) in DCM was added TEA (81.3 mL, 587 mmol). The reaction mixture was cooled to 0° C. before adding POCl$_3$ (21.6 mL, 235 mmol) dropwise. The reaction was stirred for 1 h. The solution was warmed to room temperature and saturated aqueous Na$_2$SO$_3$ was added dropwise. After 30 min, the phases were separated and the aqueous layer was washed with DCM. The combined organic layers were washed with brine, dried over MgSO$_4$ and concentrated under vacuum to give crude methyl 2-isocyanoacetate (LXXIII) as a dark brown oil (30 g). The crude product was used for the next step without purification.

Step 2

Crude methyl 2-isocyanoacetate (LXXIII) was added to a 6.7 M solution of NH$_3$ in MeOH (70 mL, 470 mmol) and stirred at room temperature overnight. The excess of ammonia and MeOH were evaporated under reduced pressure and the crude residue was dissolved in MeOH and stirred with activated carbon at 50° C. for 2 h. The mixture was filtered through Celite and the filtrate was concentrated to dryness under vacuum to give 2-isocyanoacetamide (LXXIV) as a white solid (25 g). The crude product was used for the next step without purification.

Step 3

To a cooled (~10° C.) solution of KOH (13.2 g, 235 mmol) in MeOH (50 mL) was added the solution of 2-isocyanoacetamide (LXXIV) in MeOH (60 mL) dropwise while maintaining the temperature at 10-15° C. A solution of 4-(trifluoromethyl)benzaldehyde (40.9 g, 235 mmol) in MeOH (50 mL) was then added and the reaction was stirred for an additional 2 h. The reaction mixture was cooled to −20° C. causing a white solid to precipitate. The solid was filtered and dried to give crude (5R)-5-(4-(trifluoromethyl)phenyl)-4,5-dihydrooxazole-4-carboxamide (LXXV) (62 g). The crude product was used for the next step without purification.

Step 4

(5R)-5-(4-(Trifluoromethyl)phenyl)-4,5-dihydro oxazole-4-carboxamide (LXXV) (was added to aq. 2 N HCl and refluxed for 20 h. Activated carbon was then added and the mixture was refluxed for an additional 1 h. The mixture was filtered through Celite and concentrated to ⅓ volume under vacuum. To this solution was added aq. 4 N NaOH until the pH was ~10. The solution was cooled to 5° C. followed by dropwise addition of Ac₂O (44.4 mL, 470 mmol). The reaction mixture was stirred for 30 min and then acidified with 2 N aqueous HCl to pH 2 causing a solid to precipitate. The solid was filtered to give a white solid which was recrystallized from hot EtOAc/MeOH (100:1, 40 mL) to give (R)-2-acetamido-3-hydroxy-3-(4-(trifluoromethyl)phenyl)propanoic acid (LXXVI) as a white crystalline solid (45 g, 155 mmol, 66% yield for 4 steps). $^1$H NMR (DMSO-$d_6$) δ ppm 1.72 (s, 3H), 4.56 (dd, J=2 Hz, J=9 Hz, 1H), 5.23 (d, J=2 Hz, 1H), 7.58 (d, J=9 Hz, 2H), 7.66 (d, J=9 Hz, 2H), 8.04 (d, J=9 Hz, 1H); $^{19}$F NMR (DMSO-$d_6$) δ ppm −60.12; ESIMS found for $C_{12}H_{12}F_3NO_4$ m/z 290 (M−H).

Step 5-6

(R)-2-Acetamido-3-hydroxy-3-(4-(trifluoromethyl)phenyl)propanoic acid (LXXVI) (45 g, 155 mmol) was dissolved in aq. 6 HCl (300 mL) and refluxed for 2 h. The solution was adjusted to pH 9.5 with 4 M NaOH (600 mL) before a solution of Boc₂O (43.7 g, 200 mmol) in acetone (600 mL) was added in portions. The mixture was stirred at room temperature overnight. The solution was washed with Et₂O, acidified with 2 N aqueous HCl to pH ~2 and extracted with EtOAc. The organic layer was washed with brine and dried over MgSO₄. The solvent was removed in vacuo to give (R)-2-(tert-butoxycarbonylamino)-3-hydroxy-3-(4-(trifluoromethyl)phenyl) propanoic acid (LXXVIII) as a white solid (35 g, 100 mmol, 65% yield). $^1$H NMR (DMSO-$d_6$) δ ppm 1.33 (s, 9H), 4.17 (d, J=4 Hz, 1H), 5.23 (d, J=4 Hz, 1H), 7.66 (d, J=9 Hz, 2H), 7.74 (d, J=9 Hz, 2H), 8.23 (brs, 3H); $^{19}$F NMR (DMSO-$d_6$) δ ppm −60.24; ESIMS found for $C_{15}H_{18}F_3NO_5$ m/z=248 (M−H).

Step 7

To a solution of (R)-2-(tert-butoxycarbonylamino)-3-hydroxy-3-(4-(trifluoromethyl)phenyl)propanoic acid (LXXVIII) (35 g, 100 mmol) in Et₂O (600 mL) was added quinine (34 g, 100 mmol) in portions. The reaction was stirred at room temperature for 30 min at which time the white precipitate (L-enantiomer salt) was filtered and washed with Et₂O. The solid was taken up in EtOAc/aqueous KHSO₄. The organic layer was washed with aqueous KHSO₄, brine and dried over MgSO₄. The solvent was removed in vacuo to give optically pure (Marfey test) (2S,3R)-2-(tert-butoxycarbonylamino)-3-hydroxy-3-(4-(trifluoromethyl)phenyl)propanoic acid (LXXIX) (12 g, 34 mmol, 68% yield). $^1$H NMR (DMSO-$d_6$) δ ppm 1.33 (s, 9H), 4.09 (brs, 1H), 5.13 (brs, 1H), 7.47 (d, J=8 Hz, 2H), 7.56 (d, J=8 Hz, 2H); $^{19}$F NMR (DMSO-$d_6$) δ ppm −60.15; ESIMS found for $C_{15}H_{18}F_3NO_5$ m/z 348 (M−H)

Step 8

To a solution of (2S,3R)-2-(tert-butoxycarbonylamino)-3-hydroxy-3-(4-(trifluoromethyl)phenyl)propanoic acid (LXXIX) (12 g, 34 mmol) in DMF (150 mL) was added imidazole (11.5 g, 169 mmol). The mixture was stirred at room temperature and t-BDMSCl (7.7 g, 51 mmol) was added in portions. The reaction was stirred at room temperature overnight, and the mixture was partitioned between DCM (200 mL) and 0.1N HCl (100 mL). The organic phase was collected and evaporated to produce a residue which was dissolved in Et₂O. The ether layer was washed with 10% aqueous Na₂S₂O₃ (×5), brine and dried over MgSO₄. The solvent was removed in vacuo to give the crude product (16.4 g) which was purified by flash chromatography on silica gel (DCM:MeOH 200:1) to give (5R,6S)-2,2,3,3,10,10-hexamethyl-8-oxo-5-(4-(trifluoromethyl)phenyl)-4,9-dioxa-7-aza-3-silaundecane-6-carboxylic acid (LXXX) as a white solid (14.8 g, 32 mol, 94% yield). $^1$H NMR (DMSO-$d_6$) δ ppm −0.19 (s, 3H), 0.00 (s, 3H), 0.83 (s, 9H), 1.20 (s, 9H), 4.22 (dd, J=2 Hz, J=9 Hz, 1H), 5.35 (d, J=2 Hz, 1H), 6.46 (d, J=9 Hz, 1H), 7.58 (d, J=8 Hz, 2H), 7.66 (d, J=8 Hz, 2H); $^{19}$F NMR (DMSO-$d_6$) δ ppm −60.30; ESIMS found for $C_{21}H_{32}F_3NO_5Si$ m/z 462 (M−H).

Preparation of intermediate (LXXXIII) is depicted below in Scheme 14.

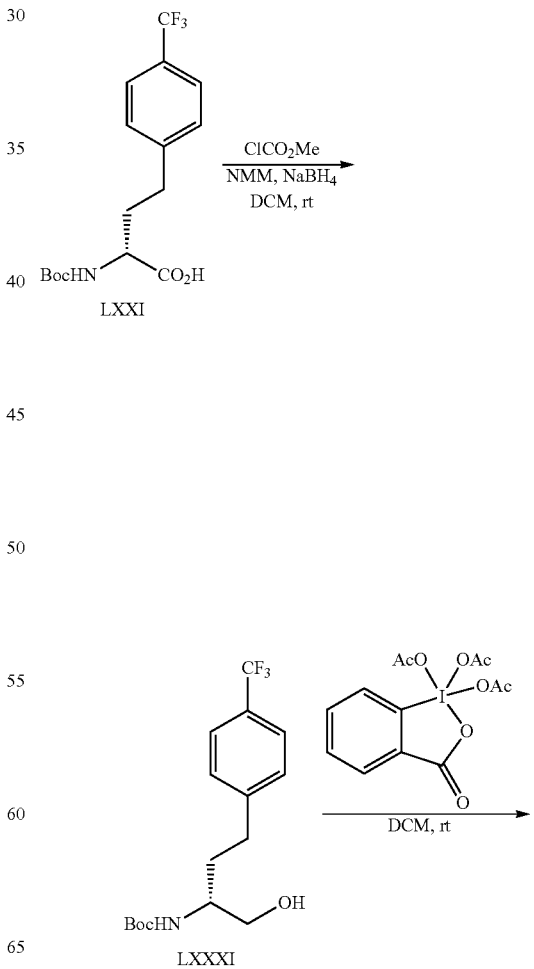

Scheme 14

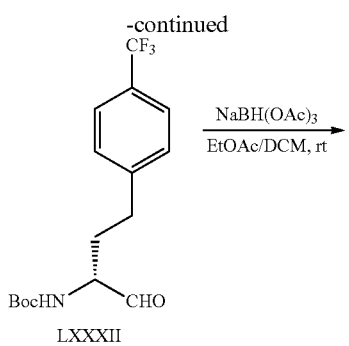

(R)-tert-butyl 1-oxo-3-(4-(trifluoromethyl)phenyl)propan-2-yl carbamate LXXXIV

Preparation of intermediate (LXXXVI) is depicted below in Scheme 15.

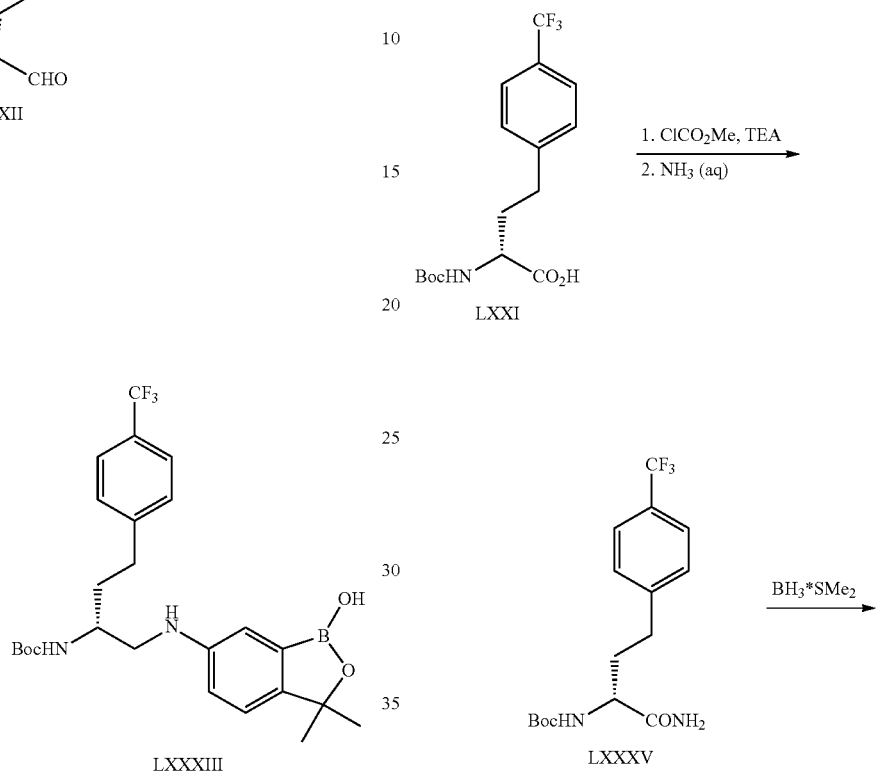

The following intermediate is prepared from (R)-2-(tert-butoxycarbonylamino)-3-(4-(trifluoromethyl)phenyl)propanoic acid (LXVI) in accordance with the procedure described in the above Scheme 14.

LXXXIV

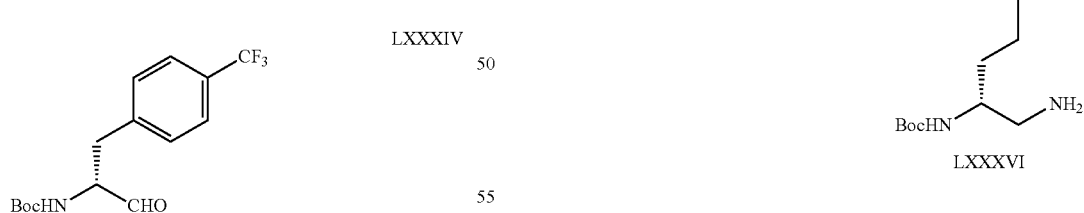

Preparation of intermediate (XCII) is depicted below in Scheme 16.

Scheme 16

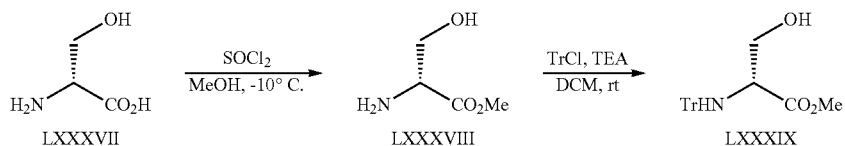

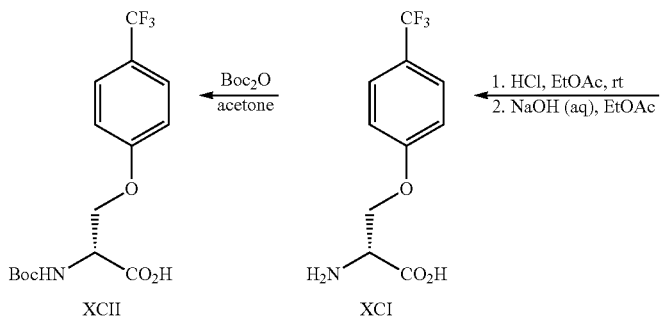

Step 1

Methanol (5 mL/mmol) was cooled −20° C. before (1.2 eq) of thionyl chloride was added dropwise while maintaining the temperature below −10° C. The cooling bath was removed and D-Ser-OH (1 eq) (LXXXVII) was added. The flask was tightly stoppered and the reaction was stirred at room temperature for 2 hours. The methanol was removed in vacuo and the crystalline residue was evaporated twice with toluene. It was then slurred with diethyl ether, filtered and dried in open air at room temperature to give pure D-Ser-OMe (LXXXVIII) (90% yield).

Step 2

To a solution of D-Ser-OMe (LXXXVIII) in dry DCM was added TEA (1.2 eq). After the solution became clear, trityl chloride (1 eq in dry DCM) was added dropwise and stirred for 2 hours. The reaction mixture was washed with 2M HCl, brine and dried over anhydrous $MgSO_4$. The solvent was removed under reduced pressure to give the crude product as a colorless oil. The oil crystallized from $Et_2O$/hexane to produce pure (R)-methyl 3-hydroxy-2-(tritylamino)propanoate (LXXXIX) as white solid (85% yield).

Step 3

To a solution of triphenylphosphine (3 eq) in dry THF under Argon was added diethylazodicarboxylate (3 eq) dropwise. The reaction mixture was stirred at room temperature for 15 minutes before adding a solution of 4-(trifluoromethyl)phenol (3 eq in dry THF) dropwise. The reaction mixture was stirred at room temperature for 1 hour before adding (R)-methyl 3-hydroxy-2-(tritylamino)propanoate (LXXXIX) in dry THF in one portion. The reaction mixture was stirred at room temperature ovenight. The mixture was concentrated to dryness, treated with hexane and filtered. The residue was concentrated to dryness and purified by silica flash chromatography (EtOAc/hexane=1:5). Pure (R)-methyl 3-(4-(trifluoromethyl)phenoxy)-2-(tritylamino)propanoate (XC) was obtained as an off-white solid (50% yield).

Step 4-5

To a solution of (R)-methyl 3-(4-(trifluoromethyl)phenoxy)-2-(tritylamino)propanoate (XC) in EtOAc was treated with HCl (4.5 M solution in EtOAc). The reaction mixture was stirred for 2 h at room temperature. The reaction was concentrated under reduced pressure, diluted with EtOAc and washed with 1M NaOH. To this basic solution containing (R)-2-amino-3-(4-(trifluoromethyl)phenoxy)propanoic acid (XCI) was added $Boc_2O$ (1.1 eq in acetone) followed by stirring overnight at room temperature. The acetone was evaporated under vacuum and the aqueous residue was washed with ether (2×200 ml). The aqueous layer was acidified with 6N HCl to pH=3 and extracted with EtOAc. The organic layer was washed with brine, dried over $MgSO_4$ and evaporated to dryness. The solid residue was purified by silica flash chromatography (DCM/MeOH=200:1) to yield pure (R)-2-(tert-butoxycarbonylamino)-3-(4-(trifluoromethyl)phenoxy)propanoic acid (XCII) as an off-white solid (60% yield).

The following intermediate is prepared from 4-(trifluoromethyl)benzenethiol in accordance with the procedure described in the above Scheme 16.

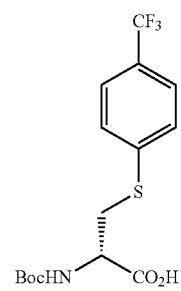

XCIII (S)-2-(tert-butoxycarbonylamino)-3-(4-(trifluoromethyl)phenylthio) propanoic acid XCIII Preparation of intermediate (XCVIII) is depicted below in Scheme 17.

Scheme 17

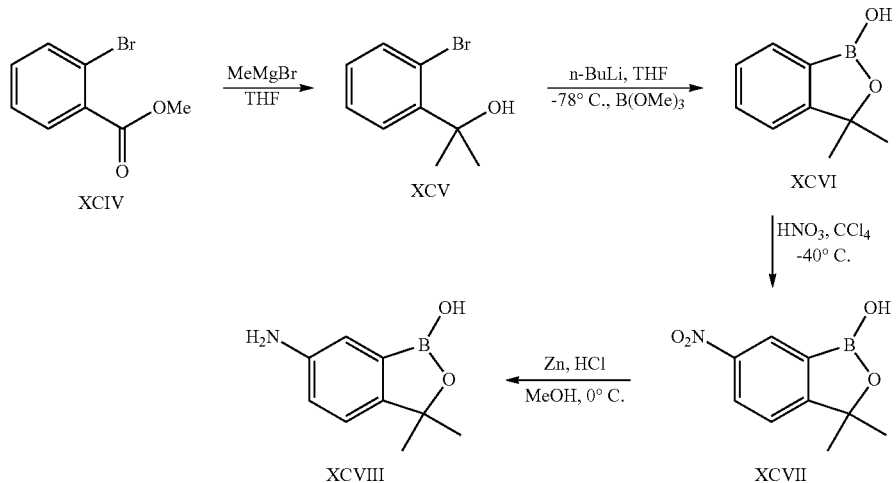

Step 1

To a stirring solution of methyl 2-bromobenzoate (XCIV) (5 g, 0.0233 mol) in THF (30 mL) under argon at 0° C. was added dropwise MeMgBr (19.4 mL, 0.058 mol), maintaining the temperature in the range of −5 to 0° C. The reaction mixture was stirred at 0° C. for 1 hour and then at room temperature overnight. The mixture was cooled to 0° C. and 1M aqueous HCl (35 mL) was added, maintaining the temperature below 5° C., after which it was allowed to reach room temperature and was stirred for 30 minutes. To this mixture EtOAc (35 mL) was added and after stirring for 5 minutes a white precipitate was removed by filtration through a Celite pad. The layers were separated and the aqueous layer was extracted with EtOAc. The combined organic fractions were concentrated, washed with brine and dried over MgSO$_4$. Crude XCV was purified by silica gel chromatography using DCM then DCM/MeOH 300/1 to give 2-(2-bromophenyl) propan-2-ol (XCV) as a light yellow oil (4.55 g; 21.2 mmol, 91% yield). $^1$H NMR (CDCl$_3$) δ ppm 1.75 (s, 6H), 2.85 (brs, 1H), 7.09 (td, J=7 Hz, J=2 Hz, 1H), 7.29 (td, J=7 Hz, J=1 Hz, 1H), 7.58 (dd, J=7, J=1, 1H), 7.67 (dd J=7, J=2, 1H).

Step 2

To a solution of n-BuLi (21.2 ml, 0.053 mol) in anhydrous THF (160 mL) at −78° C. under argon was slowly added a solution of 2-(2-bromophenyl)propan-2-ol (XCV) (0.0212 mol, 4.55 g) in anhydrous THF (50 mL) while maintaining the temperature below −65° C. After addition was complete, the reaction mixture was stirred at −75° C. for 30 min. To this mixture was added in portions trimethyl borate (0.032 mol, 3.3 g), and the reaction mixture was stirred at −78° C. for 30 min and then at room temperature overnight. The mixture was cooled to 0° C., carefully quenched with 1M aqueous HCl, and stirred at room temperature for 15 min. The mixture was acidified to pH 3 with 2M HCl and stirring was continued for 1 hour. The two phases were separated and the aqueous layer was extracted with EtOAc. The combined organic phases were dried over MgSO$_4$. The crude product was purified by silica gel chromatography using DCM followed by DCM/MeOH 300/1 to give 3,3-dimethylbenzo[c][1,2]oxaborol-1 (3H)-ol (XCVI) as a light yellow oil (1.37 g; 8.5 mmol, 40% yield). $^1$H NMR (CDCl$_3$) δ ppm 1.54 (s, 6H), 7.25-7.29 (m, 1H), 7.33 (d, J=7 Hz, 1H), 7.45 (td, J=7 Hz, J=1 Hz, 1H), 7.68 (d, J=7 Hz, 1H).

Step 3

To 100% fuming nitric acid (10 mL) at −40° C. was added dropwise a solution of 3,3-dimethylbenzo[c][1,2]oxaborol-1 (3H)-ol (XCVI) (1.37 g, 0.0085 mol) in carbon tetrachloride (40 mL), maintaining the temperature below −40° C. Stirring was continued for 20 min at −40° C. The yellow solution was poured onto ice and was stirred for 10 min at room temperature. The mixture was extracted with EtOAc. To the organic layer was added 1M aqueous NaOH to pH=7. The organic layer was separated, and washed with water, dried over MgSO$_4$ and filtered, and the solvent was removed in vacuo to give an orange viscous oil. The oily residue was triturated with hexane to give pure 3,3-dimethyl-6-nitrobenzo[c][1,2] oxaborol-1(3H)-ol (XCVII) as a yellow solid (1.20 g, 5.8 mmol, yield 68%). $^1$H NMR (CDCl$_3$) δ ppm 1.61 (s, 6H), 7.42 (s, 1H), 8.35 (d, J=8 Hz, 1H), 8.56 (d, J=8 Hz. 1H). ESIMS found for C$_9$H$_{10}$BNO$_4$ m/z 206.3 (M−H).

Step 4

To a solution of 1.20 g of 3,3-dimethyl-6-nitrobenzo[c][1, 2]oxaborol-1(3H)-ol (XCVII) (1.20 g, 5.8 mmol) in MeOH (30 mL) was added 3M aqueous HCl (30 mL), and the mixture was cooled to 0° C. To this mixture was added portionwise zinc dust (3.77 g, 0.058 mol), maintaining the temperature below 5° C. The mixture was stirred for 40 min at room temperature. A gray solid was removed by filtration through a Celite pad. The filtrate was concentrated in vacuo and the residue was dissolved in EtOAc and stirred. 1M aqueous K$_2$CO$_3$ was added to pH=7 and stirring was continued for 10 min. The two phases were separated and the aqueous layer was extracted with EtOAc. The combined organic phases were dried over MgSO$_4$ filtered and concentrated in vacuo. The crude product was purified by silica gel chromatography using DCM then DCM/MeOH 500/1→300/1→200/ 1→100/1 to give 6-amino-3,3-dimethylbenzo[c][1,2]oxaborol-1(3H)-ol (XCVIII) as an orange solid (0.62 g, 3.5 mmol, yield 60%). $^1$H NMR (DMSO-d$_6$) δ ppm 1.46 (s, 6H), 7.43 (dd, J=8 Hz, J=2 Hz, 1H), 7.55 (d. J=8 Hz, 1H), 7.67 (d, J=2 Hz, 1H), 9.95-10.72 (brs, 3H) ESIMS found for $C_9H_{12}BNO_2$ m/z 178.1 (M+H).

Preparation of intermediate (CIII) is depicted below in Scheme 18.

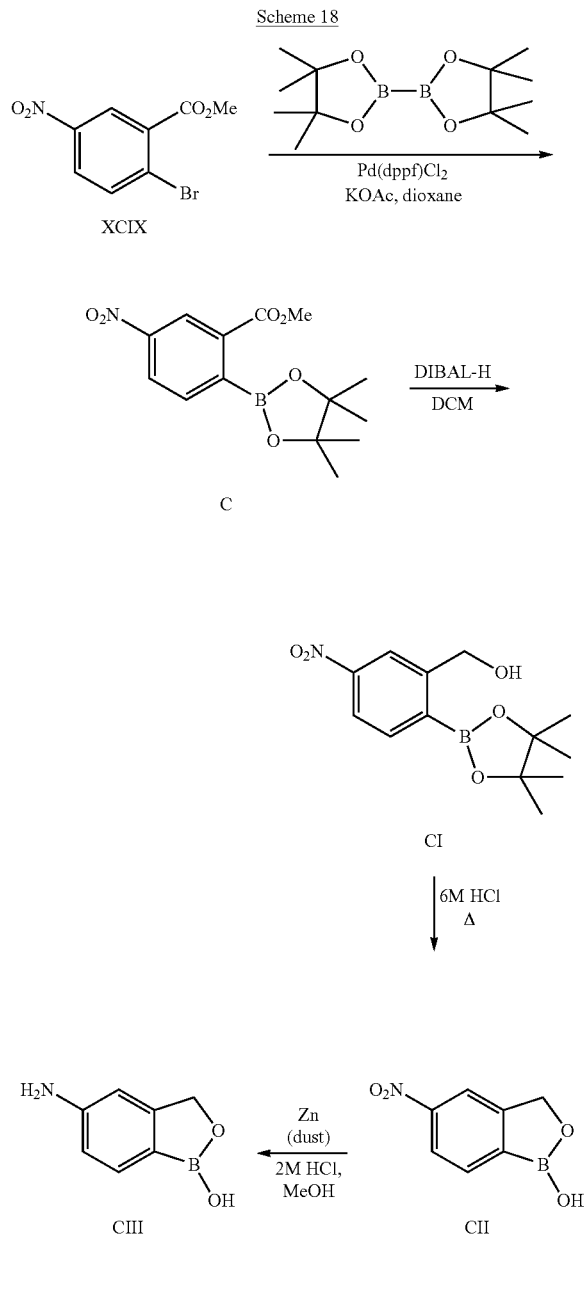

Scheme 18

Step 1

Bis-(pinacolato)diboron (3.22 g, 12.69 mmol), 1,1'-Bis(diphenyl phosphino)ferrocene]dichloropalladium (II) (754 mg, 0.923 mmol), potassium acetate (3.4 g, 34.61 mmol) were dissolved in dioxane (60 mL) and flushed with argon. Then a solution of methyl-2-bromo-5-nitrobenzoate (XCIX) (3 g, 11.54 mmol) in dioxane (20 mL) was added and the reaction mixture was heated at 70° C. overnight. The solids were removed by filtration and washed with EtOAc (50 mL). The combined filtrate was concentrated under vacuum. The residue was dissolved in EtOAc (100 mL), washed with water, brine, dried over anhydrous $MgSO_4$ and concentrated under vacuum to give 3.5 g of a black oil. The oil was purified on a silica gel column (EtOAc:hexane 1:20) to give methyl 5-nitro-2-(4,4,5,5-tetramethyl-1,3,2-dioxaborolan-2-yl)benzoate (C) as white crystals (2.5 g, 8.14 mmol, 56% yield, purity 80%). The product was used without further purification for step 2.

Step 2

Methyl 5-nitro-2-(4,4,5,5-tetramethyl-1,3,2-dioxaborolan-2-yl)benzoate (C) (2.5 g, 8.14 mmol) was dissolved in DCM (25 mL), flushed with argon and cooled in an ice bath to 0° C. A solution of 1 M diisobutylaluminum hydride in DCM (20.5 mL, 20.35 mmol) was added dropwise so that the temperature remained below 3° C. over 2 h. The black reaction mixture was stirred at 0° C. for an additional 2 h. After this time, MeOH (3 mL) was added causing a yellow precipitate to form. 1 M aqueous HCl (50 mL) was then added and reaction was stirred for 30 min at 0° C. The layers were separated and the aqueous phase was extracted with EtOAc (3×50 mL). The combined organic phases were washed with brine and dried over anhydrous $MgSO_4$ to produce (5-nitro-2-(4,4,5,5-tetramethyl-1,3,2-dioxaborolan-2-yl)phenyl)methanol (CI) as a black oil (1.25 g, 4.48 mmol, 55% yield, purity 85%). The product was used without further purification for step 3.

Step 3

(5-Nitro-2-(4,4,5,5-tetramethyl-1,3,2-dioxaborolan-2-yl)phenyl)methanol (CI) (1.25 g, 4.48 mmol) was dissolved in 6 M HCl (100 mL) at 60° C. and stirred overnight. The mixture was then cooled to the room temperature and extracted with EtOAc (2×100 mL). The organic layers were combined, washed with brine and dried over anhydrous $MgSO_4$ to give 5-nitrobenzo[c][1,2]oxaborol-1(3H)-ol (CII) as a brown solid (800 mg, 4.47 mmol, 99% yield). The crude product was used without further purification for step 4. ESIMS found for $C_7H_6BNO_4$ m/z 180.1 (M+H).

Step 4

To a solution of 5-nitrobenzo[c][1,2]oxaborol-1(3H)-ol (CII) (360 mg, 2.01 mmol) in MeOH (25 mL) was added Zn dust (1.31 g, 20.11 mmol) and 2 M HCl (30 mL, 60.33 mmol). The reaction mixture was stirred at room temperature for 2.5 h before saturating with 5% aq. $NaHCO_3$ (40 mL). The solids were filtered and filtrate was concentrated under reduce pressure to about 50 mL. The residue was diluted with EtOAc and the phases were separated. The organic layer was washed with brine, dried over $MgSO_4$, and concentrated in vacuo to give 5-aminobenzo[c][1,2]oxaborol-1(3H)-ol (CIII) as a brown oil (250 mg, 1.68 mmol, 83% yield, 80% purity). ESIMS found for $C_7H_8BNO_2$ m/z 149.9 (M+H). The crude product was used without further purification for coupling.

Preparation of intermediate (CXII) is depicted below in Scheme 19.

Scheme 19

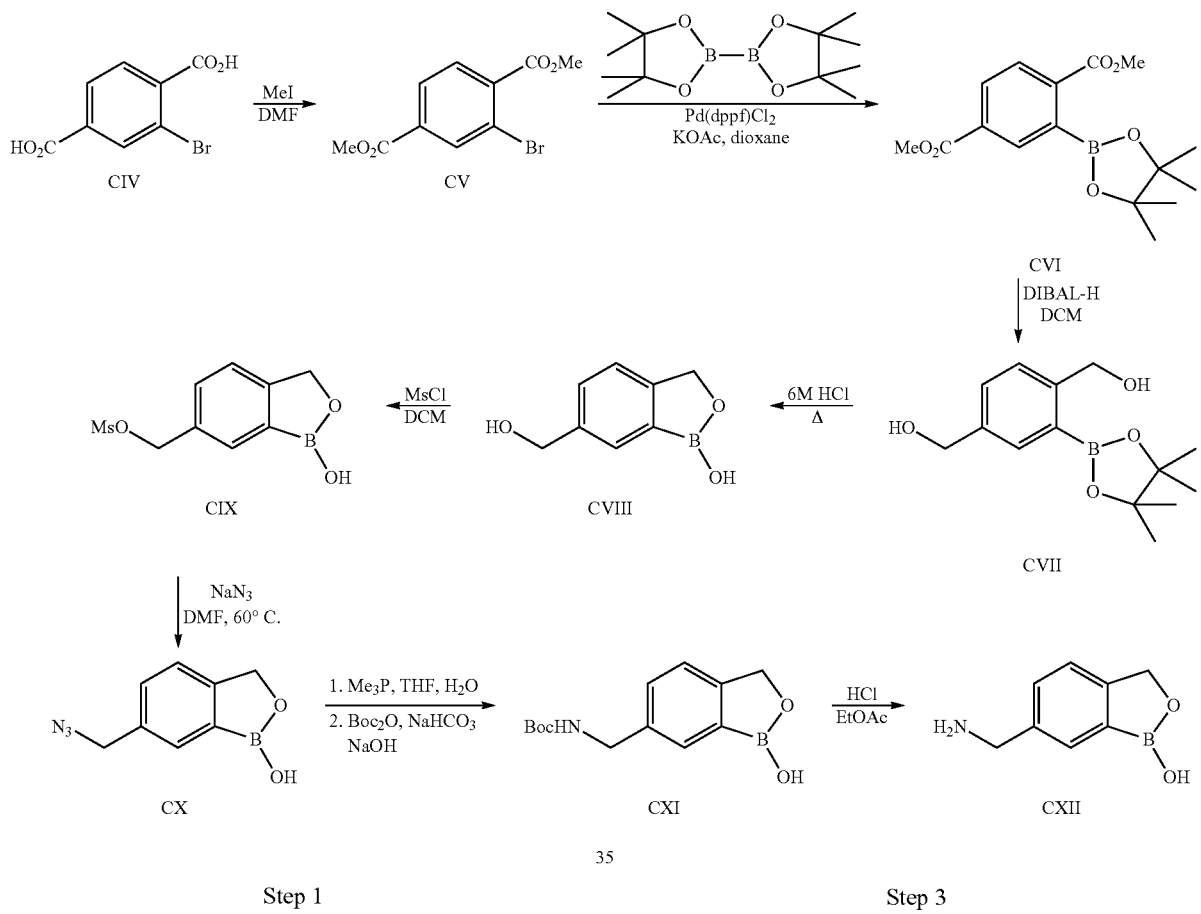

Step 1

To the solution of 2-bromoterephthalic acid (CIV) (5.0 g, 20.40 mmol) in DMF was added $K_2CO_3$ (7.9 g, 57.13 mmol) and $CH_3I$ (3.56 mL, 57.13 mmol). The reaction mixture was stirred overnight at room temperature. The reaction mixture was diluted with DCM, washed with 1 N aqueous HCl, 1 M aqueous $K_2CO_3$, 10% aqueous $Na_2S_2O_3$, brine, dried over anhydrous $MgSO_4$, and concentrated under vacuum to give dimethyl 2-bromoterephthalate (CV) (4.82 g, 17.65 mmol, 99% purity, 80% yield). ESIMS found for $C_{10}H_9BrO_4$ m/z 275.2 (M+2H).

Step 2

Bis-(pinacolato)diboron (4.93 g, 19.40 mmol), 1,1'-Bis (diphenyl phosphino)ferrocene]dichloropalladium (II) (0.72 g, 0.88 mmol), potassium acetate (5.19 g, 17.65 mmol) were dissolved in dioxane (40 ml) and flushed with argon. A solution of dimethyl 2-bromoterephthalate (CV) (4.82 g, 17.65 mmol) in dioxane (15 mL) was then added and the reaction mixture was heated at 80° C. overnight. The solids were filtered off and washed with EtOAc. The combined organic phases were concentrated under vacuum and the residue was dissolved in EtOAc, washed with water, dried over anhydrous $MgSO_4$ and concentrated to give 8.01 g of a black oil. The oil was purified by silica gel chromatography (DCM/MeOH 1000:1→500:1→200:1→100:1) to give dimethyl 2-(4,4,5,5-tetramethyl-1,3,2-dioxaborolan-2-yl)terephthalate (CVI) (2.60 g, 8.12 mmol, 51% purity, 23% yield). ESIMS found for $C_{16}H_{21}BO_6$ m/z 243.3 (M+Na).

Step 3

Dimethyl 2-(4,4,5,5-tetramethyl-1,3,2-dioxaborolan-2-yl) terephthalate (CVI) (2.60 g, 8.12 mmol) was dissolved in DCM (25 mL), flushed with argon and cooled to −10° C. A 1 M solution of diisobutylaluminum hydride in DCM (48.73 mL, 48.73 mmol) was then added dropwise and the reaction was stirred at 0° C. for 2 h. 1 N aqueous HCl (50 mL) was carefully added and stirred for 5 minutes. The reaction was extracted with DCM and the combined extracts were washed with brine, dried over anhydrous $MgSO_4$ and concentrated to give (2-(4,4,5,5-tetramethyl-1,3,2-dioxaborolan-2-yl)-1,4-phenylene)dimethanol (CVII) (2.0 g, 7.57 mmol). The crude product was used without further purification for step 4.

Step 4

(2-(4,4,5,5-Tetramethyl-1,3,2-dioxaborolan-2-yl)-1,4-phenylene)dimethanol (CVII) (2.0 g, 7.57 mmol) was dissolved in 6 M aqueous HCl (100 ml) at 60° C. and stirred overnight. The reaction mixture was concentrated under vacuum and the oily residue was triturated with $Et_2O$ to give a light-brown solid. The solid was removed by filtration and washed with $Et_2O$. The filtrate (which according to LC/MS contained the product) was concentrated under vacuum to give 6-(hydroxymethyl)benzo[c][1,2]oxaborol-1(3H)-ol (CVIII) (0.63 g, 3.84 mmol, 35% purity). ESIMS found for $C_8H_9BO_3$ m/z 163.0 (M−H). The crude product was used without further purification for Step 5.

Step 5

To the solution of 6-(hydroxymethyl)benzo[c][1,2]oxaborol-1(3H)-ol (CVIII) (0.63 g, 3.84 mmol) in DCM (20 mL) was added Et$_3$N (0.53 mL, 4.61 mmol) and methanesulfonyl chloride (0.33 mL, 4.42 mmol). The reaction mixture was stirred overnight at room temperature. The reaction mixture was diluted with DCM, washed with 2 N aqueous HCl, brine, dried over anhydrous MgSO$_4$, and concentrated under vacuum to give (1-hydroxy-1,3-dihydrobenzo[c][1,2]oxaborol-6-yl) methylmethanesulfonate (CIX) (0.48 g, 1.98 mmol, impure). The crude product was used without further purification for step 6.

Step 6

To the solution of (1-hydroxy-1,3-dihydrobenzo[c][1,2]oxaborol-6-yl)methylmethanesulfonate (CIX) (0.48 g, 1.98 mmol) in DMF (20 mL) was added NaI (0.06 g, 0.40 mmol) and NaN$_3$ (0.15 g, 2.38 mmol). The mixture was stirred at 60° C. overnight. The reaction mixture was diluted with EtOAc, washed with 10% aqueous Na$_2$S$_2$O$_3$, brine, dried over anhydrous MgSO$_4$, and concentrated under vacuum to give 6-(azidomethyl)benzo[c][1,2]oxaborol-1(3H)-ol (CX) (0.49 g, impure). The crude product was used without further purification for step 7.

Step 7

To the solution of 6-(azidomethyl)benzo[c][1,2]oxaborol-1(3H)-ol (CX) (0.49 g, theoretical 1.98 mmol) in THF/H$_2$O (27 mL/3 mL) was slowly added a 1 M solution of Me$_3$P in THF (3.97 mL, 3.97 mmol). The reaction mixture was stirred overnight at room temperature. The mixture was concentrated under vacuum to produce crude amine (0.6 g). The crude amine was dissolved in 5% aq. NaHCO$_3$ followed by the addition of 1 M aqueous NaOH until pH 11. To this mixture was then added a solution of Boc$_2$O (0.52 g, 2.38 mmol) in acetone (10 mL). The reaction mixture was stirred overnight at room temperature. The reaction mixture was concentrated to remove acetone and the residue was extracted with Et$_2$O. The combined extracts were washed with 1 N aqueous HCl, brine, dried over anhydrous MgSO$_4$ and concentrated to give tert-butyl (1-hydroxy-1,3-dihydrobenzo[c][1,2]oxaborol-6-yl)methylcarbamate (CXI) (0.27 g, 1.02 mmol, 94% purity). $^1$H NMR (CDCl$_3$) δ ppm 1.49 (s, 9H), 5.08 (s, 2H), 4.34-4.40 (brs, 2H), 7.32-7.35 (brs, 1H), 7.39-7.43 (brs, 1H), 7.66-7.70 (brs, 1H); ESIMS found for C$_{13}$H$_{18}$BNO$_4$ m/z 286.3 (M+Na).

Step 8 tert-Butyl (1-hydroxy-1,3-dihydrobenzo[c][1,2]oxaborol-6-yl)methylcarbamate (CXI) (0.27 g, 1.02 mmol) was dissolved in HCl/EtOAc (4.2 M, 7 mL/mmol) and stirred for 30 minutes at room temperature. The solvent was removed under vacuum and residue was triturated with Et$_2$O to give 6-(aminomethyl)benzo[c][1,2]oxaborol-1(3H)-ol (CXII) as a white solid (0.15 g, 0.75 mmol, 74% yield). $^1$H NMR (DMSO-d$_6$) δ ppm 4.00 (s, 2H), 4.69 (s, 2H), 7.21-7.51 (brs, 1H), 7.52-7.66 (brs, 1H), 7.67-7.88 (brs, 1H), 8.06-8.98 (brs, 3H); ESIMS found for C$_8$H$_{10}$BNO$_2$ m/z 146.7 (M–H$_2$O+1).

The following intermediate is prepared from 4-bromoisophthalic acid in accordance with the procedure described in the above Scheme 19.

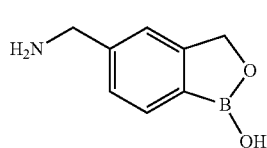

CXIII 5-(Aminomethyl)benzo[c][1,2]oxaborol-1(3H)-ol
CXIII

White solid (0.07 g, 0.35 mmol, 23% yield). ESIMS found for C$_8$H$_{10}$BNO$_2$ m/z 164.3 (M+H).

Preparation of intermediates (CXVIII) and (CXIX) is depicted below in Scheme 20.

Scheme 20

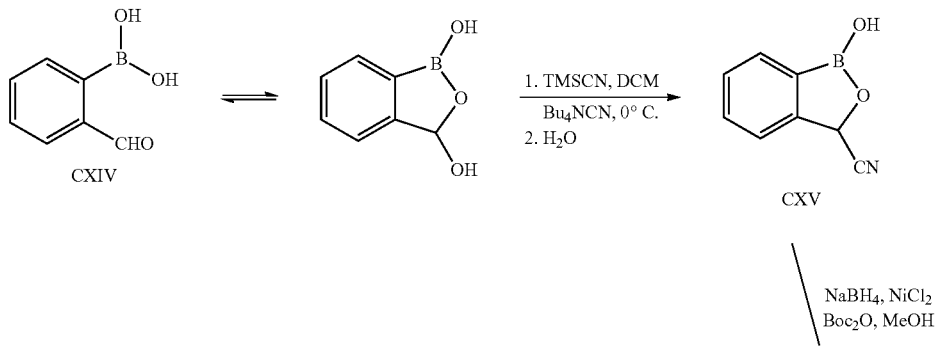

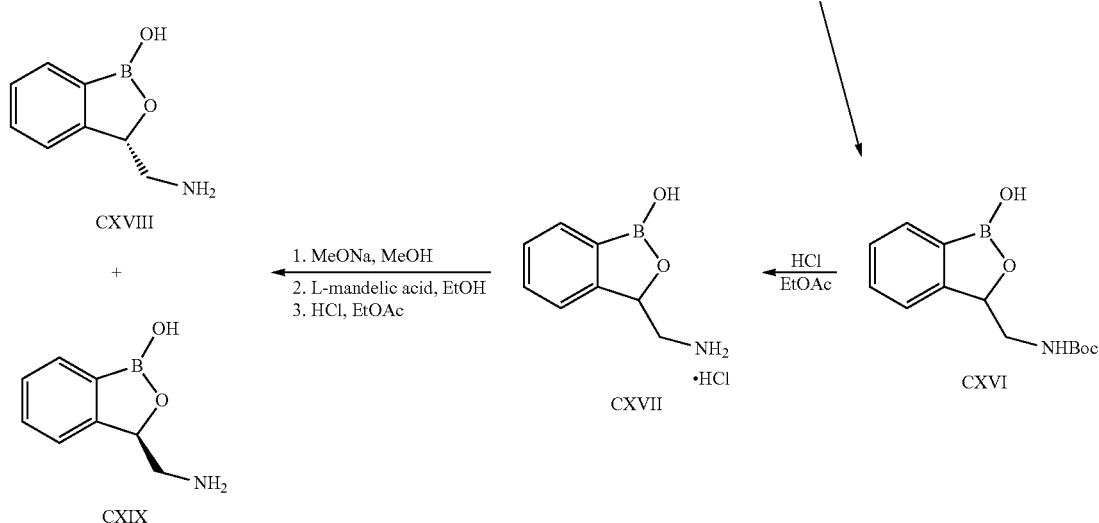

Step 1

To a solution of the 2-formylphenylboronic acid (CXIV) (27 g, 180 mmol) in dry DCM (243 mL) was added TMSCN (24.8 mL, 198 mmol) under argon at 0° C. followed by a solution of tetrabutylammonium cyanide (9.06 g, 27 mmol) in dry DCM (365 mL). The mixture was stirred at 0° C. for 60 minutes. A saturated aqueous solution of NaHCO$_3$ (1470 mL) was added and the mixture was extracted with DCM. Drying of the combined organic phases with MgSO$_4$ was followed by evaporation of the solvent in vacuo. The crude 1-hydroxy-1,3-dihydrobenzo[c][1,2]oxaborole-3-carbonitrile (CXV) was used without further purification for step 2.

Step 2

To a solution of 1-hydroxy-1,3-dihydrobenzo[c][1,2]oxaborole-3-carbonitrile (CXV) (30.7 g, 193 mmol) in MeOH (965 mL, 5 ml/mmol) at −10° C. was added NiCl$_2$*6H$_2$O (4.58 g, 19.3 mmol) and Boc$_2$O (84.2 g, 386 mmol). After 5 minutes, sodium borohydride (51.08 g, 1350 mmol) was added in small portions, as the color of the mixture changed to black. The reaction mixture was allowed to warm up to room temperature and stirred overnight. The MeOH was evaporated, EtOAc was added and the mixture was washed twice with water. The organic layer was dried over anhydrous MgSO$_4$ and concentrated under vacuum. The crude product was purified by silica gel chromatography using DCM/MeOH 200:1→150:1→100:1→50:1 to yield tert-butyl (1-hydroxy-1,3-dihydrobenzo[c][1,2]oxaborol-3-yl)methylcarbamate (CXVI) (13.09 g, 49.75 mmol, 26% yield). ESIMS found for C$_{13}$H$_{18}$BNO$_4$ m/z 262.4 (M−H).

Step 3 tert-Butyl (1-hydroxy-1,3-dihydrobenzo[c][1,2]oxaborol-3-yl) methylcarbamate (CXVI) (13.09 g, 49.75 mmol) was dissolved in HCl/EtOAc (4.2 M, 350 mL and stirred for 10 minutes at room temperature. The solvent was removed under vacuum and the residue was triturated with Et$_2$O to give 3-(aminomethyl)benzo[c][1,2]oxaborol-1(3H)-ol hydrochloride (CXVII) as a white solid (7.2 g, 36.09 mmol, 72% yield). $^1$H NMR (DMSO-d$_6$) δ ppm [2.72 (dd, J=10 Hz, J=12 Hz, 1$^{st}$ isomer), 2.80 (dd, J=8 Hz, J=12 Hz, 2$^{nd}$ isomer), 1H], 3.37-3.49 (m, 1H), [5.38 (d, J=8 Hz, 1$^{st}$ isomer), 5.47 (d, J=8 Hz, 2$^{nd}$ isomer), 1H], 7.32-7.42 (m, 1H), [7.47 (d, J=3 Hz, 1$^{st}$ isomer), 7.51 (d, J=3 Hz, 2$^{nd}$ isomer), 2H], [7.66 (d, J=7 Hz, 2$^{nd}$ isomer), 7.82 (d, J=7 Hz, 1$^{st}$ isomer)], 8.2-8.46 (brs, 3H); ESIMS found for C$_8$H$_{10}$BNO$_2$ m/z 164.2 (M+H).

Step 4

To a solution of 3-(aminomethyl)benzo[c][1,2]oxaborol-1 (3H)-ol hydrochloride (CXVII) (7.2 g, 36.09 mmol) in MeOH (40 mL, 1.1 mL/mmol) at room temperature was added MeONa (11.95 g. 36.09 mmol). After 1 hour, the solvent was evaporated and DCM was added. The resulting white precipitate was removed by filtration and washed with DCM. The filtrate was concentrated under vacuum to give the free amine (5.88 g, 36.0 mmol, 100% yield). The free amine was dissolved in absolute EtOH (140 mL) before adding L-mandelic acid (5.48 g, 36.0 mmol). After 10 minutes a white precipitate had formed. The precipitate was filtered and washed with absolute EtOH (50 mL).

The filtrate was concentrated under vacuum and the oily residue was dissolved in HCl/EtOAc (4.2 M, 250 mL) and stirred for 20 minutes at room temperature. The solvent was removed under vacuum and the residue was triturated with Et$_2$O to give (R)-3-(aminomethyl)benzo[c][1,2]oxaborol-1 (3H)-ol (CXVIII) as an off-white solid (3.0 g). Marfey test (96%/4% R/S). $^1$H NMR (DMSO-d$_6$) δ ppm 2.73-2.83 (m, 1H), 3.48 (d, J=13 Hz, 1H), 5.44 (d, J=8 Hz, 1H), 7.42 (s, 1H), 7.51 (s, 2H), 7.87 (d, J=7 Hz, 1H), 8.2-8.4 (brs, 3H); ESIMS found for C$_8$H$_{10}$BNO$_2$ m/z 164.2 (M+H).

The precipitate was dissolved in HCl/EtOAc (4.2 M, 250 mL) and stirred for 20 minutes at room temperature. The solvent was removed under vacuum and residue was triturated with Et$_2$O to give (S)-3-(aminomethyl)benzo[c][1,2] oxaborol-1(3H)-ol (CXIX) as a white solid (3.0 g). $[α]_D^{23}$=+67° (c 2.0, H$_2$O), [lit. for R-isomer, $[α]_D^{27}$=−47.5° (c 1.9, H$_2$O), WO 2008/157726]; Marfey test (97.6%/2.4% S/R). $^1$H NMR (DMSO-d$_6$) δ ppm 2.73-2.83 (m, 1H), 3.48 (d, J=13 Hz, 1H), 5.44 (d, J=8 Hz, 1H), 7.42 (s, 1H), 7.51 (s, 2H), 7.87 (d, J=7 Hz, 1H), 8.2-8.4 (brs, 3H); ESIMS found for C$_8$H$_{10}$BNO$_2$ m/z 164.2 (M+H).

Preparation of intermediate (CXXII) is depicted below in Scheme 21.

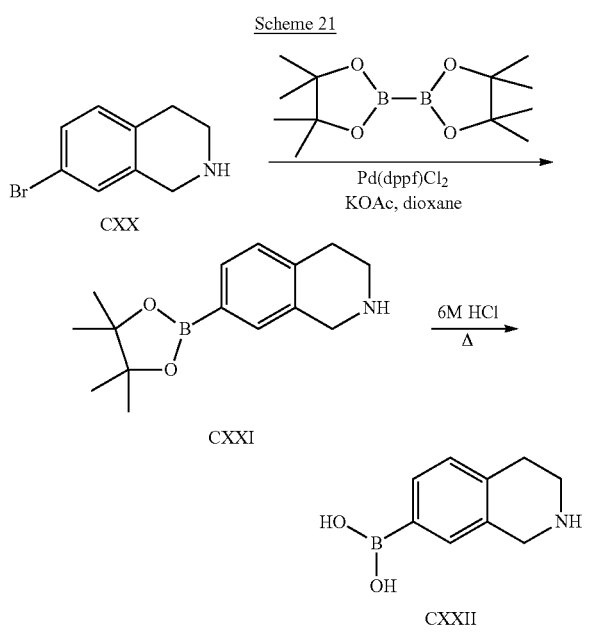

Step 1

Bis(pinacolato)diboran (0.66 g, 2.59 mmol), Pd(dppf)Cl$_2$ (0.09 g, 5 mol %), KOAc (0.69 g, 7.07 mmol) were placed in a flask under argon. Next, 7-bromo-1,2,3,4-tetrahydroisoquinoline (CXX) (0.5 g, 2.35 mmol) and dioxane (35 mL, 15 mL/mmol) were added. The reaction mixture was stirred under argon at 90° C. overnight. The reaction mixture was filtered through a pad of Celite and washed with EtOAc. The solvent was evaporated to dryness to give a brown oil which was purified on a silica gel column (5:1 DCM/MeOH) to give 7-(4,4,5,5-tetramethyl-1,3,2-dioxaborolan-2-yl)-1,2,3,4-tetrahydroisoquinoline (CXXI) (0.3 g, 1.15 mmol, 49% yield). ESIMS found for C$_{15}$H$_{22}$BNO$_2$ m/z 260 (M+H).

Step 2

7-(4,4,5,5-Tetramethyl-1,3,2-dioxaborolan-2-yl)-1,2,3,4-tetrahydroisoquinoline (CXXI) (0.3 g, 1.15 mmol) was dissolved in 6 N aqueous HCl (20 mL) and refluxed overnight. The solvent was evaporated to dryness and the residue was crystallized from MeOH/Et$_2$O to give 1,2,3,4-tetrahydroisoquinolin-7-ylboronic acid (CXXII) as a brown solid (0.21 g, 0.98 mmol, 87% yield). $^1$H NMR (DMSO-d$_6$) δ ppm 2.92-3.07 (m, 2H), 3.36 (brs, 2H), 4.22 (brs, 2H), 7.18 (d, J=7.56 Hz, 1H), 7.59 (s, 1H), 7.67 (d, J=6.87 Hz, 1H), 8.08 (brs, 1H), 9.66 (brs, 2H); ESIMS found for C$_9$H$_{12}$BNO$_2$ m/z 178 (M+H).

The following intermediates were prepared in accordance with the procedure described in the above Scheme 21.

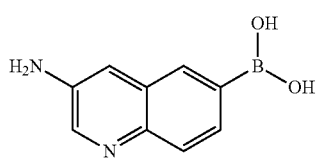

3-Aminoquinolin-6-ylboronic acid CXXIII

Brown solid (1.97 g, 7.54 mmol, 95% yield). $^1$H NMR (DMSO-d$_6$) δ ppm 7.93-7.98 (m, 2H), 8.02 (d, J=8 Hz, 1H), 8.35 (s, 1H), 8.67 (d, J=3 Hz, 1H); ESIMS found for C$_9$H$_9$BN$_2$O$_2$ m/z 189 (M+H).

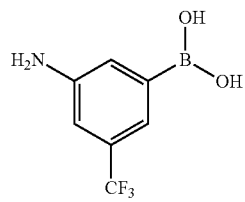

3-Amino-5-(trifluoromethyl)phenylboronic acid CXXIV

White solid (1.38 g, 5.71 mmol, 82% yield). $^1$H NMR (DMSO-d$_6$) δ ppm 7.53 (s, 1H), 7.72 (s, 1H), 7.90 (s, 1H), 8.15-8.7 (brs, 3H); $^{19}$F NMR (DMSO-d$_6$) δ ppm [three signals, −60.69 (21.9%, s), −60.65 (60.9%, s), −60.56 (17.2%, s) 3F]; ESIMS found for C$_7$H$_7$BF$_3$NO$_2$ m/z 206.4 (M+H).

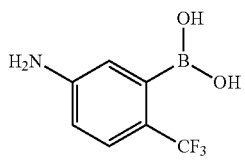

5-Amino-2-(trifluoromethyl)phenylboronic acid CXXV

White solid (0.6 g, 2.48 mmol, 71% yield). $^1$H NMR (DMSO-d$_6$) δ ppm 6.38-6.98 (brs, 3H), 6.99-7.26 (m, 2H), 7.52 (d, J=9 Hz, 1H); $^{19}$F NMR (DMSO-d$_6$) δ ppm [two signals, −56.71 (20%, s), −56.61 (80%, s), 3F]; ESIMS found for C$_7$H$_7$BF$_3$NO$_2$ m/z 206.3 (M+H).

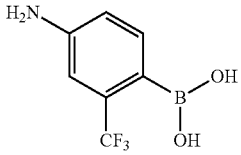

4-Amino-2-(trifluoromethyl)phenylboronic acid CXXVI

White solid (0.79 g, 3.27 mmol, 56% purity, 34% yield). $^1$H NMR (DMSO-d$_6$) δ ppm 7.36-7.63 (m, 3H), 7.83-9.41 (brs, 3H); $^{19}$F NMR (DMSO-d$_6$) δ ppm −60.83 (s, 3F); ESIMS found for C$_7$H$_7$BF$_3$NO$_2$ m/z 206.53 (M+H).

Preparation of intermediate (CXXXII) is depicted below in Scheme 22.

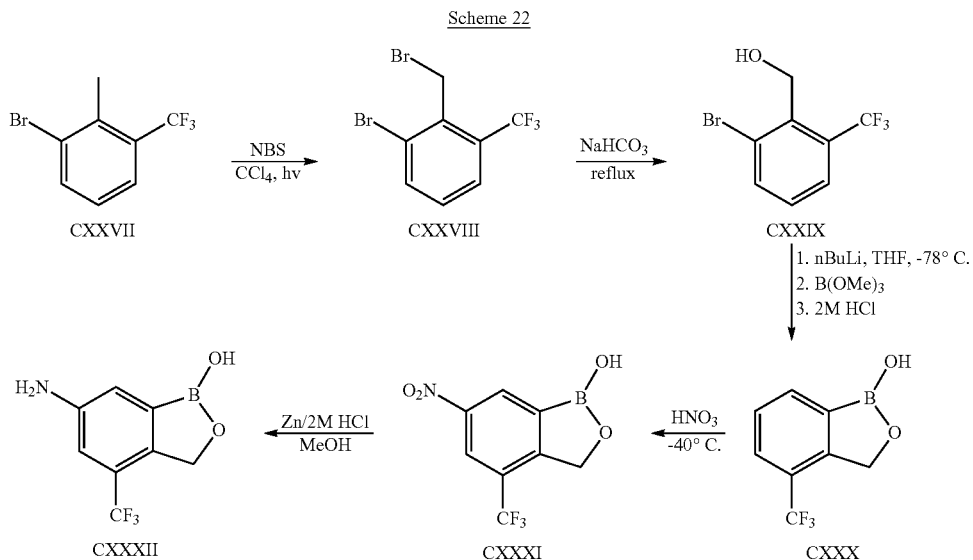

Step 1

To a solution of 1-bromo-2-methyl-3-(trifluoromethyl) benzene (CXXVII) (5.7 g, 23.86 mmol) in CCl₄ (50 mL) was added NBS (4.24 g, 23.86 mmol) and a catalytic amount of benzoyl peroxide. The reaction mixture was gently refluxed for 1 h. The reaction mixture was cooled to room temperature and the precipitate was removed by filtration. The solution was concentrated under reduced pressure and the crude product was dissolved in hexane and additional precipitate was removed by filtration. The filtrate was concentrated to dryness to give 1-bromo-2-(bromomethyl)-3-(trifluoromethyl)benzene (CXXVIII) as an orange oil (7.51 g, 23.62 mmol). $^1$H NMR (DMSO-d₆) δ ppm 4.73 (s, 2H), 7.4 (dd, J=8 Hz, J=8 Hz, 1H), 7.80 (d, J=8 Hz, 1H), 8.02 (d, J=8 Hz, 1H); $^{19}$F NMR (DMSO-d₆) δ ppm −57.85 (s, 3F). The crude product was used without further purification for step 2.

Step 2

To 1-bromo-2-(bromomethyl)-3-(trifluoromethyl)benzene (CXXVIII) (7.51 g, 23.62 mmol) was added an aqueous saturated solution of NaHCO₃ (400 mL). The reaction mixture was vigorously stirred and refluxed overnight. The reaction mixture consisted of an upper aqueous layer and a bottom oily layer, which solidified in an ice bath. The water layer was decanted and the solid was dissolved in EtOAc, dried over anhydrous MgSO₄, filtrated and evaporated to dryness to give (2-bromo-6-(trifluoromethyl)phenyl)methanol (CXXIX) as an orange oil (5.49 g, 23.16 mmol, 98%). $^1$H NMR (DMSO-d₆) δ ppm 4.67 (d, J=4 Hz, 2H), 5.23 (t, J=5 Hz, 1H), 7.43 (dd, J=8 Hz, J=8 Hz, 1H), 7.75 (d, J=8 Hz, 1H), 7.96 (d, J=8 Hz, 1H); $^{19}$F NMR (DMSO-d₆) δ ppm −56.33 (s, 3F); ESIMS found for C₈H₆BrF₃O m/z 237.3 (M+H).

Step 3

To a 2.5 M solution of n-BuLi in hexane (27.81 mL, 69.53 mmol) in dry THF (30 mL), cooled to −78° C. and under an Argon atmosphere was added a solution of (2-bromo-6-(trifluoromethyl)phenyl)methanol (CXXIX) (5.49 g, 23.16 mmol) in dry THF (30 mL) dropwise very slowly. The reaction mixture was stirred at −78° C. for 2 h before adding trimethyl borate (3.88 mL, 34.76 mmol). The reaction mixture was stirred at −78° C. for an additional 30 min, and then allowed to warm up slowly to room temperature and stirred overnight. The reaction was then cooled to 0° C. and slowly quenched with 2 M HCl and stirred for 2.5 h at room temperature. The reaction mixture was extracted with EtOAc and the organic layer was dried over anhydrous MgSO₄. The solvent was removed under reduced pressure and the crude product was purified by silica gel chromatography using (100:1 DCM/MeOH) to give 4-(trifluoromethyl)benzo[c][1,2]oxaborol-1(3H)-ol (CXXX) as an orange oil (1.17 g, 5.79 mmol, 25% yield). ESIMS found for C₈H₆BF₃O₂ m/z 201.4 (M−H).

Step 4

To 4-(trifluoromethyl)benzo[c][1,2]oxaborol-1(3H)-ol (CXXX) (1.17 g, 5.79 mmol) cooled to −40° C. was slowly added HNO₃ (10 mL, 99%). The reaction mixture was stirred for 3 h at −40° C. and then slowly quenched with crushed ice. The yellow precipitate was filtered and washed with hexane to produce 6-nitro-4-(trifluoromethyl)benzo[c][1,2]oxaborol-1(3H)-ol (CXXXI) as a yellow crystalline solid (950 mg, 3.83 mmol, 66% yield). ESIMS found for C₈H₅BF₃NO₄ m/z 246.4 (M−H).

Step 5

To a solution of 6-nitro-4-(trifluoromethyl)benzo[c][1,2]oxaborol-1(3H)-ol (CXXXI) (0.95 g, 3.83 mmol) in MeOH/2M HCl mixture (1:1) (129 mL) was added Zn (dust) (2.5 g, 38.31 nmol). The reaction mixture was stirred at room temperature for 3 hours before it was slowly neutralized by a solution of saturated aq. NaHCO₃/EtOAc (1:1, 100 mL/100 mL). Then the reaction mixture was filtered through Celite and washed with EtOAc. The organic layer was washed with 5% NaHCO₃, brine, dried over anhydrous MgSO₄, filtered and evaporated to dryness to yield 6-amino-4-(trifluoromethyl)benzo[c][1,2]oxaborol-1(3H)-ol (CXXXII) as a slightly brown crystalline solid (700 mg, 3.22 mmol, 84% yield). ESIMS found for C₈H₇BF₃NO₂ m/z 216.4 (M−H).

Preparation of intermediate (CXLI) is depicted below in Scheme 23.
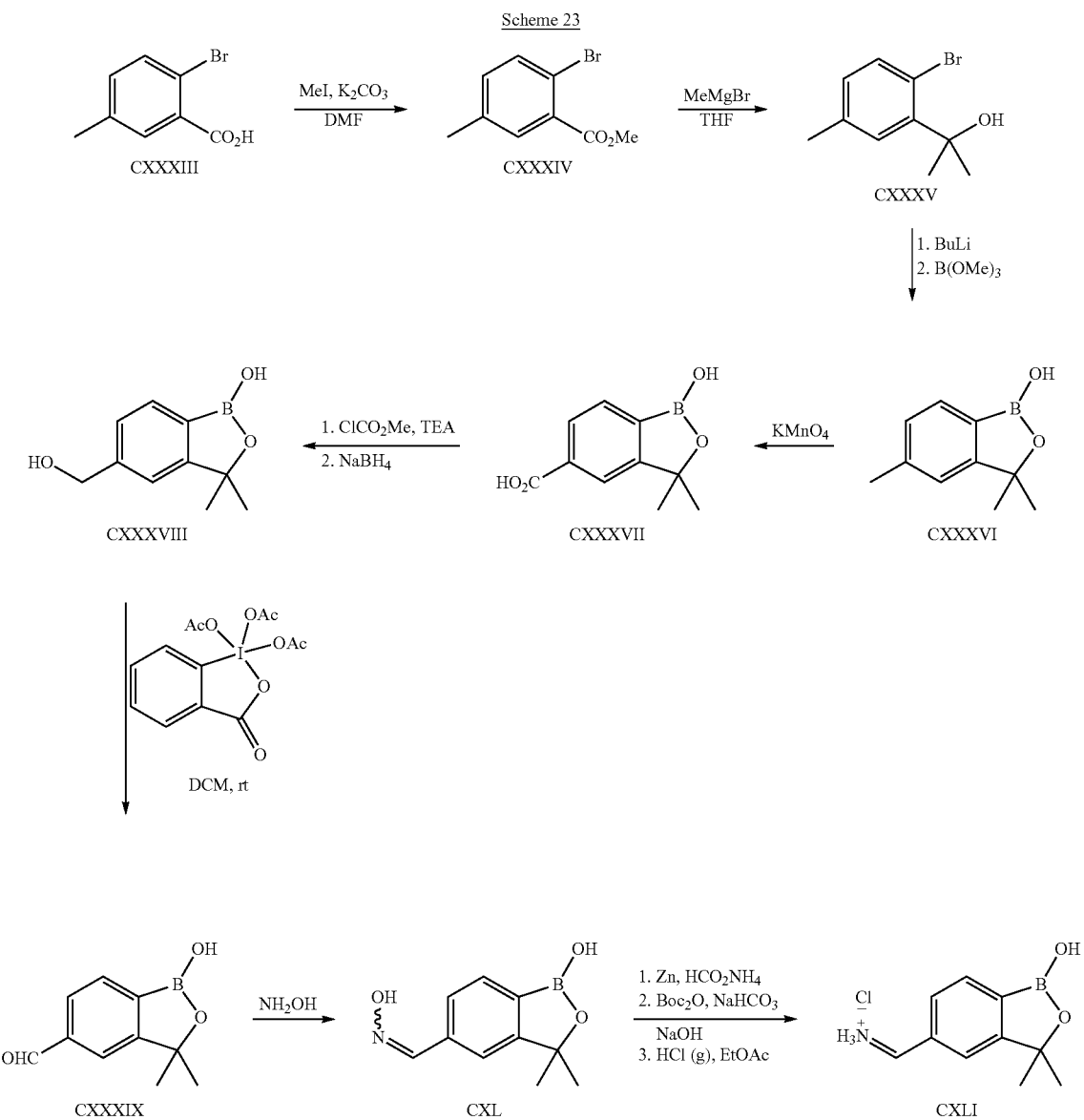
Preparation of intermediate (CXLIX) is depicted below in Scheme 24.
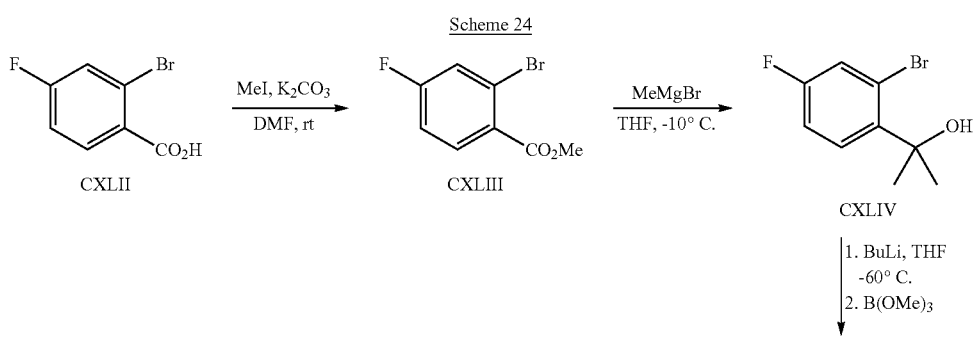

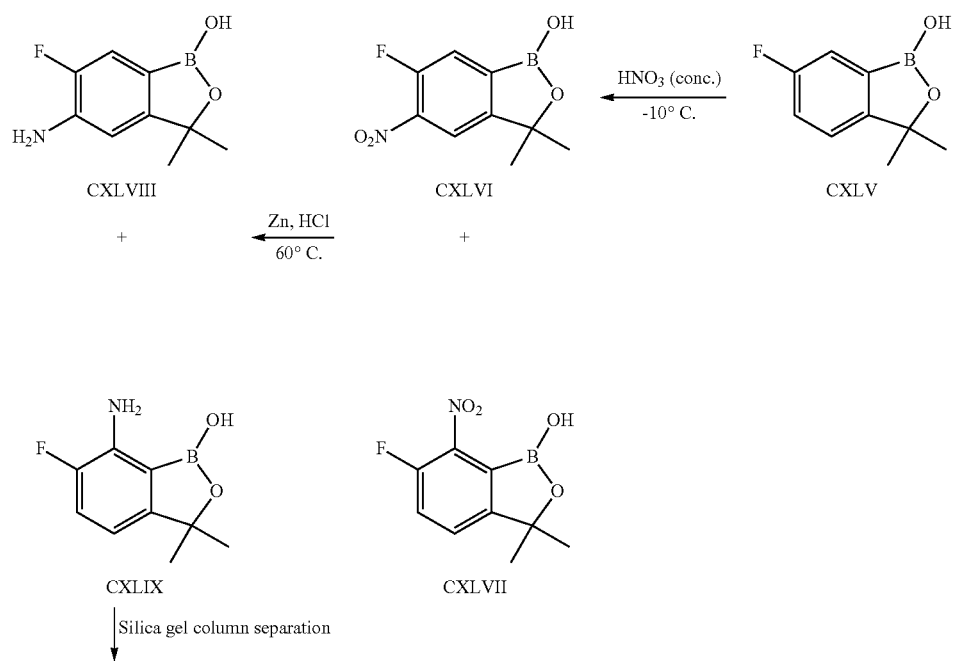
Preparation of intermediate (CLII) is depicted below in Scheme 25.
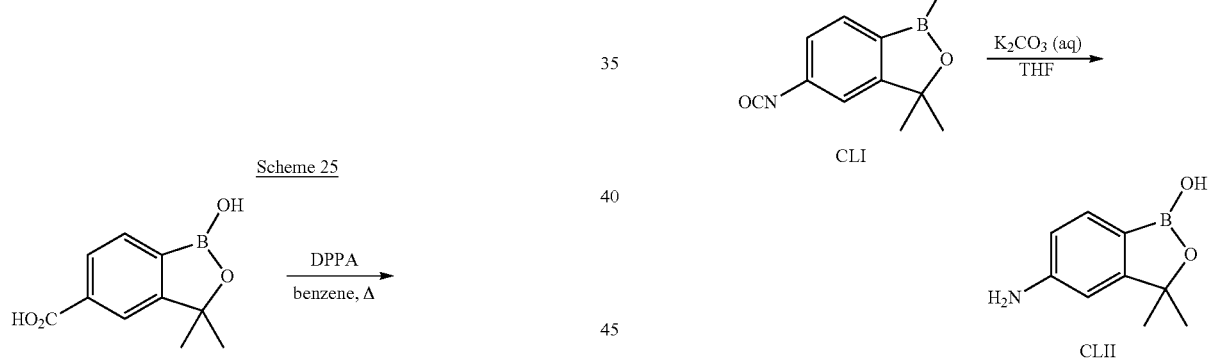
Preparation of intermediate (CLVIII) is depicted below in Scheme 26.
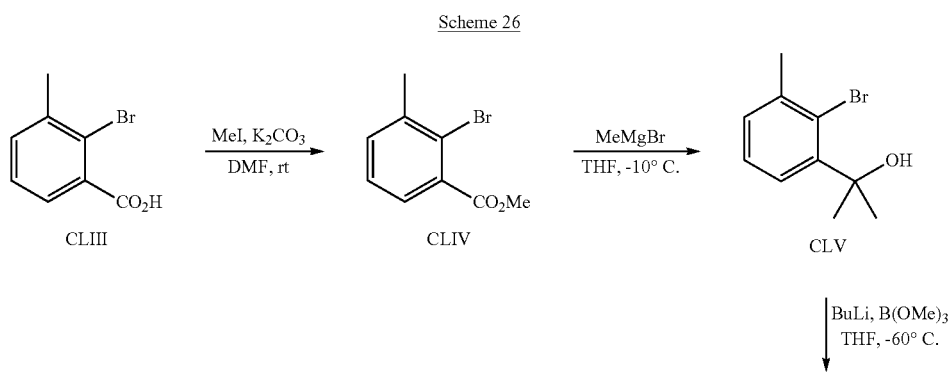

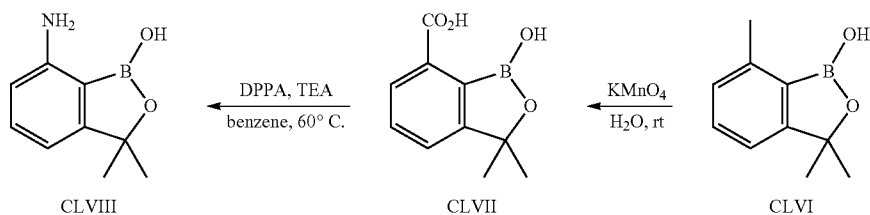
Preparation of intermediate (CLXI) is depicted below in Scheme 27.
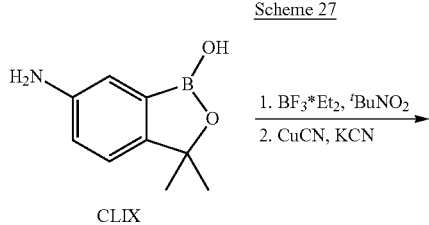
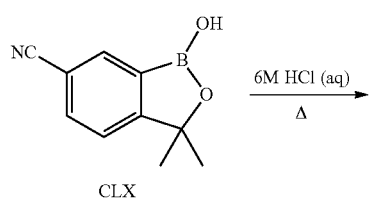
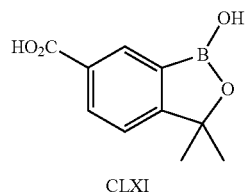
Illustrative Compound Examples
(S)-2-Amino-N5,N5-bis(2-aminoethyl)-N1-((R)-1-(1-hydroxy-3,3-dimethyl-1,3-dihydro benzo[c][1,2] oxaborol-6-ylamino)-1-oxo-3-(4-(trifluoromethyl) phenyl)propan-2-yl)pentanediamide 20
An example of the [2+2] method for the synthesis of 20 is depicted in Scheme 28 and Example 1.
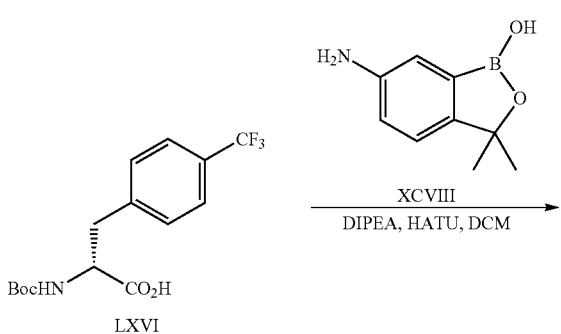

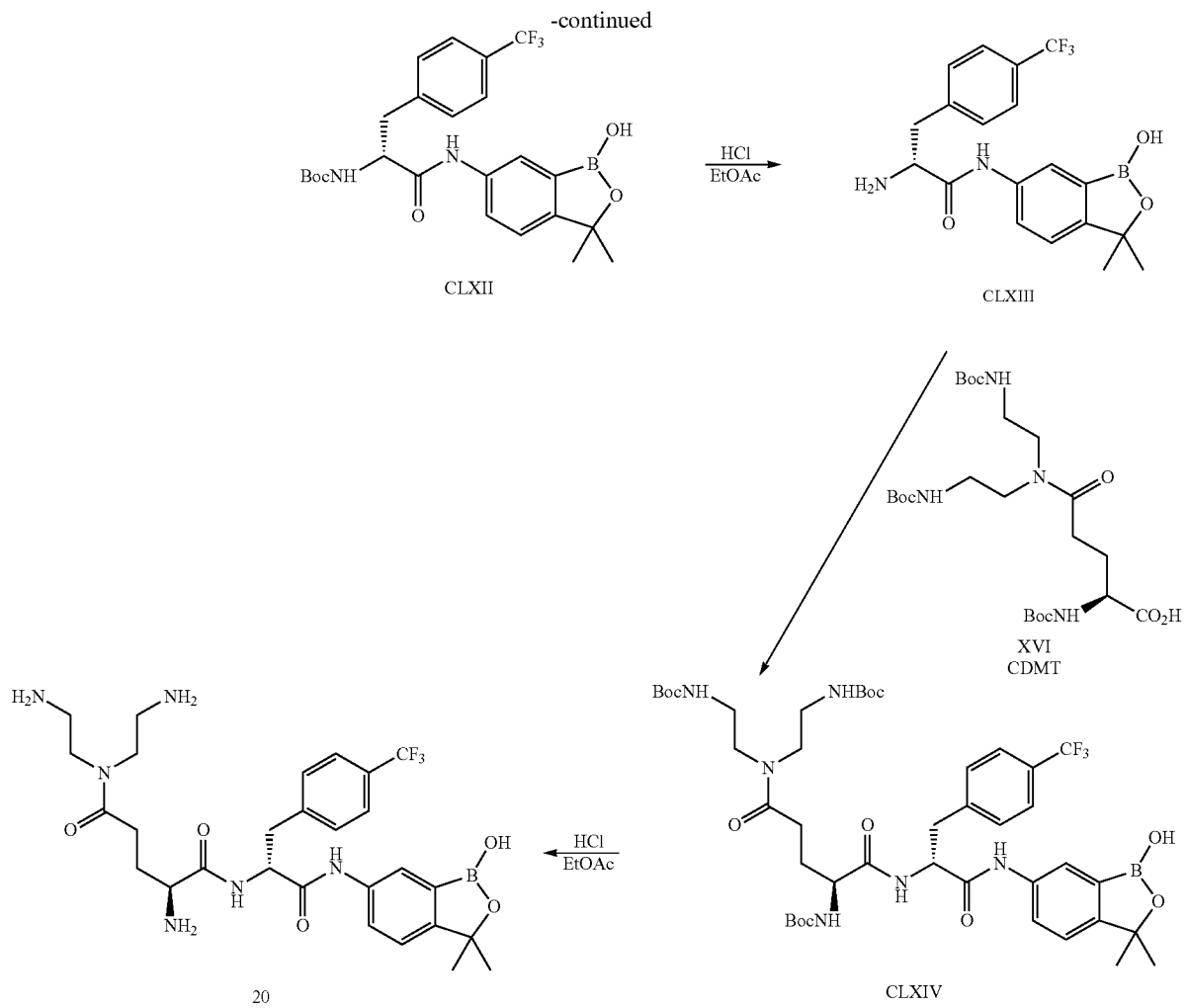

Example 1

Step 1

To a solution of (R)-2-(tert-butoxycarbonylamino)-3-(4-(trifluoromethyl)phenyl)propanoic acid (LXVI) (1.17 g, 3.5 mmol) and 6-amino-3,3-dimethylbenzo[c][1,2]oxaborol-1(3H)-ol (XCVIII) (0.62 g, 3.5 mmol) in DCM (35 mL) were added DIPEA (1 mL, 5.3 mmol) and HATU (1.4 g, 3.7 mmol). The mixture was stirred overnight at room temperature. The reaction mixture was diluted with DCM and washed sequentially with 1 M aqueous HCl, 1 M aqueous NaOH, and brine, and was dried over $MgSO_4$. The solvent was evaporated and the crude product was purified by flash chromatography using on a first column (DCM/MeOH 500/1→300/1→200/1→100/1), and on a second column (hexane/EtOAc 5/1→4/1→3/1), to give 1.00 g of pure (R)-tert-butyl 1-(1-hydroxy-3,3-dimethyl-1,3-dihydrobenzo[c][1,2]oxaborol-6-ylamino)-1-oxo-3-(4-(trifluoromethyl)phenyl)propan-2-ylcarbamate (CLXII) as an off-white solid (1.0 g, 2.03 mmol, 60% yield). $^1$H NMR ($CDCl_3$) δ ppm 1.40 (s, 9H), 1.50 (s, 6H), 3.13 (dd, J=13 Hz, J=14 Hz, 1H), 3.27 (dd, J=13 Hz, J=13 Hz, 1H), 4.48-4.60 (brs, 1H), 5.13-5.26 (brs, 1H), 7.17 (d, J=8 Hz, 1H), 7.26 (d, J=2 Hz, 1H), 7.36 (d, J=5 Hz, 2H), 7.55 (d, J=5 Hz, 2H), 7.58 (d, J=8 Hz, 1H), 8.11-8.16 (brs, 1H); $^{19}$F NMR ($CDCl_3$) δ ppm −61.88 (s, 3F); ESIMS found for $C_{24}H_{28}BF_3N_2O_5$ m/z 493.6 (M+H).

Step 2

(R)-tert-butyl 1-(1-hydroxy-3,3-dimethyl-1,3-dihydrobenzo[c][1,2]oxaborol-6-ylamino)-1-oxo-3-(4-(trifluoromethyl)phenyl)propan-2-ylcarbamate (CLXII) (1.00 g, 2.1 mmol) was treated with HCl/EtOAc (4.2 M, 15 mL) and was stirred for 30 minutes at room temperature. The solvent was removed under vacuum, and the residue was triturated with hexane to give the hydrochloride salt of (R)-2-amino-N-(1-hydroxy-3,3-dimethyl-1,3-dihydrobenzo[c][1,2]oxaborol-6-yl)-3-(4-(trifluoromethyl)phenyl)propanamide (CLXIII) as a white solid (0.86 g, 2.01 mmol, 94% yield). $^1$H NMR (DMSO-$d_6$) δ ppm 1.39 (s, 6H), 3.19 (dd, J=13 Hz, J=13 Hz, 1H), 3.29-3.32 (m, 1H), 4.33-4.40 (m, 1H), 7.34 (d, J=8 Hz, 1H), 7.55 (d, J=7 Hz, 2H), 7.60 (d, J=8 Hz, 1H), 7.66 (d, J=7 Hz, 2H), 7.86 (s, 1H), 8.45 (brs, 3H), 9.1 (s, 1H), 11.03 (s, 1H); $^{19}$F NMR (DMSO-$d_6$) δ ppm −60.25 (s, 3F). ESIMS found for $C_{19}H_{20}BF_3N_2O_3$ m/z 393.4 (M+H).

Step 3

To a solution of the hydrochloride salt of (R)-2-amino-N-(1-hydroxy-3,3-dimethyl-1,3-dihydrobenzo[c][1,2]oxaborol-6-yl)-3-(4-(trifluoromethyl)phenyl)propanamide (CLXIII) (0.86 g, 2.0 mmol) and (S)-5-(bis(2-tert-butoxycarbonylamino)ethyl)amino)-2-(tert-butoxycarbonylamino)-5-oxopentanoic acid (XVI) (1.06 g, 2.0 mmol) in DCM (20 mL) were added DIPEA (0.87 mL, 5 mmol) and HATU (0.8 g, 2.1 mol). The mixture was stirred overnight at room temperature. The solution was diluted with DCM and washed sequentially with 1 M aqueous HCl, 1 M aqueous NaOH, and brine, and was dried over MgSO$_4$. The solvent was evaporated and the crude product was purified by flash chromatography using DCM/MeOH 500/1→300/1→200/1→100/1 to give of pure product CLXIV as a white foam (1.18 g, 1.3 mmol, 65% yield). ESIMS found for C$_{43}$H$_{62}$BF$_3$N$_6$O$_{11}$ m/z 907.9 (M+H).

Step 4

Compound CLXIV (1.18 g, 1.3 mmol) was treated with HCl/EtOAc (4.2 M, 10 mL) and stirred for 30 minutes at room temperature. The solvent was removed under vacuum and the residue was triturated with Et$_2$O to give the hydrochloride salt of (S)-2-amino-N5,N5-bis(2-aminoethyl)-N1-((R)-1-(1-hydroxy-3,3-dimethyl-1,3-dihydro benzo[c][1,2]oxaborol-6-ylamino)-1-oxo-3-(4-(trifluoromethyl)phenyl)propan-2-yl) pentanediamide 20 as a white solid (0.84 g, mmol, 90% yield). $^1$H NMR (DMSO-d$_6$) δ ppm 1.42 (s, 6H), 1.70-1.79 (m, 1H), 1.81-1.89 (m, 1H), 2.90-2.98 (m, 2H), 3.00-3.10 (m, 3H), 3.28 (d, J=3 Hz, 1H), 3.45-3.64 (m, 6H), 3.93 (brs, 1H), 4.87-4.94 (m, 1H), 7.34 (d, J=9 Hz, 1H), 7.60 (d, J=8 Hz, 2H), 7.64 (d, 8 Hz, 2H), 7.66 (d, J=9 Hz, 1H), 7.93 (s, 1H), 8.14 (brs, 3H), 8.35 (brs, 3H), 8.45 (brs, 3H), 9.16 (d, J=8 Hz, 1H), 10.53 (s, 1H); $^{19}$F NMR (DMSO-d$_6$) δ ppm −60.04 (s, 3F); ESIMS found for C$_{28}$H$_{38}$BF$_3$N$_6$O$_5$ m/z 607.6 (M+H).

The following compounds are prepared in accordance with the procedure described in the above Scheme 28 and Example 1.

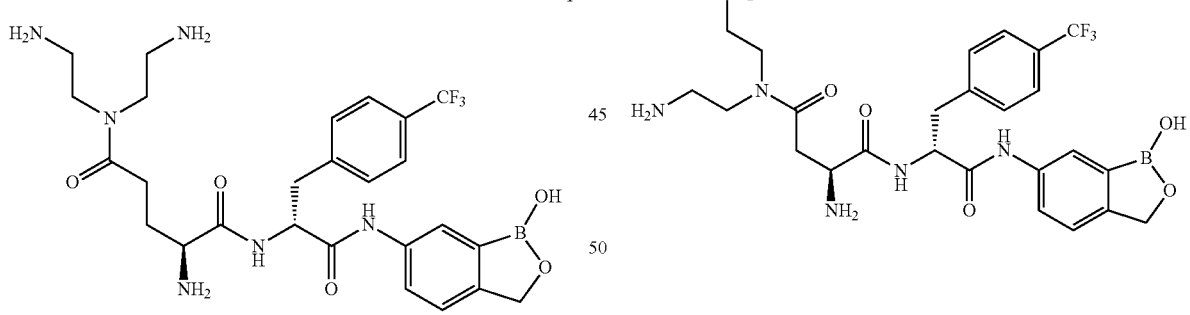

(S)-2-amino-N5,N5-bis(2-aminoethyl)-N1-((R)-1-(1-hydroxy-1,3-dihydrobenzo[c][1,2]oxaborol-6-ylamino)-1-oxo-3-(4-(trifluoromethyl)phenyl)propan-2-yl)pentanediamide 1

The final compound was isolated as the hydrochloride salt. $^1$H NMR (DMSO-d$_6$) δ ppm 1.65-1.73 (m, 1H), 1.78-1.88 (m, 1H), 2.86-2.94 (m, 2H), 2.96-3.04 (m, 2H), 3.40-3.50 (m, 1H), 3.52-3.61 (m, 4H), 3.88-3.92 (m, 1H) 4.86 (td, J=14 Hz, J=2 Hz, 1H), 4.90 (s, 2H), 7.30 (d, J=8 Hz, 1H), 7.55 (d, J=8 Hz, 2H), 7.61 (d, J=8 Hz, 2H), 7.65 (dd, J=8 Hz, J=2 Hz, 1H), 7.99 (d, J=2 Hz, 1H), 8.07 (brs, 3H), 8.29 (brs, 3H), 8.38 (brs, 3H), 9.19 (d, J=8 Hz, 1H), 10.50 (s, 1H); $^{19}$F NMR (DMSO-d$_6$) δ ppm −60.06 (s, 3F); ESIMS found for C$_{26}$H$_{34}$BF$_3$N$_6$O$_5$ m/z 579.8 (M+H).

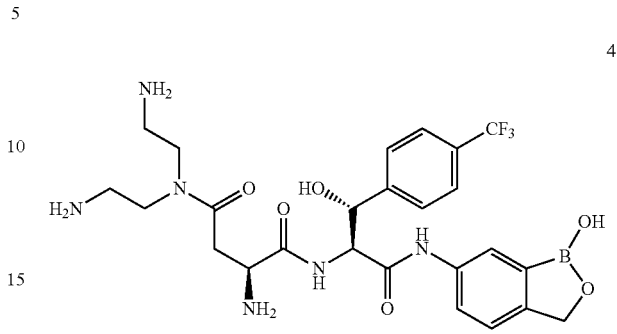

(S)-2-amino-N4,N4-bis(2-aminoethyl)-N1-((1R,2S)-1-hydroxy-3-(1-hydroxy-1,3-dihydrobenzo[c][1,2]oxaborol-6-ylamino)-3-oxo-1-(4-(trifluoromethyl)phenyl)propan-2-yl)succinamide 4

The final compound was isolated as the hydrochloride salt. $^1$H NMR (DMSO-d$_6$) δ ppm 2.91-3.00 (m, 2H), 3.00-3.12 (m, 3H), 3.12-3.21 (m, 1H), 3.54-3.67 (m, 6H), 4.23 (brs, 1H), 4.71-4.78 (m, 1H), 4.90 (s, 2H), 5.33 (brs, 1H), 7.31 (d, J=8 Hz, 1H), 7.64 (d, J=8 Hz, 3H), 7.75 (d, J=8 Hz, 2H), 8.01 (s, 1H), 8.10 (brs, 3H), 8.24 (brs, 3H), 8.33 (brs, 3H), 8.72 (d, J=8 Hz, 1H), 10.46 (s, 1H); $^{19}$F NMR (DMSO-d$_6$) δ ppm −60.08 (s, 3F); ESIMS found for C$_{25}$H$_{32}$BF$_3$N$_6$O$_6$ m/z 581.7 (M+H).

(S)-2-amino-N4,N4-bis(2-aminoethyl)-N1-((R)-1-(1-hydroxy-1,3-dihydrobenzo[c][1,2]oxaborol-6-ylamino)-1-oxo-3-(4-(trifluoromethyl)phenyl)propan-2-yl)succinamide 5

The final compound was isolated as the hydrochloride salt. $^1$H NMR (DMSO-d$_6$) δ ppm 2.90-2.98 (m, 3H), 3.00-3.12 (m, 4H), 3.15-3.21 (m, 1H), 3.48-3.54 (m, 2H), 3.54-3.62 (m, 2H), 4.18 (brs, 1H), 4.70-4.77 (m, 1H), 4.90 (s, 2H), 7.31 (d, J=8 Hz, 1H), 7.53 (d, J=8 Hz, 2H), 7.60-7.63 (m, 1H), 7.64 (d, J=8 Hz, 2H), 7.97 (s, 1H), 8.08 (brs, 3H), 8.21 (brs, 3H), 8.38 (brs, 3H), 9.04 (d, J=8 Hz, 1H), 9.22 (brs, 1H), 10.40 (s, 1H); $^{19}$F NMR (DMSO-d$_6$) δ ppm −59.98 (s, 3F); ESIMS found for C$_{25}$H$_{32}$BF$_3$N$_6$O$_5$ m/z 565.6 (M+H).

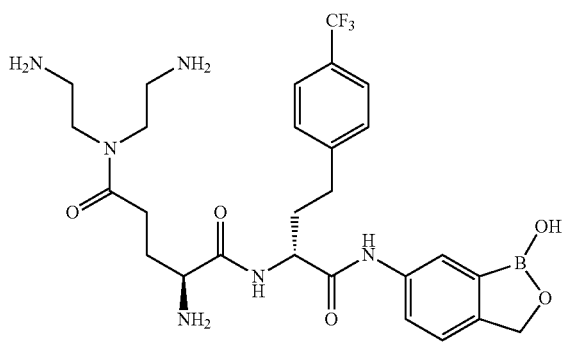

(S)-2-amino-N5,N5-bis(2-aminoethyl)-N1-((R)-1-(1-hydroxy-1,3-dihydrobenzo[c][1,2]oxaborol-6-ylamino)-1-oxo-4-(4-(trifluoromethyl)phenyl)butan-2-yl)pentanediamide 6

The final compound was isolated as the hydrochloride salt. $^1$H NMR (DMSO-$d_6$) δ ppm 1.99-2.12 (m, 4H), 2.56-2.86 (m, 4H), 2.88-2.96 (m, 2H), 2.99-3.06 (m, 2H), 3.45-3.65 (m, 4H), 3.98-4.05 (m, 1H), 4.44-4.50 (m, 1H), 4.90 (s, 2H), 7.30 (d, J=8 Hz, 1H), 7.45 (d, J=8 Hz, 2H), 7.61 (d, J=8 Hz, 2H), 7.65 (d, J=8 Hz, 1H), 7.98 (brs, 3H), 8.32 (brs, 3H), 8.38 (brs, 3H), 9.15 (d, J=8 Hz, 2H), 9.20 (s, 1H), 10.27 (s, 1H); $^{19}$F NMR (DMSO-$d_6$) δ ppm −60.07 (s, 3F); ESIMS found for $C_{27}H_{36}BF_3N_6O_5$ m/z 593.9 (M+H).

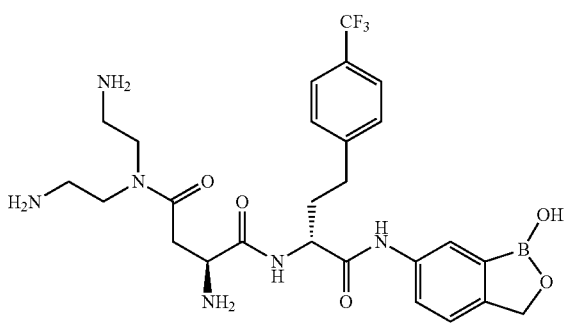

(S)-2-amino-N4,N4-bis(2-aminoethyl)-N1-((R)-1-(1-hydroxy-1,3-dihydrobenzo[c][1,2]oxaborol-6-ylamino)-1-oxo-4-(4-(trifluoromethyl)phenyl)butan-2-yl)succinamide 7

The final compound of was isolated as the hydrochloride salt. $^1$H NMR (DMSO-$d_6$) δ ppm 1.92-2.16 (m, 2H), 2.60-2.85 (m, 2H), 2.90-2.99 (m, 2H), 3.04-3.12 (m, 2H), 3.13-3.18 (m, 1H), 3.19-3.28 (m, 1H), 3.46-3.60 (m, 2H), 3.62-3.72 (m, 2H), 4.22-4.31 (m, 1H), 4.36-4.47 (m, 1H), 4.89 (brs, 2H), 7.27-7.33 (m, 1H), 7.46 (d, J=8 Hz, 2H), 7.61 (d, J=8 Hz, 2H), 7.63-7.67 (m, 1H), 7.96-8.01 (m, 1H), 8.12 (brs, 3H), 8.31 (brs, 3H), 8.38 (brs, 3H), 9.06 (d, J=8 Hz, 1H), 9.20 (brs, 1H), 10.24 (s, 1H); $^{19}$F NMR (DMSO-$d_6$) δ ppm −60.035 (s, 3F); ESIMS found for $C_{26}H_{34}BF_3N_6O_5$ m/z 579.7 (M+H).

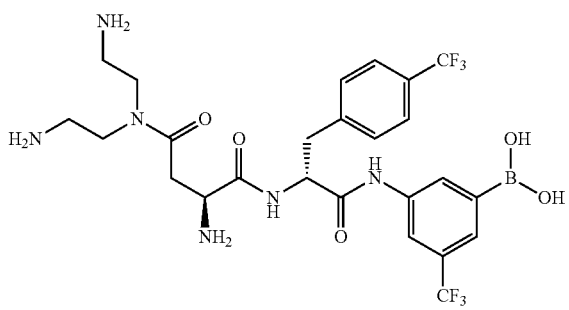

3-((R)-2-((S)-2-amino-4-(bis(2-aminoethyl)amino)-4-oxobutanamido)-3-(4-(trifluoromethyl)phenyl)propanamido)-5-(trifluoromethyl)phenylboronic acid 10

The final compound was isolated as the hydrochloride salt. $^1$H NMR (DMSO-$d_6$) δ ppm 2.89-3.31 (m, 8H), 3.41-3.71 (m, 5H), 4.23 (brs, 1H), 4.63-4.79 (m, 1H), 7.59 (d, J=8 Hz, 2H), 7.65 (d, J=8 Hz, 2H), 7.83 (s, 1H), 8.11 (brs, 6H), 8.25 (brs, 3H), 8.43 (brs, 3H), 9.11 (d, J=8 Hz, 1H), 10.69 (s, 1H); $^{19}$F NMR (DMSO-$d_6$) δ ppm −60.54 (s, 3F), −60.05 (s, 3F); ESIMS found for $C_{25}H_{31}BF_6N_6O_5$ m/z 621.9 (M+H).

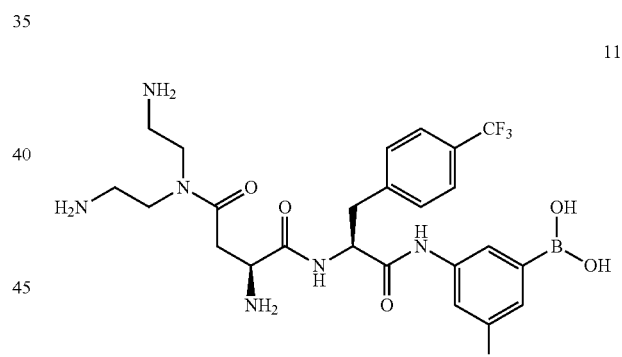

3-((S)-2-((S)-2-amino-4-(bis(2-aminoethyl)amino)-4-oxobutanamido)-3-(4-(trifluoromethyl)phenyl)propanamido)-5-(trifluoromethyl)phenylboronic acid 11

The final compound was isolated as the hydrochloride salt. $^1$H NMR (MeOD-$d_4$) δ ppm 3.12-3.22 (m, 4H), 3.23-3.36 (m, 6H), 3.74 (brs, 4H), 4.34 (brs, 1H), 7.57 (s, 4H), 7.70 (brs, 1H), 7.91 (brs, 1H), 7.99 (s, 1H); $^{19}$F NMR (MeOD-$d_4$) δ ppm [−63.35 (s, 3F), −63.48 (s, 3F)]; ESIMS found for $C_{25}H_{31}BF_6N_6O_5$ m/z 621.7 (M+H).

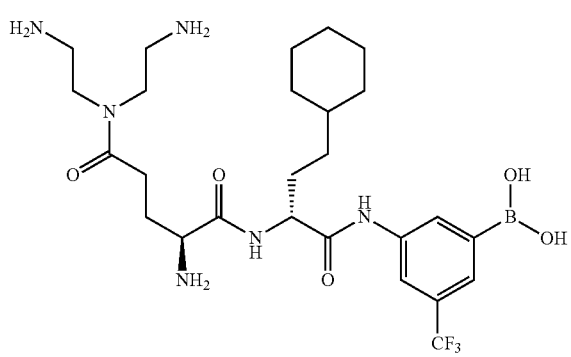

3-((R)-2-((S)-2-amino-5-(bis(2-aminoethyl)amino)-5-oxopentanamido)-4-cyclohexylbutanamido)-5-(trifluoromethyl)phenylboronic acid 12

The final compound was isolated as the hydrochloride salt. $^1$H NMR (DMSO-d$_6$) δ ppm 0.74-0.85 (m, 2H), 1.06-1.26 (m, 6H), 1.52-1.70 (m, 6H), 1.71-1.82 (m, 1H), 1.89-2.06 (m, 2H), 2.50-2.61 (m, 1H), 2.62-2.72 (m, 1H), 2.85-2.95 (m, 2H), 2.96-3.06 (m, 2H), 3.42-3.49 (m, 1H), 3.50-3.64 (m, 3H), 3.88-3.96 (m, 1H), 4.33-4.42 (m, 1H), 7.80 (s, 1H), 7.99 (brs, 3H), 8.08 (s, 1H), 8.18 (s, 1H), 8.32 (brs, 6H), 8.89 (d, J=8 Hz, 1H), 10.49 (s, 1H); $^{19}$F NMR (DMSO-d$_6$) δ ppm −60.52 (s, 3F); ESIMS found for C$_{26}$H$_{42}$BF$_3$N$_6$O$_5$ m/z 587.9 (M+H).

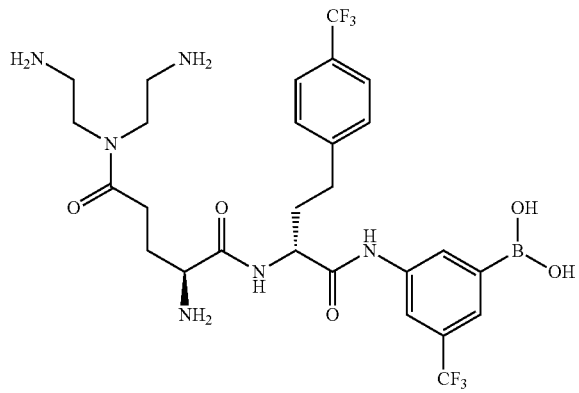

3-((R)-2-((S)-2-amino-5-(bis(2-aminoethyl)amino)-5-oxopentanamido)-4-(4-(trifluoromethyl)phenyl)butanamido)-5-(trifluoromethyl)phenylboronic acid 13

The final compound was isolated as the hydrochloride salt. $^1$H NMR (MeOD-d$_4$) δ ppm 2.11-2.22 (m, 2H), 2.23-2.28 (m, 1H), 2.29-2.39 (m, 1H), 2.78-2.99 (m, 4H), 3.14-3.22 (m, 3H), 3.23-3.28 (m, 3H), 3.65-3.83 (m, 5H), 4.20 (brs, 1H), 4.53-4.57 (m, 1H), 7.47 (d, J=8 Hz, 2H), 7.56 (d, J=8 Hz, 2H), 8.01 (brs, 1H), 8.11 (s, 1H); $^{19}$F NMR (MeOD-d$_4$) δ ppm [−63.23 (s, 3F), −63.56 (s, 3F)]; ESIMS found for C$_{27}$H$_{35}$BF$_6$N$_6$O$_5$ m/z 649.9 (M+H).

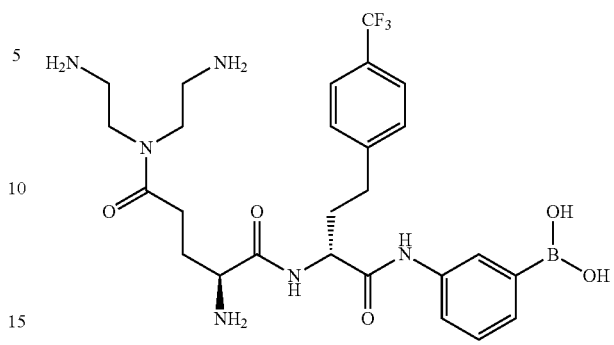

3-((R)-2-((S)-2-amino-5-(bis(2-aminoethyl)amino)-5-oxopentanamido)-4-(4-(trifluoromethyl)phenyl)butanamido)phenylboronic acid 14

The final compound was isolated as the hydrochloride salt. $^1$H NMR (DMSO-d$_6$) δ ppm 1.98-2.11 (m, 4H), 2.58-2.84 (m, 4H), 2.91 (brs, 2H), 3.01 (brs, 2H), 3.46-3.72 (m, 4H), 4.00 (brs, 1H), 4.44 (brs, 1H), 7.22 (t, J=8 Hz, 1H), 7.45 (d, J=8 Hz, 2H), 7.61 (d, J=8 Hz, 2H), 7.68 (d, J=9 Hz, 1H), 7.88 (s, 1H), 8.01 (brs, 3H), 8.32 (brs, 9H), 9.17 (d, J=8 Hz, 1H), 10.15 (s, 1H); $^{19}$F NMR (DMSO-d$_6$) δ ppm −60.06 (s, 3F); ESIMS found for C$_{26}$H$_{36}$BF$_3$N$_6$O$_5$ m/z 579.9 (M−H).

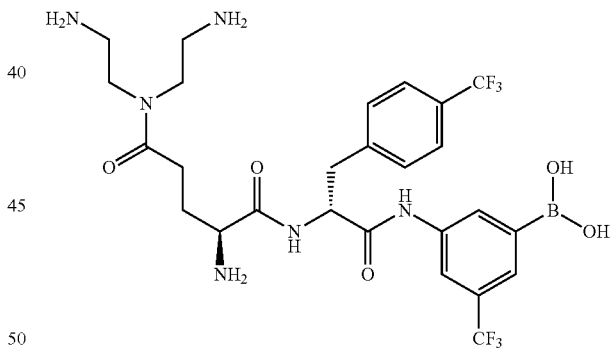

3-((R)-2-((S)-2-amino-5-(bis(2-aminoethyl)amino)-5-oxopentanamido)-3-(4-(trifluoromethyl)phenyl)propanamido)-5-(trifluoromethyl)phenylboronic acid 15

The final compound was isolated as the hydrochloride salt. $^1$H NMR (DMSO-d$_6$) δ ppm 1.64-1.94 (m, 2H), 2.3-2.59 (m, 2H), 2.87-3.14 (m, 4H), 3.19-3.68 (m, 6H), 3.92 (brs, 1H), 4.82 (brs, 1H), 7.59 (d, J=9 Hz, 2H), 7.65 (d, J=9 Hz, 2H), 7.84 (s, 1H), 7.99-8.2 (m, 5H), 8.35 (brs, 6H), 9.15 (d, J=9 Hz, 1H), 10.74 (s, 1H); $^{19}$F NMR (DMSO-d$_6$) δ ppm −60.54 (s, 3F), −60.11 (s, 3F); ESIMS found for C$_{26}$H$_{33}$BF$_6$N$_6$O$_5$ m/z 635.8 (M+H).

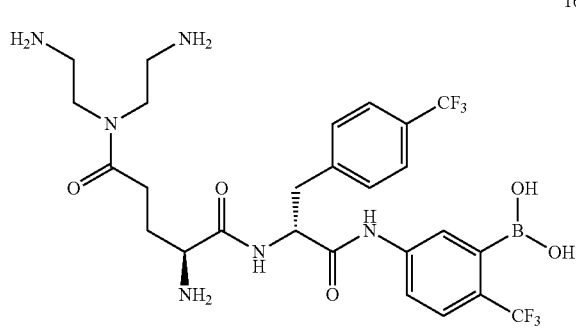

5-((R)-2-((S)-2-amino-5-(bis(2-aminoethyl)amino)-5-oxopentanamido)-3-(4-(trifluoromethyl)phenyl)propanamido)-2-(trifluoromethyl)phenylboronic acid 16

The final compound was isolated as the hydrochloride salt. $^1$H NMR (DMSO-d$_6$) δ ppm 1.77-1.95 (m, 2H), 2.49-2.60 (m, 2H), 3.09-3.30 (m, 6H), 3.49-3.68 (brs, 4H), 3.93-3.96 (m, 1H), 4.82-4.86 (m, 1H), 7.51-7.56 (m, 3H), 7.59 (d, J=8 Hz, 2H), 7.73 (s, 1H), 7.77 (d, J=8 Hz, 1H), 7.88-8.35 (brs, 9H), 8.95-9.03 (m, 1H), 10.42 (s, 1H); $^{19}$F NMR (DMSO-d$_6$) δ ppm −57.04 (s, 3F), −60.07 (s, 3F); ESIMS found for C$_{26}$H$_{33}$BF$_6$N$_6$O$_5$ m/z 633.7 (M−H).

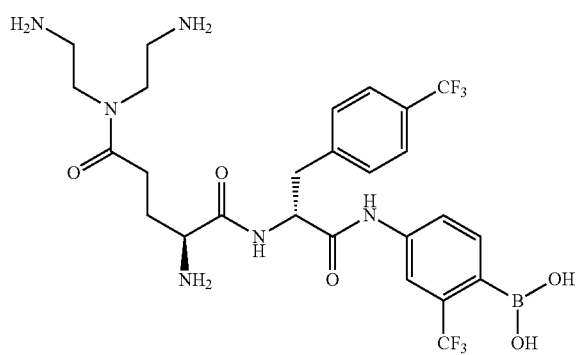

4-((R)-2-((S)-2-amino-5-(bis(2-aminoethyl)amino)-5-oxopentanamido)-3-(4-(trifluoromethyl)phenyl)propanamido)-2-(trifluoromethyl)phenylboronic acid 17

The final compound was isolated as the hydrochloride salt. $^1$H NMR (DMSO-d$_6$) δ ppm 1.65-1.75 (m, 1H), 1.76-1.85 (m, 1H), 2.89-2.96 (brs, 2H), 2.96-3.05 (m, 2H), 3.24-3.29 (m, 1H), 3.34-3.38 (m, 3H), 3.41-3.49 (m, 1H), 3.49-3.58 (m, 3H), 3.86-3.92 (m, 1H), 4.79-4.85 (m, 1H), 7.46 (d, J=8 Hz, 1H), 7.56 (d, J=8 Hz, 2H), 7.61 (d, J=8 Hz, 2H), 7.77 (d, J=8 Hz, 1H), 7.98 (s, 1H), 7.99-8.06 (brs, 3H), 8.25-8.31 (brs, 3H), 8.32-8.38 (brs, 3H), 9.13 (d, J=8 Hz, 1H), 10.80 (s, 1H); $^{19}$F NMR (DMSO-d$_6$) δ ppm −57.94 (s, 3F), −60.09 (s, 3F); ESIMS found for C$_{26}$H$_{33}$BF$_6$N$_6$O$_5$ m/z 633.8 (M−H).

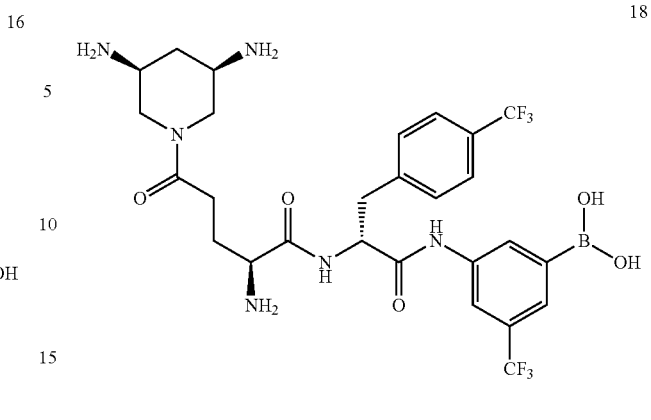

3-((R)-2-((S)-2-amino-5-((3R,5S)-3,5-diaminopiperidin-1-yl)-5-oxopentanamido)-3-(4-(trifluoromethyl)phenyl)propanamido)-5-(trifluoromethyl)phenylboronic acid 18

The final compound was isolated as the hydrochloride salt. $^1$H NMR (DMSO-d$_6$) δ ppm 1.70-1.88 (m, 2H), 2.86-3.15 (m, 2H), 3.21-3.35 (m, 8H), [3.84 (s, 1$^{st}$ rotamer), 3.91 (s, 2$^{nd}$ rotamer), 1H], [4.07 (d, J=12 Hz, 1$^{st}$ rotamer), 4.15 (d, J=12 Hz, 2$^{nd}$ rotamer), 1H], 4.67 (d, J=12 Hz, 1H), 4.81-4.91 (m, 1H), 7.58-7.68 (m, 4H), 7.85 (s, 1H), [8.15 (d, J=8 Hz, 1$^{st}$ rotamer), 8.18 (d, J=8 Hz, 2$^{nd}$ rotamer), 2H], 8.29 (brs, 3H), 8.38 (brs, 2H), 8.55 (brs, 3H), 8.66 (brs, 3H), [9.12 (d, J=8 Hz, 1$^{st}$ rotamer), 9.16 (d, J=8 Hz, 2$^{nd}$ rotamer), 1H], [10.79 (s, 1$^{st}$ rotamer), 10.87 (s, 2$^{nd}$ rotamer), 1H]; $^{19}$F NMR (DMSO-d$_6$) δ ppm [−60.13 (1$^{st}$ rotamer, s), −60.18 (2$^{nd}$ rotamer s), 3F], −60.54 (s, 3F); ESIMS found for C$_{27}$H$_{33}$BF$_6$N$_6$O$_5$ m/z 647.9 (M+H).

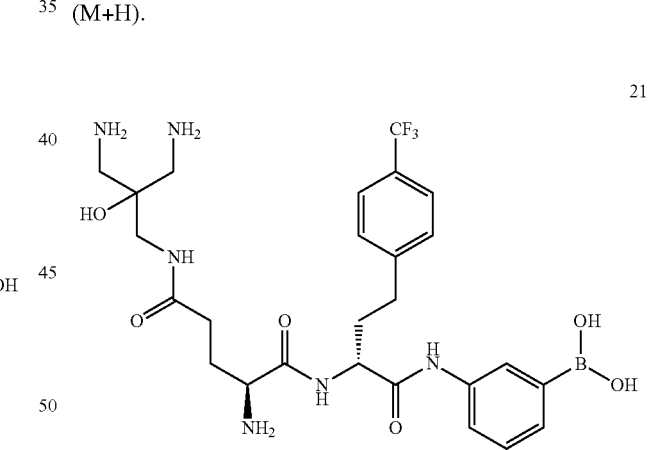

3-((R)-2-((S)-2-amino-5-(3-amino-2-(aminomethyl)-2-hydroxypropylamino)-5-oxopentanamido)-4-(4-(trifluoromethyl)phenyl)butanamido)-5-(trifluoromethyl)phenylboronic acid 21

The final compound was isolated as the hydrochloride salt. $^1$H NMR (DMSO-d$_6$) δ ppm 2.01-2.18 (m, 2H), 2.34-2.41 (m, 2H), 2.69-2.87 (m, 2H), 2.88-2.95 (m, 4H), 3.22-3.31 (m, 2H), 3.32-3.44 (m, 2H), 3.93-4.01 (m, 1H), 4.42-4.51 (m, 1H), 6.18 (s, 1H), 7.48 (d, J=8 Hz, 1H), 7.63 (d, J=8 Hz, 1H), 7.83 (s, 1H), 8.13 (s, 1H), 8.16-8.28 (m, 8H), 8.33-8.45 (m, 3H), 8.79 (t, J=6 Hz, 1H), 9.21 (d, J=8 Hz, 1H), 10.61 (s, 1H); $^{19}$F NMR (DMSO-d$_6$) δ ppm −60.53 (s, 3F), −60.09 (s, 3F); ESIMS found for $C_{27}H_{35}BF_6N_6O_6$ m/z 666.0 (M+H).

2H), 7.57-7.69 (brs, 3H), 7.91-7.98 (brs, 1H), 7.99-8.05 (brs, 3H), 8.29-8.48 (brs, 6H), 9.13-9.18 (brs, 1H), 9.89 (s, 1H); $^{19}$F NMR (DMSO-d$_6$) δ ppm −60.06 (s, 3F), −119.72 (s, 1F); ESIMS found for $C_{26}H_{35}BF_4N_6O_5$ m/z 599.9 (M+H).

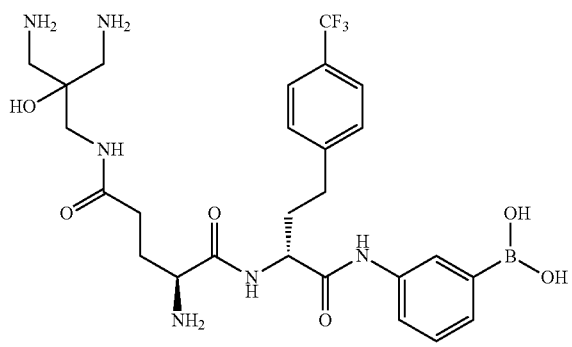

3-((R)-2-((S)-2-amino-5-(3-amino-2-(aminomethyl)-2-hydroxypropylamino)-5-oxopentanamido)-4-(4-(trifluoromethyl)phenyl)butanamido) phenylboronic acid 22

The final compound was isolated as the hydrochloride salt. $^1$H NMR (DMSO-d$_6$) δ ppm 1.94-2.15 (m, 4H), 2.33-2.41 (m, 2H), 2.66-2.85 (m, 2H), 2.92 (brs, 4H), 3.22-3.32 (m, 2H), 3.93-4.01 (m, 1H), 4.45-4.53 (m, 1H), 6.18 (s, 1H), 7.25 (t, J=8 Hz, 1H), 7.44-7.52 (m, 3H), 7.64 (d, J=8 Hz, 2H), 7.71 (d, J=8 Hz, 1H), 7.88 (s, 1H), 8.22 (brs, 6H), 8.41 (brs, 3H), 8.79 (t, J=6 Hz, 1H), 9.16 (d, J=8 Hz, 1H), 10.2 (s, 1H); $^{19}$F NMR (DMSO-d$_6$) δ ppm −60.05 (s, 3F); ESIMS found for $C_{26}H_{36}BF_3N_6O_6$ m/z 597.9 (M+H).

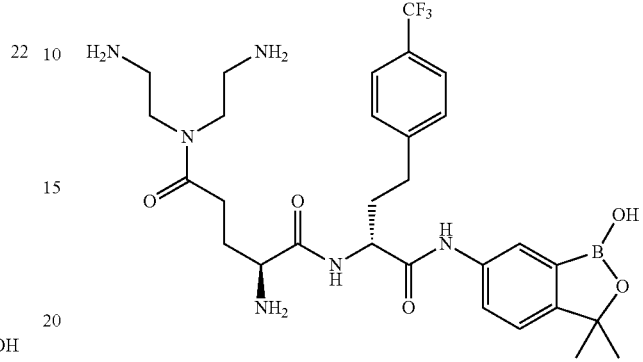

(S)-2-amino-N5,N5-bis(2-aminoethyl)-N1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)pentanediamide 26

The final compound was isolated as the hydrochloride salt. $^1$H NMR (DMSO-d$_6$) δ ppm 1.38 (s, 6H), 1.98-2.14 (m, 4H), 2.58-2.83 (m, 4H), 2.91 (brs, 2H), 3.04 (brs, 2H), 3.37-3.68 (m, 4H), 3.96-4.05 (m, 1H), 4.44-4.51 (m, 1H), 5.72 (s, 1H), 7.3 (d, J=8 Hz, 1H), 7.45 (d, J=8 Hz, 2H), 7.58-7.65 (m, 3H), 7.88 (s, 1H), 8.07 (brs, 3H), 8.42 (brs, 6H), 9.18 (d, J=8 Hz, 1H), 10.28 (s, 1H); $^{19}$F NMR (DMSO-d$_6$) δ ppm −60.07 (s, 3F); ESIMS found for $C_{29}H_{40}BF_3N_6O_5$ m/z 622.0 (M+H).

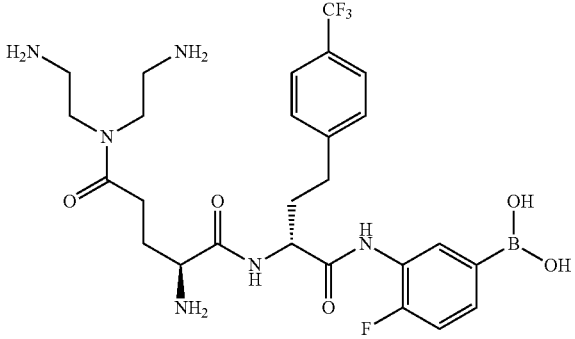

3-((R)-2-((S)-2-amino-5-(bis(2-aminoethyl)amino)-5-oxopentanamido)-4-(4-(trifluoromethyl)phenyl)butanamido)-4-fluorophenylboronic acid 25

The final compound was isolated as the hydrochloride salt. $^1$H NMR (DMSO-d$_6$) δ ppm 1.95-2.12 (m, 4H), 2.56-2.67 (m, 2H), 2.68-2.77 (m, 2H), 2.78-2.85 (m, 1H), 2.88-2.96 (brs, 2H), 2.97-2.07 (brs, 2H), 3.43-3.67 (m, 4H), 3.94-4.05 (brs, 1H), 4.48-4.58 (brs, 1H), 7.14-7.21 (brs, 1H), 7.46 (d, J=7 Hz,

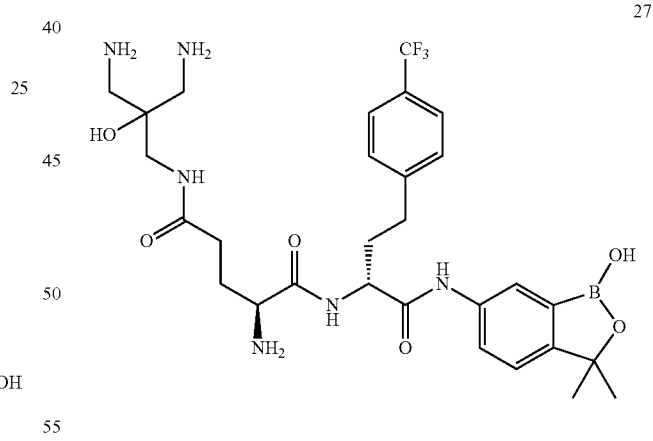

(S)-2-amino-N5-(3-amino-2-(aminomethyl)-2-hydroxypropyl)-N1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl) pentanediamide 27

The final compound was isolated as the hydrochloride salt. $^1$H NMR (DMSO-d$_6$) δ ppm 1.38 (s, 6H), 1.94-2.14 (m, 4H), 2.35 (brs, 2H), 2.66-2.82 (m, 2H), 2.89 (brs, 4H), 3.26 (brs, 2H), 3.96 (brs, 1H), 4.45-4.53 (m, 1H), 6.18 (s, 1H), 7.31 (d, J=8 Hz, 1H), 7.45 (d, J=8 Hz, 2H), 7.61 (d, J=8 Hz, 2H), 7.63-7.67 (m, 1H), 7.89 (s, 1H), 8.23 (brs, 6H), 8.42 (brs, 3H), 8.76-8.82 (m, 1H), 9.19 (d, J=8 Hz, 1H), 10.32 (s, 1H); $^{19}$F NMR (DMSO-d$_6$) δ ppm −60.05 (s, 3F); ESIMS found for C$_{29}$H$_{40}$BF$_3$N$_6$O$_6$ m/z 638.0 (M+H).

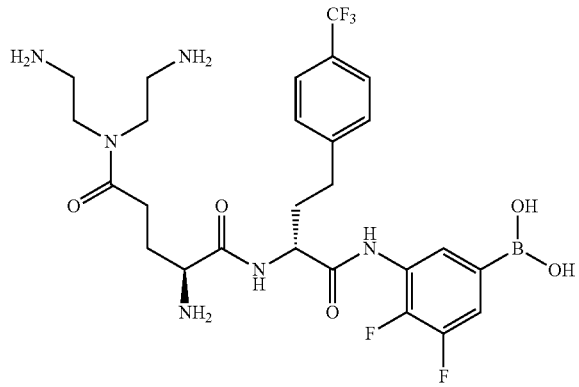

3-((R)-2-((S)-2-amino-5-(bis(2-aminoethyl)amino)-5-oxopentanamido)-4-(4-(trifluoromethyl)phenyl)butanamido)-4,5-difluorophenylboronic acid 28

The final compound was isolated as the hydrochloride salt. $^1$H NMR (DMSO-d$_6$) δ ppm 1.95-2.13 (m, 4H), 2.61 (brs, 1H), 2.66-2.86 (m, 3H), 2.91 (brs, 2H), 3.01 (brs, 2H), 3.42-3.67 (m, 4H), 4.00 (brs, 1H), 4.50 (brs, 1H), 7.46 (d, J=8 Hz, 2H), 7.54 (t, 8 Hz, 1H), 7.63 (d, J=8 Hz, 2H), 7.76 (d, J=8 Hz, 1H), 8.04 (brs, 3H), 8.27 (s, 2H), 8.37 (brs, 3H), 8.42 (brs, 3H), 9.20 (d, J=8 Hz, 1H), 10.12 (s, 1H); $^{19}$F NMR (DMSO-d$_6$) δ ppm −60.06 (s, 3F), −139.10 (d, J=22 Hz, 1F), −143.50 (d, J=22 Hz, 1F); ESIMS found for C$_{26}$H$_{34}$BF$_5$N$_6$O$_5$ m/z 617.6 (M+H).

29

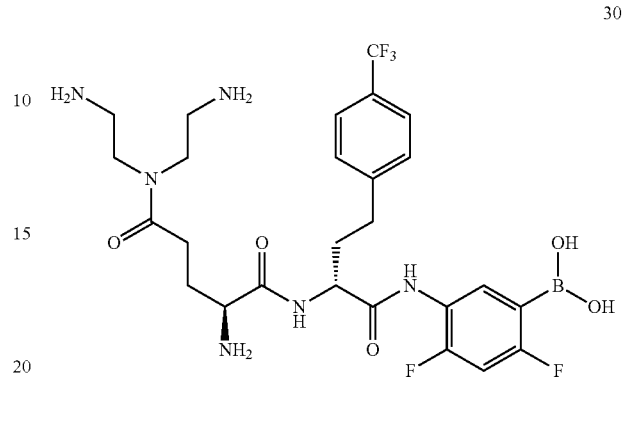

5-((R)-2-((S)-2-amino-5-(bis(2-aminoethyl)amino)-5-oxopentanamido)-4-(4-(trifluoromethyl)phenyl)butanamido)-2,4-difluorophenylboronic acid 30

The final compound was isolated as the hydrochloride salt. $^1$H NMR (MeOD-d$_4$) δ ppm 2.14-2.35 (m, 4H), 2.8-2.95 (m, 4H), 3.18 (t, J=5 Hz, 2H), 3.22-3.27 (m, 2H), 3.66-3.8 (m, 4H), 4.14-4.18 (m, 1H), 4.57-4.62 (m, 1H), 6.97-7.03 (m, 1H), 7.45 (d, J=8 Hz, 2H), 7.57 (d, J=8 Hz, 2H), 7.67-7.76 (m, 1H); $^{19}$F NMR (MeOD-d$_4$) δ ppm −118.64 (s, 1F), −105.09 (s, 1F), −63.22 (s, 3F); ESIMS found for C$_{26}$H$_{34}$BF$_5$N$_6$O$_5$ m/z 617.9 (M+H).

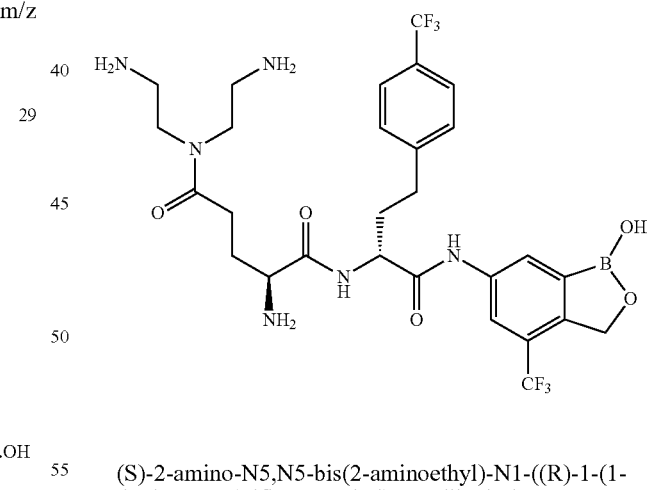

(S)-2-amino-N5,N5-bis(2-aminoethyl)-N1-((R)-1-(1-hydroxy-4-(trifluoromethyl)-1,3-dihydrobenzo[c][1,2]oxaborol-6-ylamino)-1-oxo-4-(4-(trifluoromethyl)phenyl)butan-2-yl)pentanediamide 31

4-((R)-2-((S)-2-amino-5-(bis(2-aminoethyl)amino)-5-oxopentanamido)-4-(4-(trifluoromethyl)phenyl)butanamido)-2-fluorophenylboronic acid 29

The final compound was isolated as the hydrochloride salt. $^1$H NMR (DMSO-d$_6$) δ ppm 1.92-2.14 (m, 4H), 2.56-2.81 (m, 6H), 3.44-3.70 (m, 6H), 3.93-4.02 (m, 1H), 4.39-4.48 (m, 1H), 7.34 (d, J=8 Hz, 1H), 7.44 (d, J=8 Hz, 2H), 7.48 (brs, 1H), 7.51 (brs, 1H), 7.60 (d, J=8 Hz, 2H), 8.01 (brs, 2H), 8.26 (brs, 9H), 9.17 (d, J=7 Hz, 1H), 10.57 (s, 1H); $^{19}$F NMR (DMSO-d$_6$) δ ppm −60.06 (s, 3F), −101.95 (s, 1F); ESIMS found for C$_{26}$H$_{35}$BF$_4$N$_6$O$_5$ m/z 599.6 (M+H).

The final compound was isolated as the hydrochloride salt. $^1$H NMR (DMSO-d$_6$) δ ppm 2.13 (brs, 6H), 2.65-2.74 (m, 2H), 2.74-2.83 (m, 4H), 3.64 (brs, 4H), 4.06-4.11 (m, 1H), 4.5 (brs, 1H), 5.05 (s, 2H), 7.46 (d, J=8 Hz, 2H), 7.57 (d, J=8 Hz, 2H), 8.14 (s, 1H), 8.28 (s, 1H), 8.32 (brs, 9H), 9.08-9.12 (m, 1H), 10.47 (s, 1H); $^{19}$F NMR (DMSO-d$_6$) δ ppm −60.06 (s, 3F), −60.1 (s, 3F); ESIMS found for C$_{28}$H$_{35}$BF$_6$N$_6$O$_5$ m/z 661.9 (M+H).

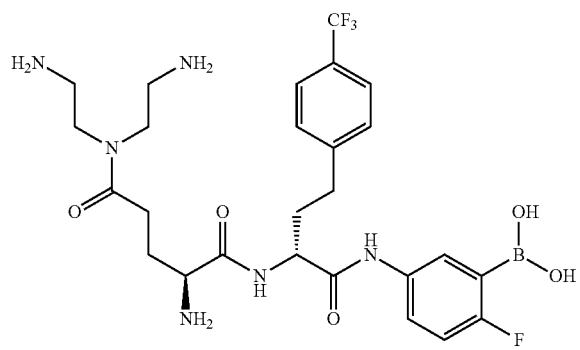

5-((R)-2-((S)-2-amino-5-(bis(2-aminoethyl)amino)-5-oxopentanamido)-4-(4-(trifluoromethyl)phenyl)butanamido)-2-fluorophenylboronic acid 32

The final compound was isolated as the hydrochloride salt. $^1$H NMR (DMSO-d$_6$) δ ppm 1.94-2.12 (m, 4H), 2.57-2.84 (m, 4H), 2.92 (brs, 2H), 3.02 (brs, 2H), 3.45-3.67 (m, 4H), 3.99 (brs, 1H), 4.41 (td, J=8 Hz, J=5 Hz, 1H), 6.96-7.02 (m, 1H), 7.44 (d, J=8 Hz, 2H), 7.61 (d, J=8 Hz, 2H), 7.65-7.71 (m, 2H), 8.04 (brs, 3H), 8.17 (s, 2H), 8.39 (brs, 6H), 9.15 (d, J=8 Hz, 1H), 10.23 (s, 1H); $^{19}$F NMR (DMSO-d$_6$) δ ppm −109.81 (s, 1F), −60.06 (s, 3F); ESIMS found for C$_{26}$H$_{35}$BF$_4$N$_6$O$_6$ m/z 599.6 (M+H).

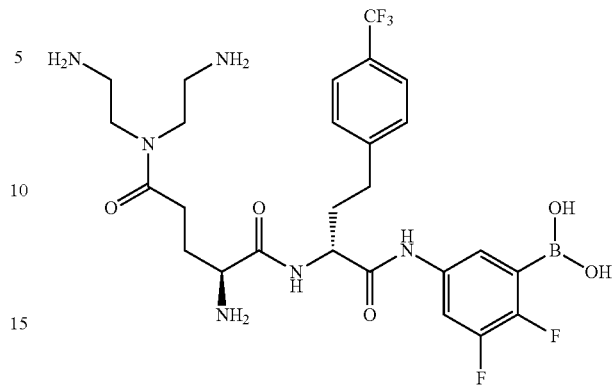

5-((R)-2-((S)-2-amino-5-(bis(2-aminoethyl)amino)-5-oxopentanamido)-4-(4-(trifluoromethyl)phenyl)butanamido)-2,3-difluorophenylboronic acid 34

The final compound was isolated as the hydrochloride salt. $^1$H NMR (DMSO-d$_6$) δ ppm 1.94-2.13 (m, 4H), 2.56-2.65 (m, 1H), 2.67-2.74 (m, 2H), 2.75-2.84 (m, 1H), 2.86-2.94 (m, 2H), 2.96-3.05 (m, 2H), 3.48-3.56 (m, 2H), 3.57-3.67 (m, 2H), 3.95-4.01 (m, 1H), 4.36-4.44 (m, 1H), 7.45 (d, J=8 Hz, 3H), 7.60 (d, J=8 Hz, 2H), 7.77-7.84 (m, 1H), 8.33 (brs, 6H), 8.39 (brs, 3H), 9.19 (d, J=8 Hz, 1H), 10.53 (s, 1H); $^{19}$F NMR (DMSO-d$_6$) δ ppm −60.6 (s, 3F), −136.5 (d, J=24 Hz, 1F), −137.7 (d, J=24 Hz, 1F); ESIMS found for C$_{26}$H$_{34}$BF$_5$N$_6$O$_5$ m/z 617.6 (M+H).

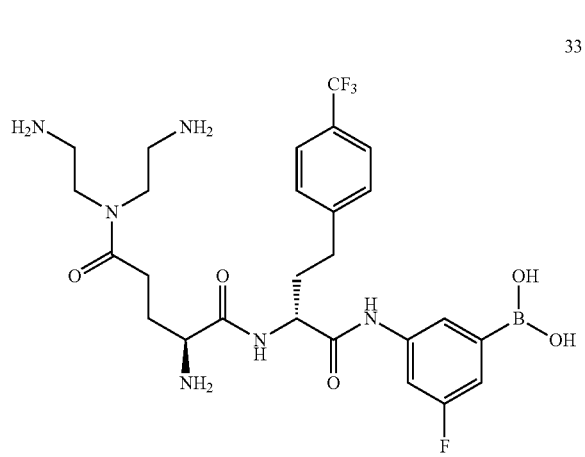 [SMILES: NCCN(CCN)C(=O)CC[C@H](N)C(=O)N[C@H](CCc1ccc(C(F)(F)F)cc1)C(=O)Nc1cc(F)c(F)c(B(O)O)c1]

3-((R)-2-((S)-2-amino-5-(bis(2-aminoethyl)amino)-5-oxopentanamido)-4-(4-(trifluoromethyl)phenyl)butanamido)-5-fluorophenylboronic acid 33

The final compound was isolated as the hydrochloride salt. $^1$H NMR (DMSO-d$_6$) δ ppm 2.05-2.2 (m, 4H), 2.66-2.9 (m, 6H), 3.65 (brs, 6H), 4.08-4.1 (m, 1H), 4.47 (brs, 1H), 7.16-7.19 (m, 1H), 7.46 (d, 2H, J=8 Hz), 7.57 (d, 2H, J=8 Hz), 7.6-7.64 (m, 1H), 7.72 (brs, 1H), 8.36 (brs, 9H), 9.07 (brs, 1H), 10.14 (s, 1H); $^{19}$F NMR (DMSO-d$_6$) δ ppm −60.06 (s, 3F), −113.09 (s, 1F); ESIMS found for C$_{26}$H$_{35}$BF$_4$N$_6$O$_5$ m/z 599.8 (M+H).

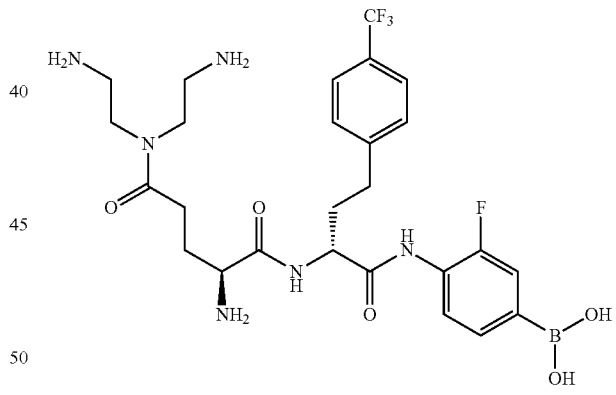

4-((R)-2-((S)-2-amino-5-(bis(2-aminoethyl)amino)-5-oxopentanamido)-4-(4-(trifluoromethyl)phenyl)butanamido)-3-fluorophenylboronic acid 35

The final compound of was isolated as the hydrochloride salt. $^1$H NMR (DMSO-d$_6$) δ ppm 1.95-2.14 (m, 4H), 2.30-2.41 (m, 2H), 2.65-2.85 (m, 2H), 2.91 (brs, 2H), 3.02 (brs, 2H), 3.93-4.02 (m, 1H), 4.16-4.25 (, m, 1H), 4.46-4.53 (m, 1H), 7.28-7.32 (m, 1H), 7.45 (d, J=7.56 Hz, 2H), 7.60 (d, J=8.24 Hz, 2H), 7.61-7.65 (m, 1H), 7.87-7.90 (m, 1H), 8.27 (brs, 6H), 8.35 (d, J=8.24 Hz, 1H), 8.41 (brs 3H), 9.04 (brs, 1H), 9.20 (d, J=8.24 Hz, 1H), 10.32 (s, 1H); $^{19}$F NMR (DMSO-d$_6$) δ ppm −60.05; ESIMS found for C$_{28}$H$_{38}$BF$_3$N$_6$O$_5$ m/z 607.8 (M+H).

36

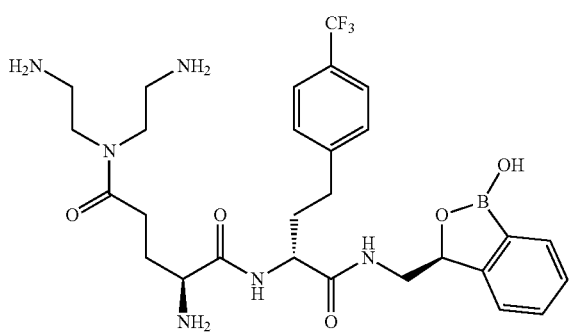

(S)-2-amino-N5,N5-bis(2-aminoethyl)-N1-((R)-1-(((R)-1-hydroxy-1,3-dihydrobenzo[c][1,2]oxaborol-3-yl)methylamino)-1-oxo-4-(4-(trifluoromethyl)phenyl)butan-2-yl)pentanediamide 36

The final compound was isolated as the hydrochloride salt. $^1$H NMR (DMSO-d$_6$) δ ppm 1.79-2.07 (m, 4H), 2.53-2.75 (m, 4H), 2.90 (brs, 2H), 3.00 (brs, 2H), 3.14-3.22 (m, 2H), 3.40-3.49 (m, 4H), 3.97 (brs, 1H), 4.26 (brs, 1H), 5.19 (brs, 1H), 7.31 (brs, 1H), 7.42 (brs, 4H), 7.62 (d, J=8 Hz, 2H), 7.71 (d, J=7 Hz, 1H), 8.05 (brs, 3H), 8.38 (brs, 4H), 8.44 (brs, 3H), 9.03 (d, J=7 Hz, 1H); $^{19}$F NMR (DMSO-d$_6$) δ ppm −60.02 (s, 3F); ESIMS found for C$_{28}$H$_{38}$BF$_3$N$_6$O$_5$ m/z 607.6 (M+H).

37

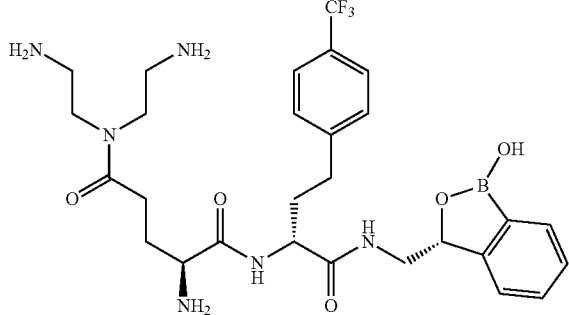

(S)-2-amino-N5,N5-bis(2-aminoethyl)-N1-((R)-1-(((R)-1-hydroxy-1,3-dihydrobenzo[c][1,2]oxaborol-3-yl)methylamino)-1-oxo-4-(4-(trifluoromethyl)phenyl)butan-2-yl)pentanediamide 37

The final compound was isolated as the hydrochloride salt. $^1$H NMR (DMSO-d$_6$) δ ppm 1.87 (brs, 3H), 1.99-2.17 (m, 2H), 2.53-2.65 (m, 2H), 2.66-2.70 (m, 1H), 2.71-2.81 (m, 1H), 3.29-3.39 (m, 2H), 3.44-3.52 (m, 2H), 3.63 (brs, 4H), 3.97-4.06 (m, 2H), 4.24-4.33 (m, 1H), 5.20 (brs, 1H), 7.25 (brs, 1H), 7.33-7.44 (m, 4H), 7.58 (d, J=8 Hz, 2H), 7.69 (d, J=7 Hz, 1H), 8.06 (s, 1H), 8.35 (brs, 9H), 8.77 (d, J=7 Hz, 1H); $^{19}$F NMR (DMSO-d$_6$) δ ppm −60.02 (s, 3F); ESIMS found for C$_{28}$H$_{38}$BF$_3$N$_6$O$_5$ m/z 607.6 (M+H).

43

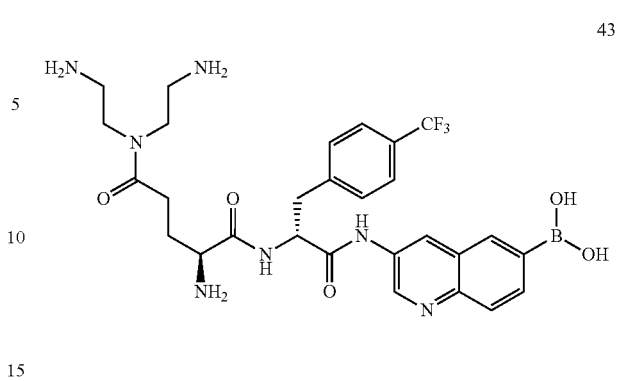

3-((R)-2-((S)-2-amino-5-(bis(2-aminoethyl)amino)-5-oxopentanamido)-3-(4-(trifluoromethyl)phenyl)propanamido)quinolin-6-ylboronic acid 43

The final compound was isolated as the hydrochloride salt. $^1$H NMR (DMSO-d$_6$) δ ppm 1.85-2.03 (m, 2H), 2.52-2.61 (m, 1H), 2.62-2.69 (m, 1H), 3.06 (brs, 4H), 3.22 (dd, J=14 Hz, J=10 Hz, 1H), 3.42 (dd, J=14 Hz, J=5 Hz, 1H), 3.66 (brs, 4H), 4.02-4.08 (m, 1H), 4.94 (td, J=9 Hz, J=6 Hz, 1H), 7.62 (m, 4H), 8.00 (d, J=8 Hz, 1H), 8.09 (d, J=8 Hz, 1H), 8.23 (brs, 10H), 8.78 (d, J=2 Hz, 1H), 9.13 (d, J=8 Hz, 1H), 9.26 (d, J=2 Hz, 1H), 10.92 (s, 1H); $^{19}$F NMR (DMSO-d$_6$) δ ppm −60.06 (s, 3F); ESIMS found for C$_{28}$H$_{35}$BF$_3$N$_7$O$_5$ m/z 619.0 (M+H).

44

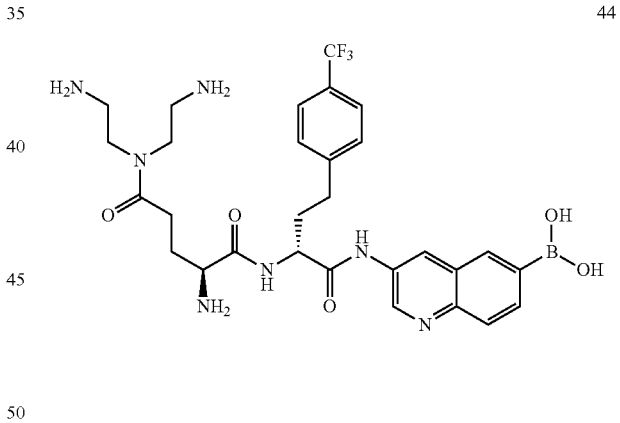

3-((R)-2-((S)-2-amino-5-(bis(2-aminoethyl)amino)-5-oxopentanamido)-4-(4-(trifluoromethyl)phenyl)butanamido)quinolin-6-ylboronic acid 44

The final compound was isolated as the hydrochloride salt. $^1$H NMR (DMSO-d$_6$) δ ppm 2.02-2.14 (m, 3H), 2.15-2.25 (m, 1H), 2.57-2.67 (m, 1H), 2.71-2.83 (m, 2H), 2.84-2.88 (m, 1H), 2.92 (brs, 2H), 3.02 (brs, 2H), 3.44-3.69 (m, 4H), 4.00-4.08 (m, 1H), 4.47-4.54 (m, 1H), 7.48 (d, J=8 Hz, 2H), 7.60 (d, J=8 Hz, 2H), 8.00-8.11 (m, 4H), 8.14 (d, J=8 Hz, 1H), 8.39 (brs, 1H), 8.47-8.55 (m, 6H), 9.01 (s, 1H), 9.33 (d, J=7 Hz, 1H), 9.38 (s, 1H), 11.28 (s, 1H); $^{19}$F NMR (DMSO-d$_6$) δ ppm −60.07 (s, 3F); ESIMS found for C$_{29}$H$_{37}$BF$_3$N$_7$O$_5$ m/z 632.6 (M+H).

45

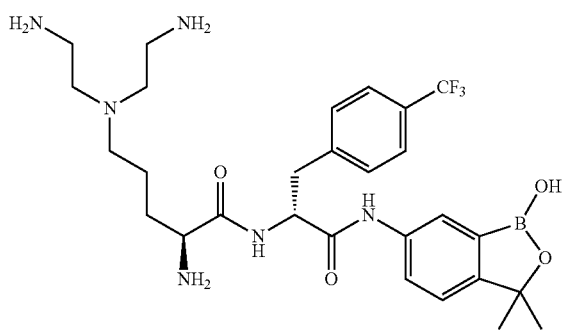

(S)-2-amino-5-(bis(2-aminoethyl)amino)-N-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)pentanamide 45

The final compound was isolated as the hydrochloride salt. $^1$H NMR (DMSO-d$_6$) δ ppm 1.42 (s, 6H), 1.54 (brs, 1H), 1.66 (brs, 1H), 1.83 (brs, 2H), 3.02-3.16 (m, 2H), 3.21-3.61 (m, 10H), 3.90 (brs, 1H), [4.77-4.82 (m, 2$^{nd}$ isomer), 4.86-4.93 (m, 1$^{st}$ isomer), 1H], 7.35 (d, J=8 Hz, 1H), 7.57-7.73 (m, 4H), [7.91 (s, 1$^{st}$ isomer), 7.95 (s, 2$^{nd}$ isomer), 1H], [8.38 (brs, 1$^{st}$ isomer), 8.40 (brs, 2$^{nd}$ isomer), 3H], 8.61 (brs, 6H), [9.17 (d, J=8 Hz, 2$^{nd}$ isomer), 9.22 (d, J=8 Hz, 1$^{st}$ isomer), 1H], [10.51 (s, 1$^{st}$ isomer), 10.62 (s, 2$^{nd}$ isomer), 1H], [11.66 (brs, 2$^{nd}$ isomer), 11.79 (brs, 1$^{st}$ isomer), 1H]; $^{19}$F NMR (DMSO-d$_6$) δ ppm [−59.98 (1$^{st}$ isomer, s), −60.09 (2$^{nd}$ isomer, s)]; ESIMS found for C$_{28}$H$_{40}$BF$_3$N$_6$O$_4$ m/z 593.7 (M+H).

46

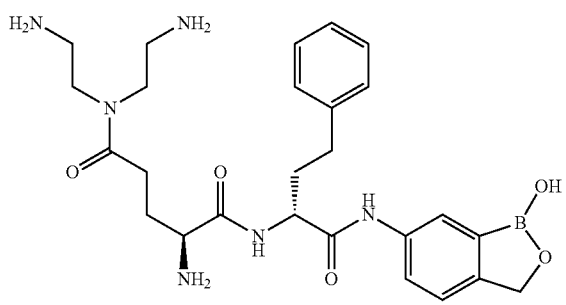

(S)-2-amino-N5,N5-bis(2-aminoethyl)-N1-((R)-1-(1-hydroxy-1,3-dihydrobenzo[c][1,2]oxaborol-6-ylamino)-1-oxo-4-phenylbutan-2-yl)pentanediamide 46

The final compound was isolated as the hydrochloride salt. $^1$H NMR (DMSO-d$_6$) δ ppm 1.44 (s, 6H), 1.97-2.14 (m, 4H), 2.65 (brs, 2H), 2.75 (brs, 2H), 2.97 (brs, 2H), 3.07 (brs, 2H), 3.48-3.68 (m, 4H), 4.04 (brs, 1H), 4.54 (brs, 1H), 7.18-7.26 (m, 3H), 7.28-7.33 (m, 2H), 7.36 (d, J=8 Hz, 1H), 7.67 (d, J=8 Hz, 1H), 7.92 (s, 1H), 8.00 (brs, 2H), 8.36 (brs, 7H), 9.06 (s, 1H), 9.11 (d, J=8 Hz, 1H), 10.25 (s, 1H); ESIMS found for C$_{28}$H$_{41}$BN$_6$O$_5$ m/z 553.6 (M+H).

47

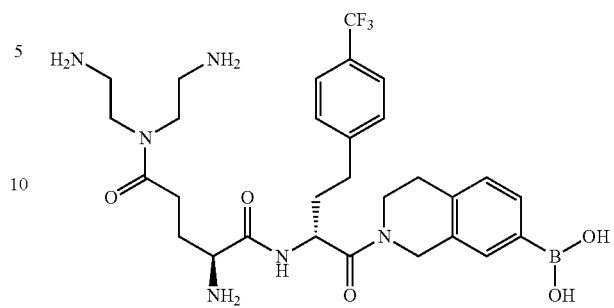

2-((R)-2-((S)-2-amino-5-(bis(2-aminoethyl)amino)-5-oxopentanamido)-4-(4-(trifluoromethyl)phenyl)butanoyl)-1,2,3,4-tetrahydroisoquinolin-7-ylboronic acid 47

The final compound was isolated as the hydrochloride salt. $^1$H NMR (DMSO-d$_6$) δ ppm 1.76-2.11 (m, 4H), 2.52-2.81 (m, 6H), 2.83-2.95 (m, 2H), 3.01 (brs, 2H), 3.43-3.65 (m, 4H), 3.68-3.79 (m, 1H), 3.90 (brs, 1H), 4.40-4.48 (m, 1H), 4.52-4.73 (m, 2H), 4.76-4.87 (m, 1H), 7.10 (d, J=8 Hz, 1H), 7.35 (d, J=8 Hz, 1H), 7.41-7.47 (m, 1H), 7.50-7.68 (m, 4H), 7.93-8.12 (m, 5H), 8.37 (brs, 6H), 9.07 (d, J=8 Hz, 1H); $^{19}$F NMR (DMSO-d$_6$) δ ppm −60.46 (s 3F); ESIMS found for C$_{29}$H$_{40}$BF$_3$N$_6$O$_5$ m/z 621.6 (M+H).

50

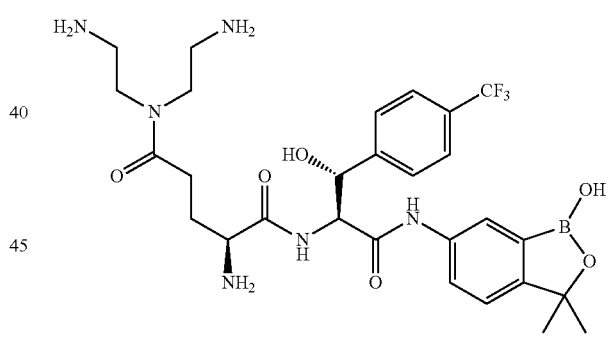

(S)-2-amino-N5,N5-bis(2-aminoethyl)-N1-((1R,2S)-1-hydroxy-3-(1-hydroxy-3,3-dimethyl-1,3-dihydrobenzo[c][1,2]oxaborol-6-ylamino)-3-oxo-1-(4-(trifluoromethyl)phenyl)propan-2-yl)pentanediamide 50

The final compound was isolated as the hydrochloride salt. $^1$H NMR (DMSO-d$_6$) δ ppm 1.41 (s, 6H), 2.01-2.15 (m, 2H), 2.67-2.85 (m, 2H), 3.04 (brs, 4H), 3.65 (brs, 4H), 3.97-4.05 (m, 1H), 4.78 (dd, J=7 Hz, J=5 Hz, 1H), 5.27 (d, J=5 Hz, 1H), 7.24 (d, J=8 Hz, 1H), 7.51 (d, J=8 Hz, 1H), 7.6 (d, J=8 Hz, 2H), 7.73 (d, J=8 Hz, 2H), 7.84 (s, 1H), 8.24 (brs, 9H), 8.65 (d, J=8 Hz, 1H), 10.06 (s, 1H); $^{19}$F NMR (DMSO-d$_6$) δ ppm −60.08 (s, 3F); ESIMS found for C$_{28}$H$_{38}$BF$_3$N$_6$O$_6$ m/z 623.6 (M+H).

51

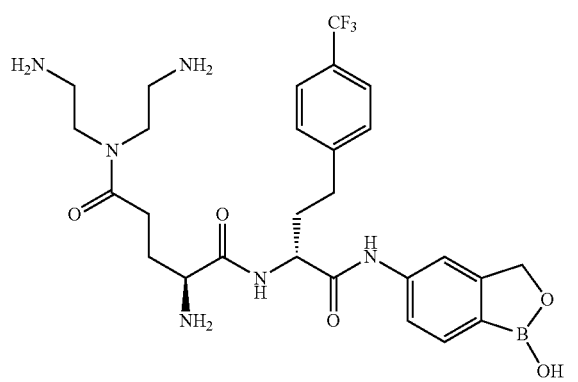

(S)-2-amino-N5,N5-bis(2-aminoethyl)-N1-((R)-1-(1-hydroxy-1,3-dihydrobenzo[c][1,2]oxaborol-5-ylamino)-1-oxo-4-(4-(trifluoromethyl)phenyl)butan-2-yl)pentanediamide 51

The final compound was isolated as the hydrochloride salt. $^1$H NMR (DMSO-$d_6$) δ ppm 2.08-2.26 (m, 4H), 2.7-2.93 (m, 4H), 3.08 (brs, 4H), 3.69 (brs, 4H), 4.08-4.15 (m, 1H), 4.52-4.59 (m, 1H), 4.95 (s, 2H), 7.5 (d, J=8 Hz, 2H), 7.58-7.65 (m, 3H), 7.67 (d, J=8 Hz, 1H), 7.78 (s, 1H), 8.41 (brs, 9H), 9.11 (d, J=7 Hz, 1H), 10.19 (s, 1H); $^{19}$F NMR (DMSO-$d_6$) δ ppm −60.07 (s, 3F); ESIMS found for $C_{27}H_{36}BF_3N_6O_5$ m/z 593.6 (M+H).

53

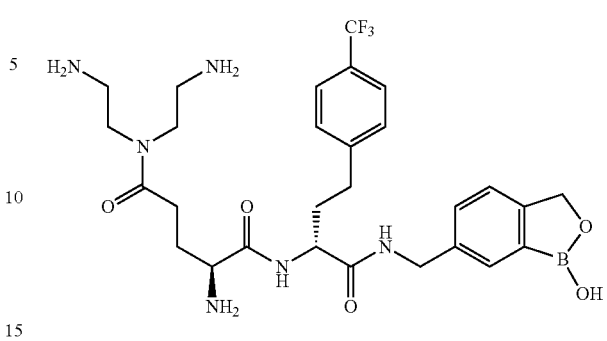

(S)-2-amino-N5,N5-bis(2-aminoethyl)-N1-((R)-1-((1-hydroxy-1,3-dihydrobenzo[c][1,2]oxaborol-6-yl)methylamino)-1-oxo-4-(4-(trifluoromethyl)phenyl)butan-2-yl)pentanediamide 53

The final compound was isolated as the hydrochloride salt. $^1$H NMR (DMSO-$d_6$) δ ppm 2.10-2.16 (brs, 2H), 2.62-2.81 (brs, 6H), 3.16-3.19 (brs, 2H), 3.56-3.70 (brs, 4H), 4.00-4.08 (brs, 2H), 4.26-4.38 (brs, 4H), 4.92 (s, 2H), 7.29 (d, J=8 Hz, 1H), 7.37-7.38 (brs, 2H), 7.40 (d, J=8 Hz, 2H), 7.57 (d, J=8 Hz, 2H), 7.66 (s, 1H), 8.19-8.38 (brs, 6H), 8.39-8.48 (brs, 3H), 8.82-8.87 (brs, 1H); $^{19}$F NMR (DMSO-$d_6$) δ ppm −60.07 (s, 3F); ESIMS found for $C_{28}H_{38}BF_3N_6O_5$ m/z 607.6 (M+H).

52

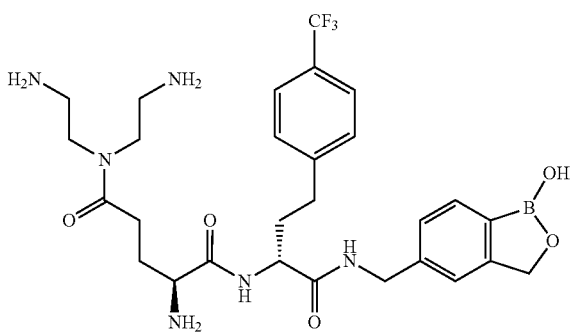

(S)-2-amino-N5,N5-bis(2-aminoethyl)-N1-((R)-1-((1-hydroxy-1,3-dihydrobenzo[c][1,2]oxaborol-5-yl)methylamino)-1-oxo-4-(4-(trifluoromethyl)phenyl)butan-2-yl)pentanediamide 52

The final compound was isolated as the hydrochloride salt. $^1$H NMR (DMSO-$d_6$) δ ppm 1.88-1.97 (m, 1H), 1.98-2.07 (m, 4H), 2.52-2.62 (m, 1H), 2.63-2.68 (m, 1H), 2.69-2.78 (m, 2H), 2.86-2.95 (m, 2H), 2.96-3.06 (m, 2H), 3.43-3.66 (m, 4H), 4.17-4.29 (m, 2H), 4.30-4.38 (m, 1H), 4.90 (s, 2H), 7.21 (d, J=7 Hz, 1H), 7.25 (s, 1H), 7.40 (d, J=8 Hz, 2H), 7.61 (d, J=8 Hz, 2H), 7.62-7.65 (m, 1H), 8.03 (brs, 3H), 8.36 (brs, 3H), 8.48 (brs, 3H), 8.72 (t, J=6 Hz, 1H), 9.09-9.16 (m, 1H); $^{19}$F NMR (DMSO-$d_6$) δ ppm −60.05 (s, 3F); ESIMS found for $C_{28}H_{38}BF_3N_6O_5$ m/z 607.6 (M+H).

56

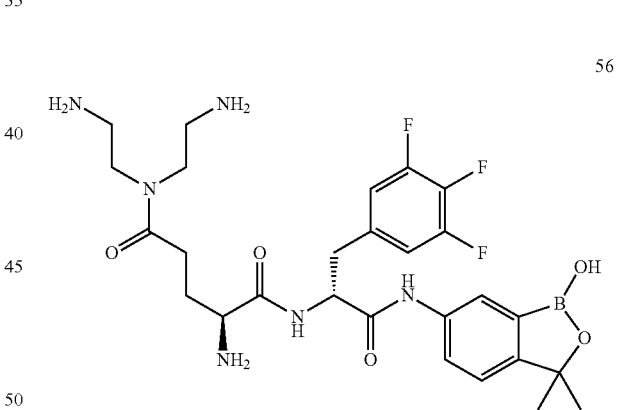

(S)-2-amino-N5,N5-bis(2-aminoethyl)-N1-((R)-1-(1-hydroxy-3,3-dimethyl-1,3-dihydrobenzo[c][1,2]oxaborol-6-ylamino)-1-oxo-3-(3,4,5-trifluorophenyl)propan-2-yl)pentanediamide 56

The final compound was isolated as the hydrochloride salt. $^1$H NMR (DMSO-$d_6$) δ ppm 1.43 (s, 6H), 1.84-1.92 (m, 1H), 1.93-2.01 (m, 1H), 2.55-2.67 (m, 2H), 2.98-3.15 (m, 9H), 3.24 (dd, 1H, J=5 Hz, J=14 Hz), 3.65 (brs, 4H), 3.98-4.03 (m, 1H), 4.84 (brs, 1H), 7.25-7.31 (m, 3H), 7.65 (dd, 1H, J=2 Hz, J=8 Hz), 7.9 (s, 1H), 8.3 (brs, 9H), 9.0 (brs, 1H), 10.14 (s, 1H); $^{19}$F NMR (DMSO-$d_6$) δ ppm −135.3 (d, 2F), −163.8 (t, 1F); ESIMS found for $C_{27}H_{36}BF_3N_6O_5$ m/z 593.7 (M+H).

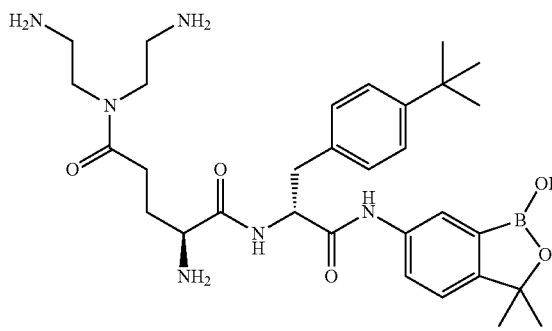

(S)-2-amino-N5,N5-bis(2-aminoethyl)-N1-((R)-3-(4-tert-butylphenyl)-1-(1-hydroxy-3,3-dimethyl-1,3-dihydrobenzo[c][1,2]oxaborol-6-ylamino)-1-oxopropan-2-yl)pentanediamide 57

The final compound was isolated as the hydrochloride salt. $^1$H NMR (DMSO-$d_6$) δ ppm 1.23 (s, 9H), 1.43 (s, 6H), 1.79 (brs, 2H), 2.32-2.72 (m, 2H), 2.88-3.19 (m, 6H), 3.35-3.71 (m, 4H), 3.92 (brs, 1H), 4.83 (brs, 1H), 7.18-7.41 (m, 5H), 7.64 (brs, 1H), 7.92 (s, 1H), 8.16 (brs, 3H), 8.36 (brs, 3H), 8.47 (brs, 3H), 9.09 (brs, 1H), 10.36 (s, 1H); ESIMS found for $C_{31}H_{47}BN_6O_5$ m/z 595.7 (M+H).

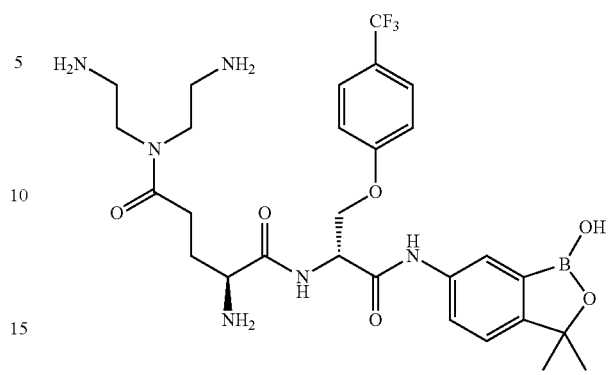

(S)-2-amino-$N^5,N^5$-bis(2-aminoethyl)-$N^1$-((R)-1-(1-hydroxy-3,3-dimethyl-1,3-dihydrobenzo[c][1,2]oxaborol-6-ylamino)-1-oxo-3-(4-(trifluoromethyl)phenoxy)propan-2-yl)pentanediamide 83

The final compound was isolated as the hydrochloride salt. $^1$H NMR (DMSO-$d_6$) δ ppm 1.37 (s, 6H), 2.00 (brd, 2H), 2.54-2.63 (m, 1H), 2.67-2.77 (m, 1H), 2.90 (brd, 2H), 2.97 (brd, 2H), 3.53-3.63 (m, 1H), 3.95-4.05 (m, 1H), 4.49 (s, 2H), 4.98 (d, 1H), 7.13 (d, 2H), 7.31 (d, 1H), 7.64 (dd, 3H), 7.92 (s, 1H), 8.10 (s, 3H), 8.41 (s, 3H), 8.48 (s, 3H), 9.27 (d, 1H), 10.46 (s, 1H); $^{19}$F NMR (DMSO-$d_6$) δ ppm −59.16 (s, 3F); ESIMS found for $C_{28}H_{38}BF_3N_6O_6$ m/z 621.7 (M−H).

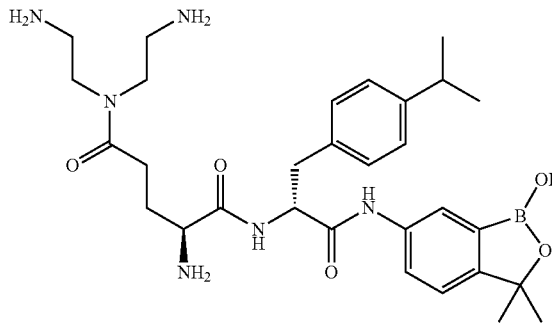

(S)-2-amino-N5,N5-bis(2-aminoethyl)-$N^1$-((R)-1-(1-hydroxy-3,3-dimethyl-1,3-dihydrobenzo[c][1,2]oxaborol-6-ylamino)-3-(4-isopropylphenyl)-1-oxopropan-2-yl)pentanediamide 78

The final compound was isolated as the hydrochloride salt. $^1$H NMR (DMSO-$d_6$) δ ppm 1.08 (d, 6H), 1.40 (s, 6H), 1.70-1.85 (m, 2H), 2.32-2.41 (m, 1H), 2.48-2.59 (m, 1H), 2.86-3.10 (m, 6H), 3.44-3.68 (m, 6H), 4.75-4.84 (q, 1H), 7.10 (d, 2H), 7.22 (d, 2H), 7.31 (d, 1H), 7.61 (d, 1H), 7.88 (s, 1H), 8.09 (brs, 3H), 8.31 (brs, 3H), 8.41 (brs, 3H), 9.04 (d, 1H), 10.32 (d, 1H); ESIMS found for $C_{30}H_{45}BN_6O_5$ m/z 579.6 (M−H).

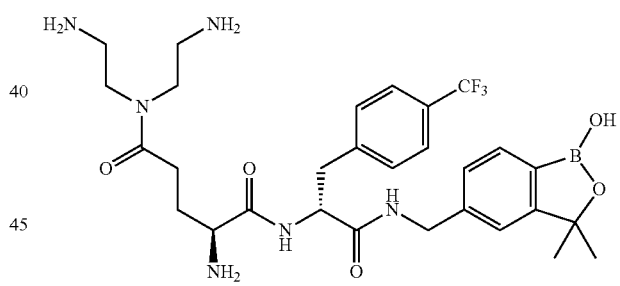

(S)-2-amino-$N^5,N^5$-bis(2-aminoethyl)-$N^1$-((R)-1-((1-hydroxy-3,3-dimethyl-1,3-dihydrobenzo[c][1,2]oxaborol-5-yl)methylamino)-1-oxo-3-(4-(trifluoromethyl)phenyl)propan-2-yl)pentanediamide 90

The final compound was isolated as the hydrochloride salt. $^1$H NMR (D$_2$O) δ ppm 1.50 (s, 3H), 1.52 (s, 3H), 1.97-2.09 (m, 2H), 2.34-2.39 (m, 1H), 2.43-2.48 (m, 1H), 3.07-3.13 (m, 1H), 3.15-3.24 (m, 5H), 3.60-3.66 (m, 3H), 3.68-3.74 (m, 1H), 4.11 (t, J=6 Hz, 1H), 4.21 (d, J=15 Hz, 1H), 4.47 (d, J=15 Hz, 1H), 4.67 (t, J=8 Hz, 1H), 7.06 (d, J=8 Hz, 1H), 7.27 (s, 1H), 7.33 (d, J=8 Hz, 2H), 7.49 (d, J=8 Hz 2H), 7.61 (d, J=8 Hz, 1H); ESIMS found for $C_{29}H_{40}BF_3N_6O_5$ m/z 621.2 (M+H).

93

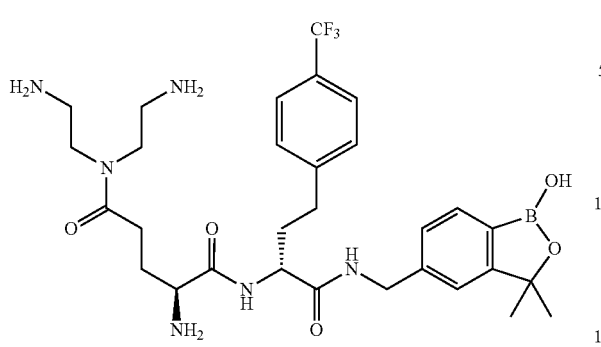

(S)-2-amino-N$^5$,N$^5$-bis(2-aminoethyl)-N$^1$-((R)-1-((1-hydroxy-3,3-dimethyl-1,3-dihydrobenzo[c][1,2]oxaborol-5-yl)methylamino)-1-oxo-4-(4-(trifluoromethyl)phenyl)butan-2-yl)pentanediamide 93

The final compound was isolated as the hydrochloride salt. $^1$H NMR (D$_2$O) δ ppm 1.43 (s, 3H), 1.44 (s, 3H), 2.05-2.12 (m, 2H), 2.12-2.21 (m, 2H), 2.60-2.69 (m, 4H), 3.19 (t, J=6 Hz, 2H), 3.23 (t, J=7 Hz, 2H), 3.65-3.72 (m, 4H), 4.15 (t, J=6.5 Hz, 1H), 4.30 (t, J=7 Hz, 1H), 4.50 (d, J=15 Hz, 1H), 7.25 (d, J=8 Hz, 2H), 7.32 (s, 1H), 7.33 (d, J=7 Hz, 1H), 7.60 (d, J=8 Hz, 2H), 7.68 (d, J=8 Hz, 1H); ESIMS found for C$_{30}$H$_{42}$BF$_3$N$_6$O$_5$ m/z 635.2 (M+H).

95

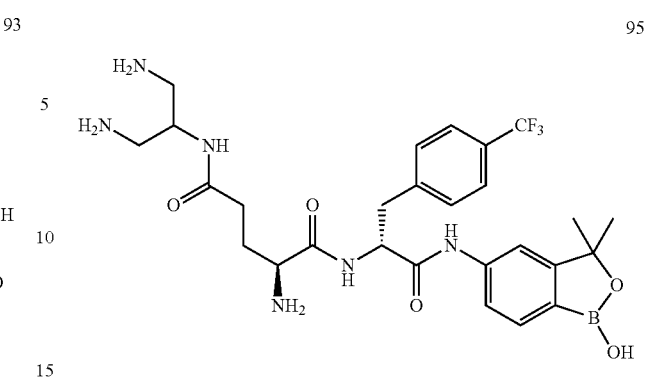

(S)-2-amino-N$^5$-(1,3-diaminopropan-2-yl)-N$^1$-((R)-1-(1-hydroxy-3,3-dimethyl-1,3-dihydrobenzo[c][1,2]oxaborol-5-ylamino)-1-oxo-3-(4-(trifluoromethyl)phenyl)propan-2-yl)pentanediamide 95

The final compound was isolated as the hydrochloride salt. $^1$H NMR (DMSO-d$_6$) δ ppm 1.42 (s, 6H), 2.18-2.34 (m, 2H), 2.91-3.14 (m, 6H), 3.22-3.29 (dd, 1H), 3.91 (brs, 1H), 4.26 (dd, 1H), 4.85 (dd, 1H), 7.52 (dd, 1H), 7.59 (dd, 1H), 7.65 (dd, 1H), 8.24-8.45 (m, 10H), 8.98 (brs, 1H), 9.18 (d, 1H), 10.59 (s, 1H); $^{19}$F NMR (DMSO-d$_6$) δ ppm −60.04 (s, 3F); ESIMS found for C$_{27}$H$_{36}$BF$_3$N$_6$O$_5$ m/z 591.7 (M−H).

94

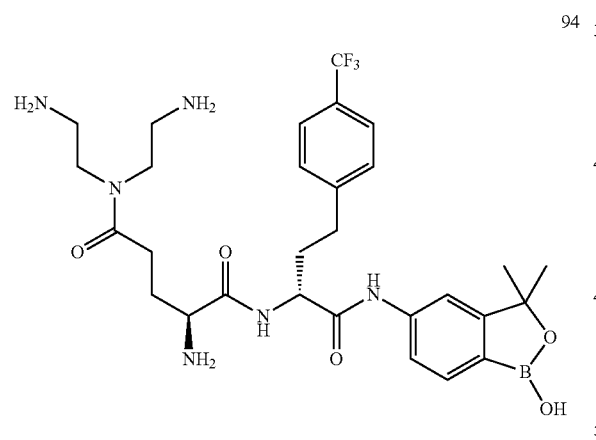

(S)-2-amino-N$^5$,N$^5$-bis(2-aminoethyl)-N$^1$-((R)-1-(1-hydroxy-3,3-dimethyl-1,3-dihydrobenzo[c][1,2]oxaborol-5-ylamino)-1-oxo-4-(4-(trifluoromethyl)phenyl)butan-2-yl)pentanediamide 94

The final compound was isolated as the hydrochloride salt. $^1$H NMR (DMSO-d$_6$) δ ppm 1.39 (s, 6H), 2.00-2.17 (m, 4H), 2.59-2.70 (m, 1H), 2.70-2.282 (m, 2H), 2.82-2.90 (m, 1H), 2.95 (d, 2H), 3.05 (d, 2H), 3.47-3.71 (m, 4H), 4.02 (brs, 1H), 4.46 (q, 1H), 7.48 (d, 2H), 7.51-7.56 (m, 1H), 7.58 (d, 1H), 7.64 (d, 2H), 7.74 (brs, 1H), 7.97-8.16 (m, 3H), 8.32-8.52 (m, 6H), 8.94 (brs, 1H), 9.18 (brs, 1H), 10.42 (brs, 1H); $^{19}$F NMR (DMSO-d$_6$) δ ppm −60.04 (s, 3F); ESIMS found for C$_{29}$H$_{40}$BF$_3$N$_6$O$_5$ m/z 619.7 (M−H).

96

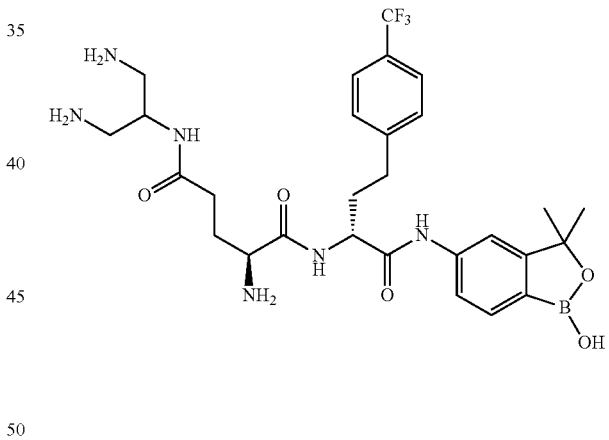

(S)-2-amino-N$^5$-(1,3-diaminopropan-2-yl)-N$^1$-((R)-1-(1-hydroxy-3,3-dimethyl-1,3-dihydrobenzo[c][1,2]oxaborol-5-ylamino)-1-oxo-4-(4-(trifluoromethyl)phenyl)butan-2-yl)pentanediamide 96

The final compound was isolated as the hydrochloride salt. $^1$H NMR (DMSO-d$_6$) δ ppm 1.38 (s, 6H), 1.96-2.15 (m, 5H), 2.29-2.45 (m, 3H), 2.68-2.78 (m, 1H), 2.78-2.97 (m, 4H), 2.98-3.11 (m, 3H), 3.98 (q, 1H), 4.16-4.27 (m, 1H), 4.50 (q, 1H), 7.47 (dd, 2H), 7.53 (dd, 1H), 7.57 (dd, 1H), 7.62 (dd, 2H), 7.73 (s, 1H), 8.17-8.32 (m, 9H), 8.35 (d, 1H), 8.39 (brs 3H), 9.21 (d, 1H), 10.46 (s, 1H); $^{19}$F NMR (DMSO-d$_6$) δ ppm −60.01 (s, 3F); ESIMS found for C$_{28}$H$_{38}$BF$_3$N$_6$O$_5$ m/z 605.6 (M−H).

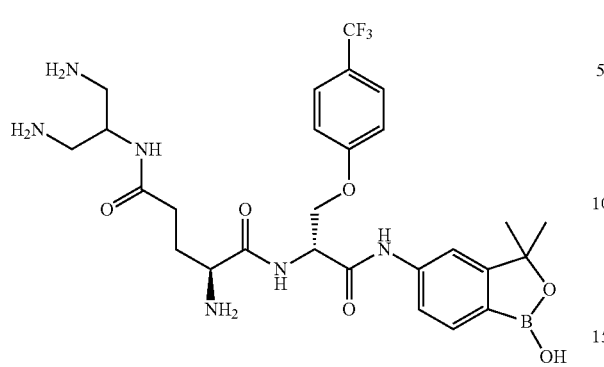

(S)-2-amino-N$^5$-(1,3-diaminopropan-2-yl)-N$^1$-((R)-1-(1-hydroxy-3,3-dimethyl-1,3-dihydrobenzo[c][1,2]oxaborol-5-ylamino)-1-oxo-3-(4-(trifluoromethyl)phenoxy)propan-2-yl)pentanediamide 97

The final compound was isolated as the hydrochloride salt. $^1$H NMR (DMSO-d$_6$) δ ppm 1.38 (s, 6H), 1.95-2.09 (m, 2H), 2.33-2.40 (m, 2H), 2.87-2.96 (m, 2H), 2.96-3.06 (m, 2H), 3.96-4.03 (m, 1H), 4.17-4.25 (m, 2H), 4.36 (dd, 1H), 4.41 (dd, 1H), 4.97 (dd, 1H), 7.18 (dd, 2H), 7.55 (dd, 1H), 7.58 (dd, 1H), 7.62 (dd, 1H), 7.76 (s, 1H), 8.28 (brs, 6H), 8.40 (dd, 1H), 8.45 (brd, 3H), 9.27 (d, 1H), 10.62 (s, 1H); $^{19}$F NMR (DMSO-d$_6$) δ ppm −59.18 (s, 3F); ESIMS found for C$_{27}$H$_{36}$BF$_3$N$_6$O$_6$ m/z 607.7 (M−H).

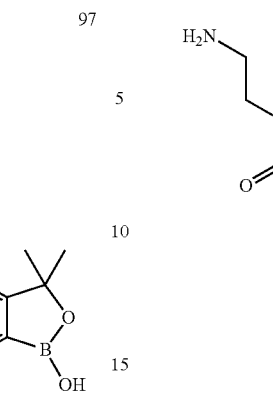

(S)-2-amino-N$^5$,N$^5$-bis(2-aminoethyl)-N$^1$-((R)-1-(1-hydroxy-3,3-dimethyl-1,3-dihydrobenzo[c][1,2]oxaborol-7-ylamino)-1-oxo-3-(4-(trifluoromethyl)phenyl)propan-2-yl)pentanediamide 101

The final compound was isolated as the hydrochloride salt. $^1$H NMR (DMSO-d$_6$) δ ppm 1.44 (d, 6H), 1.70-1.79 (m, 1H), 1.85-1.94 (m, 1H), 2.90-298 (m, 2H), 2.98-3.12 (m, 3H), 3.31-3.39 (m, 1H), 3.46-3.65 (m, 6H), 3.95 (dd, 1H), 4.87 (dd, 1H), 7.16 (dd, 1H), 7.44 (t, 1H), 7.58 (dd, 2H), 7.62 (dd, 2H), 7.86 (dd, 1H), 8.08 (brs, 3H), 8.30 (brd, 3H), 8.49 (brs, 3H), 9.25 (d, 2H), 9.43 (s, 1H); $^{19}$F NMR (DMSO-d$_6$) δ ppm −60.06 (s, 3F); ESIMS found for C$_{28}$H$_{38}$BF$_3$N$_6$O$_5$ m/z 605.7 (M−H).

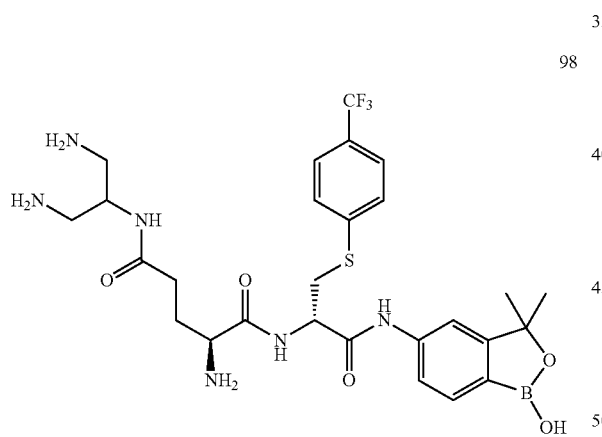

(S)-2-amino-N$^5$-(1,3-diaminopropan-2-yl)-N$^1$-((S)-1-(1-hydroxy-3,3-dimethyl-1,3-dihydrobenzo[c][1,2]oxaborol-5-ylamino)-1-oxo-3-(4-(trifluoromethyl)phenylthio)propan-2-yl)pentanediamide 98

The final compound was isolated as the hydrochloride salt. $^1$H NMR (DMSO-d$_6$) δ ppm 1.40 (s, 6H), 2.02-2.10 (m, 2H), 2.43 (t, 2H), 2.91-2.99 (m, 2H), 3.02-3.10 (m, 2H), 3.58 (dd, 1H), 3.92-3.59 (m, 1H), 4.20-4.28 (m, 1H), 4.75 (q, 1H), 7.50 (dd, 1H), 7.58 (dd, 1H), 7.61 (s, 4H), 7.75 (d, 1H), 8.25-8.38 (m, 7H), 8.39-8.47 (m, 4H), 9.32 (d, 1H), 10.62 (s, 1H); $^{19}$F NMR (DMSO-d$_6$) δ ppm −60.13 (s, 3F); ESIMS found for C$_{27}$H$_{36}$BF$_3$N$_6$O$_5$S m/z 623.8 (M−H).

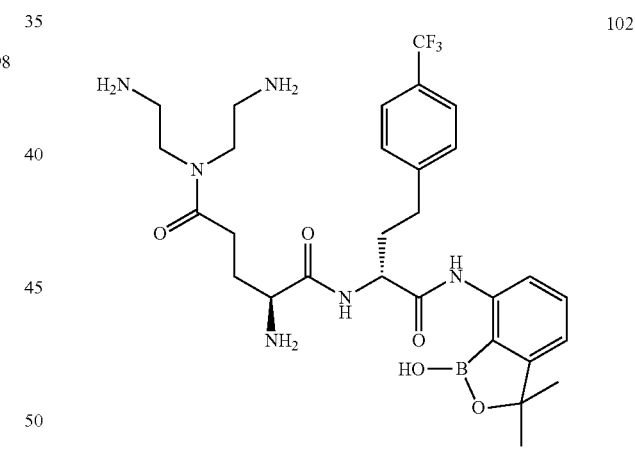

(S)-2-amino-N$^5$,N$^5$-bis(2-aminoethyl)-N$^1$-((R)-1-(1-hydroxy-3,3-dimethyl-1,3-dihydrobenzo[c][1,2]oxaborol-7-ylamino)-1-oxo-4-(4-(trifluoromethyl)phenyl)butan-2-yl)pentanediamide 102

The final compound was isolated as the hydrochloride salt. $^1$H NMR (DMSO-d$_6$) δ ppm 1.44 (s, 6H), 2.00-2.21 (m, 4H), 2.60-2.86 (m, 4H), 2.95 (brs, 2H), 3.04 (brs, 2H), 3.48-3.67 (m, 4H), 4.42 (brs, 1H), 4.59 (brs, 1H), 7.14 (d, J=7 Hz, 1H), 7.42 (t, J=8 Hz, 1H), 7.48 (d, J=8 Hz, 2H), 7.65 (d, J=8 Hz, 2H), 7.86 (d, J=8 Hz, 1H), 8.00 (brs, 3H), 8.34 (brs, 3H), 8.38 (brs, 3H), 9.23 (s, 1H), 9.27 (s, 1H), 9.32 (d, J=7 Hz, 1H); $^{19}$F NMR (DMSO-d$_6$) −60.05 (s, 3F); ESIMS found for C$_{29}$H$_{40}$BF$_3$N$_6$O$_5$ m/z 621.9 (M+H).

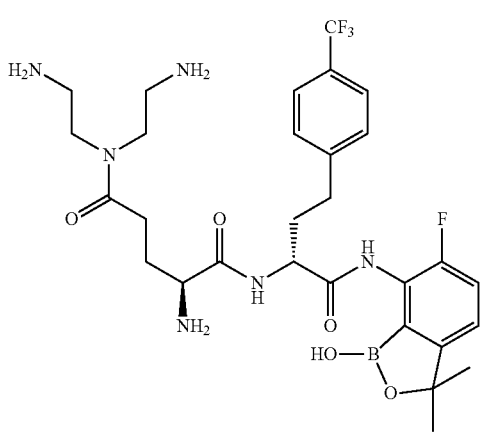

(S)-2-amino-$N^5,N^5$-bis(2-aminoethyl)-$N^1$-((R)-1-(6-fluoro-1-hydroxy-3,3-dimethyl-1,3-dihydrobenzo[c][1,2]oxaborol-7-ylamino)-1-oxo-4-(4-(trifluoromethyl)phenyl)butan-2-yl)pentanediamide 103

The final compound was isolated as the hydrochloride salt. $^1$H NMR (DMSO-$d_6$) δ ppm 1.43 (s, 6H), 1.98-2.22 (m, 4H), 2.58-2.71 (m, 2H), 2.87-2.99 (m, 4H), 2.99-3.09 (m, 3H), 3.95-3.70 (m, 3H), 3.97-4.07 (m, 1H), 4.62 (dd, 1H), 7.33 (dd, 2H), 7.46 (dd, 2H), 7.64 (dd, 2H), 8.07 (brs, 3H), 8.42 (brs, 6H), 9.09 (d, 1H), 9.94 (s, 1H); $^{19}$F NMR (DMSO-$d_6$) δ ppm −60.00 (s, 3F), −120.06 (s, 1H); ESIMS found for $C_{29}H_{39}BF_4N_6O_5$ m/z 637.7 (M−H).

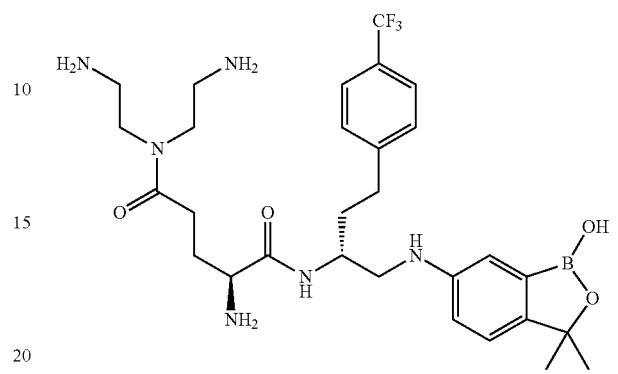

(S)-2-amino-$N^5,N^5$-bis(2-aminoethyl)-$N^1$-((R)-1-(1-hydroxy-3,3-dimethyl-1,3-dihydrobenzo[c][1,2]oxaborole-6-carboxamido)-4-(4-(trifluoromethyl) phenyl)butan-2-yl)pentanediamide 106. Compound 106 was prepared in the following manner: intermediate amine LXXXVI of Scheme 15 and the acid CLXI of Scheme 27 were coupled using the standard method which was followed by removal of Boc protection. The resulting amine was coupled by standard method to the acid intermediate XVI from Scheme 3 and the final product was obtained by removal of Boc protection of amino groups.

The final compound was isolated as the hydrochloride salt. $^1$H NMR (DMSO-$d_6$) δ ppm 1.52 (s, 6H), 1.77-1.96 (m, 3H), 1.96-2.18 (m, 4H), 2.68-2.79 (m, 2H), 2.79-2.94 (m, 1H), 2.94-3.06 (m, 2H), 3.06-3.19 (m, 2H), 3.49-3.72 (m, 5H), 3.95 (brs, 1H), 4.02 (dd, 1H), 4.09 (dd, 1H), 7.50 (d, 2H), 7.55 (d, 1H), 7.70 (d, 2H), 7.98 (d, 1H), 8.04 (d, 1H), 8.18 (brs, 1H), 8.23 (brs, 1H), 8.64 (brs, 1H), 8.84 (d, 1H), 9.22 (brs, 1H); $^{19}$F NMR (DMSO-$d_6$) δ ppm −60.17 (s, 3F); ESIMS found for $C_{30}H_{42}BF_3N_6O_5$ m/z 633.7 (M−H).

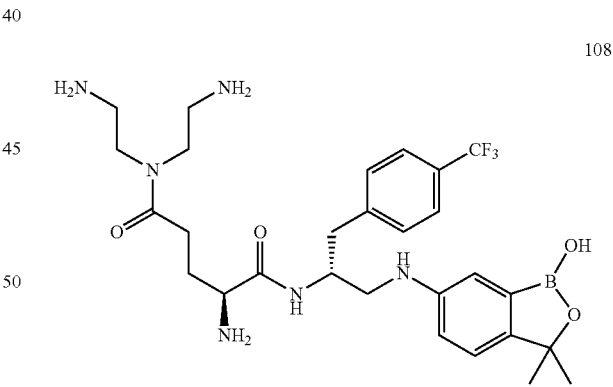

(S)-2-amino-$N^5,N^5$-bis(2-aminoethyl)-$N^1$-((R)-1-(1-hydroxy-3,3-dimethyl-1,3-dihydrobenzo[c][1,2]oxaborol-6-ylamino)-4-(4-(trifluoromethyl)phenyl)butan-2-yl)pentanediamide 107. Compound 107 was prepared in the following manner: The Boc protecting group was removed from intermediate LXXXIII of Scheme 14 and the resulting amine was coupled by the standard method to the acid intermediate XVI from Scheme 3. The final product was obtained by removal of Boc protection of amino groups.

The final compound was isolated as the hydrochloride salt. $^1$H NMR (DMSO-$d_6$) δ ppm 1.40 (s, 6H), 1.78-1.99 (m, 3H), 1.99-2.08 (m, 2H), 2.56-2.84 (m, 5H), 2.89-3.09 (m, 5H), 3.24-3.34 (m, 2H), 3.94 (brs, 1H), 4.04 (brs, 1H), 7.45 (d, 2H), 7.62 (d, 2H), 8.04 (brs, 3H), 8.38 (brs, 3H), 8.52 (brs, 3H), 9.08 (brs, 1H); $^{19}$F NMR (DMSO-$d_6$) δ ppm −60.03 (s, 3F); ESIMS found for $C_{29}H_{42}BF_3N_6O_4$ m/z 605.2 (M−H).

(S)-2-amino-$N^5,N^5$-bis(2-aminoethyl)-$N^1$-((R)-1-(1-hydroxy-3,3-dimethyl-1,3-dihydrobenzo[c][1,2]oxaborol-6-ylamino)-3-(4-(trifluoromethyl)phenyl)propan-2-yl)pentanediamide 108. Compound 108 was prepared in a manner analogous to preparation of compound 107 by using intermediate LXXXIV in place of intermediate LXXXII.

The final compound was isolated as the hydrochloride salt. $^1$H NMR (DMSO-$d_6$) δ ppm 1.40 (s, 6H), 1.89-1.95 (m, 1H), 1.99-2.10 (m, 1H), 2.55-2.84 (m, 2H), 2.87-3.15 (m, 7H), 3.16-3.30 (m, 3H), 3.83-3.93 (brs, 1H), 4.01-4.09 (m, 1H), 4.20-4.40 (m, 2H), 6.89 (dd, 1H), 7.03 (d, 1H), 7.11 (t, 1H), 7.51 (t, 2H), 7.59 (d, 2H), 8.06 (brs, 2H), 8.33 (brs, 6H), 8.85

(brs, 1H); $^{19}$F NMR (DMSO-$d_6$) δ ppm −60.06 (s, 3F); ESIMS found for $C_{28}H_{40}BF_3N_6O_4$ m/z 591.7 (M−H).

3-((R)-2-((S)-2-amino-5-(bis(2-aminoethyl)amino)-5-oxopentanamido)-4-(4-(trifluoromethyl)phenyl)butanamido)phenylboronic acid 2

An example of the [3+1] method for the synthesis of 2 is depicted in Scheme 29 and Example 2.

bonylamino)ethyl)-2,2-dimethyl-4,9,13-trioxo-15-(4-(trifluoromethyl)benzyl)-3-oxa-5,8,14-triazahexadecan-16-oate (6.1 g, 7.28 mmol, 88% yield). $^1$H NMR (DMSO-$d_6$) δ ppm 1.41 (s, 27H), 1.78-1.96 (m, 2H), 2.17 (brs, 1H), 2.59 (brs, 1H), 3.09-3.15 (m, 1H), 3.16-3.27 (m, 2H), 3.28-3.39 (m, 2H), 3.42-3.52 (m, 1H), 3.62 (brs, 1H), 4.06-4.14 (m, 1H), 4.83-4.91 (m, 1H), 5.08 (d, J=12 Hz, 1H), 5.17 (d, J=12 Hz, 1H), 5.76 (brs, 1H), 7.19 (d, J=8 Hz, 1H), 7.23-7.29 (m, 3H), 7.3-7.39 (m, 3H), 7.44 (d, J=8 Hz, 2H), 7.62 (brs, 1H); $^{19}$F

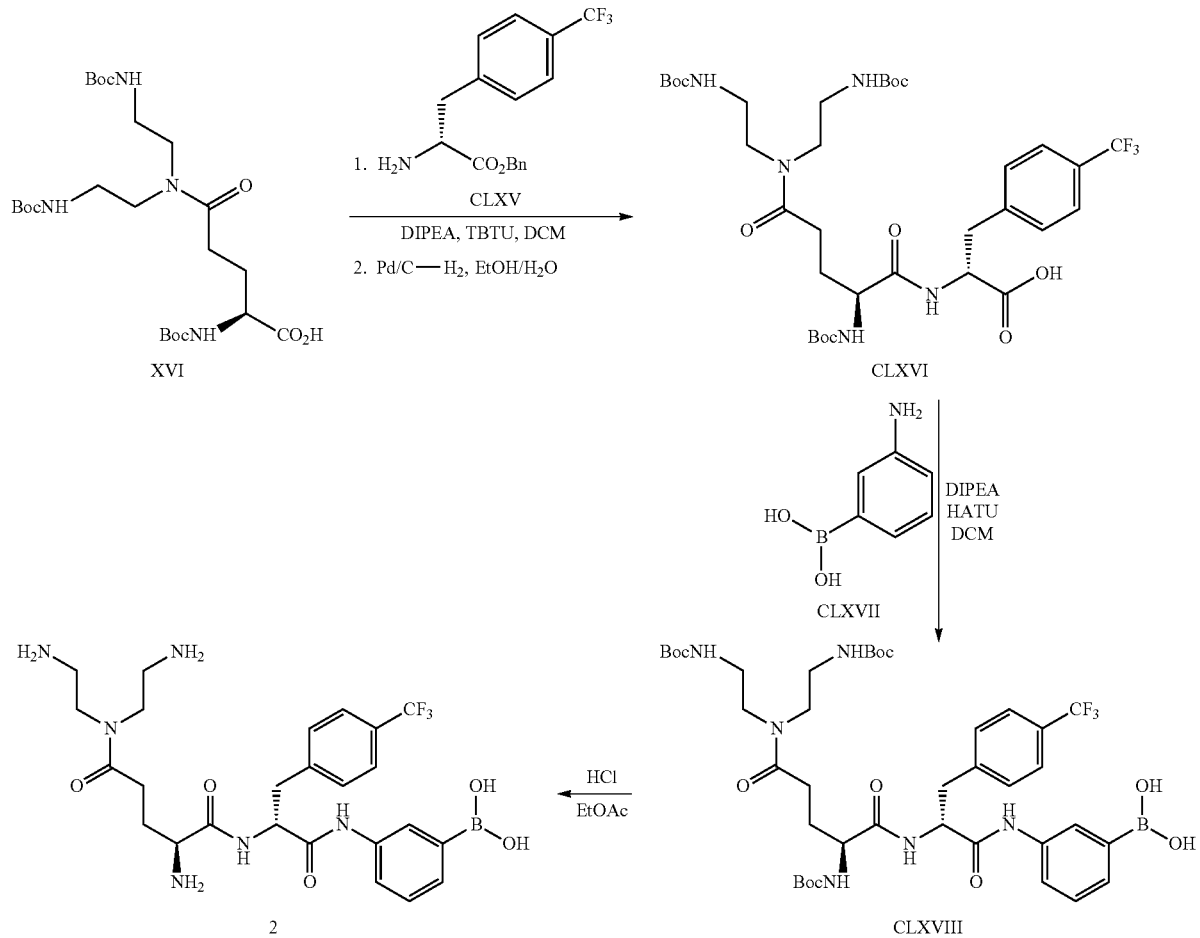

Scheme 29

Example 2

Step 1

To a suspension of (R)-benzyl 2-amino-3-(4-(trifluoromethyl)phenyl)propanoate (CLXV) (3 g, 8.33 mmol) in DCM (25 mL) was added diisopropylethylamine (3.57 mL, 20.83 mmol). To this solution was added (S)-5-(bis(2-(tert-butoxycarbonylamino)ethyl)amino)-2-(tert-butoxycarbonylamino)-5-oxopentanoic acid (XVI) (4.88 g, 9.16 mmol) and TBTU (2.94 g, 9.16 mmol). The reaction mixture was stirred at room temperature overnight. The mixture was then diluted with DCM (50 mL) and washed with 2 N aqueous HCl, 1 N aqueous NaOH, brine, dried over MgSO$_4$ and concentrated under vacuum to dryness. The residue was purified on a silica gel column using DCM:MeOH (100:1) to yield (12S,15R)-benzyl 12-(tert-butoxycarbonylamino)-8-(2-(tert-butoxycar- NMR (DMSO-$d_6$) δ ppm −61.84 (s, 3F); ESIMS found for $C_{41}H_{58}F_3N_5O_{10}$ m/z 838.9 (M+H).

Step 2

To a solution of (12S,15R)-benzyl 12-(tert-butoxycarbonylamino)-8-(2-(tert-butoxycarbonylamino)ethyl)-2,2-dimethyl-4,9,13-trioxo-15-(4-(trifluoromethyl)benzyl)-3-oxa-5,8,14-triazahexadecan-16-oate (3 g, 3.58 mmol) in a mixture of EtOH/H$_2$O (18 mL/2 mL) was added palladium (wet) on carbon (catalytic amount). The reaction mixture was stirred under an atmosphere of hydrogen at room temperature overnight. The catalyst was filtered through a pad of Celite. The filtrate was evaporated under reduced pressure to give (12S, 15R)-12-(tert-butoxycarbonylamino)-8-(2-(tert-butoxycarbonylamino)ethyl)-2,2-dimethyl-4,9,13-trioxo-15-(4-(trifluoromethyl)benzyl)-3-oxa-5,8,14-triazahexadecan-16-oic acid (CLXVI) as white crystals (2.66 g, 3.56 mmol, 99% yield). $^{1}$H NMR (DMSO-d$_{6}$) δ ppm 1.32 (s, 27H), 1.52-1.78 (m, 2H), 2.07-2.26 (m, 2H), 2.9-3.03 (m, 4H), 3.14-3.23 (m, 4H), 3.31 (brs, 2H), 3.83-3.92 (m, 1H), 4.4-4.46 (m, 1H), 6.74-6.85 (m, 2H), 6.88-6.94 (m, 1H), 7.38 (d, J=8 Hz, 2H), 7.55 (d, J=8 Hz, 2H), 7.94-8.01 (m, 1H); $^{19}$F NMR (DMSO-d$_{6}$) δ ppm −60.24 (s, 3F); ESIMS found for C$_{34}$H$_{52}$F$_{3}$N$_{5}$O$_{10}$ m/z 748.9 (M+H).

Step 3

To a solution of 3-aminophenylboronic acid (CLXVII) (100 mg, 0.73 mmol) in DCM (7 mL) was added diisopropylethylamine (0.137 mL, 0.803 mmol) and (12S,15R)-12-(tert-butoxycarbonylamino)-8-(2-(tert-butoxycarbonylamino)ethyl)-2,2-dimethyl-4,9,13-trioxo-15-(4-(trifluoromethyl)benzyl)-3-oxa-5,8,14-triazahexadecan-16-oic acid (CLXVI) (546 mg, 0.73 mmol). HATU (277 mg, 0.73 mmol) was then added and the reaction mixture was stirred at room temperature overnight. The reaction mixture was diluted with DCM (30 mL), washed with 1 M aqueous HCl (30 mL), 5% aqueous NaHCO$_{3}$ (30 mL), brine, dried over anhydrous MgSO$_{4}$ and evaporated under vacuum to dryness. The residue was dissolved in a very little amount of Et$_{2}$O, then hexane (30 mL) was added to cause 3-((12S,15R)-12-(tert-butoxycarbonylamino)-8-(2-(tert-butoxycarbonylamino)ethyl)-2,2-dimethyl-4,9,13-trioxo-15-(4-(trifluoromethyl)benzyl)-3-oxa-5,8,14-triazahexadecanamido)phenylboronic acid (CLXVIII) to precipitate as white crystals (550 mg, 0.64 mmol, 87% yield). $^{1}$H NMR (DMSO-d$_{6}$) δ ppm 1.35 (brs, 27H), 1.52-1.62 (m, 1H), 1.63-1.74 (m, 1H), 2.06-2.21 (m, 2H), 2.91-3.03 (m, 5H), 3.14-3.25 (m, 5H), 3.82-3.93 (m, 1H), 4.65-4.73 (m, 1H), 6.74-6.83 (m, 1H), 6.84-6.96 (m, 2H), 7.24 (t, J=8 Hz, 1H), 7.43-7.49 (m, 3H), 4.81 (d, J=8 Hz, 2H), 7.69 (d, J=8 Hz, 1H), 7.82 (s, 1H), 8.03 (s, 2H), 8.21 (d, J=8 Hz, 1H); $^{19}$F NMR (DMSO-d$_{6}$) δ ppm −60.17 (s, 3F); ESIMS found for C$_{40}$H$_{58}$BF$_{3}$N$_{6}$O$_{11}$ m/z 867.9 (M+H).

Step 4

To a solution of 3-((12S,15R)-12-(tert-butoxycarbonylamino)-8-(2-(tert-butoxycarbonylamino)ethyl)-2,2-dimethyl-4,9,13-trioxo-15-(4-(trifluoromethyl)benzyl)-3-oxa-5,8,14-triazahexadecanamido)phenylboronic acid (CLXVIII) (140 mg, 0.162 mmol) in EtOAc (2 mL) was added 5.5 M HCl/EtOAc (10 mL). The reaction mixture was stirred at room temperature for 0.5 h before adding Et$_{2}$O (25 mL) causing white crystals to precipitate. The crystals was filtered and washed with Et$_{2}$O (2×10 mL) to give 3-((R)-2-((S)-2-amino-5-(bis(2-aminoethyl)amino)-5-oxopentanamido-3-(4-(trifluoromethyl)phenyl)propanamido)phenylboronic acid (2) (109 mg, 0.161 mmol, 100% yield) as the hydrochloride salt. $^{1}$H NMR (DMSO-d$_{6}$) δ ppm 1.64-1.86 (m, 2H), 2.39 (brs, 2H), 2.87-2.95 (m, 2H), 2.96-3.05 (m, 2H), 3.23 (dd, J=13 Hz, J=3 Hz, 1H), 3.38-3.62 (m, 5H), 3.84-3.92 (m, 1H), 4.79-4.86 (m, 1H), 7.24 (t, J=8 Hz, 1H), 7.48 (d, J=8 Hz, 1H), 7.55 (d, J=8 Hz, 2H), 7.61 (d, J=8 Hz, 2H), 7.69 (d, J=8 Hz, 1H), 7.85 (s, 1H), 8.1 (brs, 3H), 8.29 (brs, 3H), 8.41 (brs, 3H), 9.1 (d, J=8 Hz, 1H), 10.33 (s, 1H); $^{19}$F NMR (DMSO-d$_{6}$) δ ppm −60.05 (s, 3F); ESIMS found for C$_{25}$H$_{34}$BF$_{3}$N$_{6}$O$_{5}$ m/z 567.7 (M+H).

The following compounds are prepared in accordance with the procedure described in the above Scheme 29 and Example 2.

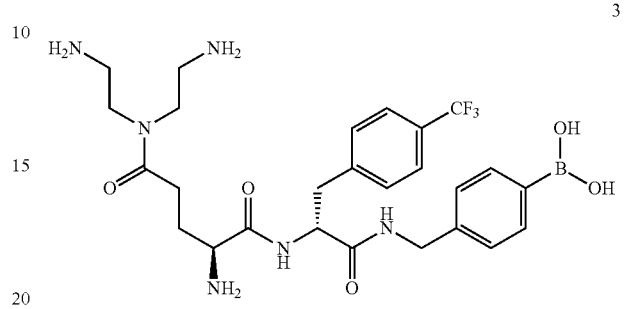

3

4-(((R)-2-((S)-2-amino-5-(bis(2-aminoethyl)amino)-5-oxopentanamido)-3-(4-(trifluoromethyl)phenyl)propanamido)methyl)phenylboronic acid 3

The final compound was isolated as the hydrochloride salt. $^{1}$H NMR (DMSO-d$_{6}$) δ ppm 1.62-1.83 (m, 2H), 2.3-2.45 (m, 2H), 2.86-3.04 (m, 4H), 3.14-3.21 (m, 1H), 3.33-3.59 (m, 5H), 3.82-3.89 (m, 1H), 4.24 (d, J=5 Hz, 2H), 4.65 (td, J=5 Hz, J=9 Hz, 1H), 7.18 (d, J=8 Hz, 1H), 7.22 (t, J=8 Hz, 1H), 7.45 (d, J=8 Hz, 2H), 7.57 (d, J=8 Hz, 2H), 7.63 (d, J=8 Hz, 1H), 7.66 (s, 1H), 8.06 (brs, 3H), 8.31 (brs, 3H), 8.37 (brs, 3H), 8.72-8.78 (m, 1H), 8.98 (d, J=8 Hz, 1H); $^{19}$F NMR (DMSO-d$_{6}$) δ ppm −60.06 (s, 3F); ESIMS found for C$_{26}$H$_{36}$BF$_{3}$N$_{6}$O$_{5}$ m/z 581.7 (M+H).

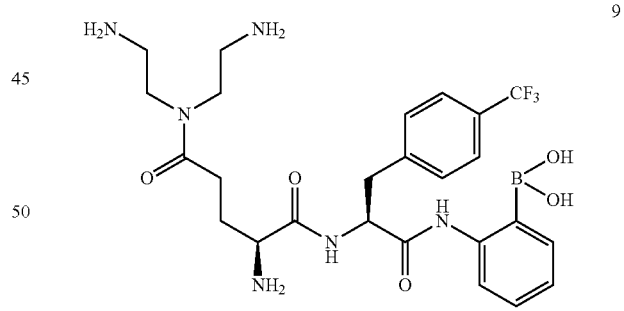

9

2-((S)-2-((S)-2-amino-5-(bis(2-aminoethyl)amino)-5-oxopentanamido)-3-(4-(trifluoromethyl)phenyl)propanamido)phenylboronic acid 9

The final compound was isolated as the hydrochloride salt. $^{1}$H NMR (CDCl$_{3}$) δ ppm 1.98-2.08 (m, 1H), 2.12-2.22 (m, 1H), 3.10-3.18 (m, 2H), 3.22-3.30 (m, ), 3.37-3.47 (m, 1H), 3.52-3.62 (m, 2H), 3.63-3.70 (m, 2H), 3.72-3.78 (m, 1H), 3.80-3.88 (m, 1H), 3.95-4.05 (m, 1H), 4.09 (dd, J=11.7 Hz, 3.4 Hz, 1H), 4.92-4.99 (m, 1H), 7.04 (d, J=7.6 Hz, 1H), 7.28-7.38 (m, 3H), 7.38 (dd, J=7.1 Hz, 1.6 Hz, 1H), 7.63 (d, J=8.2 Hz, 2H), 7.75 (d, J=8.2 Hz, 2H); ESIMS found for $C_{25}H_{34}BF_3N_6O_5$ m/z 549 (M+H−$H_2O$).

84

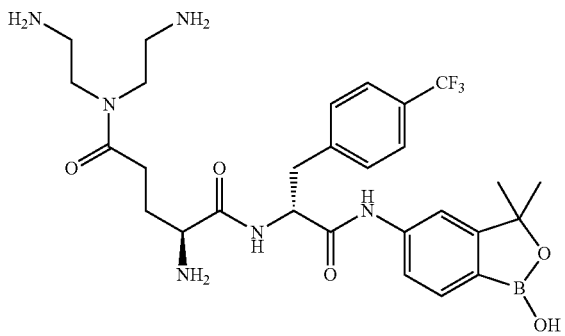

(S)-2-amino-$N^5$,$N^5$-bis(2-aminoethyl)-$N^1$-((R)-1-(1-hydroxy-3,3-dimethyl-1,3-dihydrobenzo[c][1,2]oxaborol-5-ylamino)-1-oxo-3-(4-(trifluoromethyl)phenyl)propan-2-yl)pentanediamide 84

The final compound was isolated as the hydrochloride salt. $^1$H NMR (DMSO-$d_6$) δ ppm 1.39 (s, 6H), 1.65-1.75 (m, 1H), 1.75-1.87 (m, 1H), 2.32-2.43 (m, 1H), 2.87-2.97 (m, 2H), 2.97-3.08 (m, 3H), 3.14 (brs, 1H), 3.27 (d, 1H), 3.42-3.63 (m, 4H), 3.89 (brs, 1H), 4.85 (brs, 1H), 7.52 (d, 1H), 7.55-7.66 (m, 5H), 7.68 (s, 1H), 7.95-8.53 (brd, 9H), 8.96 (s, 1H), 9.13 (d, 1H), 10.62 (s, 1H); $^{19}$F NMR (DMSO-$d_6$) δ ppm −60.05 (s, 3F); ESIMS found for $C_{28}H_{38}BF_3N_6O_5$ m/z 605.7 (M−H).

(S)-2-amino-N5-((1s,3R,5S)-3,5-diamino cyclohexyl)-N1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)pentanediamide 38

An example of the [1+3] method for the synthesis of 38 is depicted in Scheme 30 and Example 3.

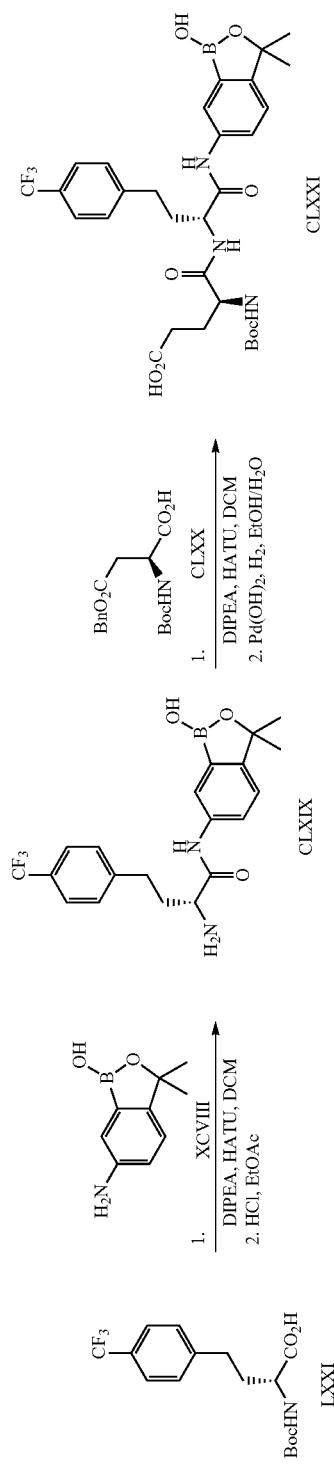
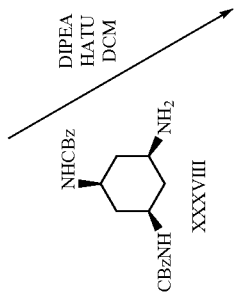
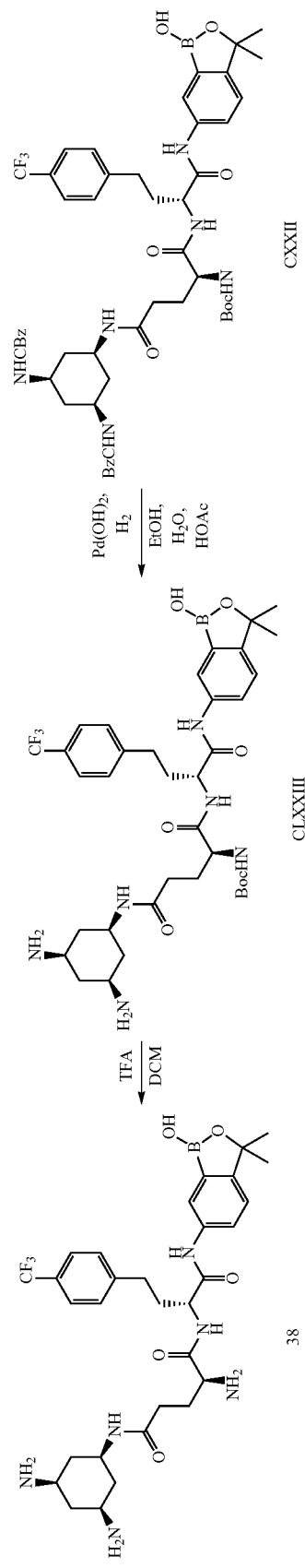

Example 3

Step 1

To a suspension of (R)-2-(tert-butoxycarbonylamino)-4-(4-(trifluoromethyl)phenyl)butanoic acid (LXXI) (1 g, 2.88 mmol) and 6-amino-3,3-dimethylbenzo[c][1,2]oxaborol-1(3H)-ol (XCVIII) (0.615 g, 2.88 mmol) in dry DCM (10 mL) was added DIPEA (1.47 mL, 8.64 mmol). To this solution was added HATU (1.09 g, 2.88 mmol) and the mixture was stirred at room temperature overnight. The mixture was washed with 2 N aqueous HCl, 1 M aqueous $K_2CO_3$, brine, dried over $MgSO_4$ and evaporated under vacuum to give (R)-tert-butyl 1-(1-hydroxy-3,3-dimethyl-1,3-dihydrobenzo[c][1,2]oxaborol-6-ylamino)-1-oxo-4-(4-(trifluoromethyl)phenyl)butan-2-ylcarbamate (1.44 g, 2.84 mmol, 99% yield). ESIMS found for $C_{25}H_{30}BF_3N_2O_5$ m/z 507.5 (M+H).

Step 2

(R)-tert-butyl 1-(1-hydroxy-3,3-dimethyl-1,3-dihydrobenzo[c][1,2]oxaborol-6-ylamino)-1-oxo-4-(4-(trifluoromethyl)phenyl)butan-2-ylcarbamate (1.44 g, 2.844 mmol) was stirred with 4.4 M HCl/EtOAc (10 mL) at room temperature for 30 min. The solution was evaporated to dryness under vacuum to produce (R)-2-amino-N-(1-hydroxy-3,3-dimethyl-1,3-dihydrobenzo[c][1,2]oxaborol-6-yl)-4-(4-(trifluoromethyl)phenyl)butanamide (CLXIX) as a light orange solid (1.22 g, 2.75 mmol, 97% yield). $^1$H NMR (DMSO-$d_6$) δ ppm 1.46 (s, 6H), 2.22-2.29 (m, 2H), 2.83-2.91 (m, 2H), 4.17-4.22 (m, 1H), 7.35 (d, 1H, J=8 Hz), 7.47 (d, 2H, J=8 Hz), 7.62 (d, 2H, J=8 Hz), 7.65-7.68 (m, 1H), 7.92 (s, 1H), 8.53 (brs, 3H), 10.76 (s, 1H); $^{19}$F NMR (DMSO-$d_6$) δ ppm −60.17 (s, 3F); ESIMS found for $C_{20}H_{22}BF_3N_2O_3$ m/z 407.4 (M+H), 405.3 (M−H).

Step 3

To a suspension of (R)-2-amino-N-(1-hydroxy-3,3-dimethyl-1,3-dihydrobenzo[c][1,2]oxaborol-6-yl)-4-(4-(trifluoromethyl)phenyl)butanamide (CLXIX) (1.2 g, 2.71 mmol) and Boc-Glu(OBzl)-OH (CLXX) (0.915 g, 2.71 mmol) in DCM (10 mL) was added DIPEA (1.39 mL, 8.13 mmol). To this solution was added HATU (1.03 g, 2.71 mmol) and the mixture was stirred at room temperature overnight. The mixture was washed with 2 N aqueous HCl, 1 M aqueous $K_2CO_3$, brine and dried over $MgSO_4$. The solution was evaporated to dryness under vacuum to give (S)-benzyl 4-(tert-butoxycarbonylamino)-5-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-5-oxopentanoate as an orange foam (1.83 g, 2.52 mmol, 93% yield). $^1$H NMR (DMSO-$d_6$) δ ppm 1.33 (s, 9H), 1.4 (s, 6H), 1.8-1.88 (m, 1H), 1.9-1.96 (m, 2H), 2.08 (brs, 1H), 2.42 (brs, 2H), 2.6-2.66 (m, 1H), 2.7-2.76 (m, 1H), 3.98-4.05 (m, 1H), 4.4 (brs, 1H), 5.07 (s, 2H), 7.1 (brs, 1H), 7.28-7.34 (m, 6H), 7.37-7.44 (m, 2H), 7.55-7.63 (m, 3H), 7.89 (s, 1H), 8.34 (brs, 1H), 9.0 (s, 1H), 9.86 (s, 1H); $^{19}$F NMR (DMSO-$d_6$) δ ppm −60.11 (s, 3F); ESIMS found for $C_{37}H_{43}BF_3N_3O_8$ m/z 726.7 (M+H).

Step 4

To a solution of (S)-benzyl 4-(tert-butoxycarbonylamino)-5-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-5-oxopentanoate (1.8 g, 2.48 mmol) in a mixture of EtOH/$H_2O$ (20 mL/2 mL) was added Pd(OH)$_2$/C (cat.). The mixture was stirred under a $H_2$ atmosphere for 2 h. The mixture was filtered through Celite and washed with MeOH. The filtrate was evaporated to dryness under vacuum to produce (S)-4-(tert-butoxycarbonylamino)-5-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-5-oxopentanoic acid (CLXXI) as a white foam (1.57 g, 2.48 mmol, 100% yield). ESIMS found for $C_{30}H_{37}BF_3N_3O_3$ m/z 634.6 (M−H).

Step 5

To a suspension of benzyl (1R,3S,5R)-5-amino cyclohexane-1,3-diyldicarbamate (XXXVIII) (1.06 g, 2.44 mmol) and (S)-4-(tert-butoxycarbonylamino)-5-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-5-oxopentanoic acid (CLXXI) (1.55 g, 2.44 mmol) in DCM (10 mL) was added DIPEA (1.25 mL, 7.32 mmol) and HATU (0.925 g, 2.44 mmol). The mixture was stirred at room temperature overnight at which time a thick oil formed. The oil was separated and washed with DCM, and residual solvent was removed under vacuum to give crude tert-butyl (S)-5-((1R,3R,5S)-3,5-b is (2-phenyl acetamido)cyclohexylamino)-1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-1,5-dioxopentan-2-ylcarbamate (CLXXII) (1.55 g). ESIMS found for $C_{52}H_{62}BF_3N_6O_{11}$ m/z 1016 (M+H), 1014.3 (M−H). The crude product was used without further purification for step 6.

Step 6

To a solution of tert-butyl (S)-5-((1r,3R,5S)-3,5-bis(2-phenylacetamido)cyclohexylamino)-1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-1,5-dioxopentan-2-ylcarbamate (CLXXII) (1.55 g) in EtOH/$H_2O$/HOAc (20/2/2 mL) was added Pd(OH)$_2$/C (cat.). The reaction was flushed with $H_2$ and stirred at room temperature overnight. The reaction was filtered through Celite and evaporated to give crude tert-butyl (S)-5-((1S,3R,5S)-3,5-diaminocyclohexylamino)-1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-1,5-dioxopentan-2-ylcarbamate (CLXXIII) (1.5 g). ESIMS found for $C_{36}H_{50}BF_3N_6O_7$ m/z 747.8 (M+H), 745.8 (M−H). The crude product was used without further purification for step 7.

Step 7

To a suspension of tert-butyl (S)-5-((1S,3R,5S)-3,5-diaminocyclohexylamino)-1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-ylamino)-1,5-dioxopentan-2-ylcarbamate (CLXXIII) (1.5 g) in DCM (35 mL) was added TFA (7 mL). The suspension dissolved and was stirred at room temperature for 1 h. The solvent was evaporated and Et$_2$O was added causing a solid to precipitate. The solid was filtered, washed with Et$_2$O and dried to give 1.25 g of an impure residue. The residue was purified on preparative HPLC (120 min, 10-50% MeCN, λ=220 nm) to yield (S)-2-amino-N5-((1S,3R,5S)-3,5-diaminocyclohexyl)-N1-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)pentanediamide (38) (0.3 g, 0.32 mmol). ESIMS found for $C_{36}H_{50}BF_3N_6O_7$ m/z 647.7 (M+H), 646.8 (M−H).

The following compounds are prepared in accordance with the procedure described in the above Scheme 30 and Example 3.

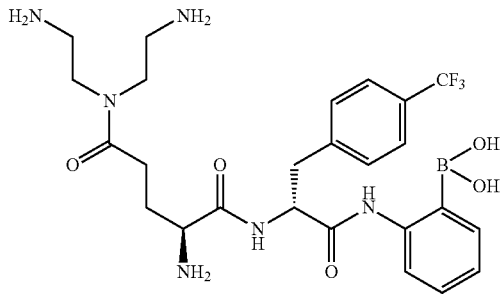

2-((R)-2-((S)-2-amino-5-(bis(2-aminoethyl)amino)-5-oxopentanamido)-3-(4-(trifluoromethyl)phenyl)propanamido)phenylboronic acid 8

The final compound was isolated as the hydrochloride salt. $^1$H NMR (CDCl$_3$) δ ppm 1.98-2.08 (m, 1H), 2.12-2.22 (m, 1H), 2.78-2.88 (m, 2H), 3.18-3.28 (m, 4H), 3.40-3.48 (m, 2H), 3.55-3.60 (m, 1H), 3.65-3.75 (m, 7H), 4.05-4.12 (m, 1H), 5.02 (t, J=7.8 Hz, 1H), 7.06 (dd, J=6.9 Hz, 2 Hz, 1H), 7.25-7.35 (m, 2H), 7.44 (dd, J=6.9 Hz, 1.9 Hz, 1H), 7.59 (d, J=8.4 Hz, 2H), 7.62 (d, J=8.4 Hz, 2H); ESIMS found for C$_{25}$H$_{34}$BF$_3$N$_6$O$_5$ m/z 549 [M+H−H$_2$O].

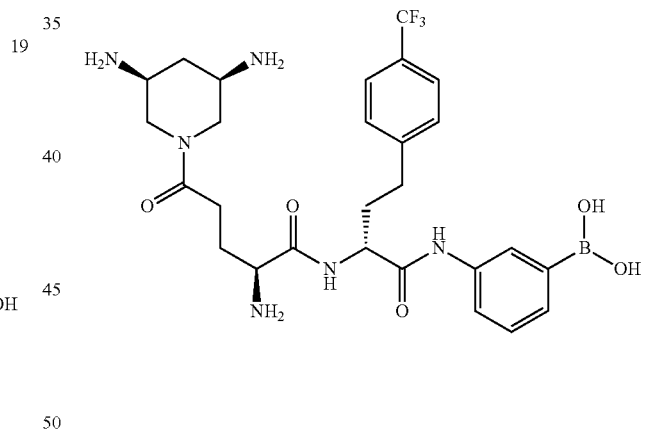

3-((R)-2-((S)-2-amino-5-((1R,3R,5S)-3,5-diaminocyclohexylamino)-5-oxopentanamido)-3-(4-(trifluoromethyl)phenyl)propanamido)-5-(trifluoromethyl)phenyl)boronic acid 19

The final compound was isolated as the hydrochloride salt. $^1$H NMR (DMSO-d$_6$) δ ppm 1.84-1.92 (m, 2H), 2.1-2.2 (m, 4H), 2.38 (d, 1H, J=12 Hz), 3.08-3.16 (m, 3H), 3.18-3.26 (m, 3H), 3.32 (dd, 1H, J=5 Hz, J=12 Hz), 3.7-3.8 (m, 1H), 3.92 (brs, 1H), 3.9-3.93 (m, 1H), 4.85 (brs, 1H), 7.56 (d, 2H, J=8 Hz), 7.61 (d, 2H, J=8 Hz), 7.81 (s, 1H), 8.08-8.14 (m, 2H), 8.16 (s, 1H), 8.3 (brs, 9H), 8.95 (brs, 1H), 10.4 (s, 1H); $^{19}$F NMR (DMSO-d$_6$) δ ppm −60.12 (s, 3F), −60.55 (s, 3F); ESIMS found for C$_{27}$H$_{32}$F$_3$N$_7$O$_4$ m/z 661.9 (M+H).

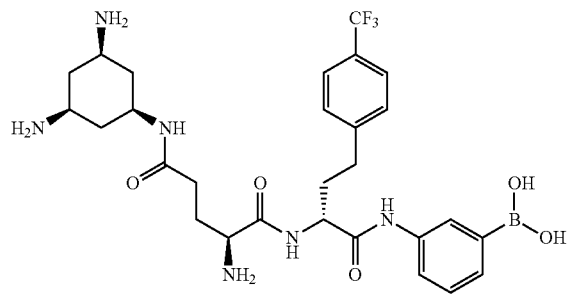

3-((R)-2-((S)-2-amino-5-((1S,3R,5S)-3,5-diaminocyclohexylamino)-5-oxopentanamido)-4-(4-(trifluoromethyl)phenyl)butanamido)phenylboronic acid 23

The final compound was isolated as the hydrochloride salt. $^1$H NMR (DMSO-d$_6$) δ ppm 2.03-2.2 (m, 7H), 2.32-2.4 (m, 3H), 2.72-2.88 (m, 2H), 3.2 (brs, 2H), 3.7-3.8 (m, 2H), 4.0 (t, 1H, J=6 Hz), 4.55-4.48 (m, 2H), 7.24 (t, 1H, J=8 Hz), 7.46 (d, 2H, J=8 Hz), 7.48 (d, 1H, J=7 Hz), 7.6 (d, 2H, J=8 Hz), 7.66-7.7 (m, 1H), 7.91 (s, 1H), 8.2 (d, 1H, J=8 Hz), 8.37 (brs, 9H), 8.95 (d, 1H, J=8 Hz), 9.84 (s, 1H); $^{19}$F NMR (DMSO-d$_6$) δ ppm −60.05 (s, 3F); ESIMS found for C$_{28}$H$_{38}$BF$_3$N$_6$O$_5$ m/z 608 (M+H), 606.1 (M−H).

3-((R)-2-((S)-2-amino-5-((3R,5S)-3,5-diaminopiperidin-1-yl)-5-oxopentanamido)-4-(4-(trifluoromethyl)phenyl)butanamido)phenylboronic acid 24

The final compound was isolated as the hydrochloride salt. $^1$H NMR (DMSO-d$_6$) δ ppm 1.64-1.77 (m, 2H), 1.93-2.15 (m, 4H), 2.62-2.73 (m, 2H), 2.74-2.84 (m, 2H), 2.91-3.07 (m, 1H), 3.05-3.15 (m, 2H), 3.87-4.01 (m, 1H), 4.05-4.27 (m, 2H), 4.38-4.50 (m, 1H), 4.60-4.69 (m, 1H), 7.18-7.27 (m, 1H), 7.40-7.51 (m, 2H), 7.59-7.65 (m, 2H), 7.66-7.73 (m, 1H), 7.83-7.90 (m, 1H), 7.96-8.08 (m, 1H), 8.48 (brs, 9H), [9.13 (brs, 1$^{st}$ rotamer); 9.07 (brs, 2$^{st}$ rotamer), 1H], [10.18 (s, 1$^{st}$ rotamer); 10.13 (s, 2$^{st}$ rotamer), 1H]; $^{19}$F NMR (DMSO-d$_6$) δ ppm −60.46 (s, 3F); ESIMS found for C$_{27}$H$_{36}$BF$_3$N$_6$O$_5$ m/z 593.6 (M+H).

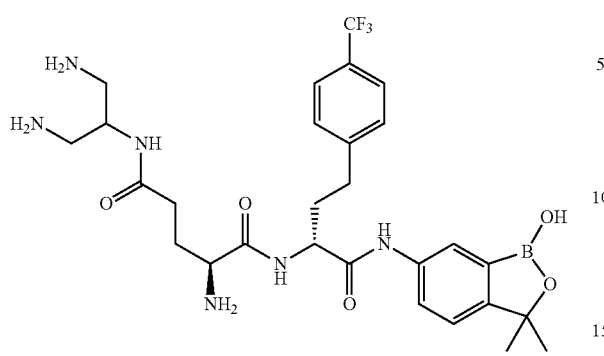

(S)-2-amino-N⁵-(1,3-diaminopropan-2-yl)-N¹-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)pentanediamide 39

The final compound was isolated as the hydrochloride salt. $^{1}$H NMR (DMSO-d$_{6}$) δ ppm 1.38 (s, 6H), 1.95-2.14 (m, 6H), 2.2-2.27 (m, 3H), 2.44-2.5 (m, 3H), 2.65-2.72 (m, 1H), 2.73-2.8 (m, 1H), 3.17 (brs, 2H), 3.68-3.77 (m, 1H), 3.9-4.2 (m, 1H), 4.46-4.52 (m, 1H), 7.3 (d, 1H, J=8 Hz), 7.42 (d, 2H<J=8 Hz), 7.61 (d, 3H, J=8 Hz), 7.87 (s, 1H), 8.36 (brs, 9H), 9.06 (s, 1H), 9.12 (d, 1H, J=8 Hz, 10.3 (s, 1H); $^{19}$F NMR (DMSO-d$_{6}$) δ ppm −60.05 (s, 3F); ESIMS found for C$_{31}$H$_{42}$BF$_{3}$N$_{6}$O$_{5}$ m/z 647.8 (M+H).

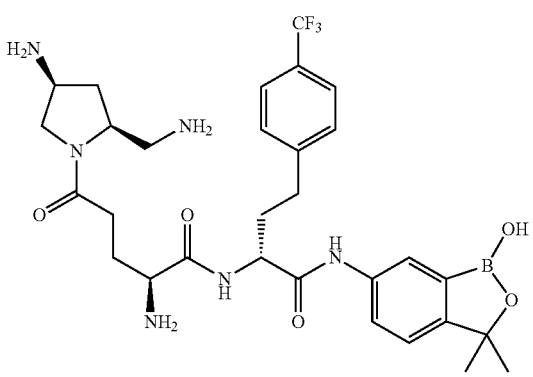

(S)-2-amino-5-((2S,4S)-4-amino-2-(aminomethyl)pyrrolidin-1-yl)-N-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)-5-oxopentanamide 41

The final compound was isolated as the hydrochloride salt. $^{1}$H NMR (DMSO-d$_{6}$) δ ppm 1.01-1.10 (m, 1H), 1.22 (brs, 3H), 1.40 (s, 6H), 2.09 (brs, 4H), 2.54 (brs, 2H), 2.68-2.88 (m, 2H), 3.31-3.42 (m, 1H), 3.50-3.61 (m, 1H), 3.64-3.78 (m, 1H), 3.86-3.97 (m, 1H), 4.02 (brs, 1H), 4.16-4.28 (m, 1H), 4.45-4.56 (m, 1H), 7.26 (d, J=7 Hz, 1H), 7.44 (d, J=7 Hz, 2H), 7.58 (d, J=7 Hz, 2H), 7.63 (d, J=7 Hz, 1H), 7.88 (s, 1H), 8.34 (brs, 9H), 9.07 (brs, 1H), 10.01 (s, 1H); $^{19}$F NMR (DMSO-d$_{6}$) δ ppm −60.05 (s, 3F); ESIMS found for C$_{30}$H$_{40}$BF$_{3}$N$_{6}$O$_{5}$ m/z 633.7 (M+H).

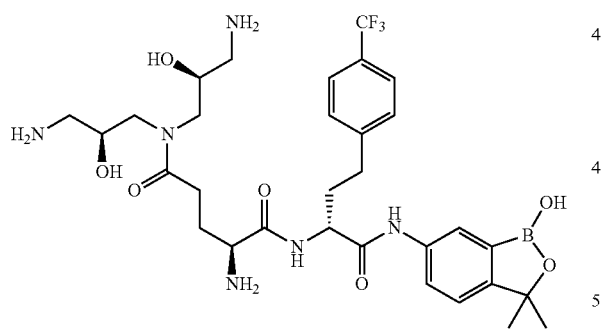

(S)-2-amino-N⁵,N⁵-bis((S)-3-amino-2-hydroxypropyl)-N¹-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)pentanediamide 40

The final compound was isolated as the hydrochloride salt in 85% yield. $^{1}$H NMR (MeOD-d$_{4}$) δ ppm 7.76 (s, 1H), 7.64 (d, J=6.6 Hz, 2H), 7.57 (d, J=7.6 Hz, 2H), 7.47 (d, J=7.6 Hz, 2H), 7.29 (d, J=6.6 Hz, 2H), 4.54 (t, J=5.62 Hz, 1H), 4.18-4.09 (m, 3H), 3.67-3.51 (m, 4H), 3.16-2.79 (m, 6H), 2.30-2.2.15 (m, 4H), 1.50 (s, 6H); ESIMS found for C$_{31}$H$_{44}$BF$_{3}$N$_{6}$O$_{7}$ m/z 681.3 (M+H).

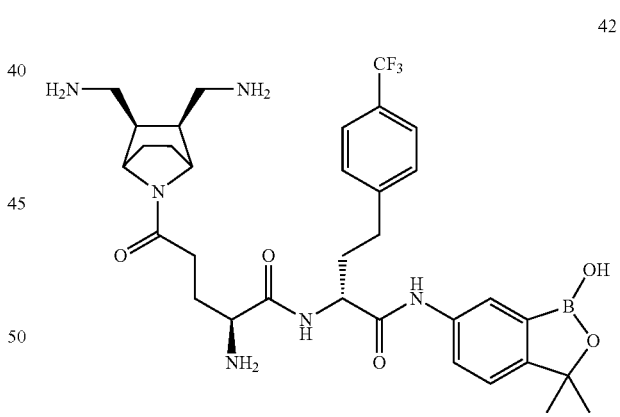

(2S)-2-amino-5-((2R,3S)-2,3-bis(amino methyl)-7-azabicyclo[2.2.1]heptan-7-yl)-N-((R)-1-(1-hydroxy-3,3-dimethyl-1,3-dihydrobenzo[c][1,2]oxaborol-6-ylamino)-1-oxo-4-(4-(trifluoromethyl)phenyl)butan-2-yl)-5-oxopentanamide 42

The final compound was isolated as the hydrochloride salt. $^{1}$H NMR (DMSO-d$_{6}$) δ ppm 1.38 (s, 6H), 1.59-1.75 (m, 4H), 1.96-2.16 (m, 6H), 2.32-2.39 (m, 2H), 2.61-2.92 (m, 6H), 2.97-3.04 (m, 1H), 3.92-4.03 (m, 1H), 4.43-4.54 (m, 2H), 7.30 (d, J=8 Hz, 1H), 7.42-7.44 (m, 2H), 7.59-7.62 (m, 3H), 7.88 (s, 1H), 8.20 (brs, 3H), 8.36 (brs, 3H), 8.41 (brs, 3H), 9.12 (brs, 1H), 10.28 (s, 1H); $^{19}$F NMR (DMSO-$d_6$) δ ppm −60.06 (s 3F); ESIMS found for $C_{33}H_{44}BF_3N_6O$ m/z 673.8 (M+H).

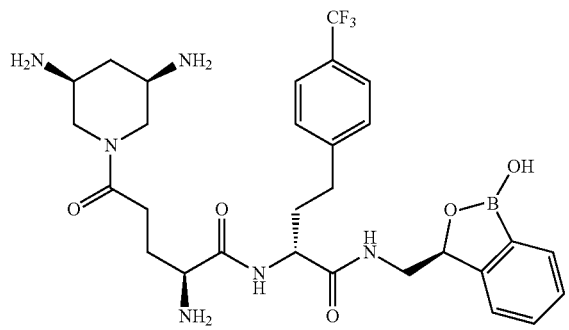

(S)-2-amino-5-((3R,5S)-3,5-diaminopiperidin-1-yl)-
N-((R)-1-(((R)-1-hydroxy-1,3-dihydrobenzo[c][1,2]
oxaborol-3-yl)methylamino)-1-oxo-4-(4-(trifluoromethyl)phenyl)butan-2-yl)-5-oxopentanamide 48

The final compound was isolated as the hydrochloride salt. $^1$H NMR (DMSO-$d_6$) δ ppm 2.04-2.18 (m, 2H), 2.49-2.66 (m, 4H), 3.04 (brs, 4H), 3.21 (brs, 4H), 3.31-3.54 (m, 2H), 3.97 (brs, 1H), 4.31 (brs, 2H), 5.21 (brs 1H), 7.25 (brs, 1H), 7.32-7.41 (m, 5H), 7.59 (d, J=8 Hz, 2H), 7.67 (d, J=8 Hz, 1H), 8.02 (brs, 1H), 8.51 (brs, 9H), 8.66 (d, J=8 Hz, 2H); $^{19}$F NMR (DMSO-$d_6$) δ ppm −60.01 (s, 3F); ESIMS found for $C_{29}H_{38}BP_3N_6O_5$ m/z 619.6 (M+H).

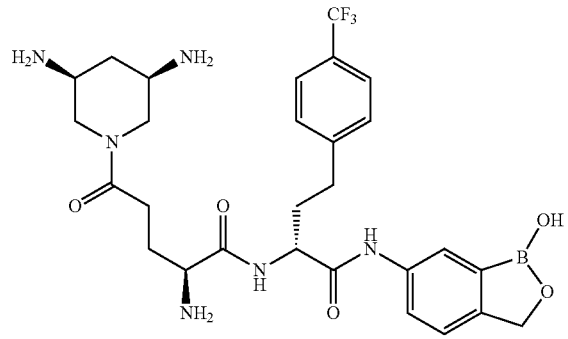

(S)-2-amino-5-((3R,5S)-3,5-diaminopiperidin-1-yl)-
N-((R)-1-(1-hydroxy-1,3-dihydrobenzo[c][1,2]oxaborol-6-ylamino)-1-oxo-4-(4-(trifluoromethyl)phenyl)butan-2-yl)-5-oxopentanamide 49

The final compound was isolated as the hydrochloride salt. $^1$H NMR (DMSO-$d_6$) δ ppm 2.01-2.20 (brs, 4H), 2.50-2.58 (brs, 2H), 2.58-2.71 (brs, 2H), 2.72-2.81 (brs, 2H), 2.81-2.89 (brs, 2H), 3.13-3.32 (brs, 4H), 3.99-4.08 (brs, 1H), 4.46-4.56 (brs, 1H), 4.91 (s, 2H), 7.28 (d, J=8 Hz, 1H), 7.45 (d, J=8 Hz, 2H), 7.58 (d, J=8 Hz, 2H), 7.67 (d, J=8 Hz, 2H), 7.98 (d, J=8 Hz, 2H), 8.37-8.86 (brs, 6H), 8.86-9.09 (brs, 3H), 10.00 (s, 1H); $^{19}$F NMR (DMSO-$d_6$) δ ppm −60.06 (s, 3F); ESIMS found for $C_{28}H_{36}BF_3N_6O_5$ m/z 605.6 (M+H).

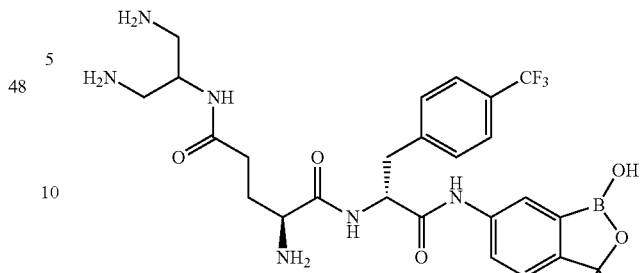

(S)-2-amino-$N^5$-(1,3-diaminopropan-2-yl)-$N^1$–((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)pentanediamide 54

The final compound was isolated as the hydrochloride salt. $^1$H NMR (DMSO-$d_6$) δ ppm 1.38 (s, 6H), 1.75-1.90 (m, 2H), 2.17-2.32 (m, 2H), 2.90 (brs, 2H), 2.98-3.10 (m, 3H), 3.16-3.24 (m, 1H), 3.83-3.92 (m, 1H) 4.17-4.26 (m, 1H), 4.82-4.88 (m, 1H), 7.31 (d, J=8 Hz, 1H), 7.53 (d, J=8 Hz, 2H), 7.58 (d, J=8 Hz, 1H), 7.63 (d, J=8 Hz, 2H), 7.84 (s, 1H), 8.28 (brs, 8H), 8.34 (d, J=8 Hz, 2H), 9.07 (s, 1H), 9.13 (d, J=8 Hz, 1H), 10.40 (s, 1H); $^{19}$F NMR (DMSO-$d_6$) δ ppm −60.05 (s, 3F); ESIMS found for $C_{27}H_{36}BF_3N_6O_5$ m/z 593.6 (M+H).

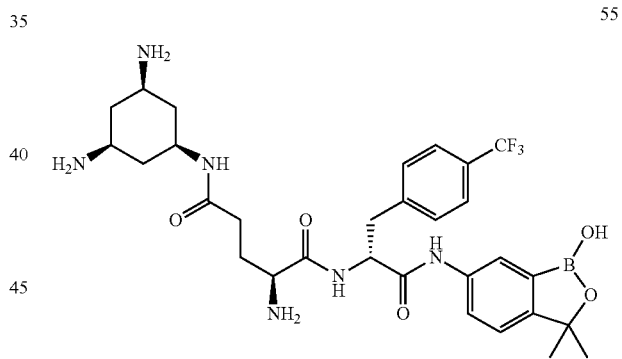

(2S)-2-amino-$N^5$-((3R,5S)-3,5-diaminocyclohexyl)-
$N^1$-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)pentanediamide 55

The final compound was isolated as the hydrochloride salt. $^1$H NMR (DMSO-$d_6$) δ ppm 1.41 (s, 6H), 1.79-1.90 (m, 2H), 2.06-2.18 (m, 4H), 2.32-2.40 (m, 1H), 3.05-3.12 (m, 2H), 3.13-3.22 (m, 3H), 3.26 (d, J=5 Hz, 1H), 3.29 (d, J=6 Hz, 1H), 3.67-3.78 (m, 1H), 3.86-3.92 (m, 1H), 4.79-4.87 (m, 1H), 7.27 (d, J=8 Hz, 1H), 7.53 (d, J=8 Hz, 2H), 7.58 (d, J=8 Hz, 2H), 7.62 (d, J=8 Hz, 1H), 7.87 (s, 1H), 8.13 (d, J=7 Hz, 1H), 8.38 (brs, 9H), 8.99 (d, J=8 Hz, 1H), 10.12 (s, 1H); $^{19}$F NMR (DMSO-$d_6$) δ ppm −60.07 (s, 3F); ESIMS found for $C_{30}H_{40}BF_3N_6O_5$ m/z 633.6 (M+H).

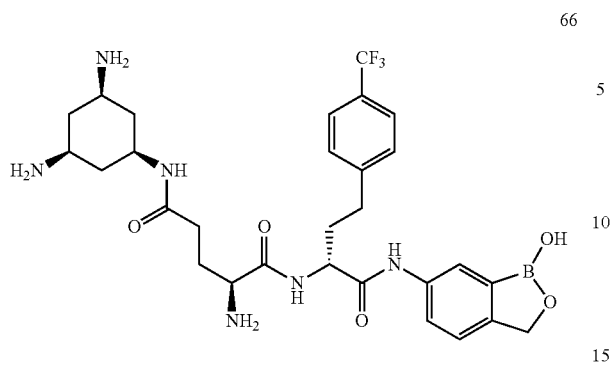

66

(S)-2-amino-N⁵-((1s,3R,5S)-3,5-diaminocyclo-hexyl)-N¹-((R)-1-(1-hydroxy-1,3-dihydrobenzo[c][1,2]oxaborol-6-ylamino)-1-oxo-4-(4-(trifluoromethyl)phenyl)butan-2-yl)pentanediamide 66

The final compound was isolated as the hydrochloride salt. ¹H NMR (DMSO-d₆) δ ppm 1.95-2.08 (m, 6H), 2.08-2.18 (m, 1H), 2.22-2.30 (m, 4H), 2.66-2.75 (m, 1H), 2.75-2.84 (m, 1H), 3.16-3.26 (m, 2H), 3.91-3.98 (m, 2H), 4.46-4.58 (m, 1H), 4.94 (s, 2H), 7.34 (d, 1H), 7.45 (d, 2H), 7.60-7.69 (m, 3H), 8.00 (s, 1H), 8.25-8.41 (m, 10H), 9.12 (d, 1H), 10.34 (s, 1H); ¹⁹F NMR (DMSO-d₆) δ ppm −60.06 (s, 3F); ESIMS found for $C_{29}H_{38}BF_3N_6O_5$ m/z 617.7 (M−H).

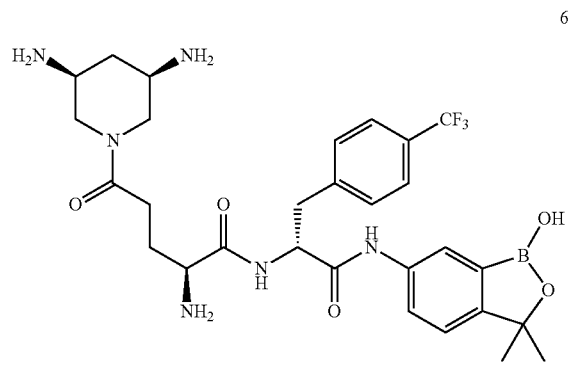

67

(S)-2-amino-5-((3R,5S)-3,5-diaminopiperidin-1-yl)-N-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)-5-oxopentanamide 67

The final compound was isolated as the hydrochloride salt. ¹H NMR (DMSO-d₆) δ ppm 1.44 (s, 6H), 1.69-1.89 (m, 3H), 1.91-2.02 (m, 0.5H), 2.23-2.34 (m, 0.5H), 2.89-3.20 (m, 3H), 3.20-3.34 (m, 2H), 3.80-3.97 (2×brd, 1H), 4.05-4.21 (2×brd, 1H), 4.69 (d, 1H), 4.85-4.97 (m, 1H), 7.37 (dd, 1H), 7.53-7.71 (m, 5H), 7.93 (d, 1H), 8.30 (brs, 3H), 8.54 (brs, 3H), 8.69 (brd, 3H), 9.05-9.19 (m, 2H), 10.50 (s, 0.5H), 10.57 (s, 0.5H); ¹⁹F NMR (DMSO-d₆) δ ppm −60.08 (s, 3F), −60.15 (s, 3F); ESIMS found for $C_{29}H_{38}BF_3N_6O_5$ m/z 617.6 (M−H).

74

(S)-2-amino-5-((3S,5S)-3,5-diamino piperidin-1-yl)-N-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)-5-oxopentanamide 74

The final compound was isolated as the hydrochloride salt. ¹H NMR (DMSO-d₆) δ ppm 1.44 (s, 6H), 1.82-1.92 (m, 1H), 1.92-2.02 (m, 1H), 2.16-2.25 (m, 2H), 2.46-2.56 (m, 1H), 2.56-2.67 (m, 1H), 3.09-3.20 (m, 2H), 3.28-3.35 (dd, 2H), 3.55-3.86 (m, 4H), 4.00 (t, 1H), 4.86 (dd, 1H), 7.28 (d, 1H), 7.52-7.66 (m, 5H), 7.89 (s, 1H), 8.49 (brs, 9H), 8.98 (d, 1H), 10.11 (s, 1H); ¹⁹F NMR (DMSO-d₆) δ ppm −60.08 (s, 3F); ESIMS found for $C_{29}H_{38}BF_3N_6O_5$ m/z 617.7 (M+H).

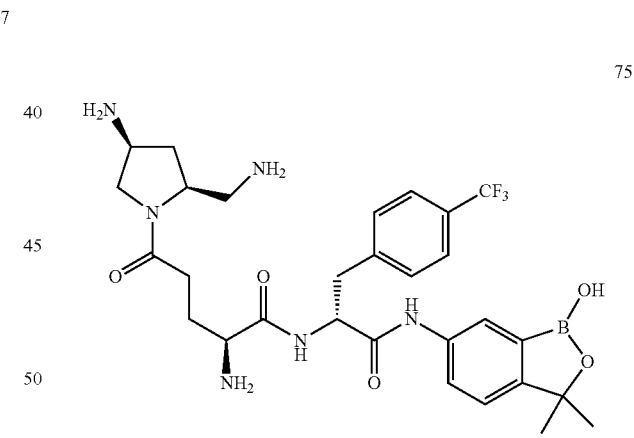

75

(S)-2-amino-5-((2S,4S)-4-amino-2-(aminomethyl)pyrrolidin-1-yl)-N-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)-5-oxopentanamide 75

The final compound was isolated as the hydrochloride salt. ¹H NMR (DMSO-d₆) δ ppm 1.46 (s, 6H), 1.82-1.97 (m, 2H), 2.08-2.16 (m, 1H), 2.30-2.64 (m, 4H), 3.19-3.28 (m, 1H), 3.29-3.38 (m, 1H), 3.38-3.46 (m, 1H), 3.55-3.66 (m, 1H), 3.72-3.84 (m, 1H), 3.89-4.03 (m, 2H), 4.22-4.35 (m, 1H), 4.86-4.97 (m, 1H), 7.28-7.37 (m, 2H), 7.54-7.72 (m, 5H), 7.92 (s, 1H), 8.42 (brs, 8H), 9.10 (brs, 1H), 10.17 (s, 1H); $^{19}$F NMR (DMSO-$d_6$) δ ppm −60.02 (s, 3F); ESIMS found for $C_{29}H_{38}BF_3N_6O_5$ m/z 617.7 (M−H).

(S)-2-amino-5-(3-amino-2-(aminomethyl)propanamido)-N-((R)-1-(1-hydroxy-3,3-dimethyl-1,3-dihydrobenzo[c][1,2]oxaborol-6-ylamino)-1-oxo-3-(4-(trifluoromethyl)phenyl)propan-2-yl)pentanamide 104

The final compound was isolated as the hydrochloride salt. $^1$H NMR (DMSO-$d_6$) δ ppm 0.81-0.93 (m, 1H), 1.12-1.23 (m, 1H), 1.42 (s, 6H), 1.44-1.54 (m, 1H), 2.80-3.03 (m, 4H), 31.0 (brs, 5H), 3.30 (dd, 1H), 3.80 (brd, 1H), 4.92 (dd, 1H), 7.36 (d, 1H), 7.59 (d, 2H), 7.67 (d, 3H), 7.92 (s, 1H), 8.26 (brs, 10H), 8.60 (t, 1H), 9.11 (brs, 1H), 9.17 (d, 1H), 10.54 (s, 1H); $^{19}$F NMR (DMSO-$d_6$) δ ppm −60.06 (s, 3F); ESIMS found for $C_{28}H_{38}BF_3N_6O_5$ m/z 605.6 (M−H).

Illustrative compounds of Formula (I) are shown in Table 1. Some structures are shown with defined configurations at selected stereocenters but the shown stereochemistries are not meant to be limiting and all possible stereoisomers of the shown structures are encompassed in the present invention. Compounds of any absolute and relative configurations at the stereocenters as well as mixtures of enantiomers and diastereoisomers of any given structure are also encompassed in the present invention.

TABLE 1

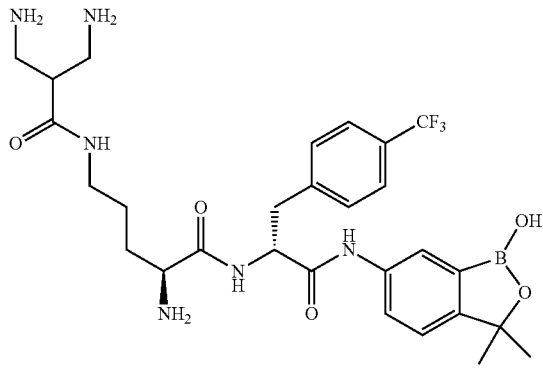

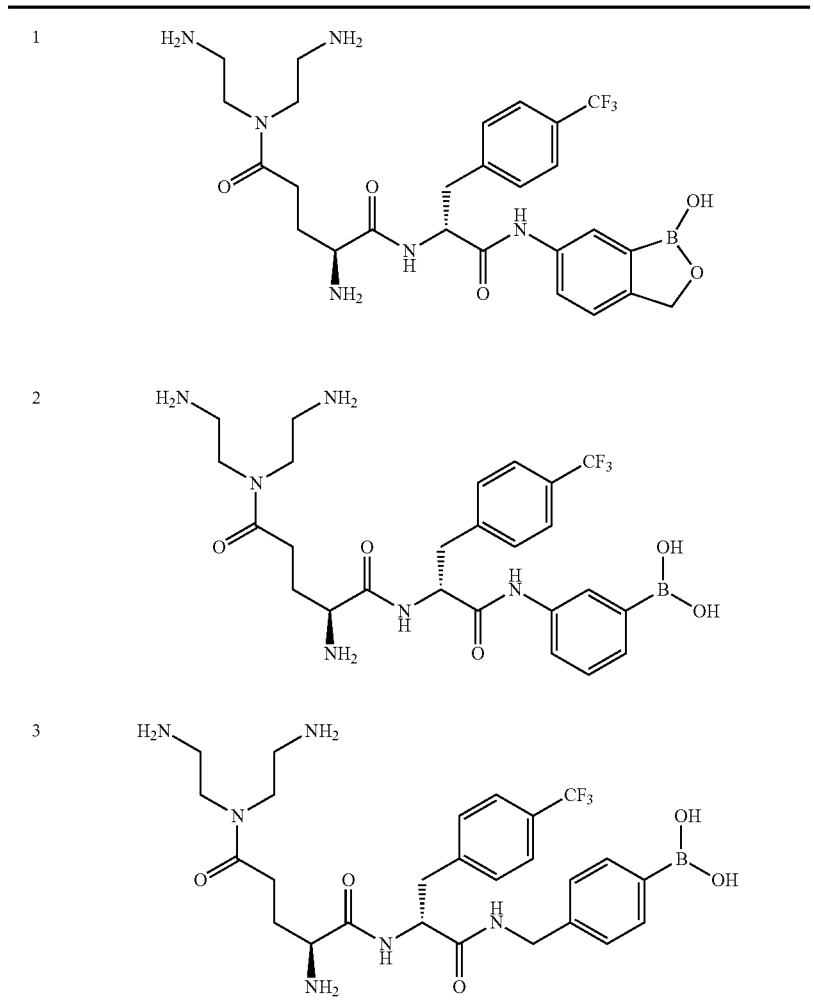

TABLE 1-continued
4 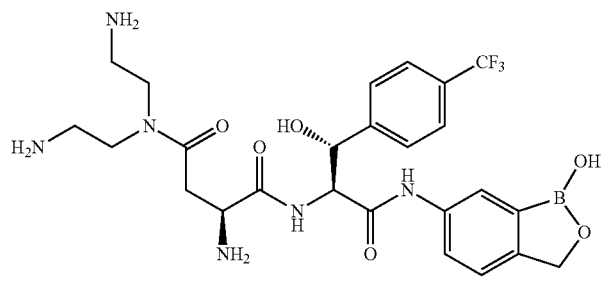 [SMILES: NCCN(CCN)C(=O)C[C@H](N)C(=O)N[C@H](C(=O)Nc1ccc2c(c1)B(O)OC2)[C@H](O)c1ccc(C(F)(F)F)cc1]
5 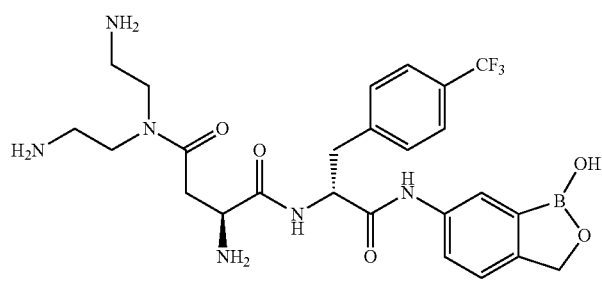 [SMILES: NCCN(CCN)C(=O)C[C@H](N)C(=O)N[C@H](Cc1ccc(C(F)(F)F)cc1)C(=O)Nc1ccc2c(c1)B(O)OC2]
6 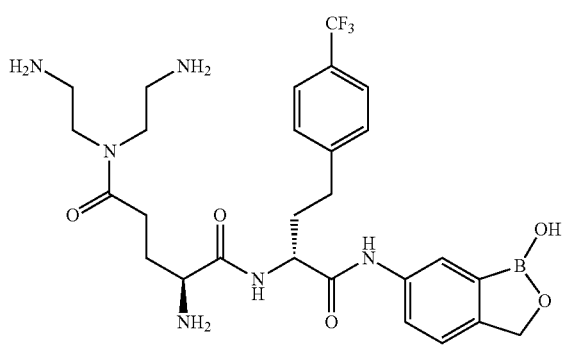 [SMILES: NCCN(CCN)C(=O)CC[C@H](N)C(=O)N[C@H](CCc1ccc(C(F)(F)F)cc1)C(=O)Nc1ccc2c(c1)B(O)OC2]
7 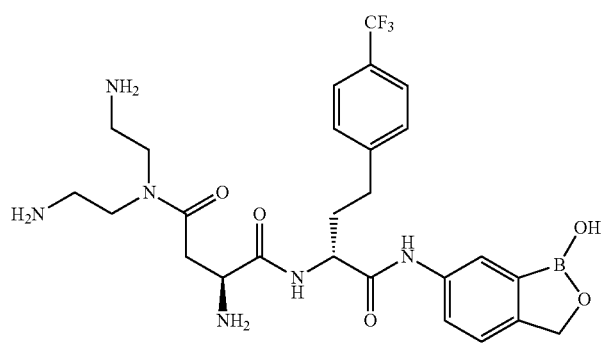 [SMILES: NCCN(CCN)C(=O)C[C@H](N)C(=O)N[C@H](CCc1ccc(C(F)(F)F)cc1)C(=O)Nc1ccc2c(c1)B(O)OC2]
8 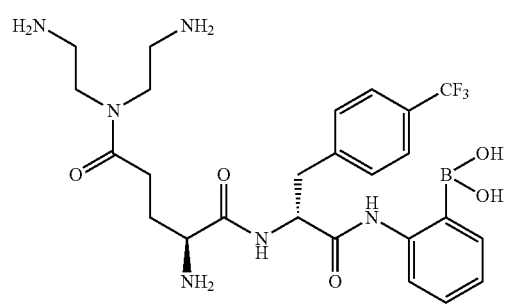 [SMILES: NCCN(CCN)C(=O)CC[C@H](N)C(=O)N[C@H](Cc1ccc(C(F)(F)F)cc1)C(=O)Nc1ccccc1B(O)O]

TABLE 1-continued
9 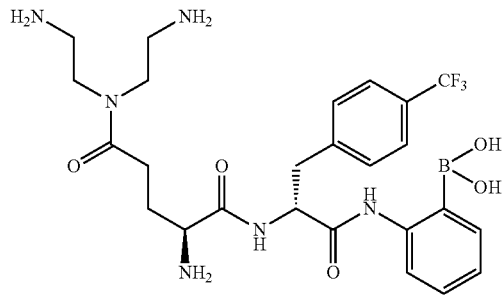 [SMILES: NCCN(CCN)C(=O)CC[C@H](N)C(=O)N[C@H](Cc1ccc(C(F)(F)F)cc1)C(=O)Nc1ccccc1B(O)O]
10 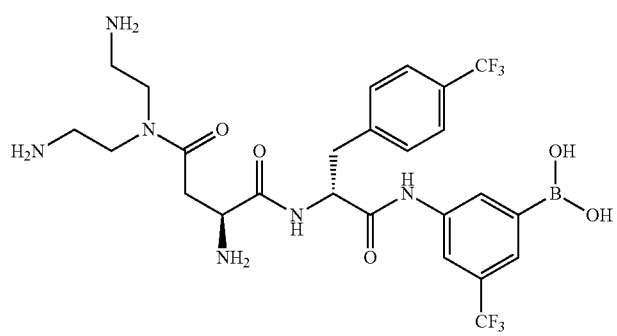 [SMILES: NCCN(CCN)C(=O)C[C@H](N)C(=O)N[C@H](Cc1ccc(C(F)(F)F)cc1)C(=O)Nc1cc(B(O)O)cc(C(F)(F)F)c1]
11 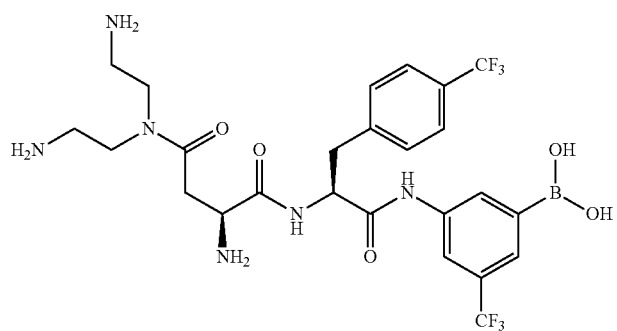 [SMILES: NCCN(CCN)C(=O)C[C@H](N)C(=O)N[C@@H](Cc1ccc(C(F)(F)F)cc1)C(=O)Nc1cc(B(O)O)cc(C(F)(F)F)c1]
12 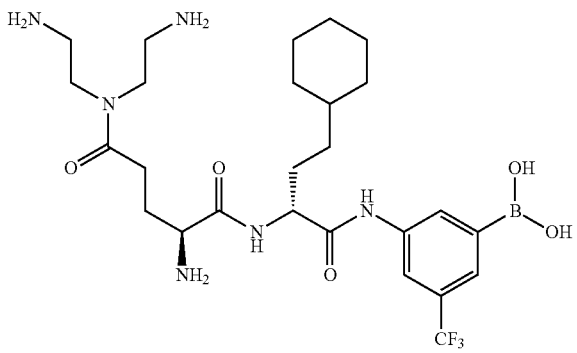 [SMILES: NCCN(CCN)C(=O)CC[C@H](N)C(=O)N[C@H](CCC1CCCCC1)C(=O)Nc1cc(B(O)O)cc(C(F)(F)F)c1]

TABLE 1-continued
13
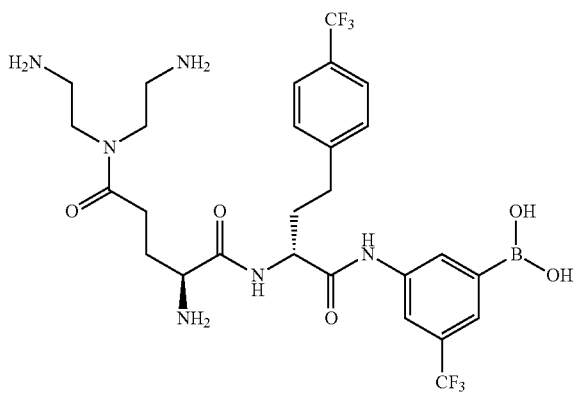 [SMILES: NCCN(CCN)C(=O)CC[C@H](N)C(=O)N[C@H](CCc1ccc(C(F)(F)F)cc1)C(=O)Nc1cc(B(O)O)cc(C(F)(F)F)c1]
14
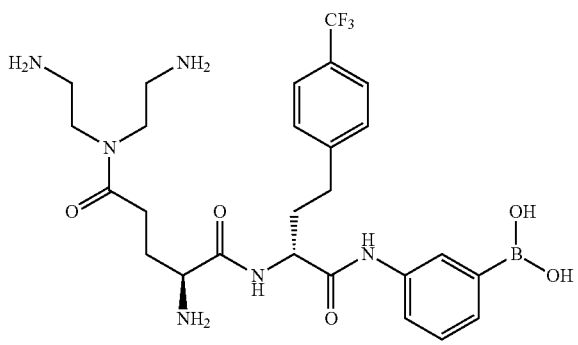 [SMILES: NCCN(CCN)C(=O)CC[C@H](N)C(=O)N[C@H](CCc1ccc(C(F)(F)F)cc1)C(=O)Nc1cccc(B(O)O)c1]
15
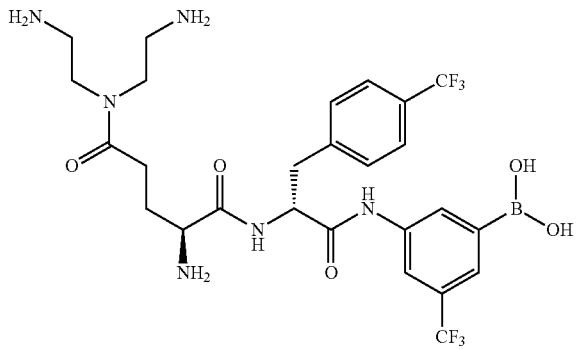 [SMILES: NCCN(CCN)C(=O)CC[C@H](N)C(=O)N[C@H](Cc1ccc(C(F)(F)F)cc1)C(=O)Nc1cc(B(O)O)cc(C(F)(F)F)c1]
16
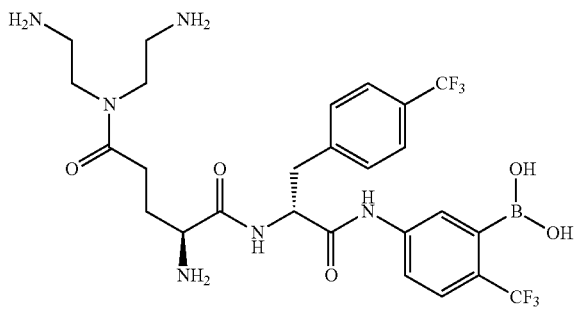 [SMILES: NCCN(CCN)C(=O)CC[C@H](N)C(=O)N[C@H](Cc1ccc(C(F)(F)F)cc1)C(=O)Nc1ccc(C(F)(F)F)c(B(O)O)c1]

TABLE 1-continued
17 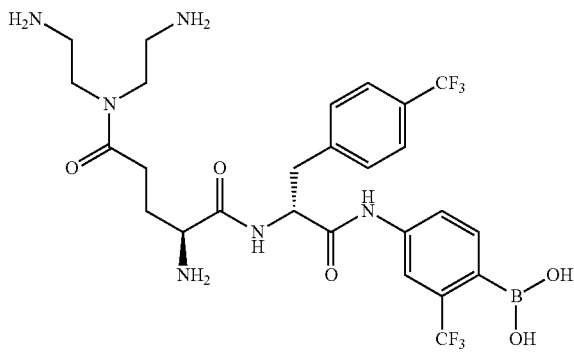 [SMILES: NCCN(CCN)C(=O)CC[C@H](N)C(=O)N[C@H](Cc1ccc(C(F)(F)F)cc1)C(=O)Nc1ccc(B(O)O)c(C(F)(F)F)c1]
18 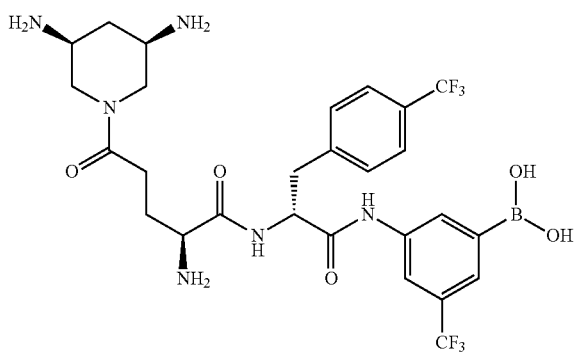 [SMILES: N[C@@H]1C[C@H](N)CN(C(=O)CC[C@H](N)C(=O)N[C@H](Cc2ccc(C(F)(F)F)cc2)C(=O)Nc2cc(B(O)O)cc(C(F)(F)F)c2)C1]
19 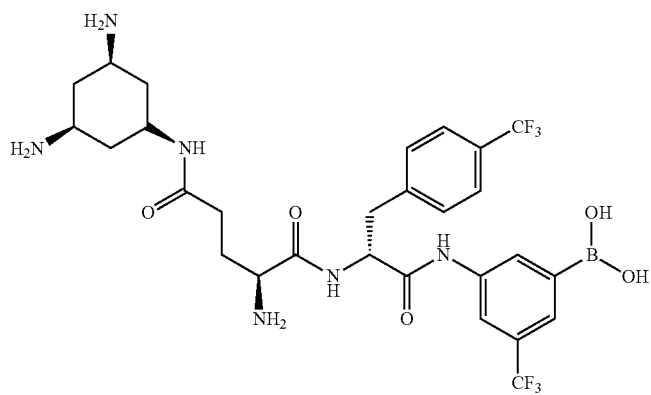
20 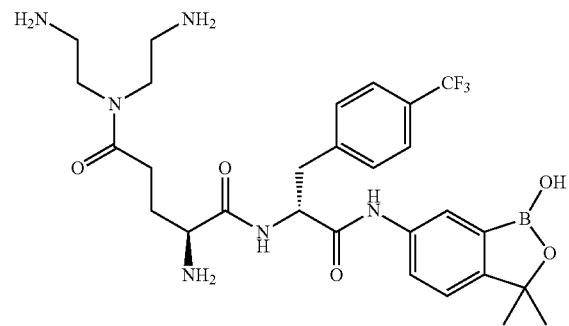 [SMILES: CC1(C)OB(O)c2cc(NC(=O)[C@@H](Cc3ccc(C(F)(F)F)cc3)NC(=O)[C@@H](N)CCC(=O)N(CCN)CCN)ccc21]

TABLE 1-continued
| 21 | 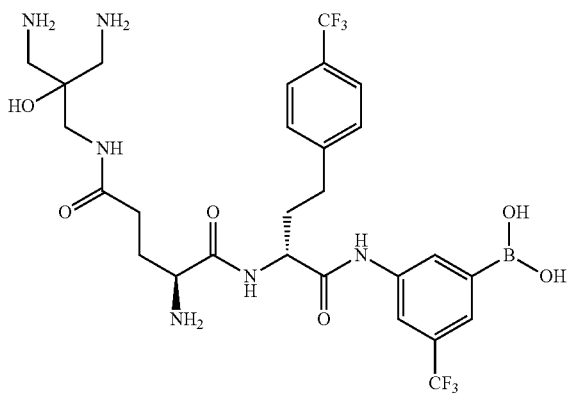 [SMILES: NCC(O)(CN)CNC(=O)CC[C@H](N)C(=O)N[C@H](CCc1ccc(C(F)(F)F)cc1)C(=O)Nc1cc(B(O)O)cc(C(F)(F)F)c1] |
| --- | --- |
| 22 | 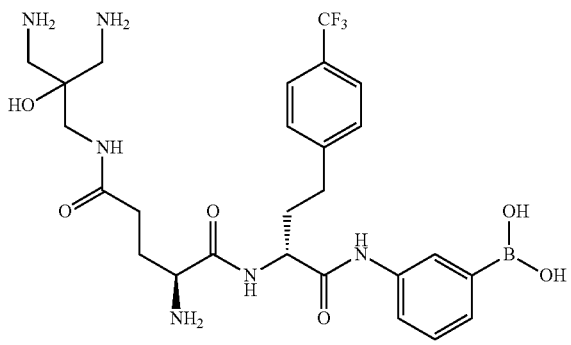 [SMILES: NCC(O)(CN)CNC(=O)CC[C@H](N)C(=O)N[C@H](CCc1ccc(C(F)(F)F)cc1)C(=O)Nc1cccc(B(O)O)c1] |
| 23 | 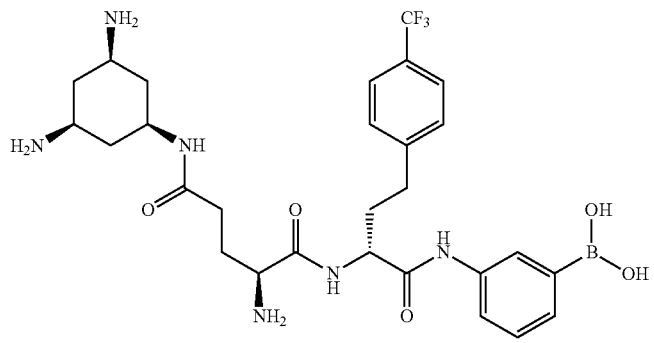 [SMILES: N[C@@H]1C[C@H](N)C[C@H](NC(=O)CC[C@H](N)C(=O)N[C@H](CCc2ccc(C(F)(F)F)cc2)C(=O)Nc2cccc(B(O)O)c2)C1] |
| 24 | 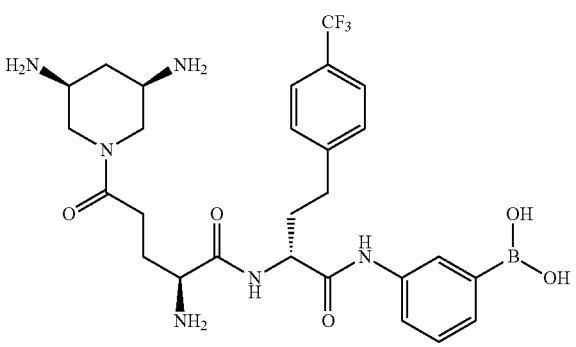 [SMILES: N[C@@H]1C[C@H](N)CN(C(=O)CC[C@H](N)C(=O)N[C@H](CCc2ccc(C(F)(F)F)cc2)C(=O)Nc2cccc(B(O)O)c2)C1] |

TABLE 1-continued
25 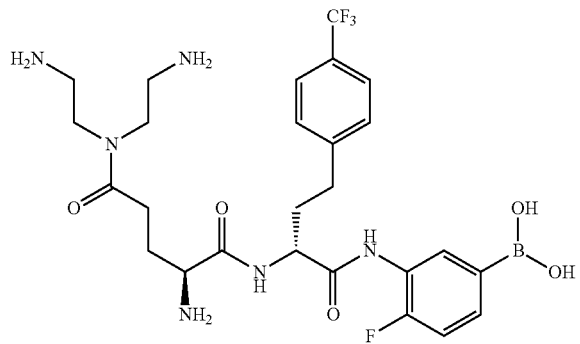 [SMILES: NCCN(CCN)C(=O)CC[C@H](N)C(=O)N[C@H](CCc1ccc(C(F)(F)F)cc1)C(=O)Nc1cc(B(O)O)ccc1F]
26 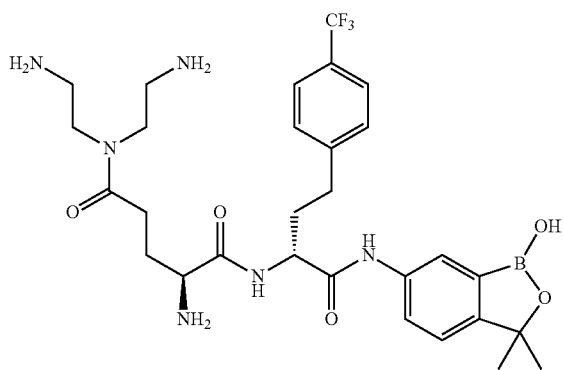
27 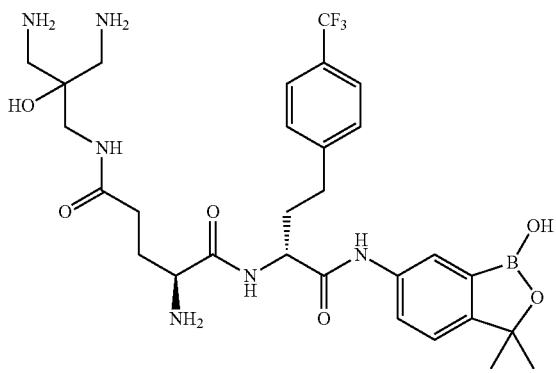 [SMILES: CC1(C)OB(O)c2cc(NC(=O)[C@@H](CCc3ccc(C(F)(F)F)cc3)NC(=O)[C@@H](N)CCC(=O)NCC(O)(CN)CN)ccc21]
28 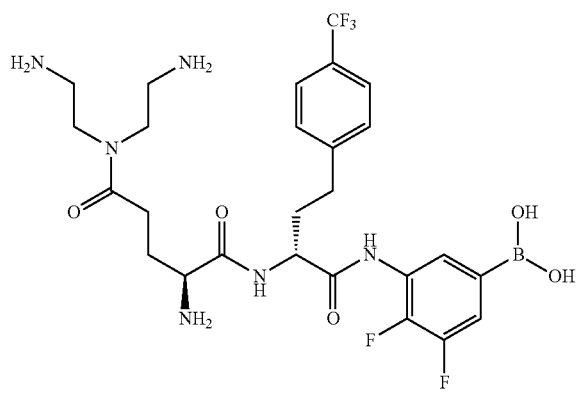 [SMILES: NCCN(CCN)C(=O)CC[C@H](N)C(=O)N[C@H](CCc1ccc(C(F)(F)F)cc1)C(=O)Nc1cc(B(O)O)cc(F)c1F]

TABLE 1-continued
29
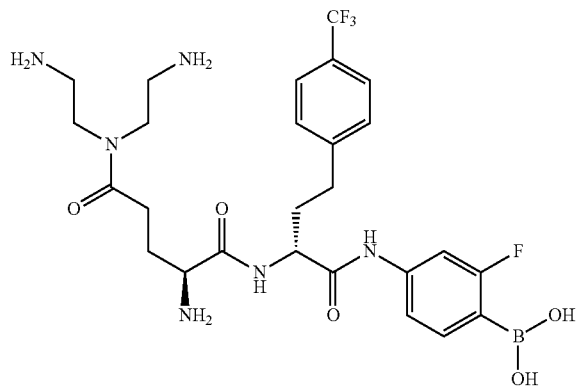 [SMILES: NCCN(CCN)C(=O)CC[C@H](N)C(=O)N[C@H](CCc1ccc(C(F)(F)F)cc1)C(=O)Nc1ccc(B(O)O)c(F)c1]
30
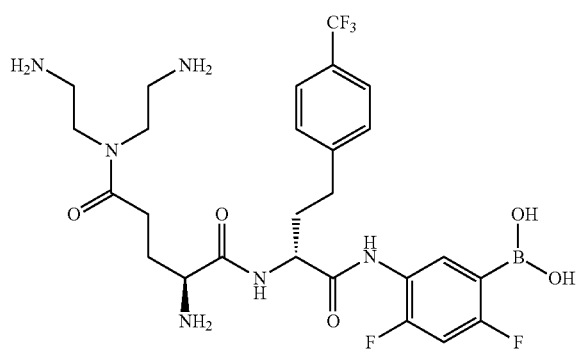 [SMILES: NCCN(CCN)C(=O)CC[C@H](N)C(=O)N[C@H](CCc1ccc(C(F)(F)F)cc1)C(=O)Nc1cc(B(O)O)c(F)cc1F]
31
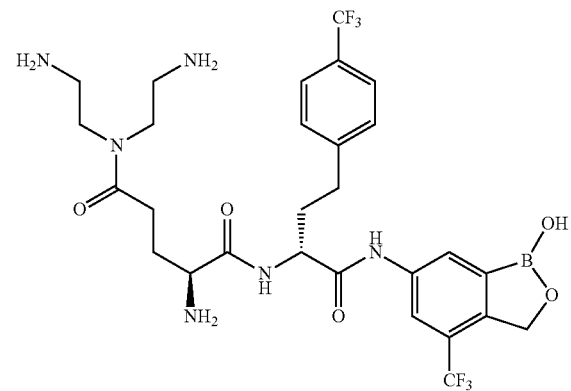 [SMILES: NCCN(CCN)C(=O)CC[C@H](N)C(=O)N[C@H](CCc1ccc(C(F)(F)F)cc1)C(=O)Nc1cc2c(c(C(F)(F)F)c1)COB2O]
32
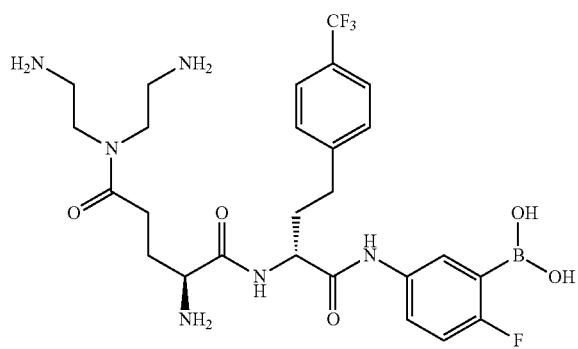 [SMILES: NCCN(CCN)C(=O)CC[C@H](N)C(=O)N[C@H](CCc1ccc(C(F)(F)F)cc1)C(=O)Nc1ccc(F)c(B(O)O)c1]

TABLE 1-continued
33 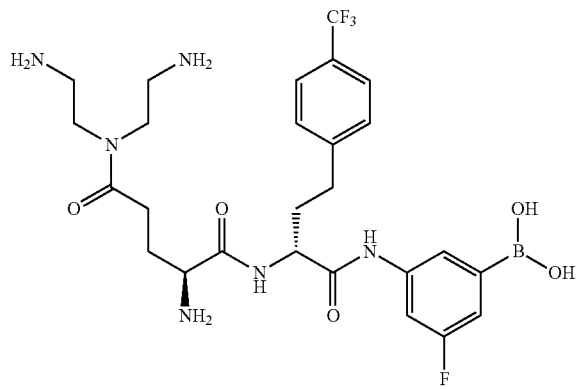 [SMILES: NCCN(CCN)C(=O)CC[C@H](N)C(=O)N[C@H](CCc1ccc(C(F)(F)F)cc1)C(=O)Nc1cc(F)cc(B(O)O)c1]
34 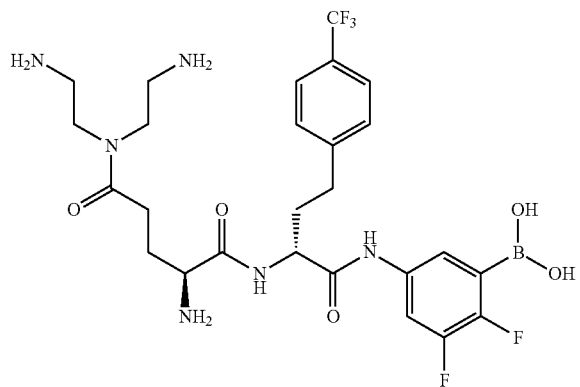 [SMILES: NCCN(CCN)C(=O)CC[C@H](N)C(=O)N[C@H](CCc1ccc(C(F)(F)F)cc1)C(=O)Nc1cc(F)c(F)c(B(O)O)c1]
35 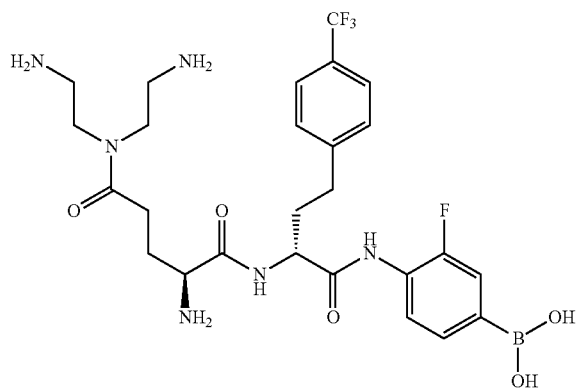 [SMILES: NCCN(CCN)C(=O)CC[C@H](N)C(=O)N[C@H](CCc1ccc(C(F)(F)F)cc1)C(=O)Nc1ccc(B(O)O)cc1F]
36 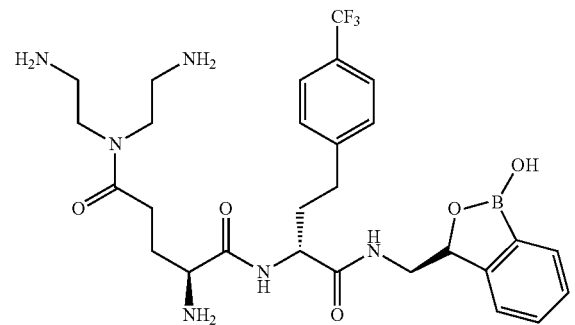

TABLE 1-continued
37 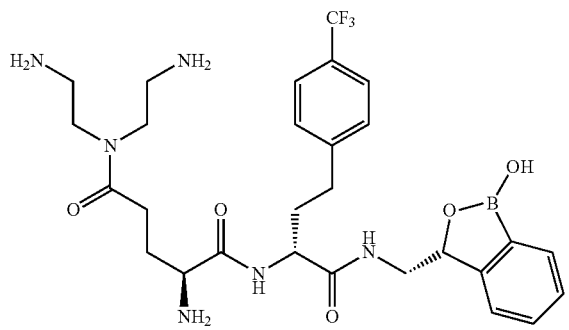
38 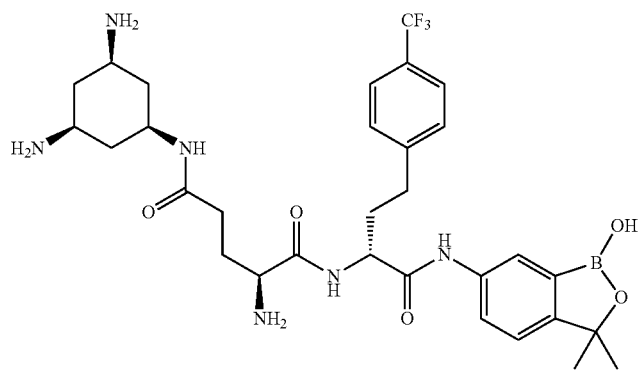 [SMILES: CC1(C)OB(O)c2cc(NC(=O)[C@@H](CCc3ccc(C(F)(F)F)cc3)NC(=O)[C@@H](N)CCC(=O)N[C@@H]3C[C@H](N)C[C@H](N)C3)ccc21]
39 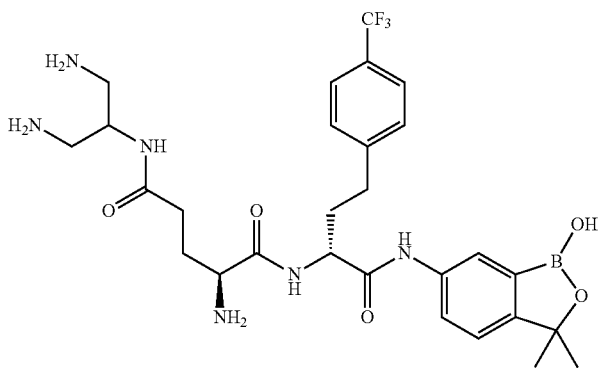 [SMILES: CC1(C)OB(O)c2cc(NC(=O)[C@@H](CCc3ccc(C(F)(F)F)cc3)NC(=O)[C@@H](N)CCC(=O)NC(CN)CN)ccc21]
40 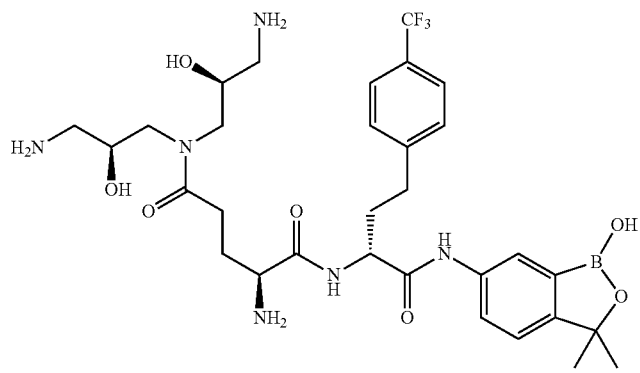 [SMILES: CC1(C)OB(O)c2cc(NC(=O)[C@@H](CCc3ccc(C(F)(F)F)cc3)NC(=O)[C@@H](N)CCC(=O)N(C[C@@H](O)CN)C[C@@H](O)CN)ccc21]

TABLE 1-continued
41
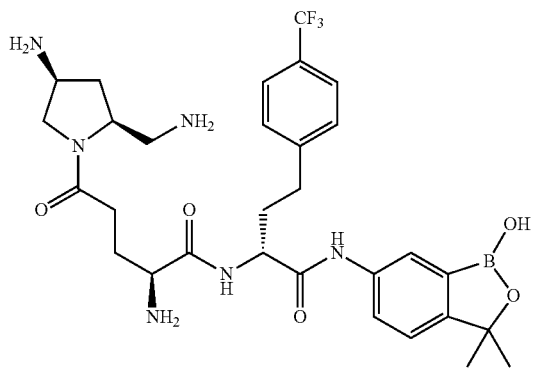 [SMILES: CC1(C)OB(O)c2cc(NC(=O)[C@@H](CCc3ccc(C(F)(F)F)cc3)NC(=O)[C@@H](N)CCC(=O)N3C[C@@H](N)C[C@H]3CN)ccc21]
42
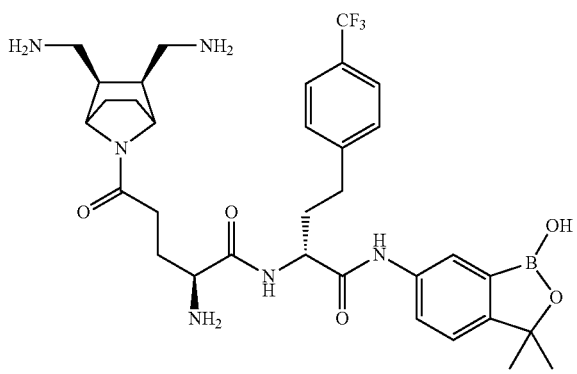 [SMILES: CC1(C)OB(O)c2cc(NC(=O)[C@@H](CCc3ccc(C(F)(F)F)cc3)NC(=O)[C@@H](N)CCC(=O)N3C4CCC3[C@H](CN)[C@@H]4CN)ccc21]
43
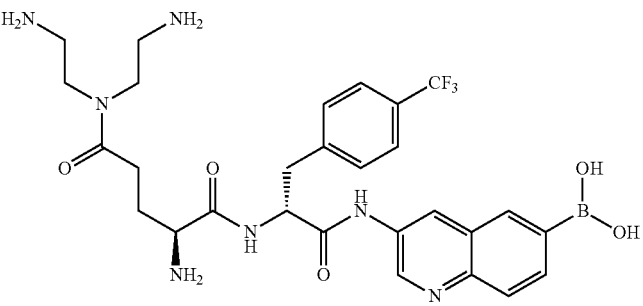 [SMILES: NCCN(CCN)C(=O)CC[C@H](N)C(=O)N[C@H](Cc1ccc(C(F)(F)F)cc1)C(=O)Nc1cnc2ccc(B(O)O)cc2c1]
44
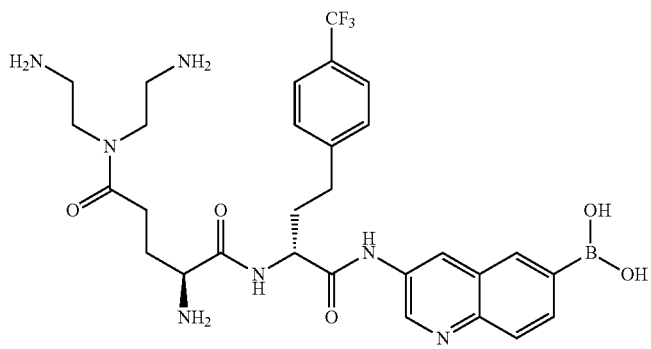 [SMILES: NCCN(CCN)C(=O)CC[C@H](N)C(=O)N[C@H](CCc1ccc(C(F)(F)F)cc1)C(=O)Nc1cnc2ccc(B(O)O)cc2c1]

TABLE 1-continued
45 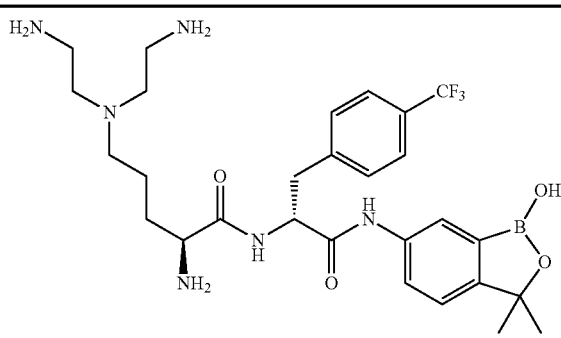
46 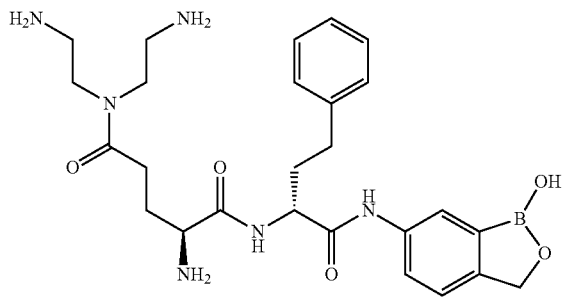 [SMILES: NCCN(CCN)C(=O)CC[C@H](N)C(=O)N[C@H](CCc1ccccc1)C(=O)Nc1ccc2c(c1)B(O)OC2]
47 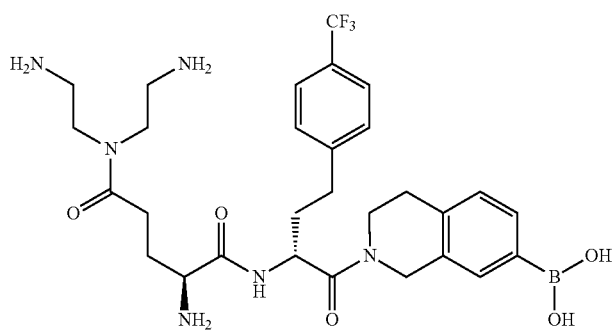 [SMILES: NCCN(CCN)C(=O)CC[C@H](N)C(=O)N[C@H](CCc1ccc(C(F)(F)F)cc1)C(=O)N1CCc2ccc(B(O)O)cc2C1]
48 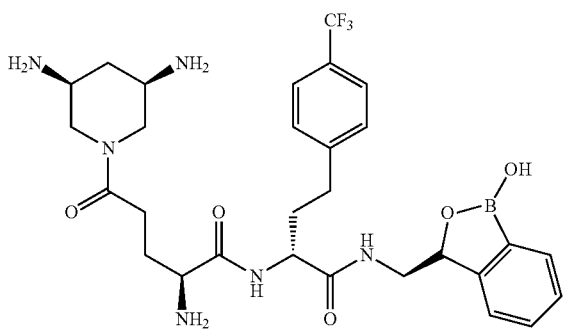
49 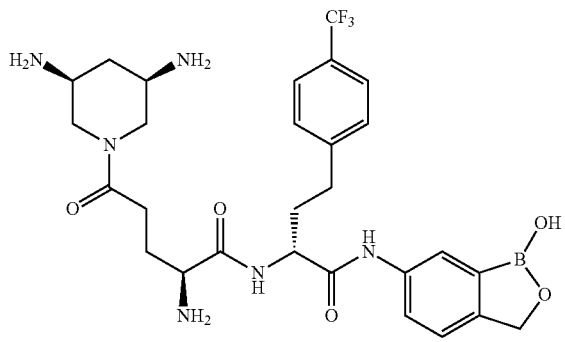 [SMILES: N[C@@H]1C[C@H](N)CN(C(=O)CC[C@H](N)C(=O)N[C@H](CCc2ccc(C(F)(F)F)cc2)C(=O)Nc2ccc3c(c2)B(O)OC3)C1]

TABLE 1-continued
| 50 | 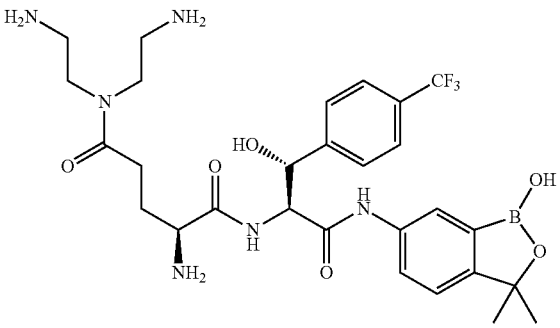 [SMILES: CC1(C)OB(O)c2cc(NC(=O)[C@@H](NC(=O)[C@@H](N)CCC(=O)N(CCN)CCN)[C@H](O)c3ccc(C(F)(F)F)cc3)ccc21] |
| --- | --- |
| 51 | 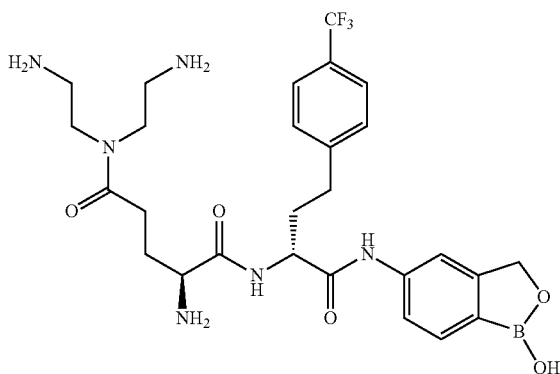 [SMILES: NCCN(CCN)C(=O)CC[C@H](N)C(=O)N[C@H](CCc1ccc(C(F)(F)F)cc1)C(=O)Nc1ccc2c(c1)COB2O] |
| 52 | 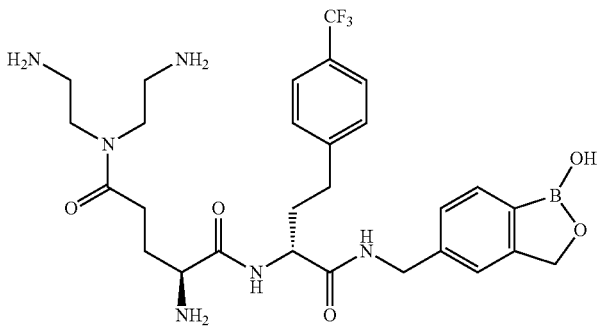 [SMILES: NCCN(CCN)C(=O)CC[C@H](N)C(=O)N[C@H](CCc1ccc(C(F)(F)F)cc1)C(=O)NCc1ccc2c(c1)COB2O] |
| 53 | 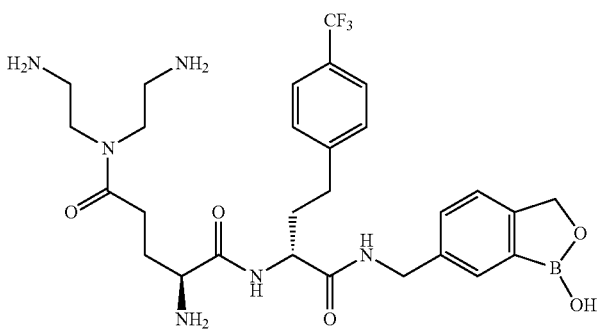 [SMILES: NCCN(CCN)C(=O)CC[C@H](N)C(=O)N[C@H](CCc1ccc(C(F)(F)F)cc1)C(=O)NCc1ccc2c(c1)B(O)OC2] |

TABLE 1-continued
54 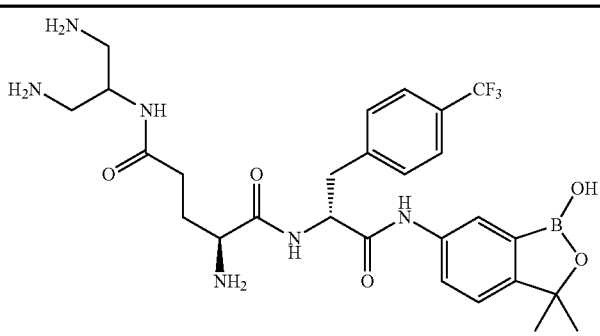
55 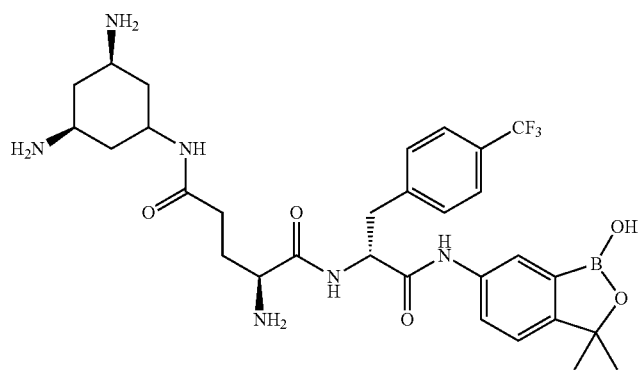 [SMILES: CC1(C)OB(O)c2cc(NC(=O)[C@@H](Cc3ccc(C(F)(F)F)cc3)NC(=O)[C@@H](N)CCC(=O)NC3C[C@@H](N)C[C@@H](N)C3)ccc21]
56 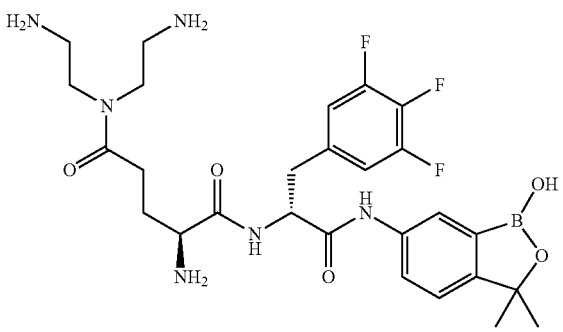 [SMILES: CC1(C)OB(O)c2cc(NC(=O)[C@@H](Cc3cc(F)c(F)c(F)c3)NC(=O)[C@@H](N)CCC(=O)N(CCN)CCN)ccc21]
57 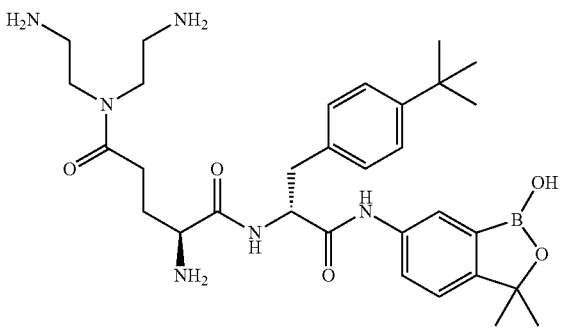 [SMILES: CC(C)(C)c1ccc(C[C@@H](NC(=O)[C@@H](N)CCC(=O)N(CCN)CCN)C(=O)Nc2ccc3c(c2)B(O)OC3(C)C)cc1]
58 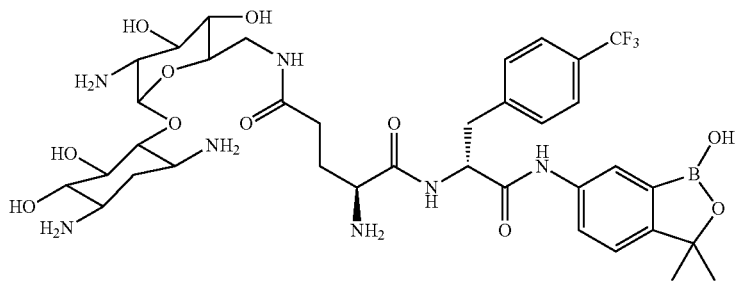 [SMILES: CC1(C)OB(O)c2cc(NC(=O)[C@@H](Cc3ccc(C(F)(F)F)cc3)NC(=O)[C@@H](N)CCC(=O)NCC3OC(OC4C(N)CC(N)C(O)C4O)C(N)C(O)C3O)ccc21]

TABLE 1-continued
| 59 | 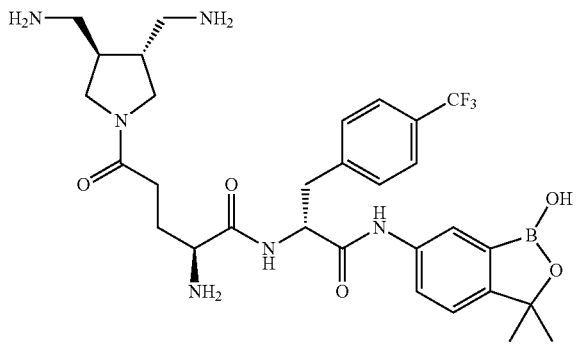 [SMILES: CC1(C)OB(O)c2cc(NC(=O)[C@@H](Cc3ccc(C(F)(F)F)cc3)NC(=O)[C@@H](N)CCC(=O)N3C[C@@H](CN)[C@H](CN)C3)ccc21] |
| 60 | 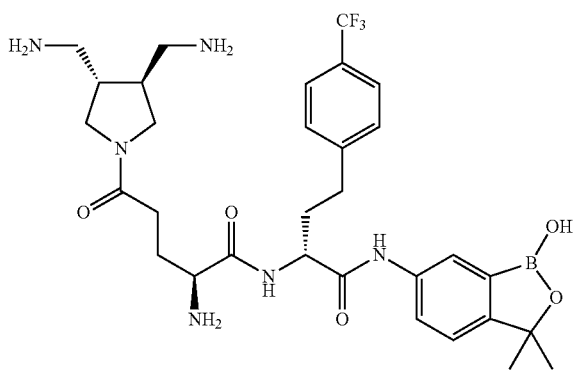 [SMILES: CC1(C)OB(O)c2cc(NC(=O)[C@@H](CCc3ccc(C(F)(F)F)cc3)NC(=O)[C@@H](N)CCC(=O)N3C[C@H](CN)[C@@H](CN)C3)ccc21] |
| 61 | 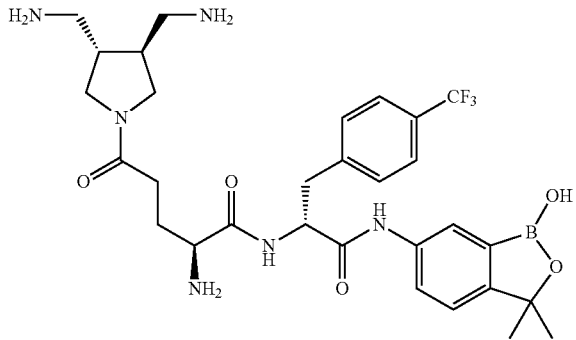 [SMILES: CC1(C)OB(O)c2cc(NC(=O)[C@@H](Cc3ccc(C(F)(F)F)cc3)NC(=O)[C@@H](N)CCC(=O)N3C[C@H](CN)[C@@H](CN)C3)ccc21] |
| 62 | 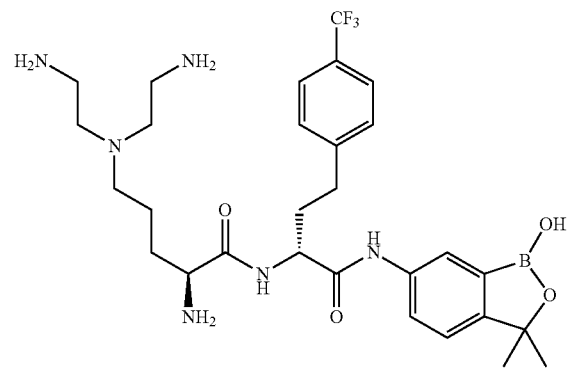 [SMILES: CC1(C)OB(O)c2cc(NC(=O)[C@@H](CCc3ccc(C(F)(F)F)cc3)NC(=O)[C@@H](N)CCCN(CCN)CCN)ccc21] |

TABLE 1-continued
63
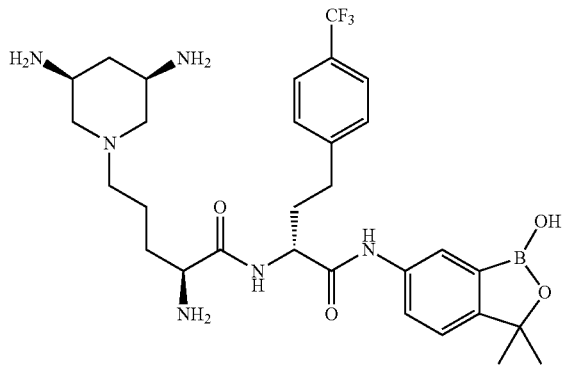 [SMILES: CC1(C)OB(O)c2cc(NC(=O)[C@@H](CCc3ccc(C(F)(F)F)cc3)NC(=O)[C@@H](N)CCCN3C[C@H](N)C[C@H](N)C3)ccc21]
64
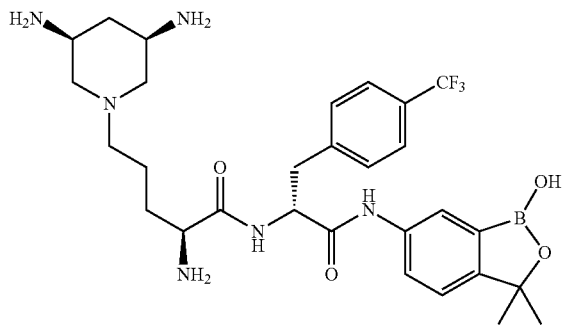 [SMILES: CC1(C)OB(O)c2cc(NC(=O)[C@@H](Cc3ccc(C(F)(F)F)cc3)NC(=O)[C@@H](N)CCCN3C[C@H](N)C[C@H](N)C3)ccc21]
65
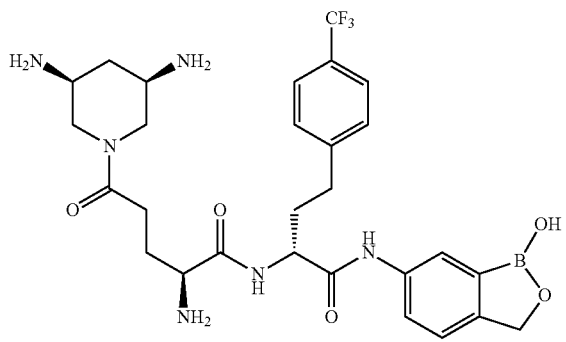 [SMILES: N[C@@H]1C[C@H](N)CN(C(=O)CC[C@H](N)C(=O)N[C@H](CCc2ccc(C(F)(F)F)cc2)C(=O)Nc2ccc3c(c2)B(O)OC3)C1]
66
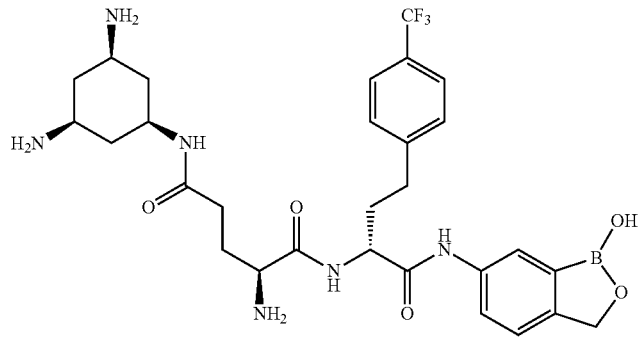 [SMILES: N[C@@H]1C[C@H](N)C[C@H](NC(=O)CC[C@H](N)C(=O)N[C@H](CCc2ccc(C(F)(F)F)cc2)C(=O)Nc2ccc3c(c2)B(O)OC3)C1]

TABLE 1-continued
| 67 | 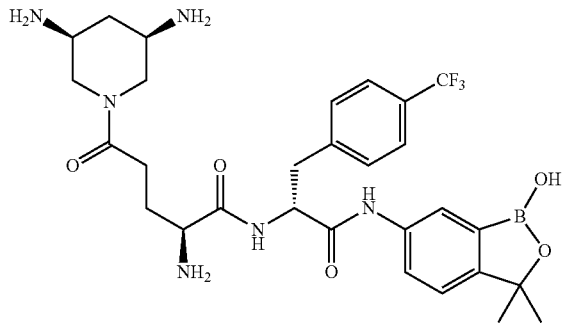 [SMILES: CC1(C)OB(O)c2cc(NC(=O)[C@@H](Cc3ccc(C(F)(F)F)cc3)NC(=O)[C@@H](N)CCC(=O)N3C[C@H](N)C[C@H](N)C3)ccc21] |
| --- | --- |
| 68 | 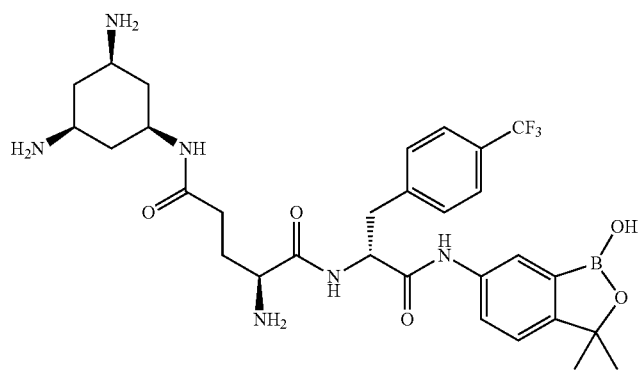 [SMILES: CC1(C)OB(O)c2cc(NC(=O)[C@@H](Cc3ccc(C(F)(F)F)cc3)NC(=O)[C@@H](N)CCC(=O)N[C@@H]3C[C@H](N)C[C@H](N)C3)ccc21] |
| 69 | 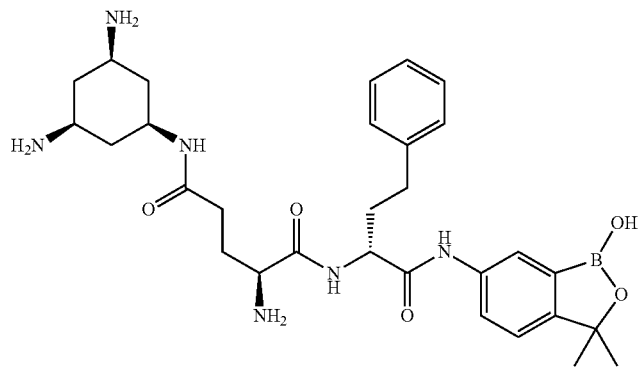 [SMILES: CC1(C)OB(O)c2cc(NC(=O)[C@@H](CCc3ccccc3)NC(=O)[C@@H](N)CCC(=O)N[C@@H]3C[C@H](N)C[C@H](N)C3)ccc21] |
| 70 | 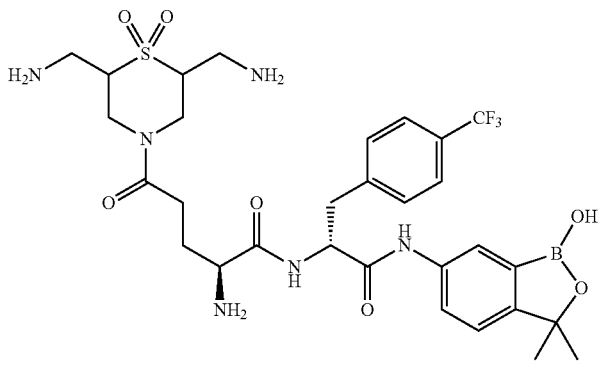 [SMILES: CC1(C)OB(O)c2cc(NC(=O)[C@@H](Cc3ccc(C(F)(F)F)cc3)NC(=O)[C@@H](N)CCC(=O)N3CC(CN)S(=O)(=O)C(CN)C3)ccc21] |

TABLE 1-continued
| | |
|---|---|
| 71 | 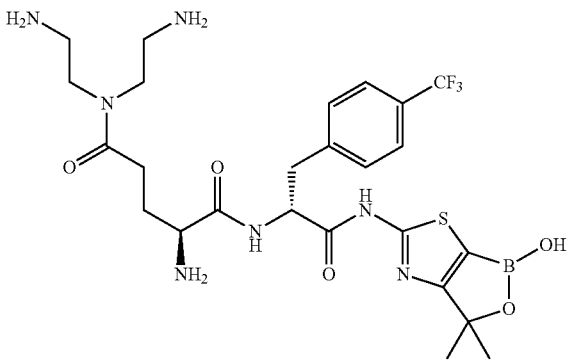 [SMILES: CC1(C)OB(O)c2sc(NC(=O)[C@@H](Cc3ccc(C(F)(F)F)cc3)NC(=O)[C@@H](N)CCC(=O)N(CCN)CCN)nc21] |
| 72 | 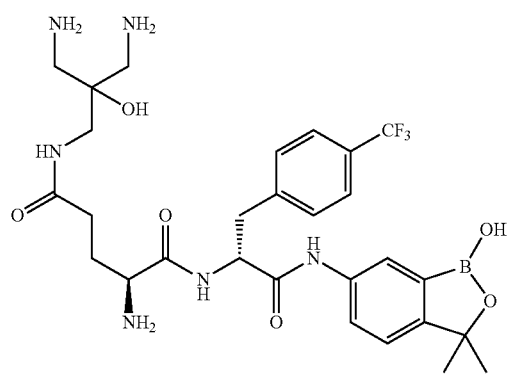 [SMILES: CC1(C)OB(O)c2cc(NC(=O)[C@@H](Cc3ccc(C(F)(F)F)cc3)NC(=O)[C@@H](N)CCC(=O)NCC(O)(CN)CN)ccc21] |
| 73 | 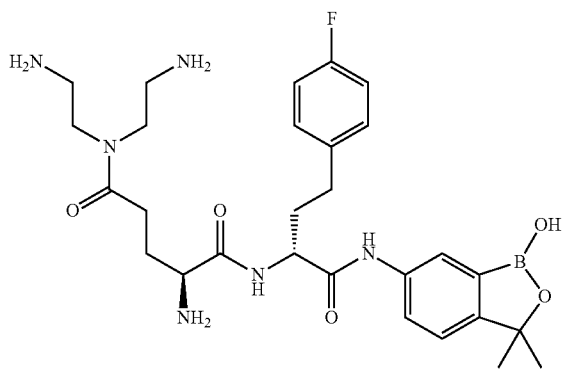 [SMILES: CC1(C)OB(O)c2cc(NC(=O)[C@@H](CCc3ccc(F)cc3)NC(=O)[C@@H](N)CCC(=O)N(CCN)CCN)ccc21] |
| 74 | 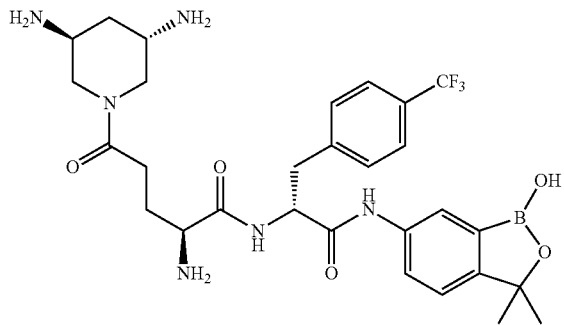 [SMILES: CC1(C)OB(O)c2cc(NC(=O)[C@@H](Cc3ccc(C(F)(F)F)cc3)NC(=O)[C@@H](N)CCC(=O)N3C[C@@H](N)C[C@H](N)C3)ccc21] |

TABLE 1-continued
| 75 | 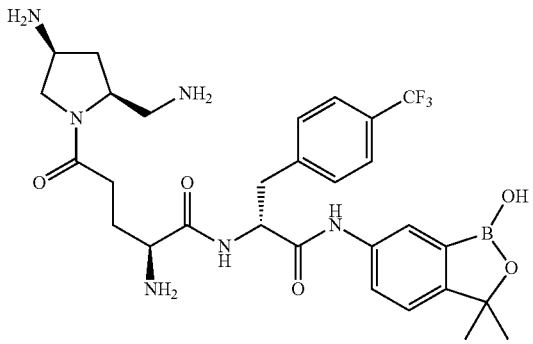 [SMILES: CC1(C)OB(O)c2cc(NC(=O)[C@@H](Cc3ccc(C(F)(F)F)cc3)NC(=O)[C@@H](N)CCC(=O)N3C[C@@H](N)C[C@H]3CN)ccc21] |
| 76 | 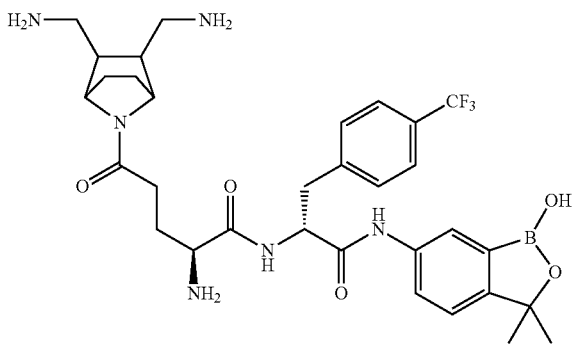 [SMILES: CC1(C)OB(O)c2cc(NC(=O)[C@@H](Cc3ccc(C(F)(F)F)cc3)NC(=O)[C@@H](N)CCC(=O)N3C4CCC3C(CN)C4CN)ccc21] |
| 77 | 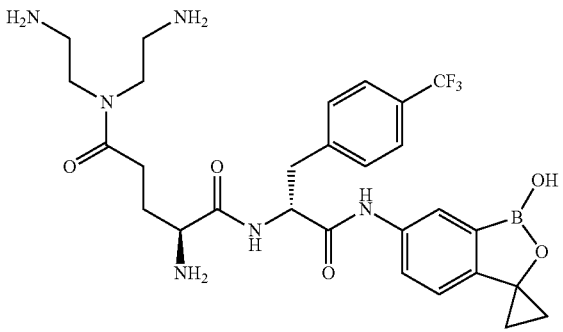 [SMILES: NCCN(CCN)C(=O)CC[C@H](N)C(=O)N[C@H](Cc1ccc(C(F)(F)F)cc1)C(=O)Nc1ccc2c(c1)B(O)OC21CC1] |
| 78 | 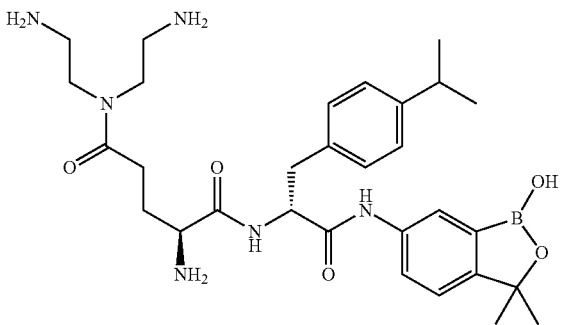 [SMILES: CC(C)c1ccc(C[C@@H](NC(=O)[C@@H](N)CCC(=O)N(CCN)CCN)C(=O)Nc2ccc3c(c2)B(O)OC3(C)C)cc1] |

TABLE 1-continued
79 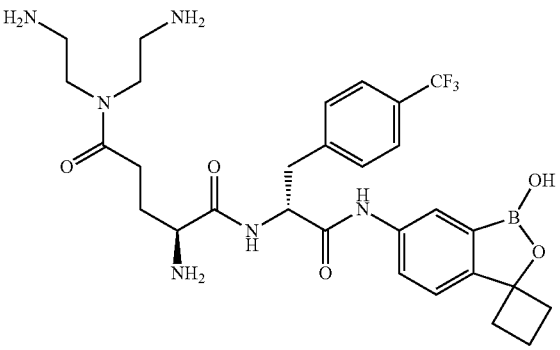 [SMILES: NCCN(CCN)C(=O)CC[C@H](N)C(=O)N[C@H](Cc1ccc(C(F)(F)F)cc1)C(=O)Nc1ccc2c(c1)B(O)OC21CCC1]
80 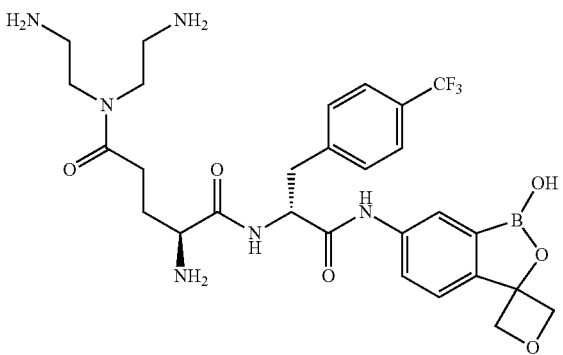 [SMILES: NCCN(CCN)C(=O)CC[C@H](N)C(=O)N[C@H](Cc1ccc(C(F)(F)F)cc1)C(=O)Nc1ccc2c(c1)B(O)OC21COC1]
81 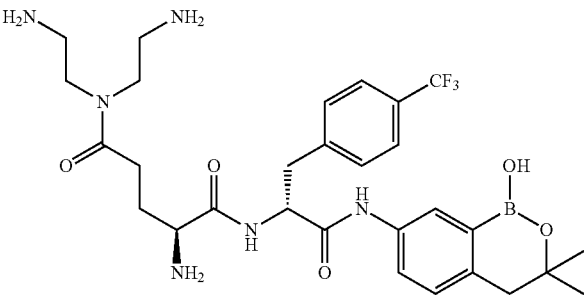 [SMILES: CC1(C)Cc2ccc(NC(=O)[C@@H](Cc3ccc(C(F)(F)F)cc3)NC(=O)[C@@H](N)CCC(=O)N(CCN)CCN)cc2B(O)O1]
82 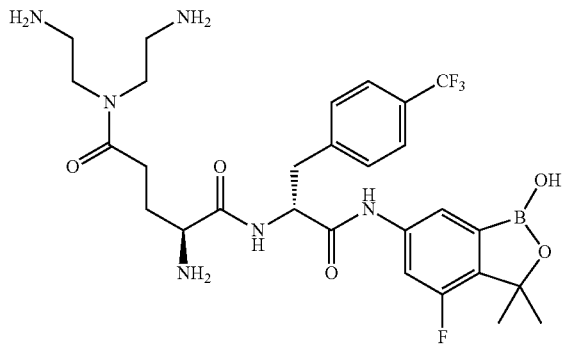 [SMILES: CC1(C)OB(O)c2cc(NC(=O)[C@@H](Cc3ccc(C(F)(F)F)cc3)NC(=O)[C@@H](N)CCC(=O)N(CCN)CCN)cc(F)c21]

TABLE 1-continued
83
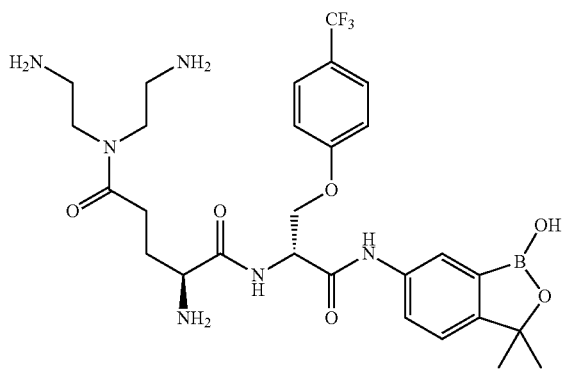 [SMILES: CC1(C)OB(O)c2cc(NC(=O)[C@@H](COc3ccc(C(F)(F)F)cc3)NC(=O)[C@@H](N)CCC(=O)N(CCN)CCN)ccc21]
84
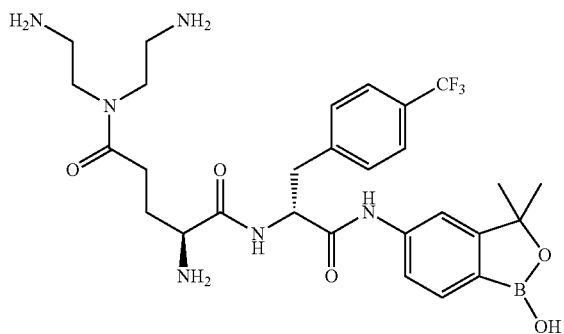 [SMILES: CC1(C)OB(O)c2ccc(NC(=O)[C@@H](Cc3ccc(C(F)(F)F)cc3)NC(=O)[C@@H](N)CCC(=O)N(CCN)CCN)cc21]
85
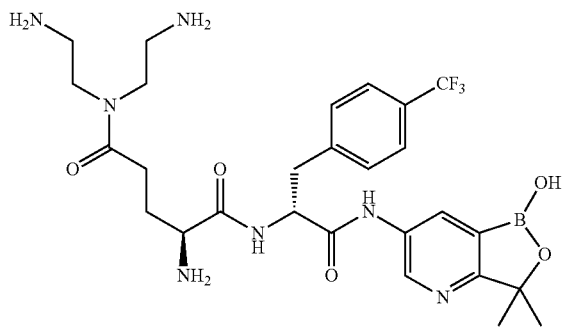 [SMILES: CC1(C)OB(O)c2cc(NC(=O)[C@@H](Cc3ccc(C(F)(F)F)cc3)NC(=O)[C@@H](N)CCC(=O)N(CCN)CCN)cnc21]
86
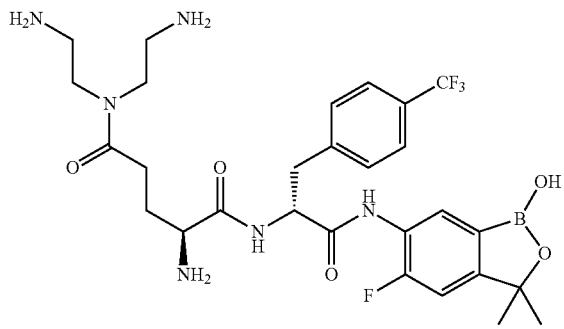 [SMILES: CC1(C)OB(O)c2cc(NC(=O)[C@@H](Cc3ccc(C(F)(F)F)cc3)NC(=O)[C@@H](N)CCC(=O)N(CCN)CCN)c(F)cc21]

TABLE 1-continued
| 87 | 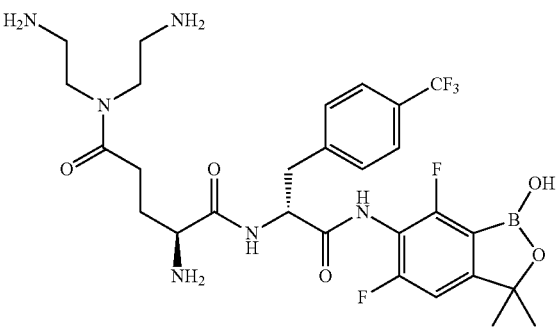 [SMILES: CC1(C)OB(O)c2c1cc(F)c(NC(=O)[C@@H](Cc1ccc(C(F)(F)F)cc1)NC(=O)[C@@H](N)CCC(=O)N(CCN)CCN)c2F] |
| --- | --- |
| 88 | 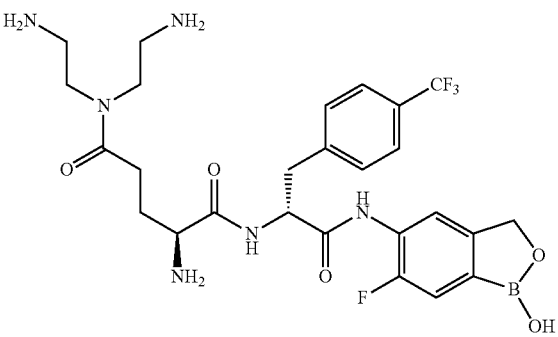 [SMILES: NCCN(CCN)C(=O)CC[C@H](N)C(=O)N[C@H](Cc1ccc(C(F)(F)F)cc1)C(=O)Nc1cc2c(cc1F)B(O)OC2] |
| 89 | 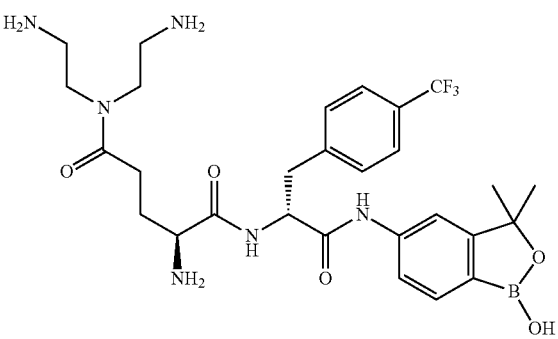 [SMILES: CC1(C)OB(O)c2ccc(NC(=O)[C@@H](Cc3ccc(C(F)(F)F)cc3)NC(=O)[C@@H](N)CCC(=O)N(CCN)CCN)cc21] |
| 90 | 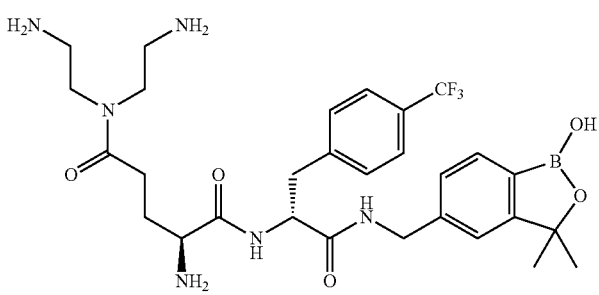 [SMILES: CC1(C)OB(O)c2ccc(CNC(=O)[C@@H](Cc3ccc(C(F)(F)F)cc3)NC(=O)[C@@H](N)CCC(=O)N(CCN)CCN)cc21] |
| 91 | 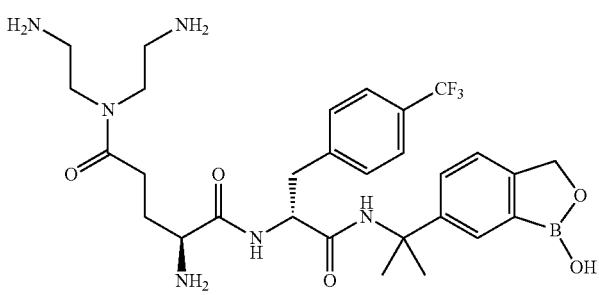 [SMILES: CC(C)(NC(=O)[C@@H](Cc1ccc(C(F)(F)F)cc1)NC(=O)[C@@H](N)CCC(=O)N(CCN)CCN)c1ccc2c(c1)B(O)OC2] |

TABLE 1-continued
92 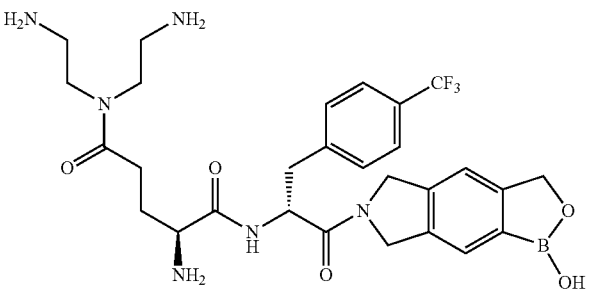 [SMILES: NCCN(CCN)C(=O)CC[C@H](N)C(=O)N[C@H](Cc1ccc(C(F)(F)F)cc1)C(=O)N1Cc2cc3c(cc2C1)B(O)OC3]
93 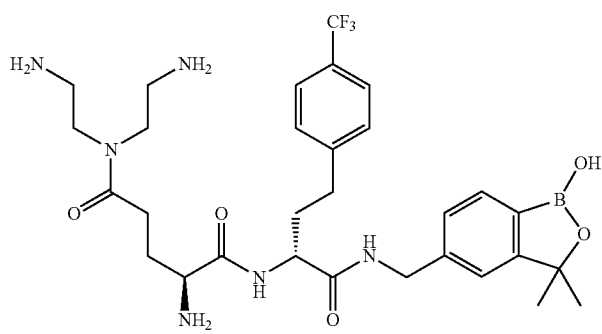 [SMILES: CC1(C)OB(O)c2ccc(CNC(=O)[C@@H](CCc3ccc(C(F)(F)F)cc3)NC(=O)[C@@H](N)CCC(=O)N(CCN)CCN)cc21]
94 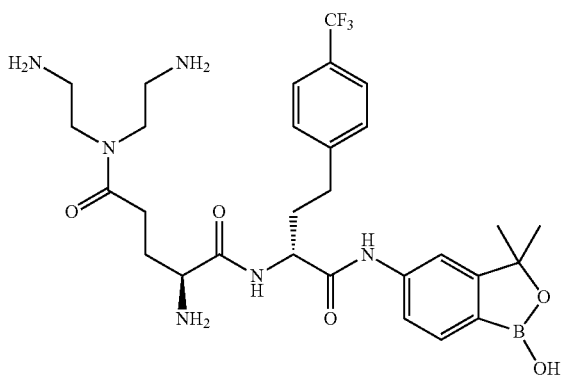 [SMILES: CC1(C)OB(O)c2ccc(NC(=O)[C@@H](CCc3ccc(C(F)(F)F)cc3)NC(=O)[C@@H](N)CCC(=O)N(CCN)CCN)cc21]
95 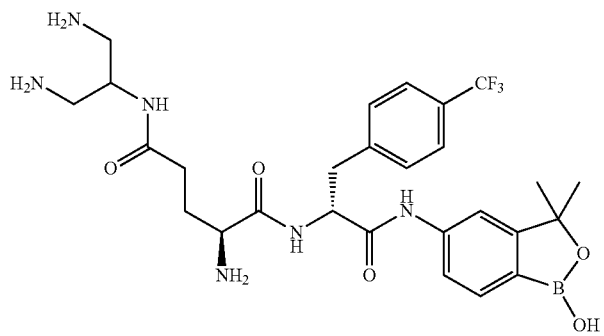 [SMILES: CC1(C)OB(O)c2ccc(NC(=O)[C@@H](Cc3ccc(C(F)(F)F)cc3)NC(=O)[C@@H](N)CCC(=O)NC(CN)CN)cc21]

TABLE 1-continued
96
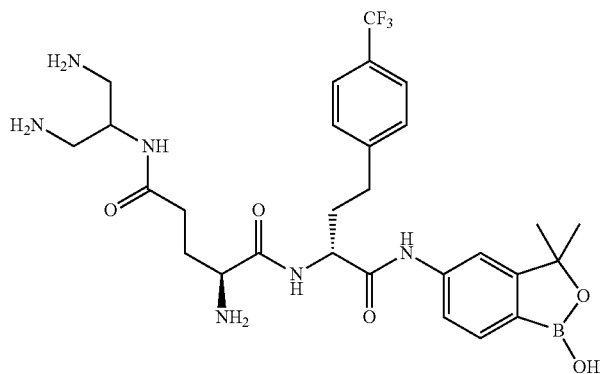
97
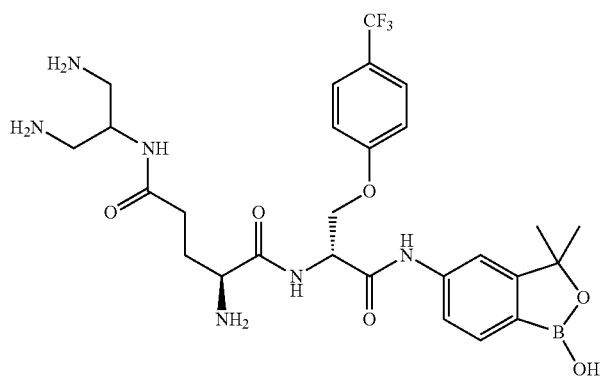
98
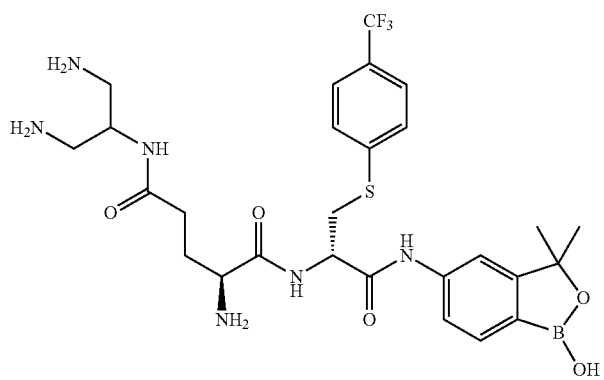 [SMILES: CC1(C)OB(O)c2ccc(NC(=O)[C@@H](CCc3ccc(C(F)(F)F)cc3)NC(=O)[C@@H](N)CCC(=O)NC(CN)CN)cc21]
99
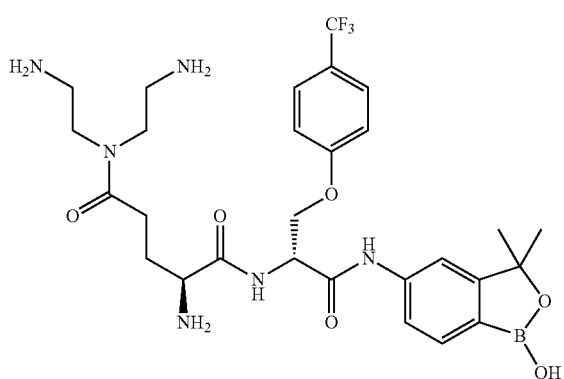

TABLE 1-continued
100 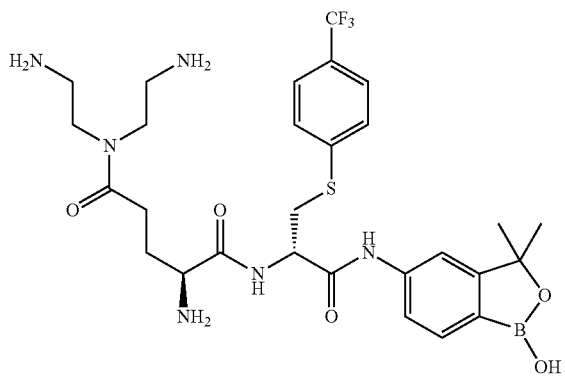 [SMILES: CC1(C)OB(O)c2ccc(NC(=O)[C@@H](COc3ccc(C(F)(F)F)cc3)NC(=O)[C@@H](N)CCC(=O)N(CCN)CCN)cc21]
101 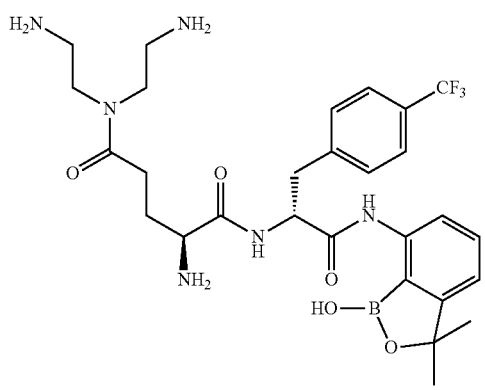 [SMILES: CC1(C)OB(O)c2c(NC(=O)[C@@H](Cc3ccc(C(F)(F)F)cc3)NC(=O)[C@@H](N)CCC(=O)N(CCN)CCN)cccc21]
102 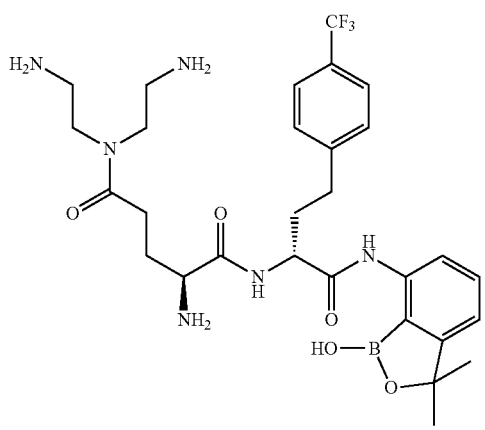 [SMILES: CC1(C)OB(O)c2c(NC(=O)[C@@H](CCc3ccc(C(F)(F)F)cc3)NC(=O)[C@@H](N)CCC(=O)N(CCN)CCN)cccc21]
103 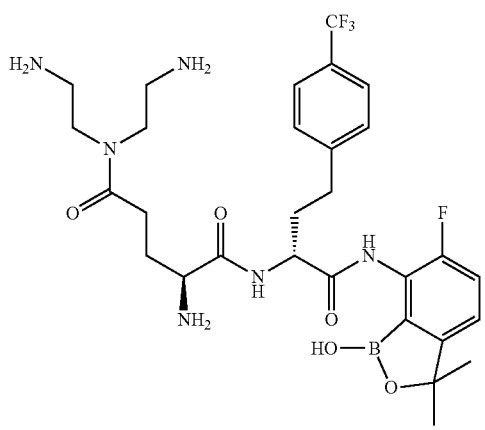 [SMILES: CC1(C)OB(O)c2c1ccc(F)c2NC(=O)[C@@H](CCc1ccc(C(F)(F)F)cc1)NC(=O)[C@@H](N)CCC(=O)N(CCN)CCN]

TABLE 1-continued
| 104 | 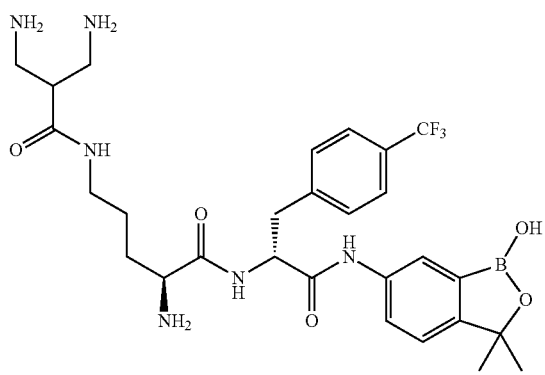 [SMILES: CC1(C)OB(O)c2cc(NC(=O)[C@@H](Cc3ccc(C(F)(F)F)cc3)NC(=O)[C@@H](N)CCCNC(=O)C(CN)CN)ccc21] |
| 105 | 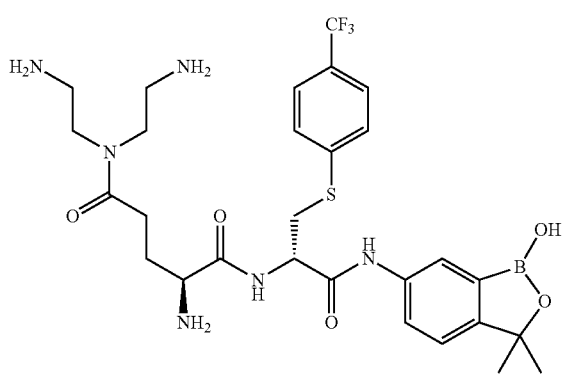 |
| 106 | 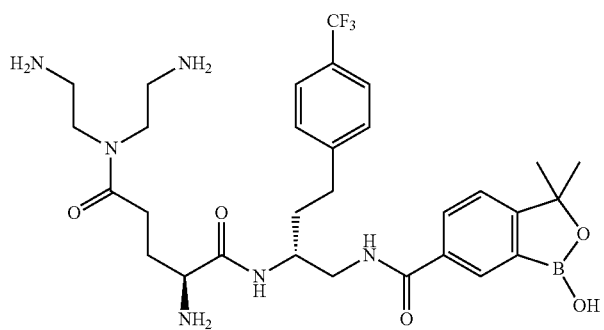 [SMILES: CC1(C)OB(O)c2cc(C(=O)NC[C@@H](CCc3ccc(C(F)(F)F)cc3)NC(=O)[C@@H](N)CCC(=O)N(CCN)CCN)ccc21] |
| 107 | 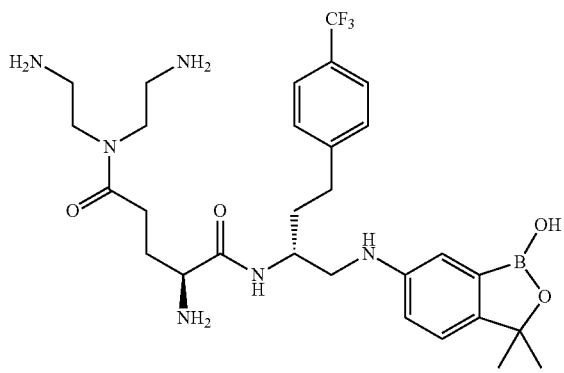 [SMILES: CC1(C)OB(O)c2cc(NC[C@@H](CCc3ccc(C(F)(F)F)cc3)NC(=O)[C@@H](N)CCC(=O)N(CCN)CCN)ccc21] |

TABLE 1-continued

108 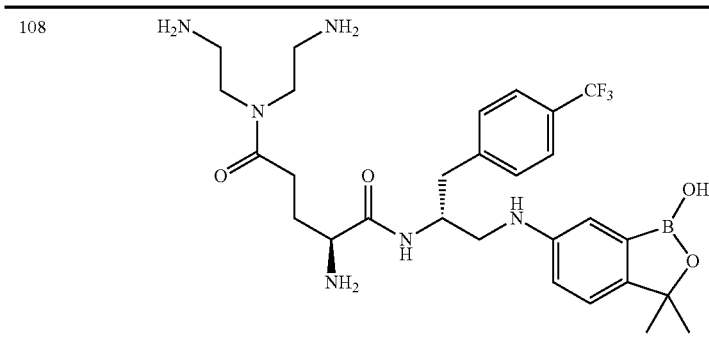

Example 4

Potentiation of Levofloxacin by Polybasic Efflux Pump Inhibitors

EPI activity was recorded as concentration of an EPI compound that is necessary to increase susceptibility to levofloxacin of the strain of *P. aeruginosa*, PAM1723, overexpressing the MexAB-OprM efflux pump eight-fold. The levofloxacin potentiating activity of the test compounds was assessed by the checkerboard assay (Antimicrobial Combinations, Antibiotics in Laboratory Medicine, Ed. Victor Lorian, M.D., Fourth edition, 1996, pp 333-338, which is incorporated herein by reference in its entirety) using a broth microdilution method performed as recommended by the NCCLS (National Committee for Clinical Laboratory Standards (NCCLS), 1997, Methods for Dilution of Antimicrobial Susceptibility Tests for Bacteria That Grow Aerobically, Fourth Edition; Approved Standard. NCCLS Document M7-A4, Vol 17 No. 2, which is incorporated herein by reference in its entirety). In this assay, multiple dilutions of two drugs, namely an EPI and levofloxacin, were tested, alone and in combination, at concentrations equal to, above and below their respective minimal inhibitory concentrations (MICs). All EPI compounds were readily soluble in water and stock solutions were prepared at a final concentration of 10 mg/ml. Stock solutions were further diluted, according to the needs of the particular assay, in Mueller Hinton Broth (MHB). Stock solution was stored at 80° C.

The checkerboard assay was performed in microtiter plates. Levofloxacin was diluted in the x-axis, each column containing a single concentration of levofloxacin. EPIs were diluted in the y-axis, each row containing a single concentration of an EPI. The result of these manipulations was that each well of the microtiter plate contained a unique combination of concentrations of the two agents. The assay was performed in MHB with a final bacterial inoculum of 5 times $10^5$ CFU/ml (from an early-log phase culture). Microtiter plates were incubated during 20 h at 35° C. and were read using a microtiter plate reader (Molecular Devices) at 650 nm as well as visual observation using a microtiter plate-reading mirror. The reported antibacterial results are those where the visible growth of the organism was completely inhibited.

In the experiment depicted in Table 2, potentiating activities of selected inhibitors are reported as Minimum Potentiating Concentration $MPC_8$ values which correspond to the lowest concentration of the inhibitor required to achieve antibacterial activity in combination with the concentration of levofloxacin equal to ⅛ of the levofloxacin concentration required to achieve the same antibacterial effect alone (MIC of levofloxacin).

TABLE 2

| Compound | MPC8 (µg/mL) |
|---|---|
| 1 | C |
| 2 | B |
| 3 | C |
| 4 | C |
| 5 | C |
| 6 | B |
| 7 | B |
| 8 | C |
| 9 | C |
| 10 | B |
| 11 | B |
| 12 | A |
| 13 | B |
| 14 | B |
| 15 | B |
| 16 | C |
| 17 | C |
| 18 | B |
| 19 | B |
| 20 | A |
| 21 | B |
| 22 | B |
| 23 | B |
| 24 | B |
| 25 | B |
| 26 | A |
| 27 | B |
| 28 | A |
| 29 | B |
| 30 | C |
| 31 | B |
| 32 | B |
| 33 | A |
| 34 | C |
| 35 | B |
| 36 | B |
| 37 | A |
| 38 | A |
| 39 | A |
| 40 | B |
| 41 | B |
| 42 | A |
| 43 | B |
| 44 | A |
| 66 | B |
| 67 | B |
| 74 | B |
| 75 | B |
| 78 | A |
| 84 | B |
| 90 | B |
| 93 | B |
| 94 | A |
| 95 | B |
| 96 | A |
| 97 | B |

TABLE 2-continued

| Compound | MPC8 (µg/mL) |
|---|---|
| 98 | B |
| 101 | B |
| 102 | B |
| 103 | B |
| 104 | B |
| 106 | B |
| 107 | A |
| 108 | A |

A = MPC$_8$ of less than 2.5 µg/mL.
B = MPC$_8$ of 2.5 µg/ml to less than 10 µg/mL.
C = MPC$_8$ of 10 µg/mL or greater.

Example 5

Rat Pneumonia Model of *Pseudomonas aeruginosa*

Rats are made neutropenic by administration of a 75 mg/kg dose of cyclophosphamide 2 days prior to infection. Immediately prior to infection, rats are anesthetized with isoflurane. Lung infection is established by intratracheal instillation of ~1×10$^7$ CFU/lung. *P. aeruginosa* PAM3062, which overexpresses the MexAB-OprM efflux pump, is used for infection. All treatments are initiated 4 hours after infection and are administered by 1.5 hr IV infusion twice daily. Rats are sacrificed 24 hours after the start of treatment; lungs are homogenized, serially diluted, and plated to determine colony counts.

In the experiment depicted in Table 3, activities of selected inhibitors are reported as Δlog CFU values which corresponds to the change in the number of *P. aeruginosa* colonies when combined with a constant concentration of levofloxacin compared against the effect of levofloxacin alone.

TABLE 3

| Compound | Levofloxacin 24 hr dose (mg/kg) | EPI 24 hr dose (mg/kg) | Δlog CFU |
|---|---|---|---|
| none | 100 (50 BID) | none | 0.77 |
| 2 | 100 (50 BID) | 40 (20 BID) | −1.74 |
| 6 | 100 (50 BID) | 16 (8 BID) | −2.99 |
| 14 | 100 (50 BID) | 20 (10 BID) | −1.13 |
| 20 | 100 (50 BID) | 10 (5 BID) | −1.75 |

What is claimed is:

1. A compound having the structure of formula I or pharmaceutically acceptable salt thereof:

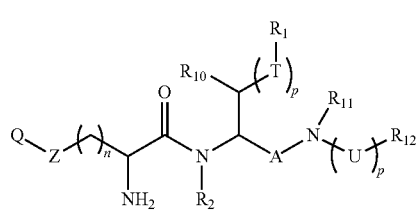

I wherein:
$R_1$ is selected from the group consisting of $C_1$-$C_6$ alkyl, $C_3$-$C_7$ carbocyclyl, heterocyclyl, aryl and heteroaryl, each optionally substituted with one or more substituents independently selected from the group consisting of a halogen, $C_1$-$C_4$ alkyl optionally substituted with one or more halogen, $C_3$-$C_7$ carbocyclyl, —OR$_2$, —SR$_2$, —SO$_2$R$_2$, —SO$_2$NHR$_2$, —N(R$_2$)$_2$, —CN, and —CO$_2$C$_1$-C$_4$ alkyl;

each $R_2$ is independently selected from the group consisting of H and $C_1$-$C_6$ alkyl optionally substituted with one or more halogen;

A is —C(O)— or CH$_2$;

Z is selected from the group consisting of —CH$_2$—, —C(O)—, —S(O)$_2$—, —C(O)O—, —C(O)S—, —C(O)NH— and —S(O)$_2$NH—;

Q is selected from the group consisting of —NR$_3$R$_4$, —CHR$_3$R$_4$,

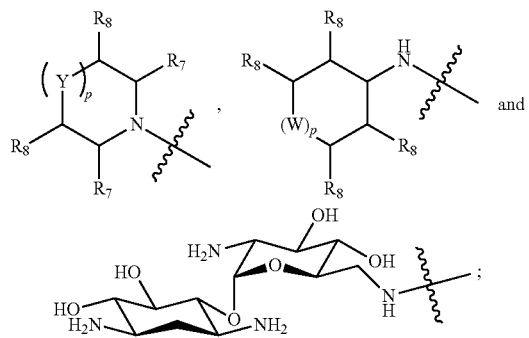

$R_3$ is selected from the group consisting of —CH$_2$[CH(R$_5$)]$_p$CH(R$_6$)NH$_2$, —CH(CHR$_6$NH$_2$)$_2$ and —CH$_2$C(OH)(CH$_2$NH$_2$)$_2$;

$R_4$ is selected from the group consisting of H and —CH$_2$[CH(R$_5$)]$_p$CH(R$_6$)NH$_2$;

each $R_5$ is independently selected from the group consisting of H, —OH, halogen, and $C_1$-$C_4$ alkyl substituted with one or more —OH or halogen;

each $R_6$ is independently selected from the group consisting of H and $C_1$-$C_4$ alkyl substituted with one or more —OH or halogen;

each $R_7$ is independently selected from the group consisting of H and $C_1$-$C_4$ alkyl substituted with one or more —OH or NH$_2$, or optionally, two $R_7$ can be linked by —(CH$_2$)$_m$— to form a bicyclic ring, wherein m is an integer of 1 to 3;

each $R_8$ is independently selected from the group consisting of H, —NH$_2$, —CH$_2$NH$_2$, —OH and —CH$_2$OH;

Y is selected from the group consisting of CHR$_9$, O, S, SO$_2$ and NR$_2$;

W is CHR$_8$;

$R_9$ is selected from the group consisting of H, —NH$_2$, —OH and $C_1$-$C_4$ alkyl substituted with one or more —OH or NH$_2$;

T is selected from the group consisting of CH$_2$, O, S and NR$_2$;

$R_{10}$ is selected from the group consisting of H and OH, with the limitation that when $R_{10}$ is OH, T is CH$_2$;

$R_{11}$ is selected from the group consisting of H and $C_1$-$C_6$ alkyl, wherein when $R_{11}$ is $C_1$-$C_6$ alkyl, it is optionally linked to $R_{12}$ to form a ring;

U is selected from the group consisting of $C_1$-$C_4$ alkyl, C=O, spirocyclic $C_3$-$C_7$ carbocyclyl, and 3-7 membered spirocyclic heterocyclyl;

$R_{12}$ is —(X)$_p$—V—B(OH)(OR$_{13}$);

X is CH$_2$;

V is selected from the group consisting of $C_3$-$C_7$ carbocyclyl, heterocyclyl, aryl and heteroaryl, each optionally substituted with one or more $C_1$-$C_4$ alkyl optionally substituted with one or more halogen, halogen, $C_1$-$C_4$ alkoxy optionally substituted with one or more halogen, or —CN;

$R_{13}$ is selected from the group consisting of H; —$(CR_{19}R_{20})_p$-spirocyclic $C_3$-$C_7$ carbocyclyl-$(CR_{21}R_{22})_p$—; —$(CR_{19}R_{20})_p$-three- to seven-membered spirocyclic heterocyclyl-$(CR_{21}R_{22})_p$— optionally substituted with $C_{1-6}$ alkyl; and $C_1$-$C_4$ alkyl optionally substituted with one or more halogen, $C_1$-$C_4$ alkyl optionally substituted with one or more halogen, $C_1$-$C_4$ alkoxy optionally substituted with one or more halogen, and oxo; wherein when $R_{13}$ is optionally substituted $C_1$-$C_4$ alkyl, —$(CR_{19}R_{20})_p$-spirocyclic $C_3$-$C_7$ carbocyclyl-$(CR_{21}R_{22})_p$—, or —$(CR_{19}R_{20})_p$-three- to seven-membered spirocyclic heterocyclyl —$(CR_{21}R_{22})_p$— optionally substituted with $C_{1-6}$ alkyl, it is linked to X or V to form a ring;

or optionally, $R_{13}$ is a bond linked directly to X to form a ring;

$R_{19}$ and $R_{20}$ are independently selected from the group consisting of H, halogen, $C_1$-$C_4$ alkyl optionally substituted with one or more halogen, and $C_1$-$C_4$ alkoxy optionally substituted with one or more halogen;

$R_{21}$ and $R_{22}$ are independently selected from the group consisting of H, halogen, $C_1$-$C_4$ alkyl optionally substituted with one or more halogen, and $C_1$-$C_4$ alkoxy optionally substituted with one or more halogen, or together they are oxo;

n is equal to 1, 2 or 3; and each p is independently equal to 0 or 1.

2. The compound of claim 1, wherein $R_{12}$ is selected from the group consisting of:

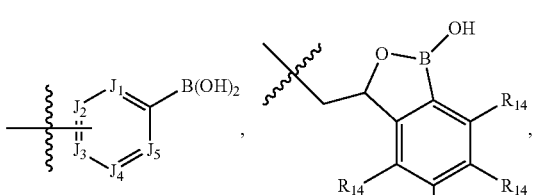

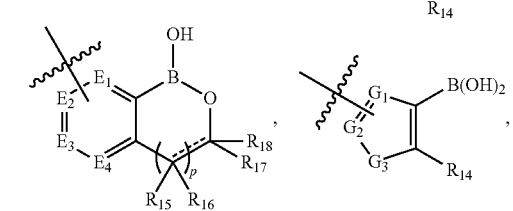

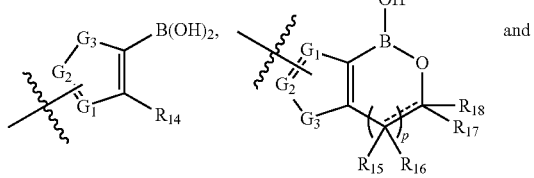

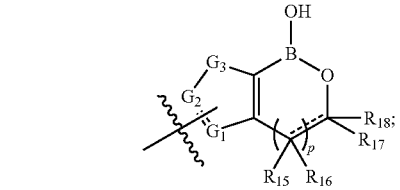

one $J_1$, $J_2$, $J_3$, $J_4$, and $J_5$ is

and is the attachment point to the rest of the molecule and the remaining $J_1$, $J_2$, $J_3$, $J_4$, and $J_5$ is independently selected from the group consisting of $CR_{14}$ and N;

one of $E_1$, $E_2$, $E_3$ and $E_4$ is

and is the attachment point to the rest of the molecule and the remaining $E_1$, $E_2$, $E_3$ and $E_4$ are independently selected from the group consisting of $CR_{14}$ and N;

$G_1$ and $G_2$ are independently selected from the group consisting of N and

which is the attachment point to the rest of the molecule;

$G_3$ is selected from the group consisting of O, —S and $NR_2$;

each $R_{14}$ is independently selected from the group consisting of H, $C_1$-$C_4$ alkyl, halogen, $C_1$-$C_4$ alkoxy, —$CF_3$, —$OCF_3$ and —CN;

$R_{15}$ and $R_{16}$ are independently selected from the group consisting of H, halogen, $C_1$-$C_4$ alkyl optionally substituted with one or more halogen, and $C_1$-$C_4$ alkoxy optionally substituted with one or more halogen, or together they are oxo, or together they form a spirocyclic $C_3$-$C_7$ carbocyclyl or a three- to seven-membered heterocyclyl containing one or two heteroatoms selected from the group consisting of O, S and $NR_2$;

$R_{17}$ and $R_{18}$ are independently selected from the group consisting of H, halogen, $C_1$-$C_4$ alkyl optionally substituted with one or more halogen, and $C_1$-$C_4$ alkoxy optionally substituted with one or more halogen, or together they form a spirocyclic $C_3$-$C_7$ carbocyclyl or a three- to seven-membered spirocyclic heterocyclyl containing one or two heteroatoms selected from the group consisting of O, S and $NR_2$; and bonds indicated by a dashed and solid line are selected from the group consisting of a single bond and a double bond, wherein when the bond is a double bond, $R_{16}$ and $R_{17}$ are absent.

3. The compound of claim 2, wherein $R_{12}$ is selected from the group consisting of:

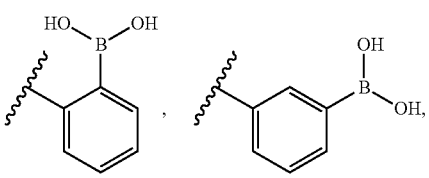

-continued
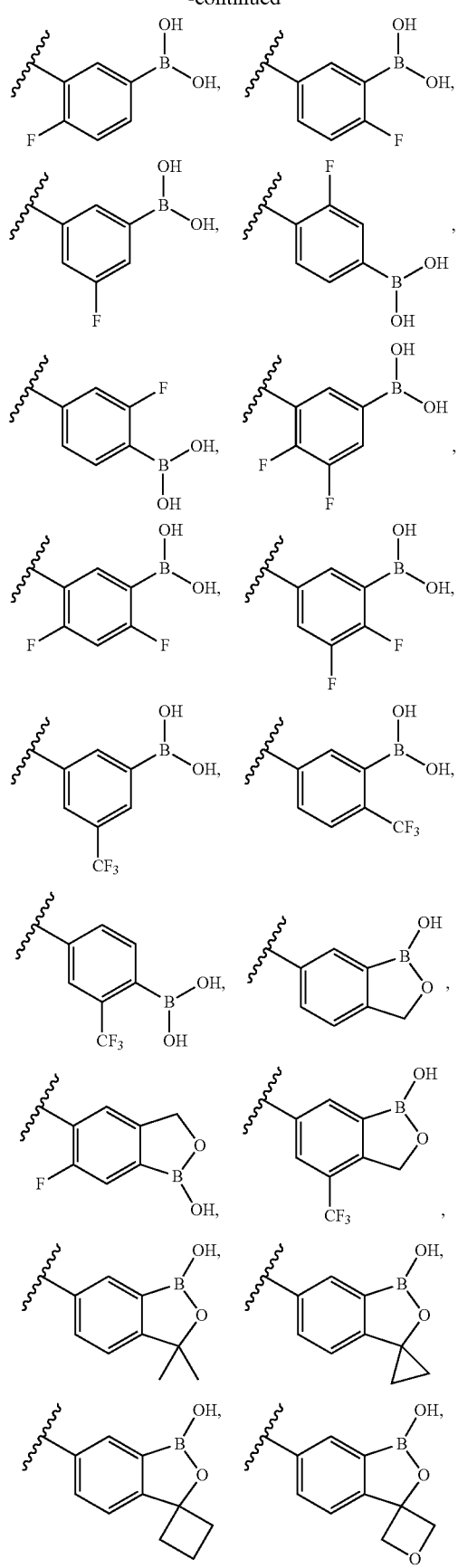
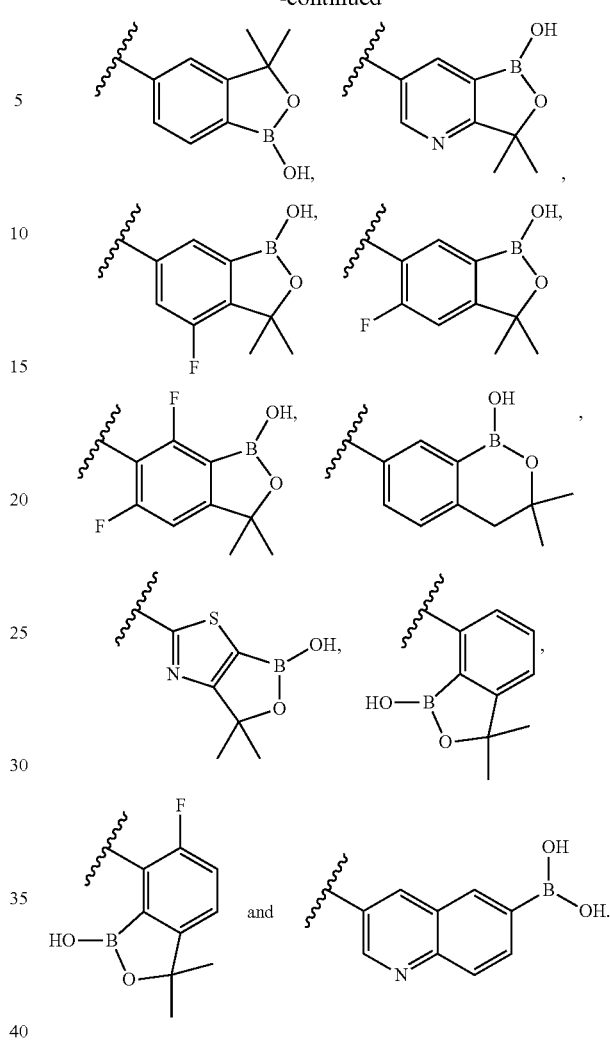
4. The compound of claim 1, wherein U is selected from the group consisting of —CH$_2$—, —C(CH$_3$)$_2$, C═O,
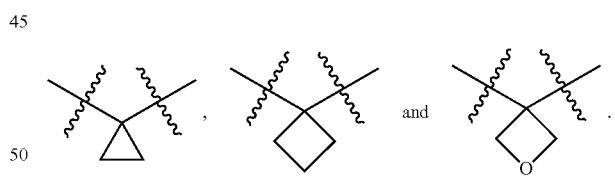
5. The compound of claim 1, wherein V is selected from the group consisting of C$_3$-C$_7$ carbocyclyl, heterocyclyl, aryl and heteroaryl, each optionally substituted with one or more C$_1$-C$_4$ alkyl, halogen, C$_1$-C$_4$ alkoxy, —CF$_3$, —OCF$_3$ or —CN.
6. The compound of claim 1, wherein
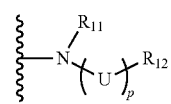

is selected from the group consisting of:

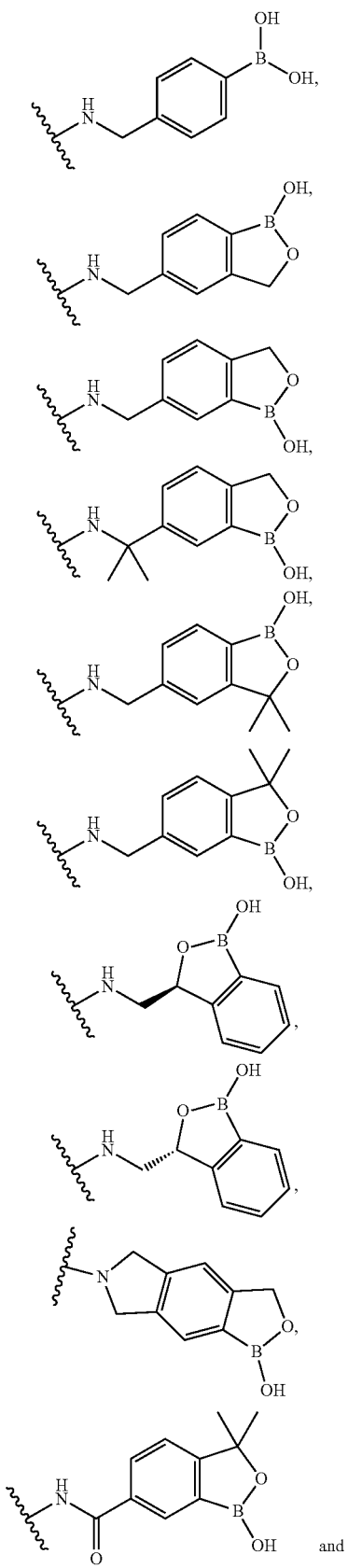

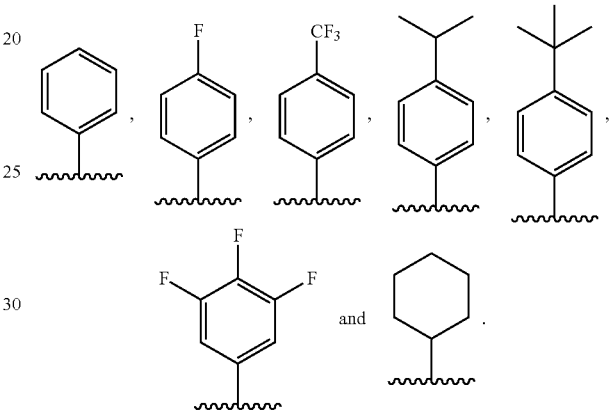

7. The compound of claim 1, wherein $R_1$ is substituted or unsubstituted carbocyclyl or substituted or unsubstituted aryl.

8. The compound of claim 7, wherein $R_1$ is carbocyclyl or aryl optionally substituted with one or more halogen, $C_1$-$C_4$ alkyl, —$CF_3$, and —$OCF_3$.

9. The compound of claim 8, wherein $R_1$ is selected from the group consisting of:

10. The compound of claim 1, wherein $R_1$ is substituted or unsubstituted carbocyclyl or substituted or unsubstituted aryl, T is $CH_2$ or O and p of $(T)_p$ is 1.

11. The compound of claim 1, wherein $R_1$ is substituted or unsubstituted carbocyclyl or substituted or unsubstituted aryl and p of $(T)_p$ is 0.

12. The compound of claim 1, wherein Z is —$CH_2$— and n is 2.

13. The compound of claim 1, wherein Z is —C(O)— and n is 1.

14. The compound of claim 1, wherein Z is —C(O)— and n is 2.

15. The compound of claim 1, wherein Q is selected from the group consisting of:

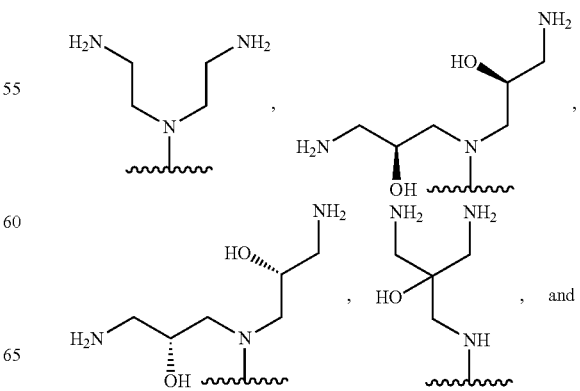

-continued

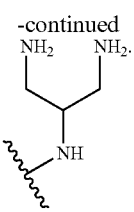

16. The compound of claim 1, wherein Q is selected from the group consisting of

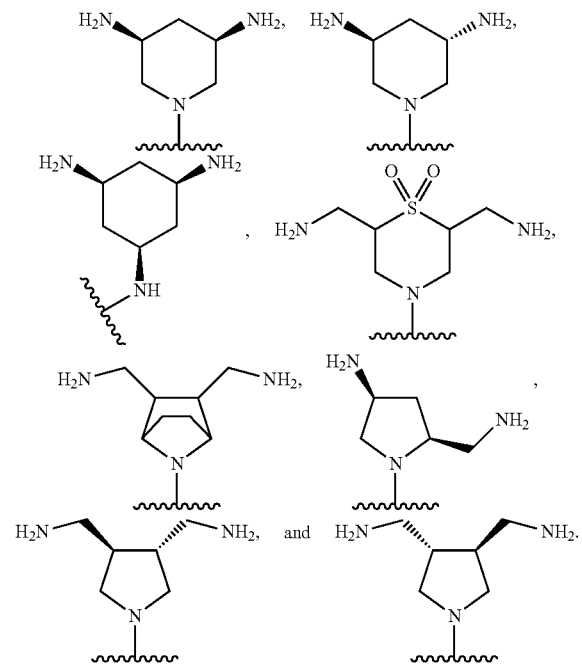

17. The compound of claim 1, wherein:

each $R_5$ is independently selected from the group consisting of H, —OH, $CH_2OH$, halogen, and $CH_2F$;

each $R_6$ is independently selected from the group consisting of H, —OH, $CH_2OH$, halogen, and $CH_2F$;

each $R_7$ is independently selected from the group consisting of H, —$CH_2OH$ and —$CH_2NH_2$; and $R_9$ is selected from the group consisting of H, —$NH_2$, —OH, —$CH_2OH$ and —$CH_2NH_2$.

18. The compound of claim 1, wherein:

$R_1$ is selected from the group consisting of $C_1$-$C_6$ alkyl, $C_3$-$C_7$ carbocyclyl, heterocyclyl, aryl and heteroaryl, each optionally substituted with one or more substituents independently selected from the group consisting of a halogen, $C_1$-$C_4$ alkyl, $C_3$-$C_7$ cycloalkyl, —$OR_2$, —$SR_2$, —$SO_2R_2$, —$SO_2NHR_2$, —$CF_3$, —$OCF_3$, —$N(R_2)_2$, —CN, and —$CO_2C_1$-$C_4$ alkyl;

each $R_2$ is independently selected from the group consisting of H and $C_1$-$C_6$ alkyl;

A is —C(O)—;

Z is selected from the group consisting of —$CH_2$—, —C(O)—, —$S(O)_2$—, —C(O)NH— and —$S(O)_2NH$—;

Q is selected from the group consisting of —$NR_3R_4$,

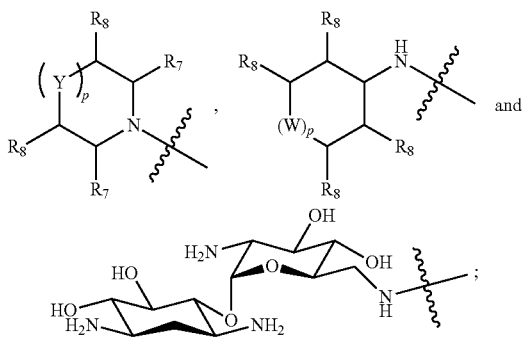

each $R_5$ is independently selected from the group consisting of H, —OH, —$CH_2OH$, halogen, and —$CH_2F$;

each $R_6$ is independently selected from the group consisting of H, —$CH_2OH$, and —$CH_2F$;

each $R_7$ is independently selected from the group consisting of H—$CH_2NH_2$ and —$CH_2OH$, or optionally, two $R_7$ can be linked by —$(CH_2)_m$— to form a bicyclic ring, wherein m is an integer of 1 to 3;

$R_9$ is selected from the group consisting of H, —$NH_2$, —$CH_2NH_2$, —OH and —$CH_2OH$;

U is selected from the group consisting of —$CH_2$—, —$C(CH_3)_2$, and

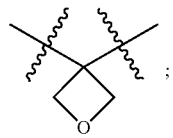 [SMILES: *C1(*)COC1]

V is selected from the group consisting of $C_3$-$C_7$ carbocyclyl, heterocyclyl, aryl and heteroaryl, each optionally substituted with one or more $C_1$-$C_4$ alkyl, halogen, $C_1$-$C_4$ alkoxy, —$CF_3$, —$OCF_3$ or —CN;

$R_{13}$ is selected from the group consisting of H; —$(CH_2)_p$-spirocyclic $C_3$-$C_7$ carbocyclyl-$(CH_2)_p$—; —$(CH_2)_p$-three- to seven-membered spirocyclic heterocyclyl-$(CH_2)_p$— optionally substituted with $C_{1-6}$ alkyl; and $C_1$-$C_4$ alkyl optionally substituted with one or more halogen, $C_1$-$C_4$ alkyl, $C_1$-$C_4$ alkoxy, and oxo;

or optionally, $R_{13}$ is a bond linked directly to X to form a ring; and n is equal to 1 or 2;

provided that when Y is O, S, $SO_2$, or $NR_2$, $R_8$ is not $NH_2$ or OH.

19. The compound of claim 1, having the structure:

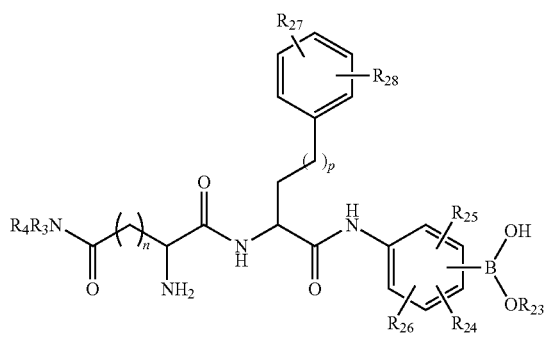

wherein:

$R_{23}$ is selected from the group consisting of H, spirocyclic $C_3$-$C_7$ carbocyclyl linked to the phenyl ring to which the boron is attached, three- to seven-membered spirocyclic heterocyclyl linked to the phenyl ring to which the boron is attached, and $C_1$-$C_4$ alkyl linked to the phenyl ring to which the boron is attached;

$R_{24}$, $R_{25}$, and $R_{26}$ are each independently selected from the group consisting of absent, hydrogen, $C_1$-$C_4$ alkyl optionally substituted with one or more halogen, halogen, $C_1$-$C_4$ alkoxy optionally substituted with one or more halogen, and —CN; and $R_{27}$ and $R_{28}$ are each independently selected from the group consisting of hydrogen, halogen, $C_1$-$C_4$ alkyl optionally substituted with one or more halogen, $C_3$-$C_7$ carbocyclyl, —$OR_2$, —$SR_2$, —$SO_2R_2$, —$SO_2NHR_2$, —$N(R_2)_2$, —CN, and —$CO_2C_1$-$C_4$ alkyl.

20. The compound of claim 1, having a structure selected from the group consisting of:

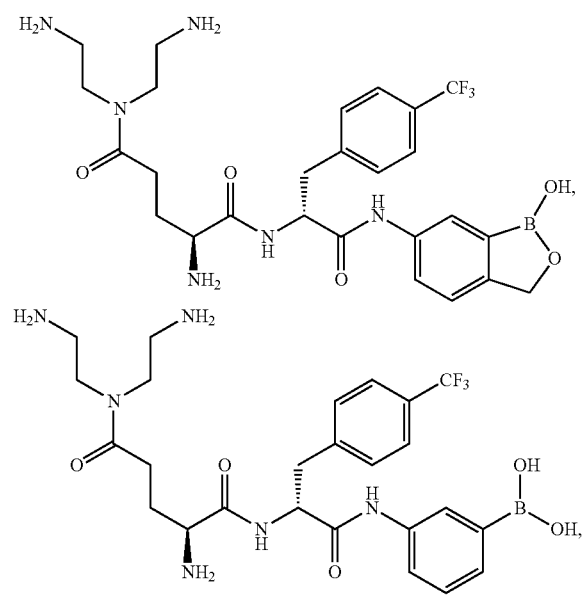

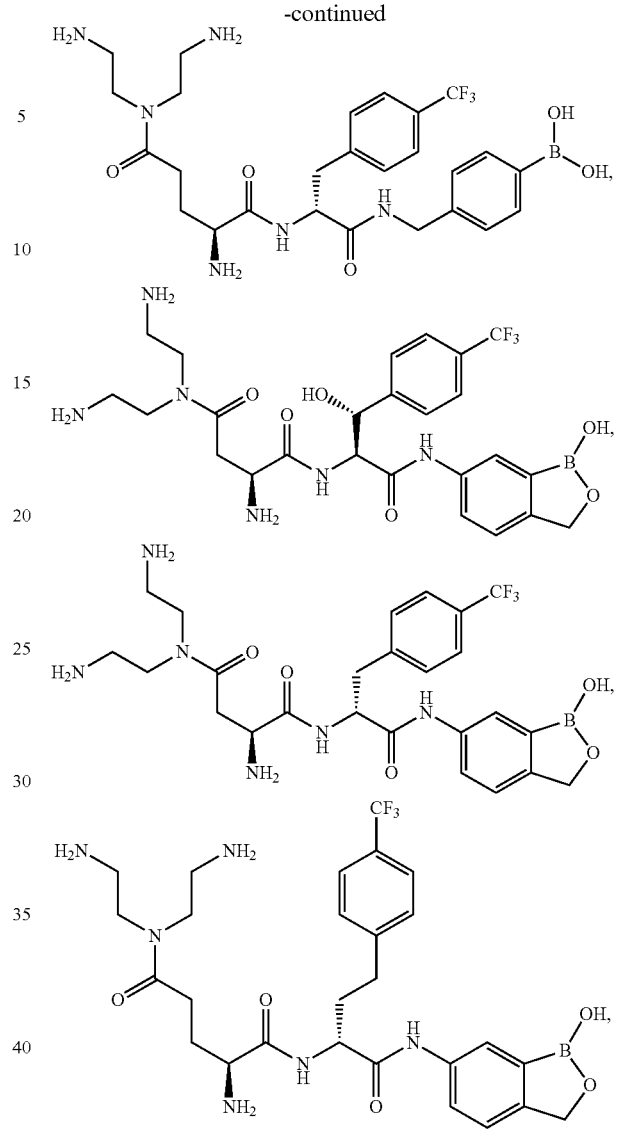

199
-continued
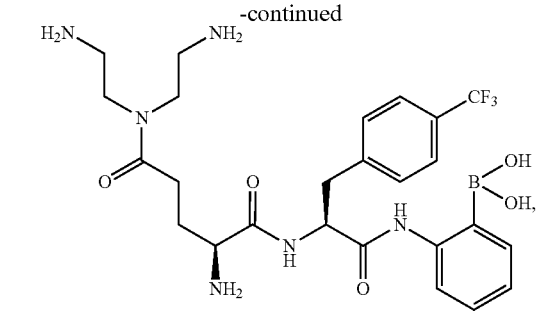
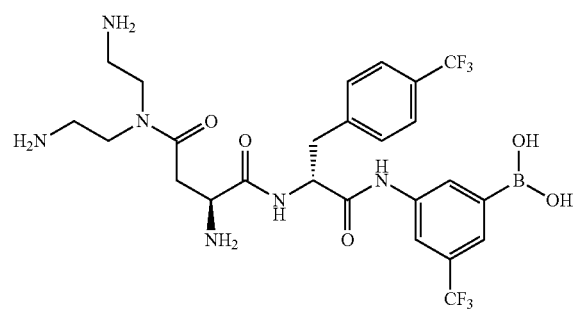
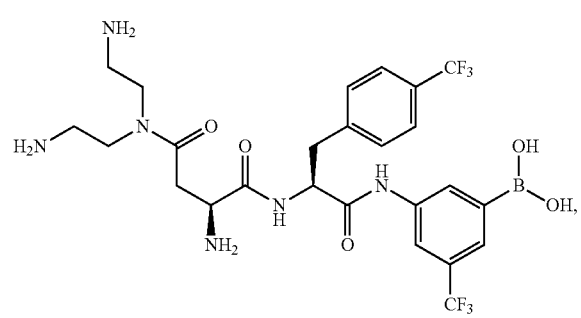
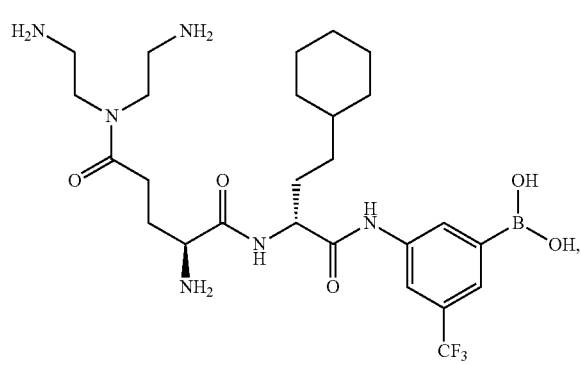
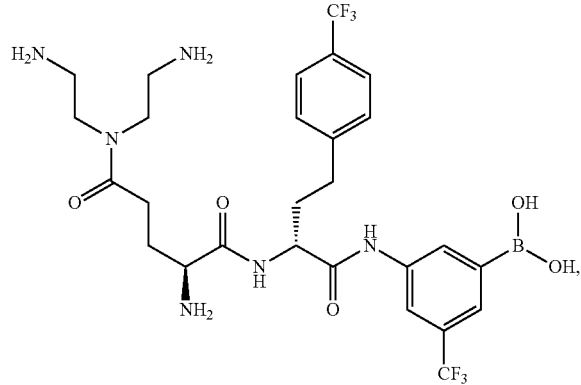
200
-continued
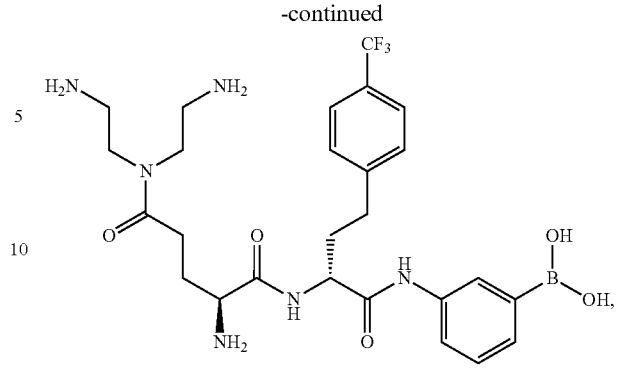
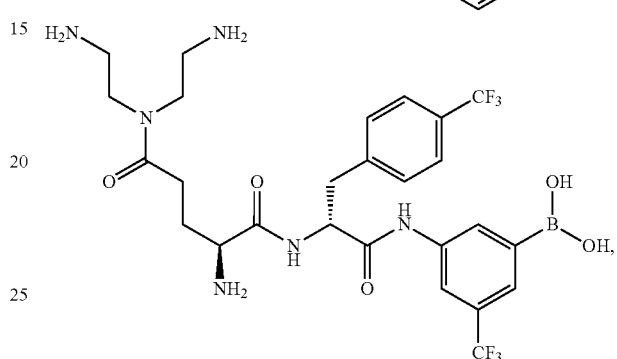
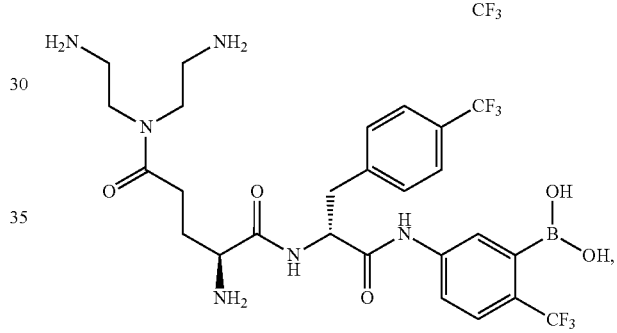
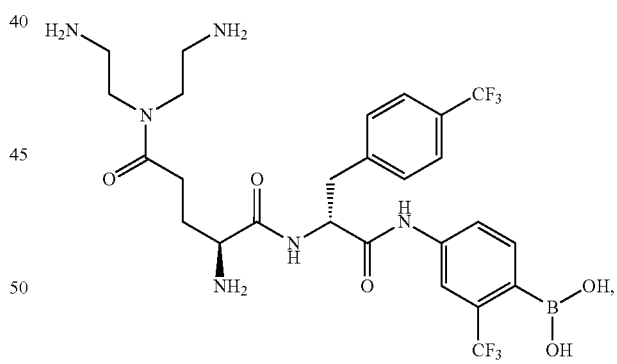
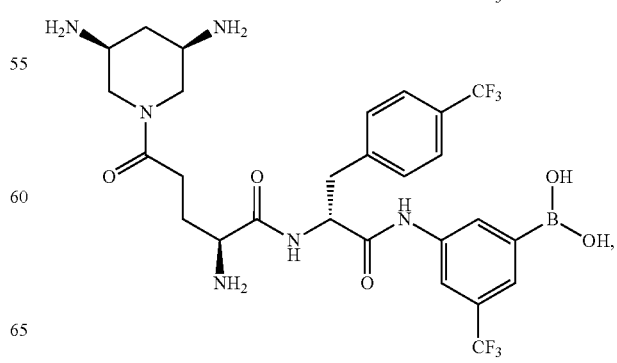

201
-continued
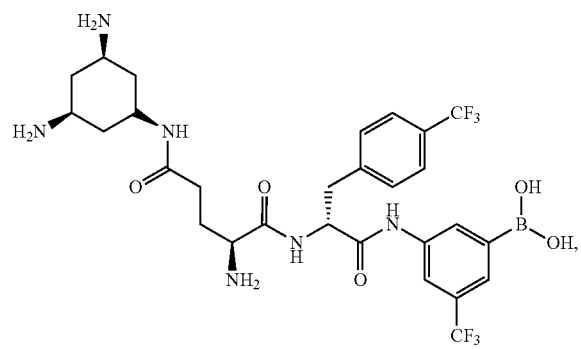
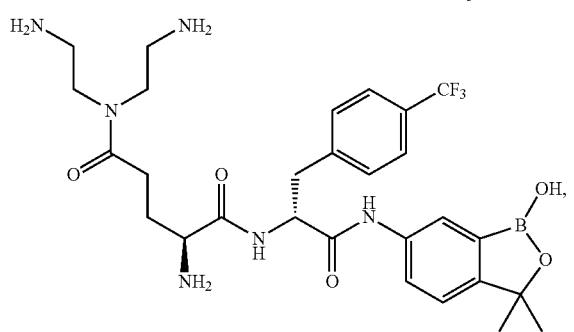
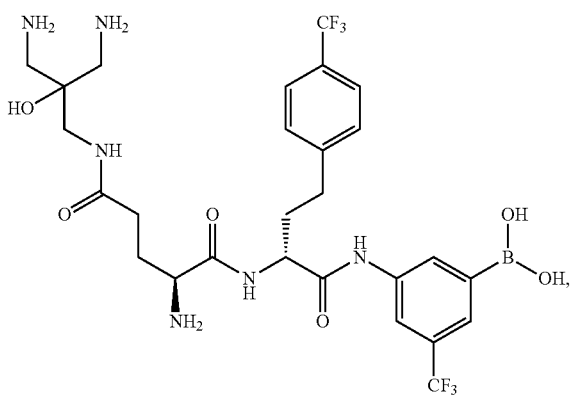
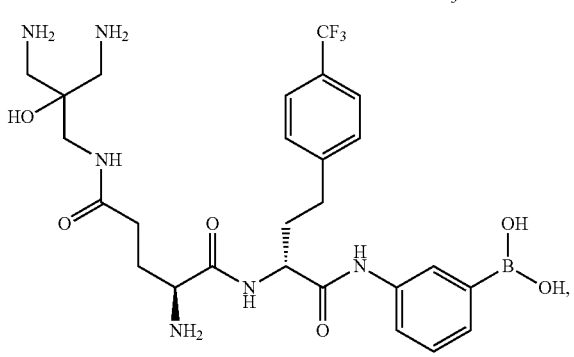
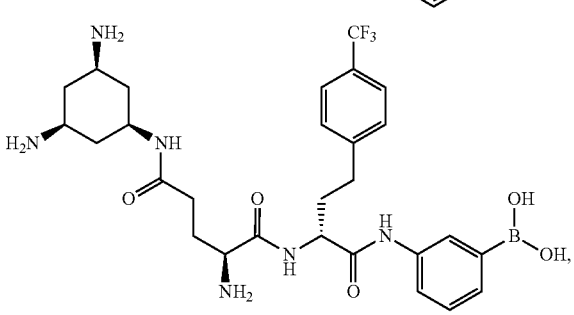
202
-continued
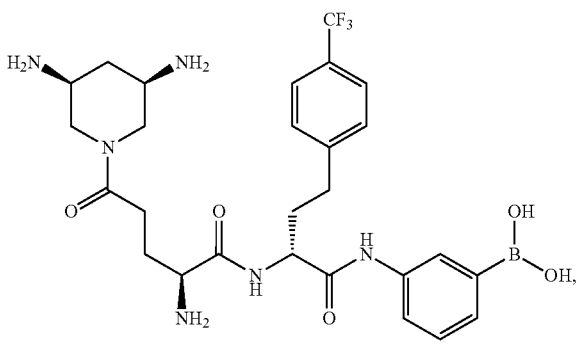
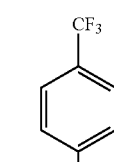
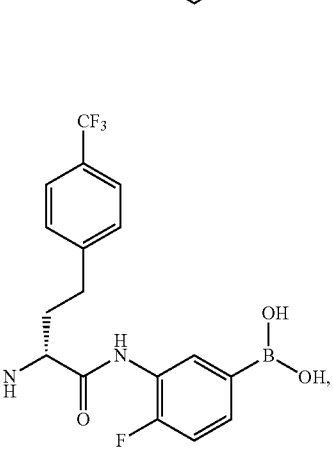
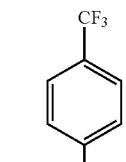
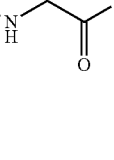
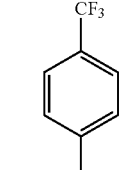
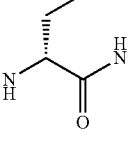

203
-continued
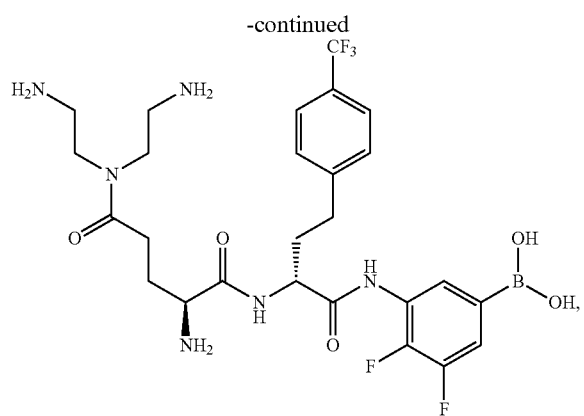
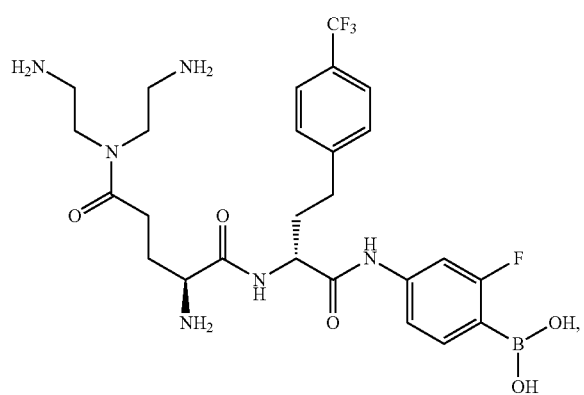
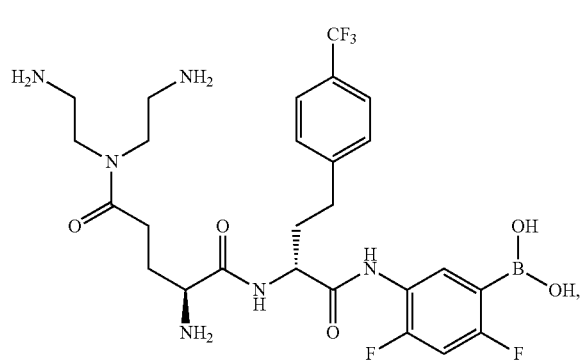
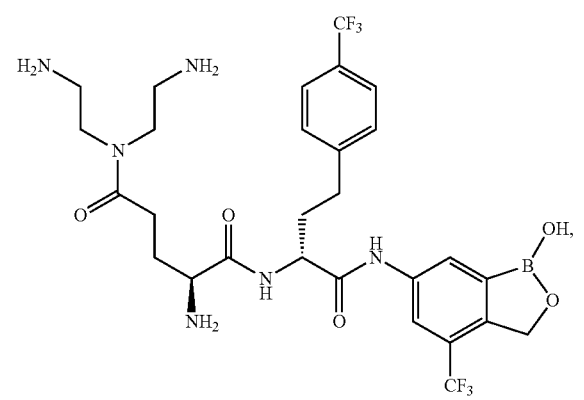
204
-continued
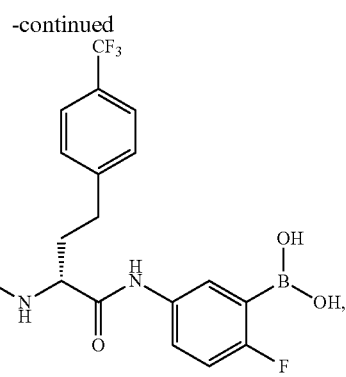
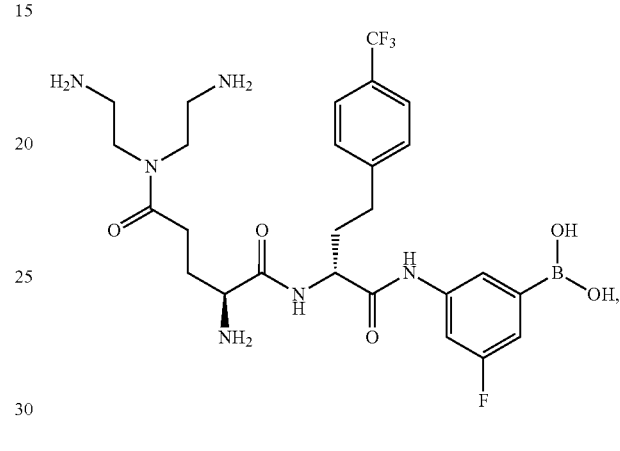
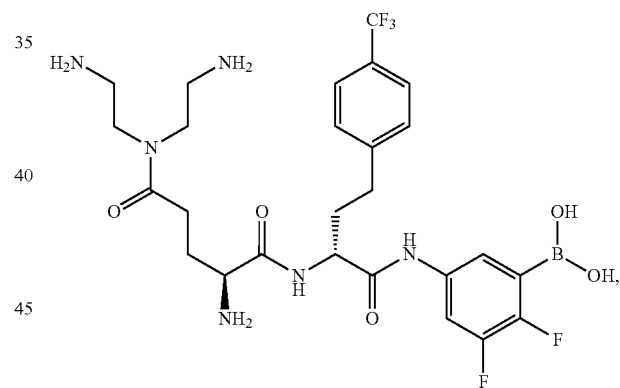
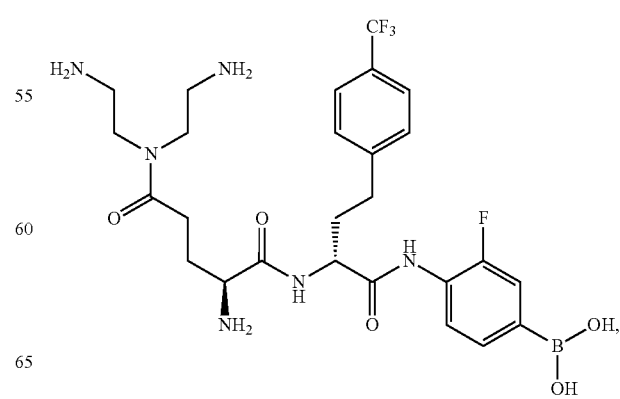

205
-continued
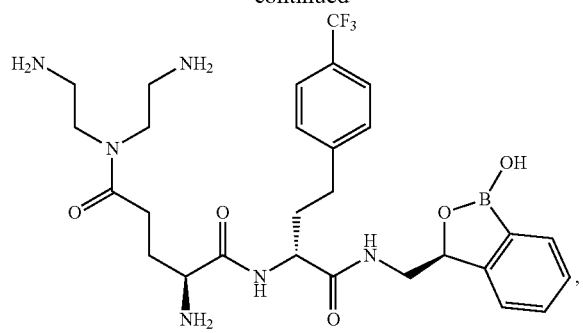
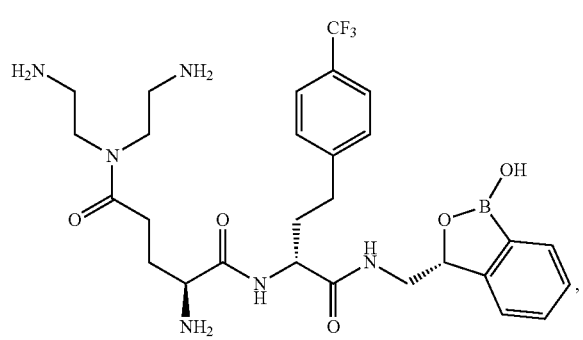
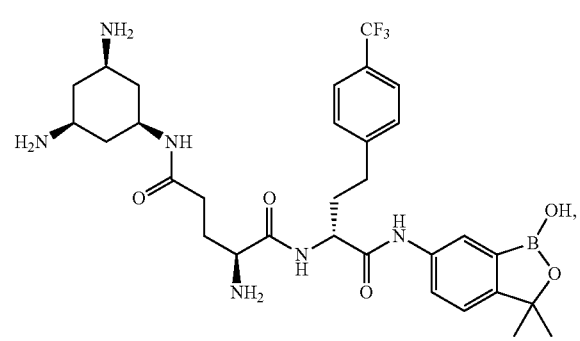
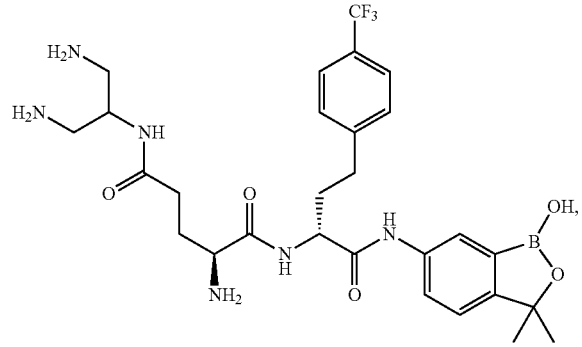
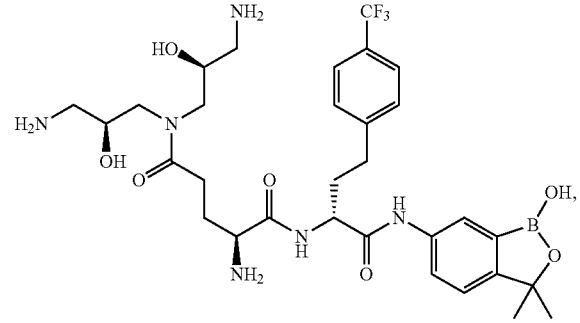
206
-continued
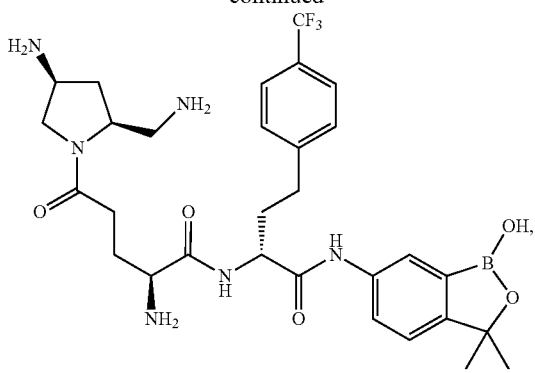
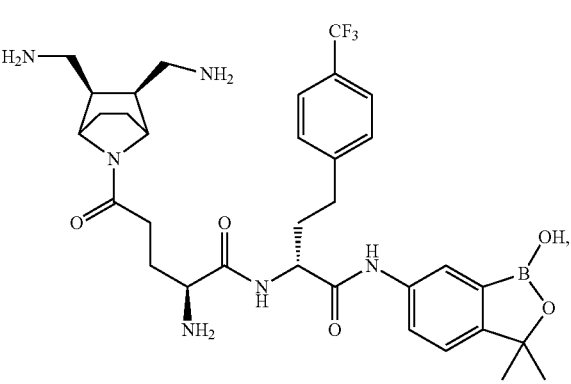
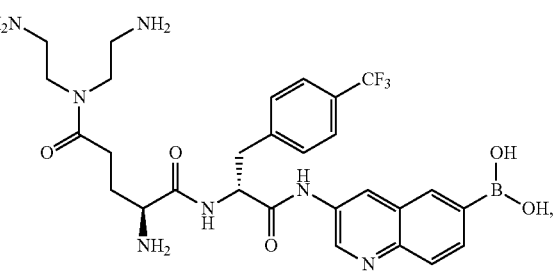
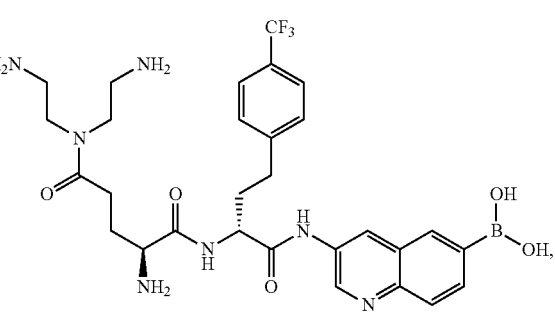
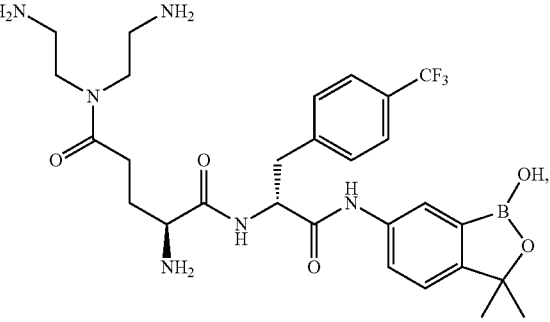

207
-continued
208
-continued
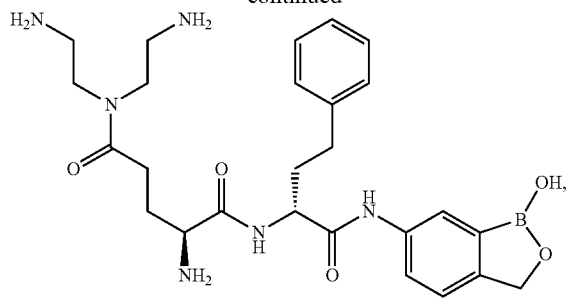
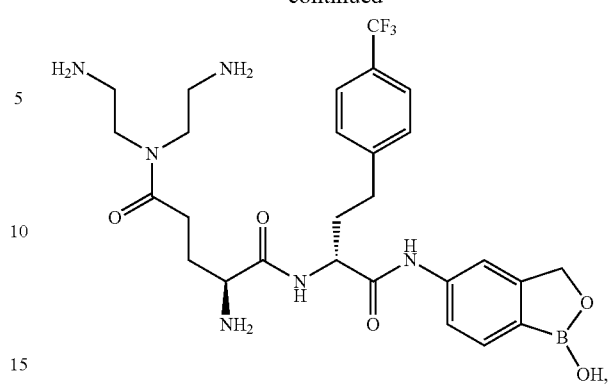
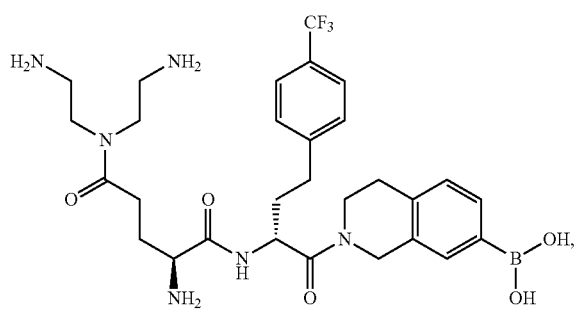
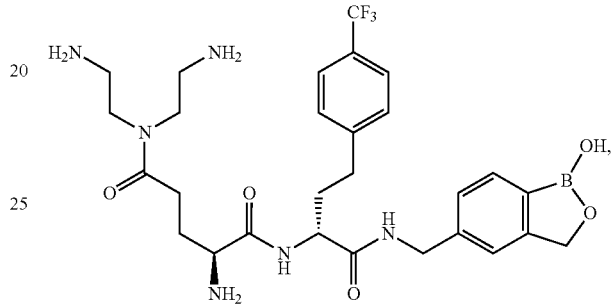
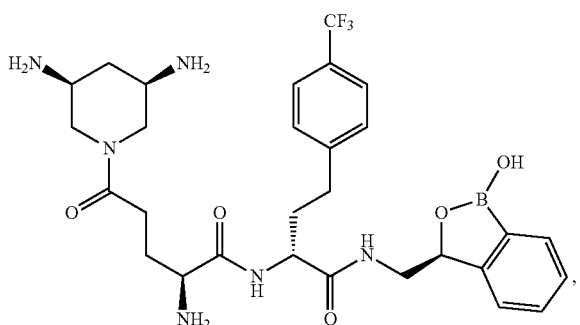
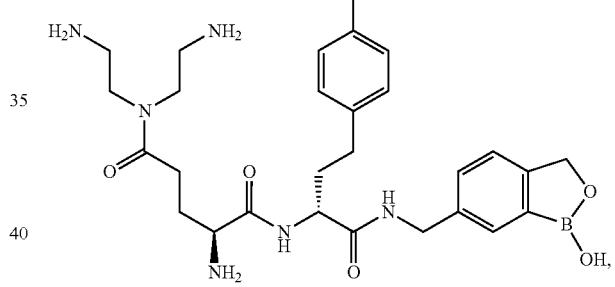
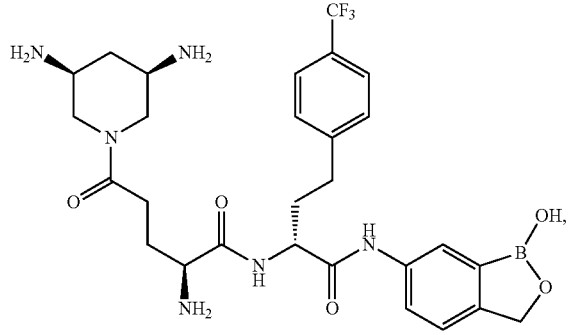
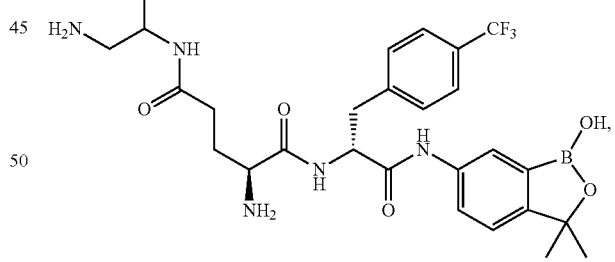
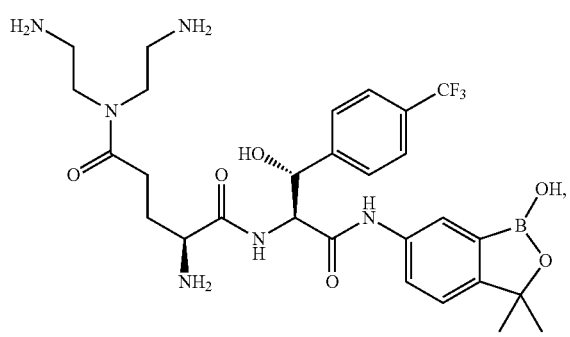
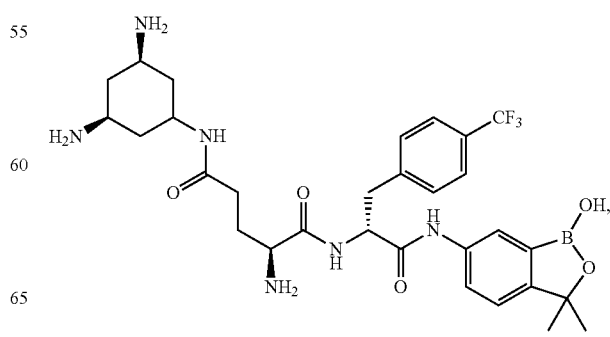

209
-continued
210
-continued
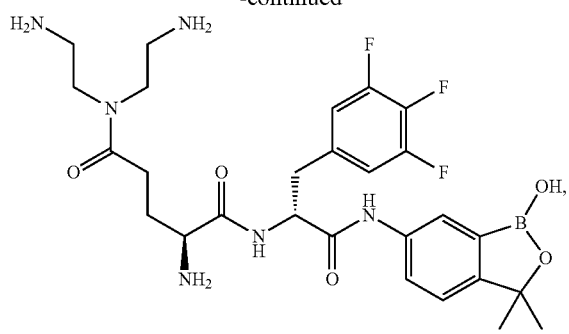
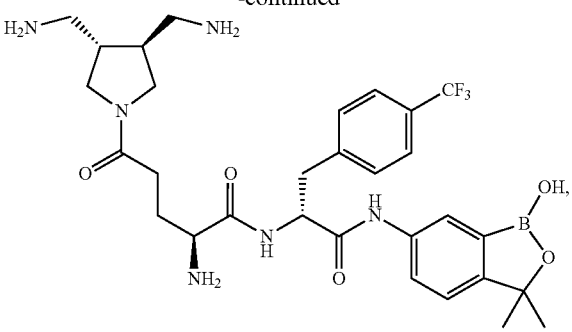
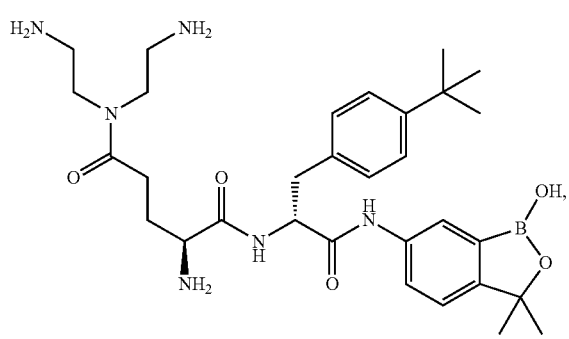
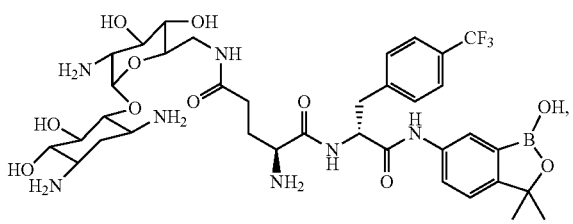
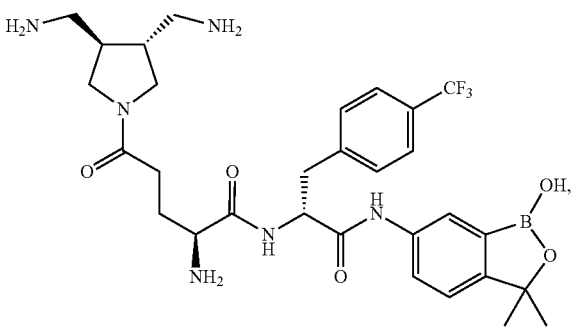
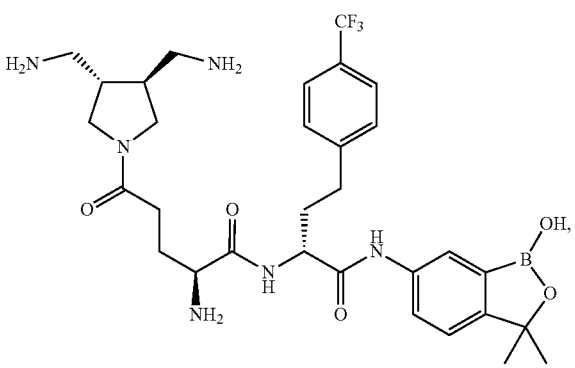

211
-continued
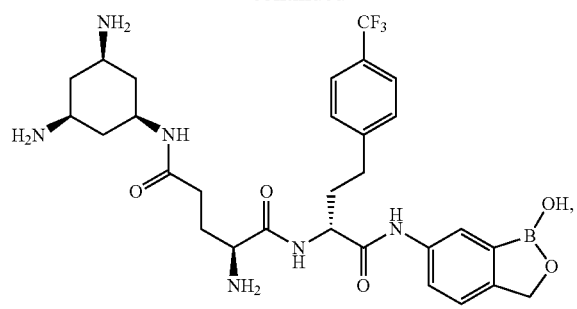
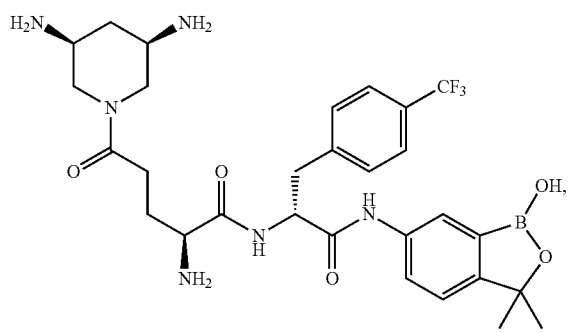
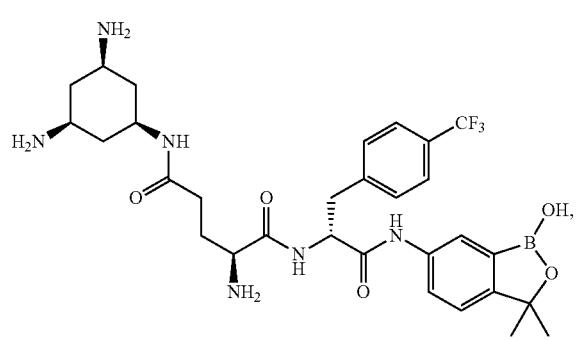
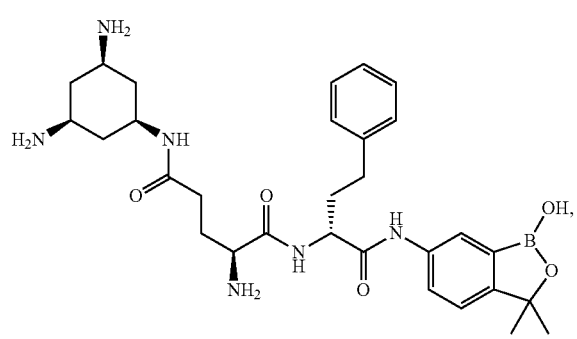
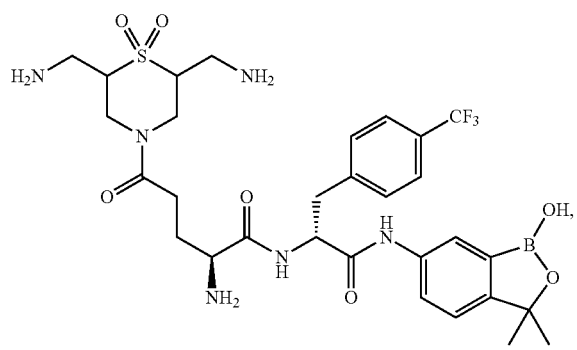
212
-continued
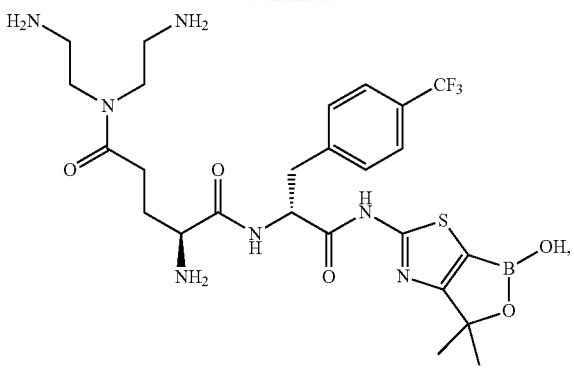
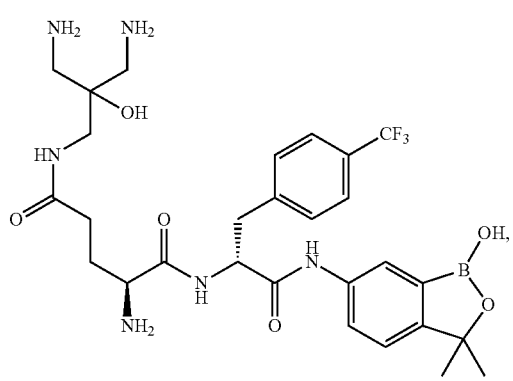
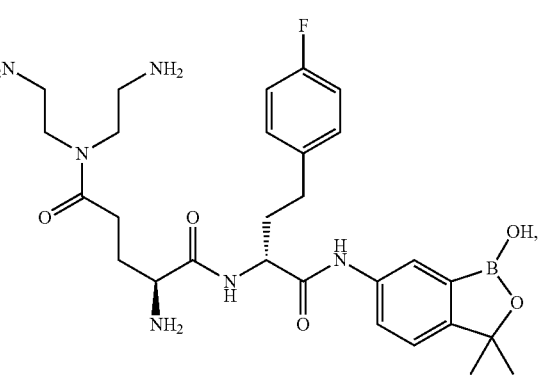
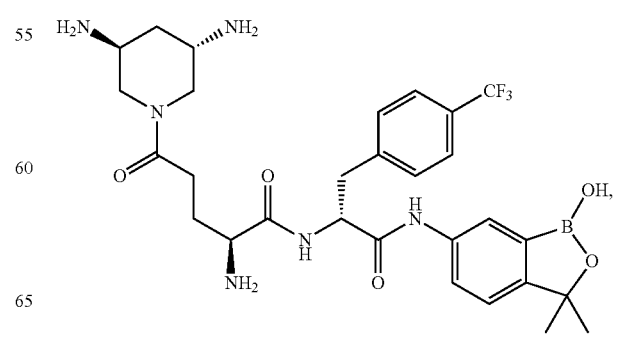

213
-continued
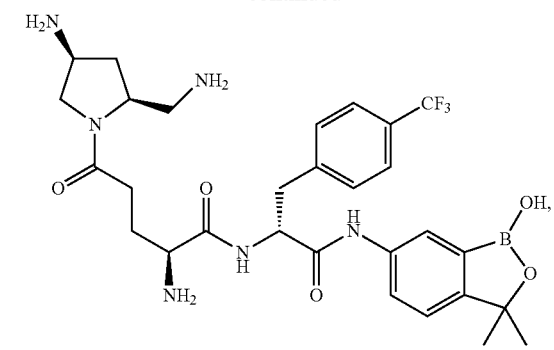
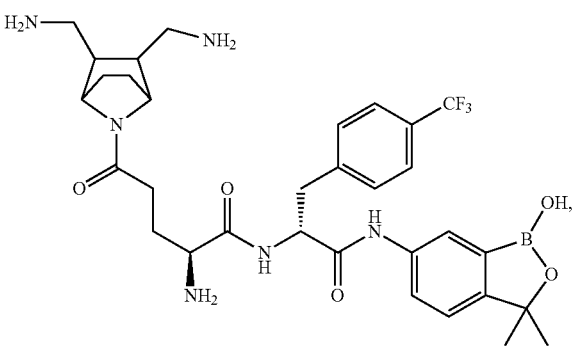
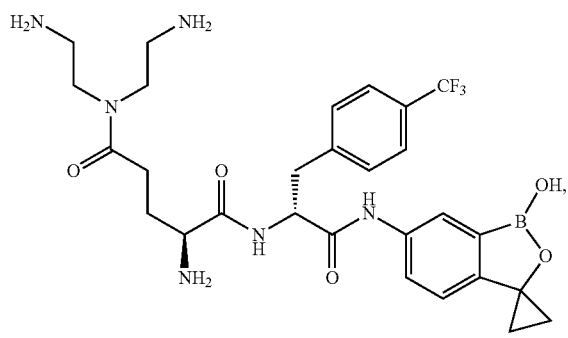
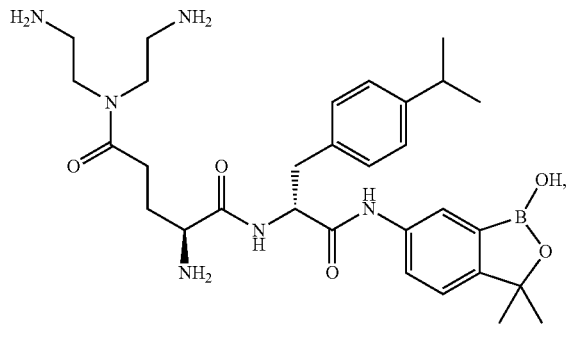
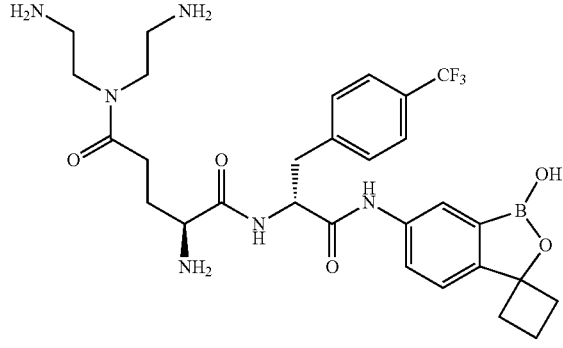
214
-continued
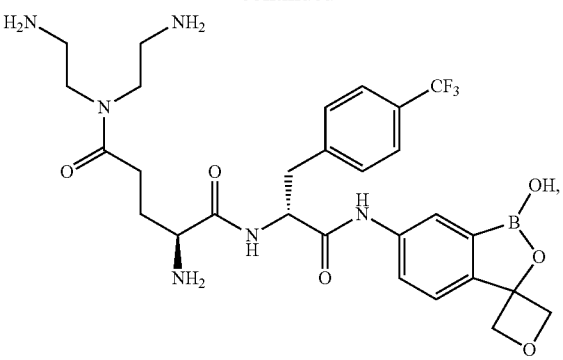
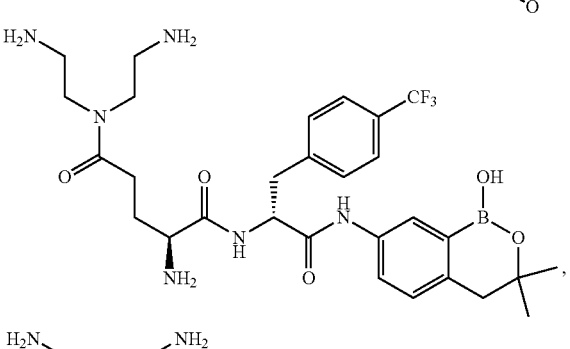
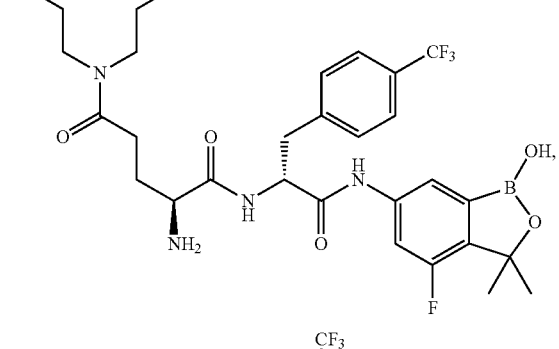
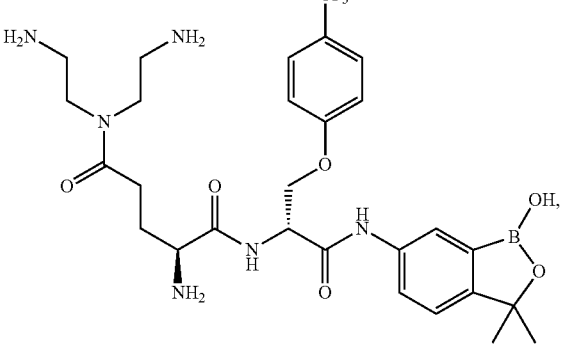
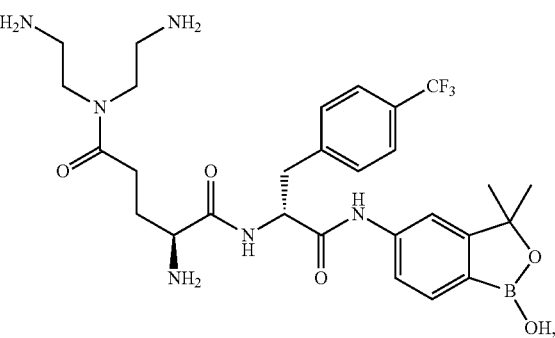

215
-continued
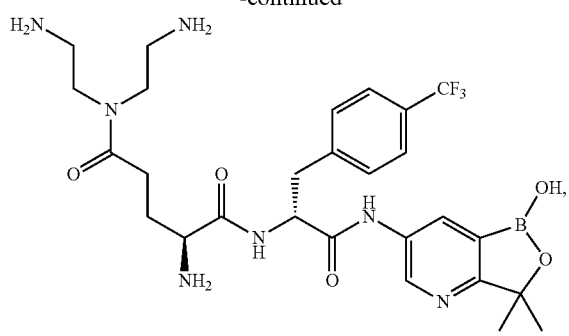
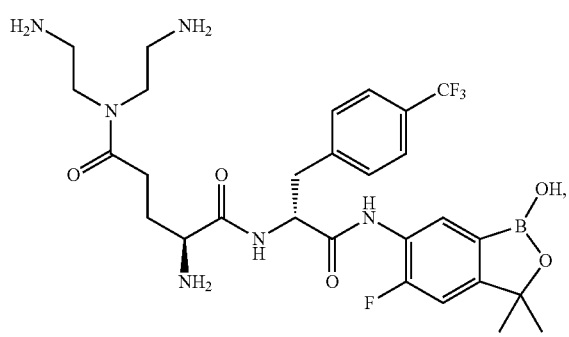
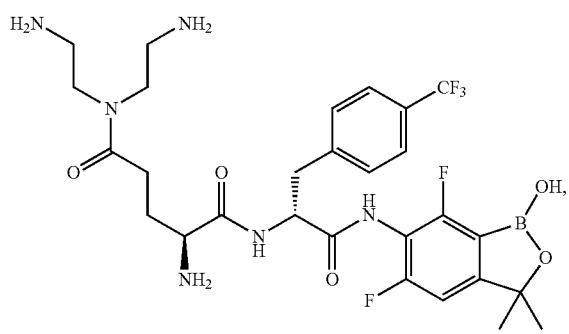
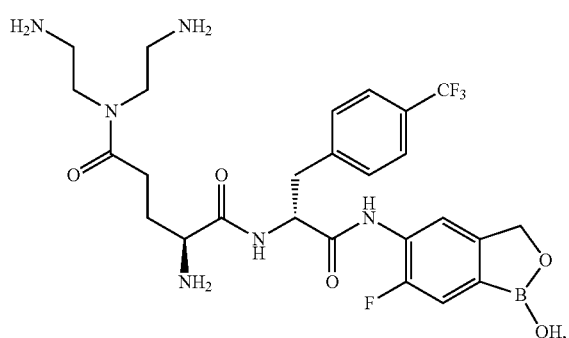
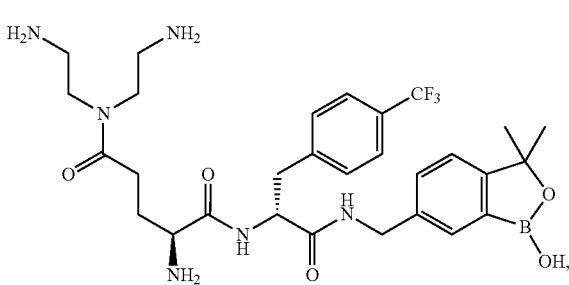
216
-continued
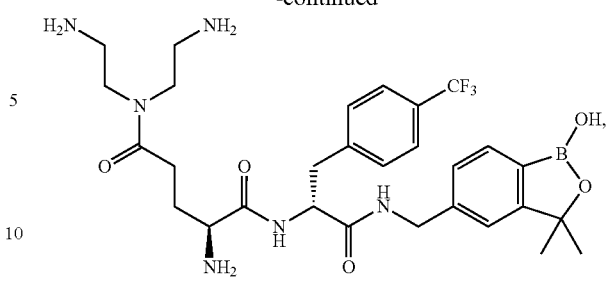
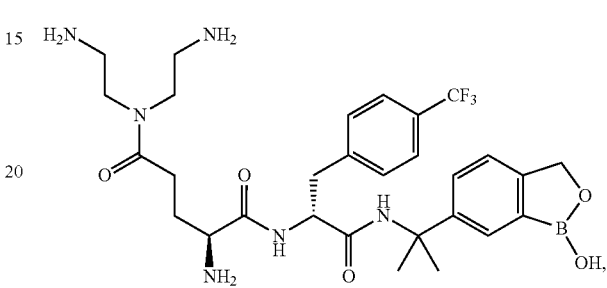
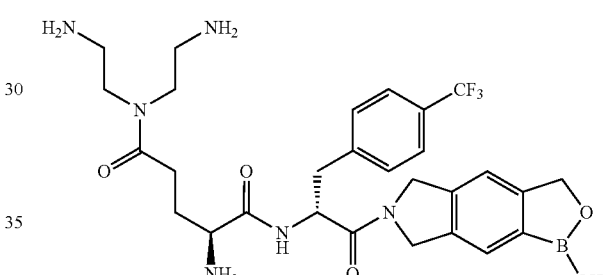
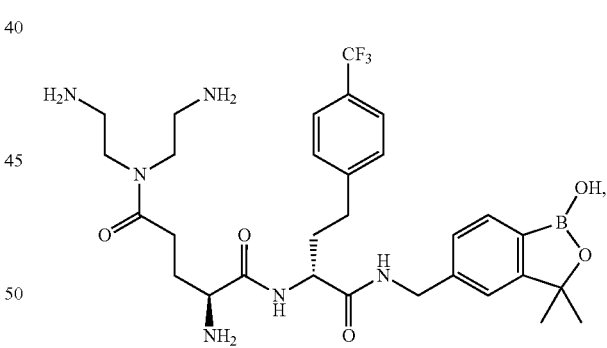
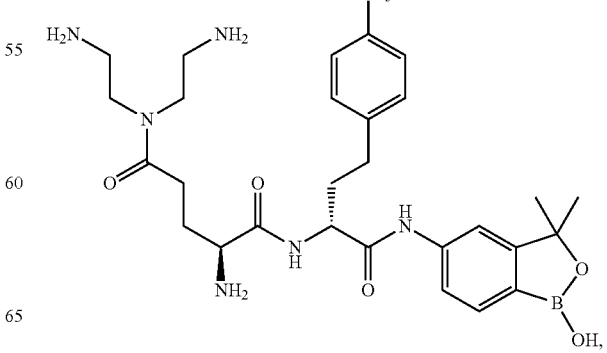

217
-continued
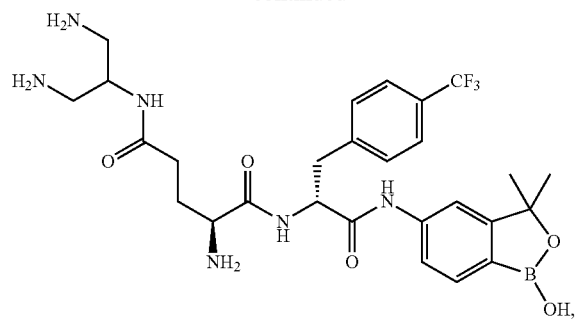
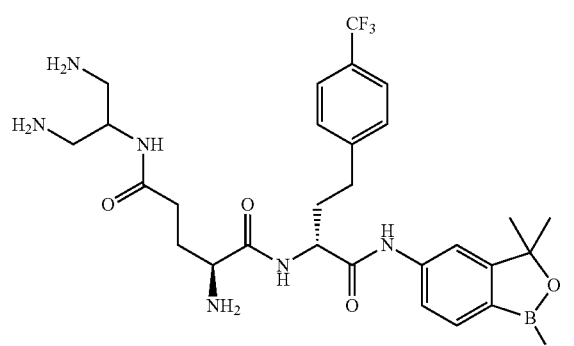
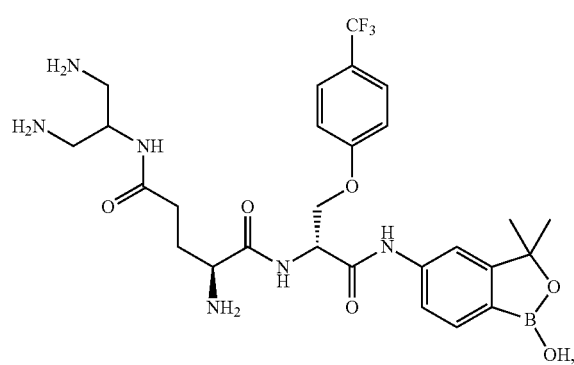
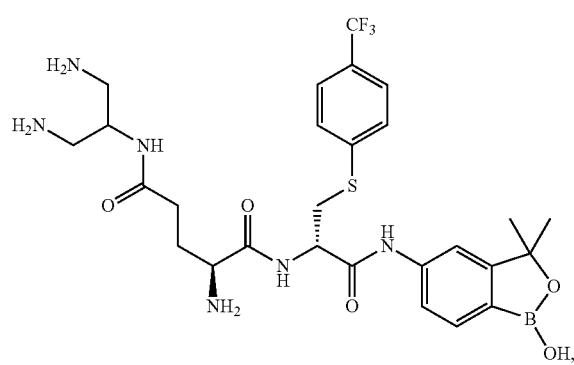
218
-continued
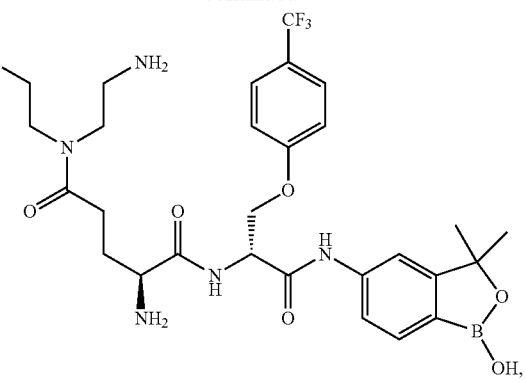
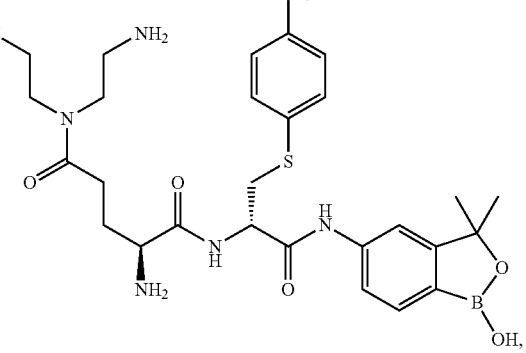
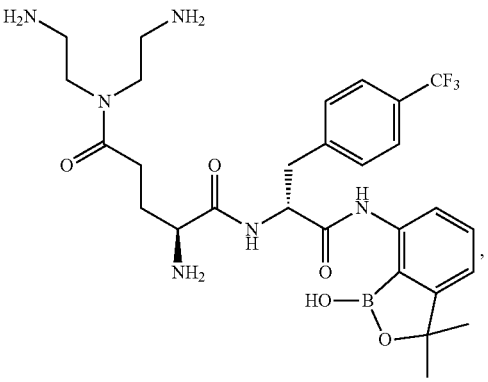
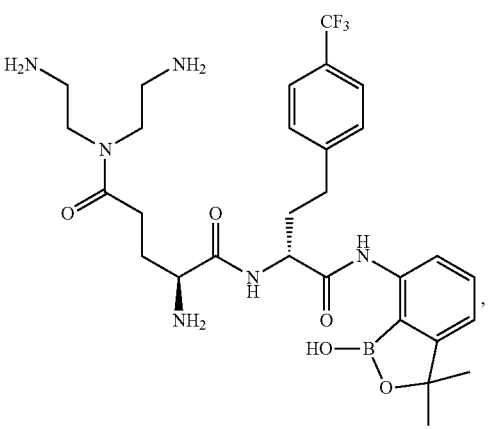

219
-continued
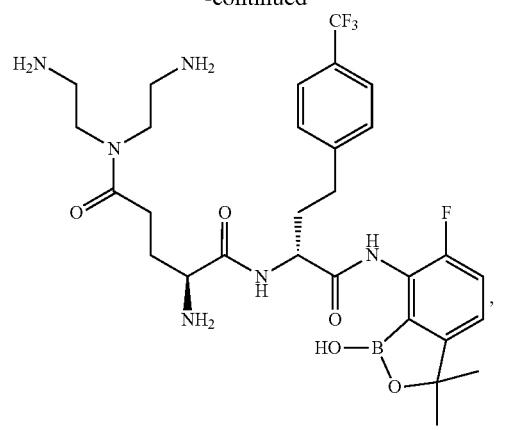
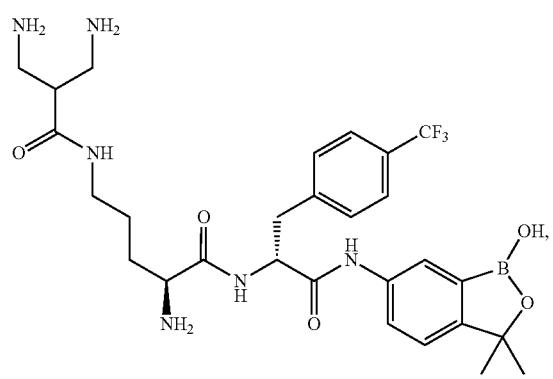
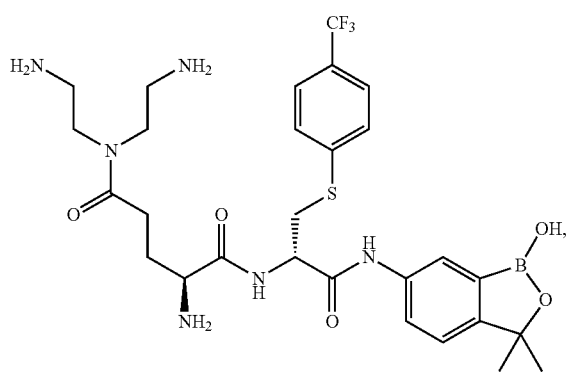
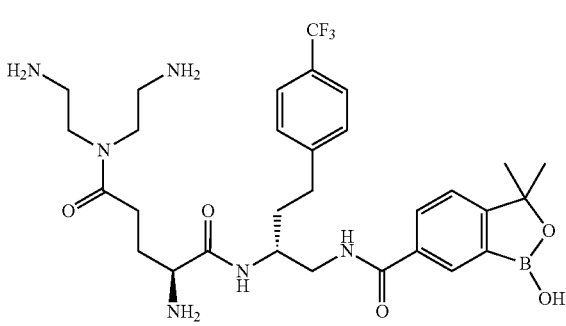
220
-continued
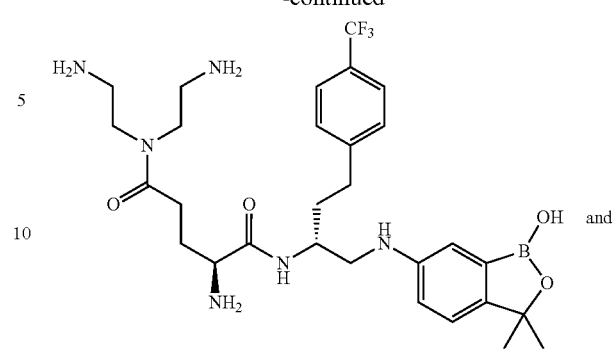
21. The compound of claim 1, having a structure selected from the group consisting of:
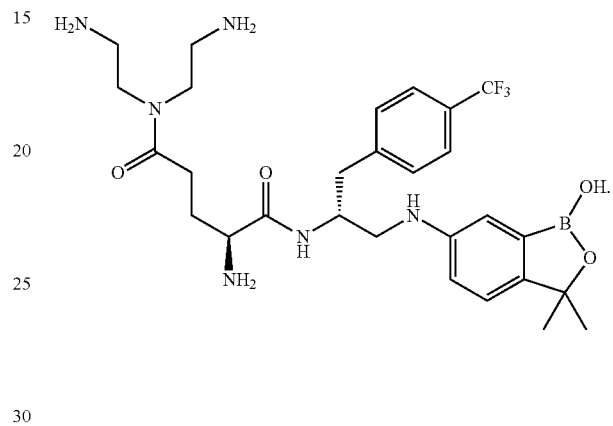
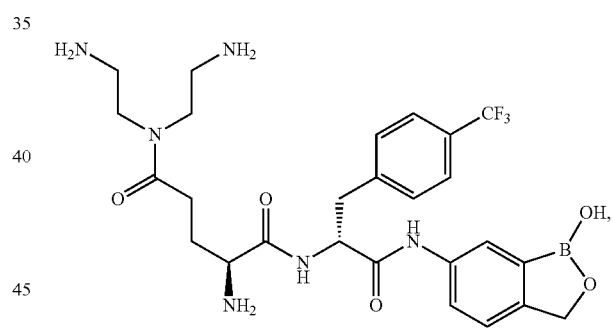
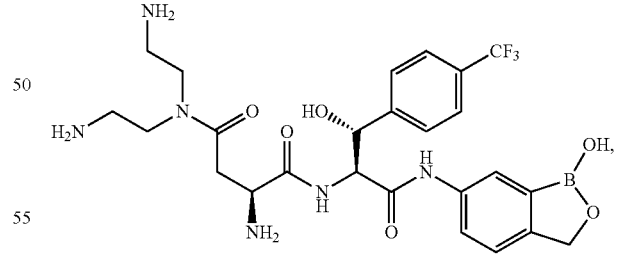
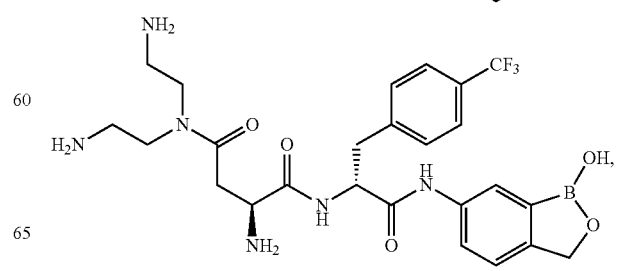

221
-continued
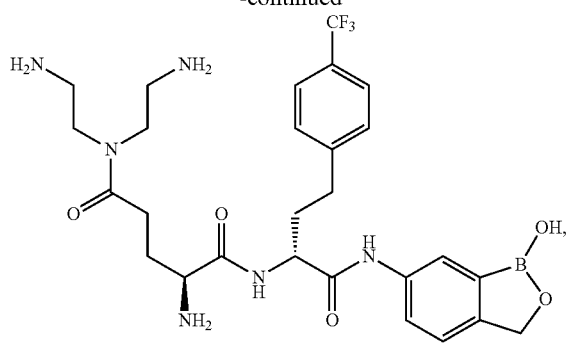
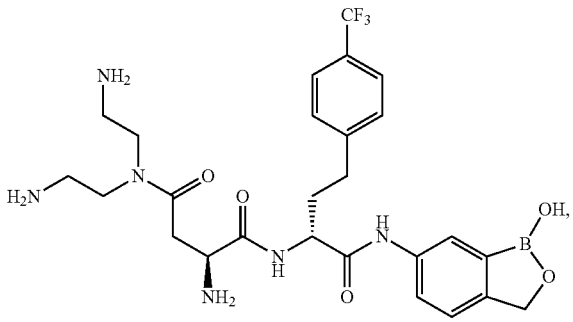
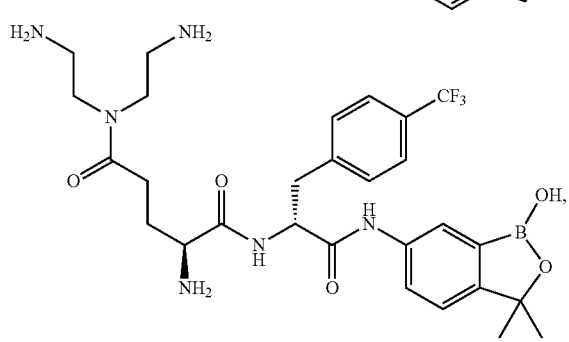
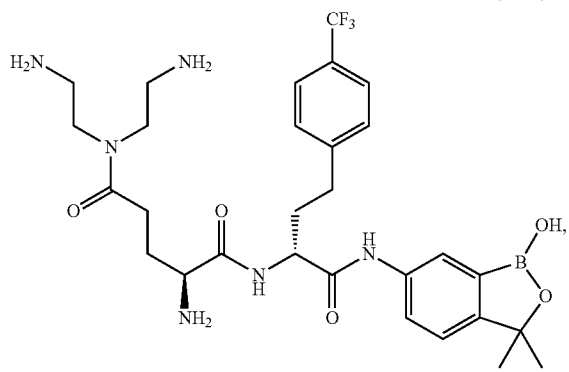
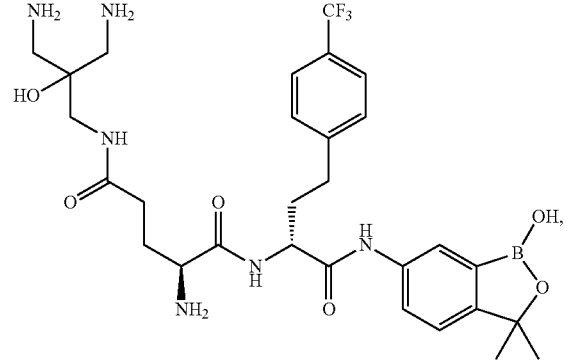
222
-continued
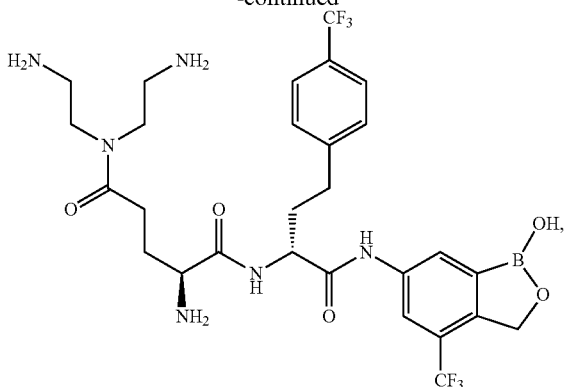
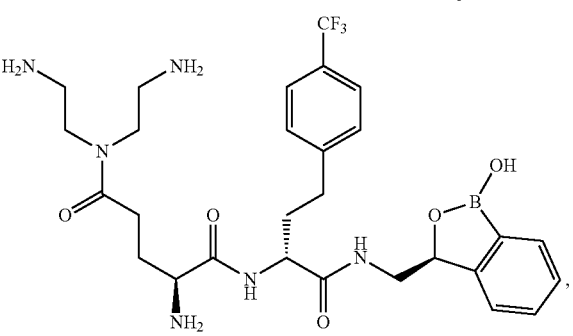
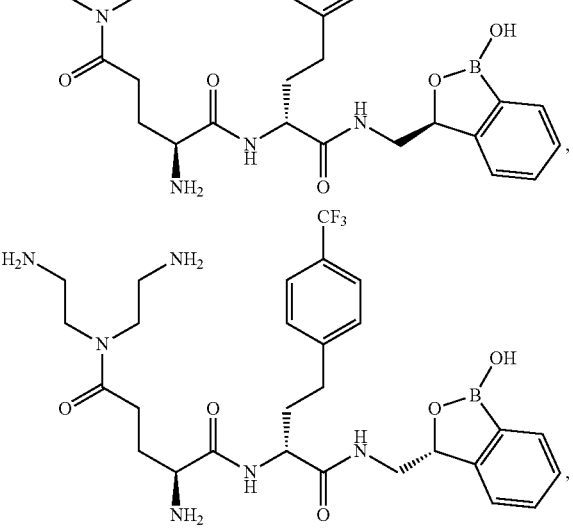
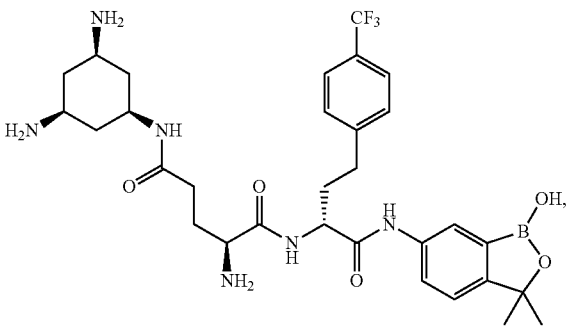
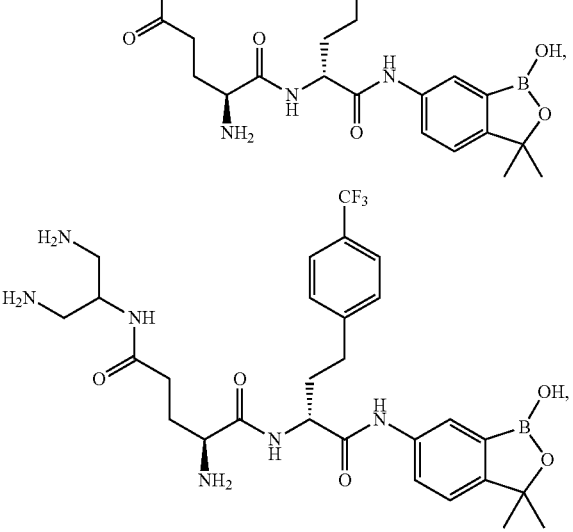

223
-continued
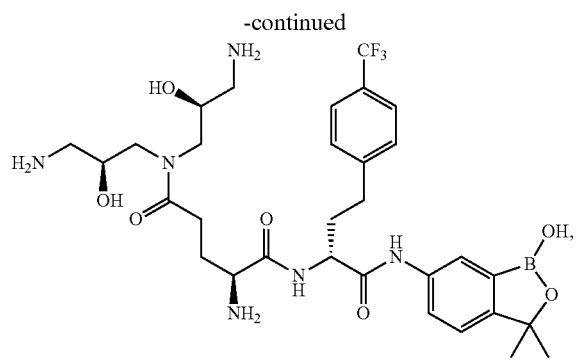
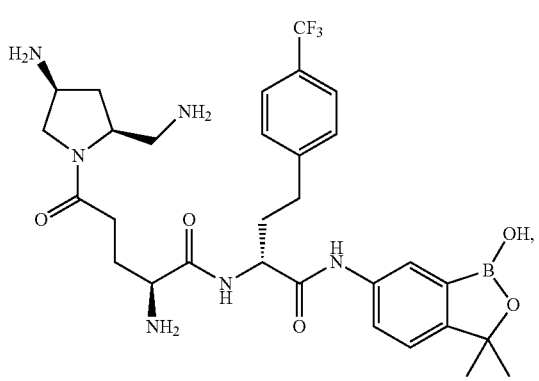
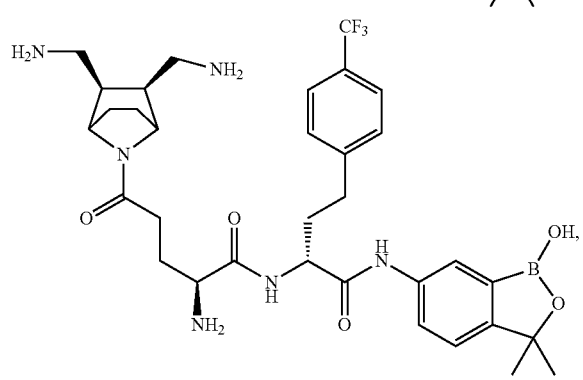
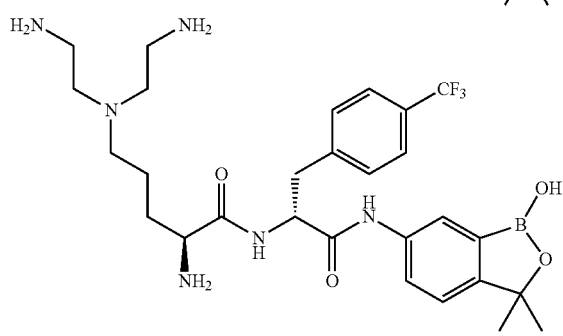
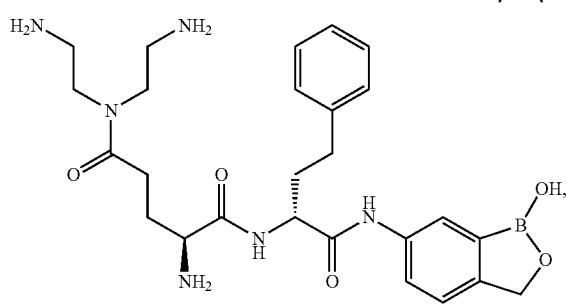
224
-continued
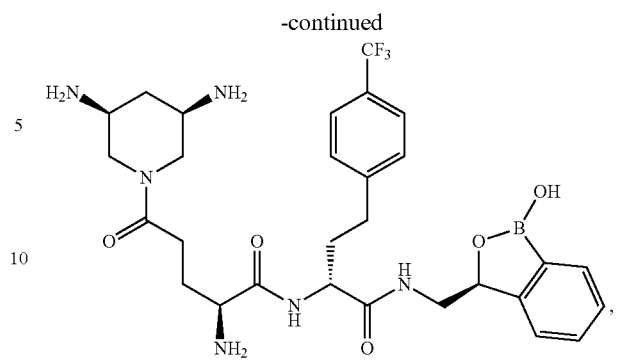
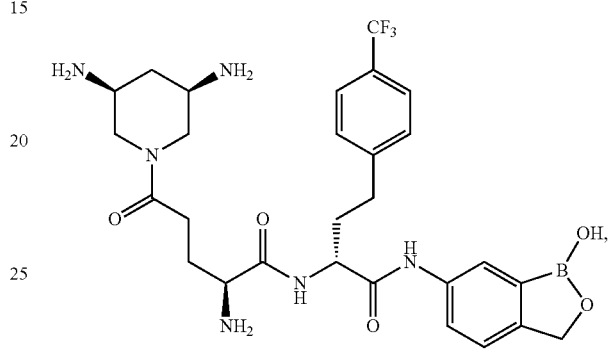
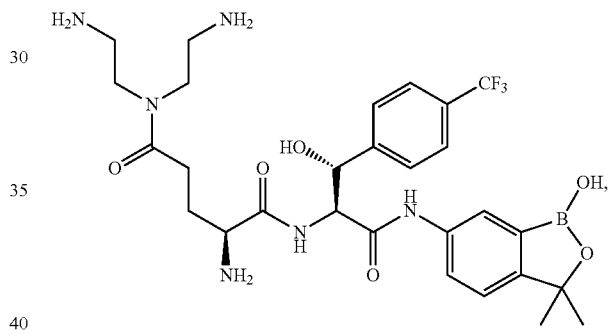
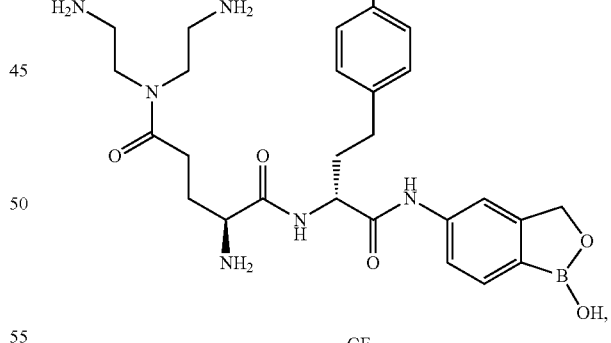
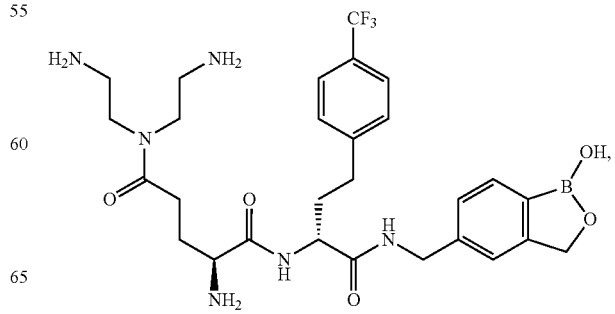

225
-continued
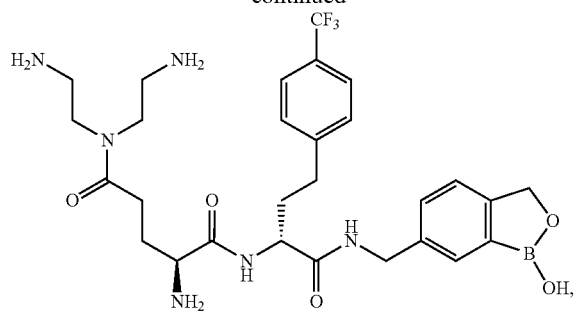
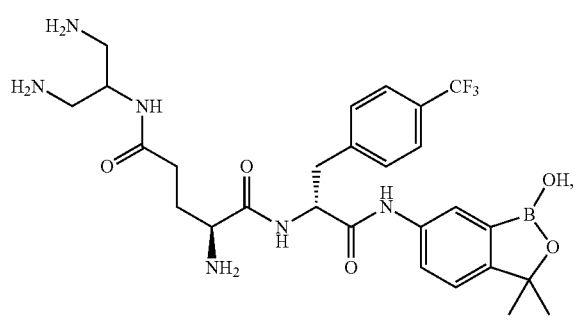
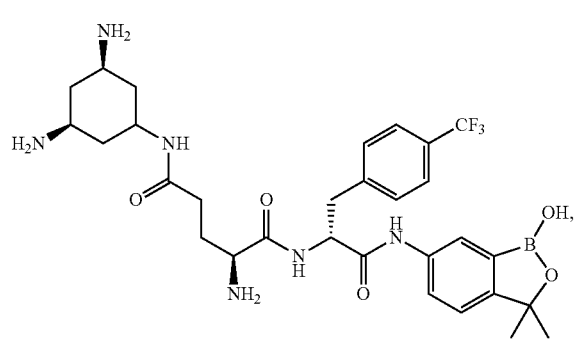
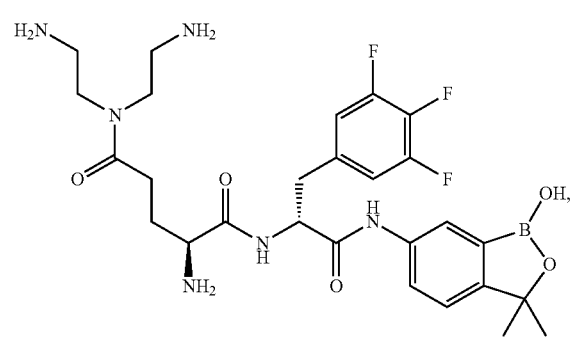
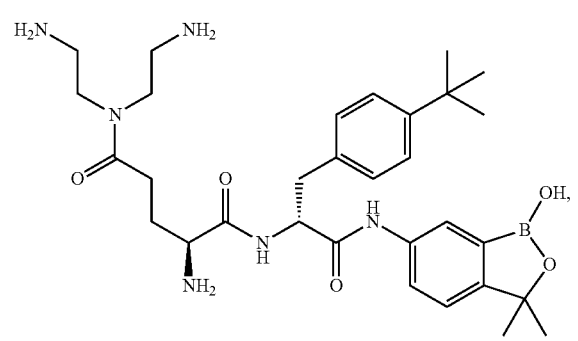
226
-continued
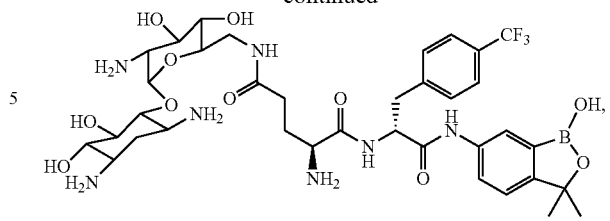
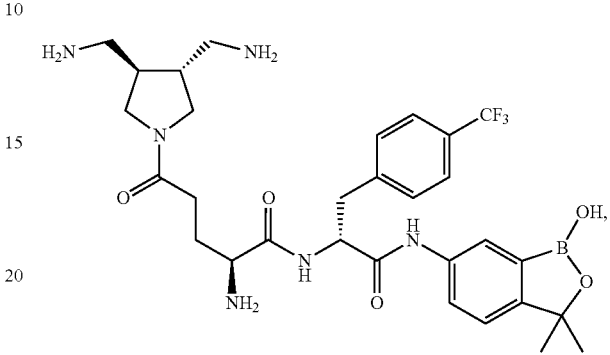
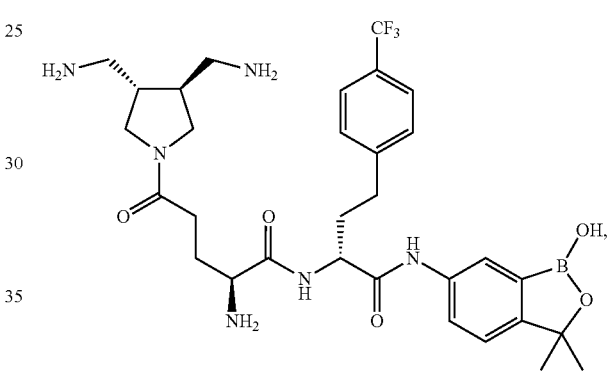
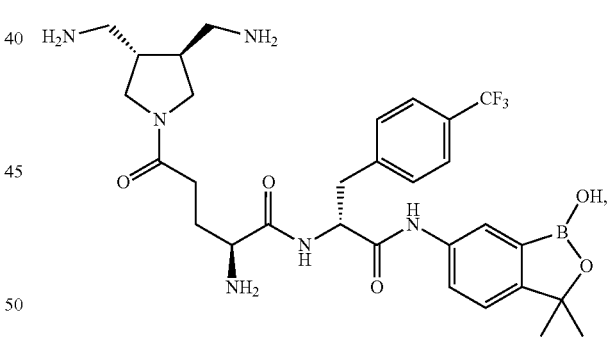
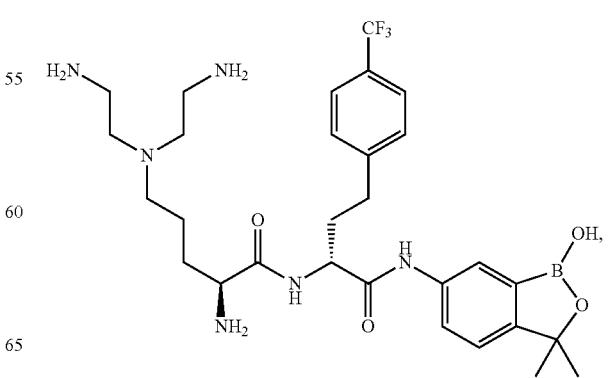

227
-continued
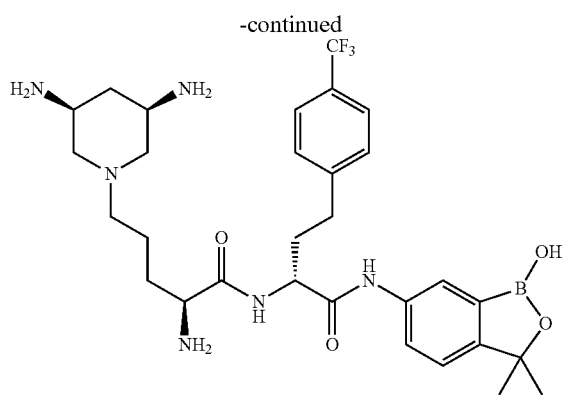
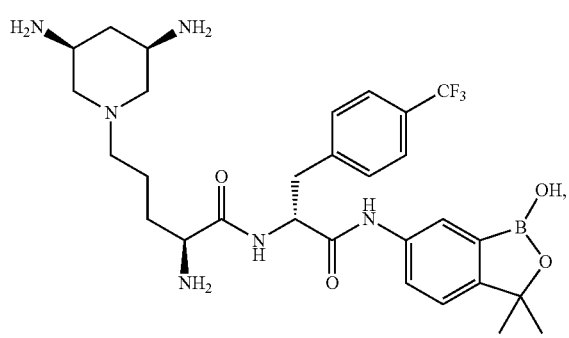
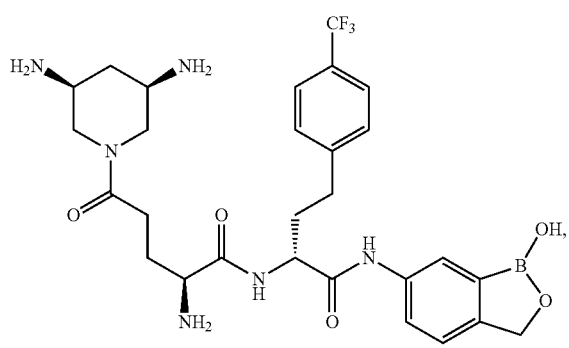
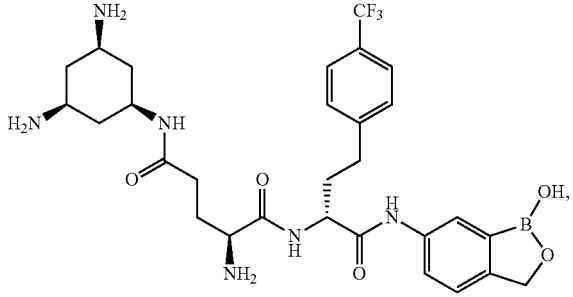
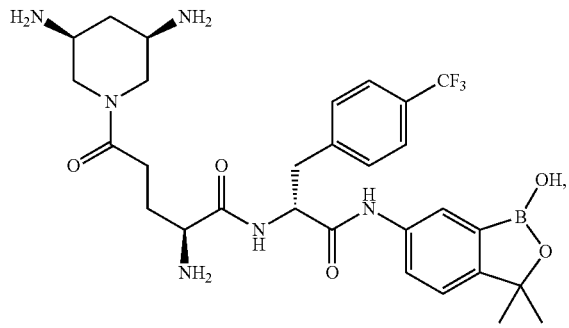
228
-continued
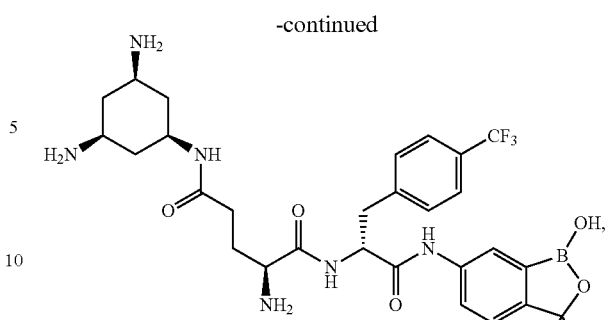
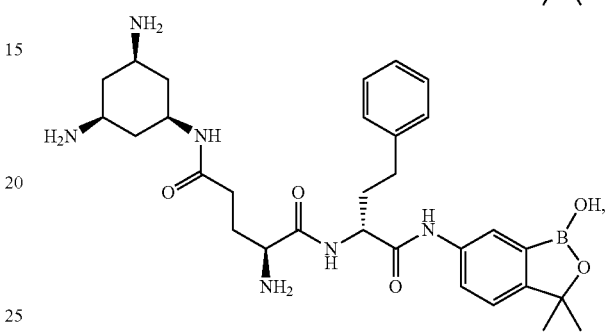
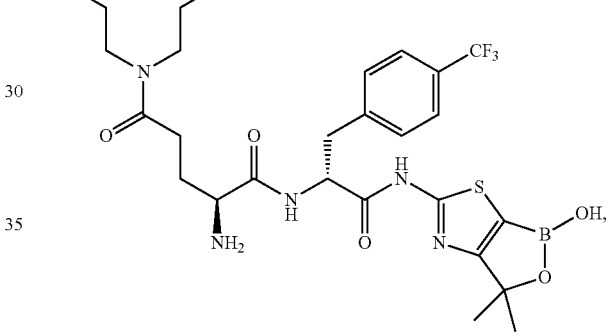
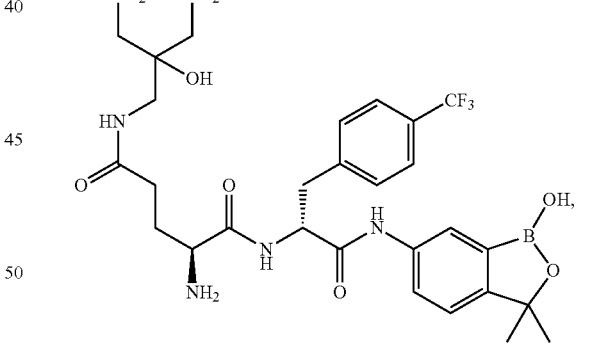
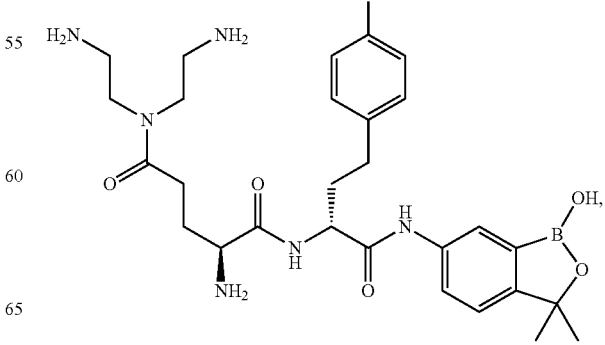

229
-continued
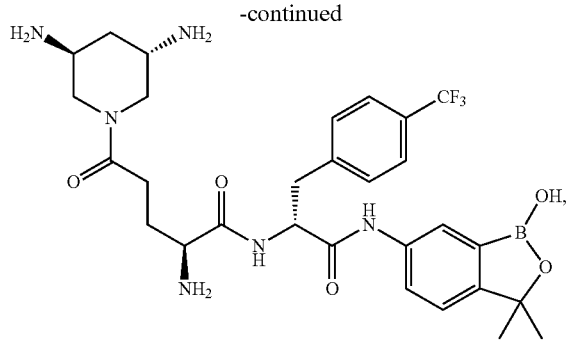
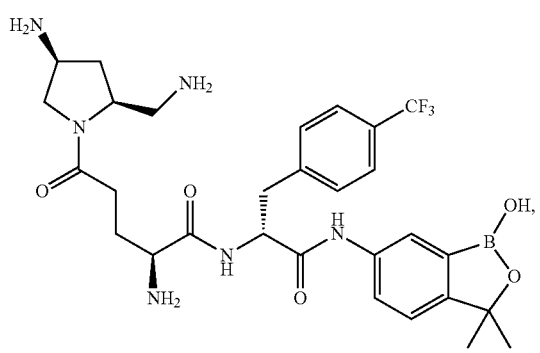
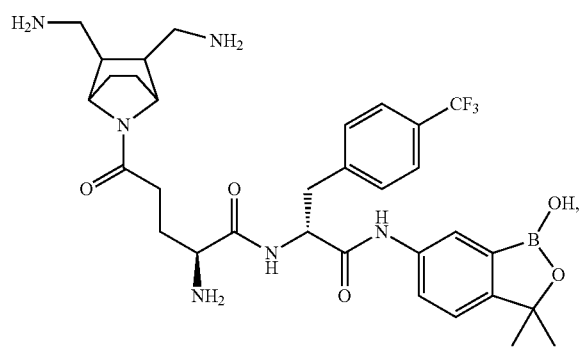
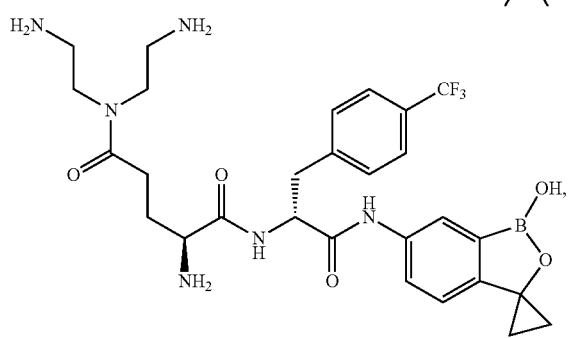
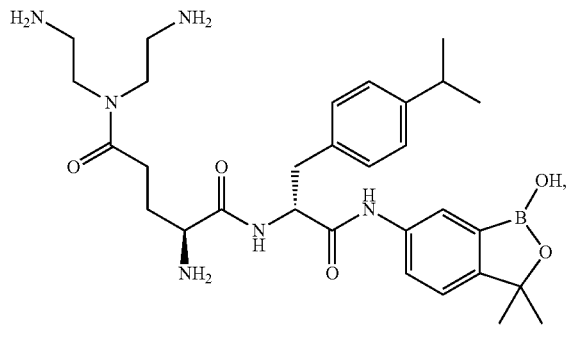
230
-continued
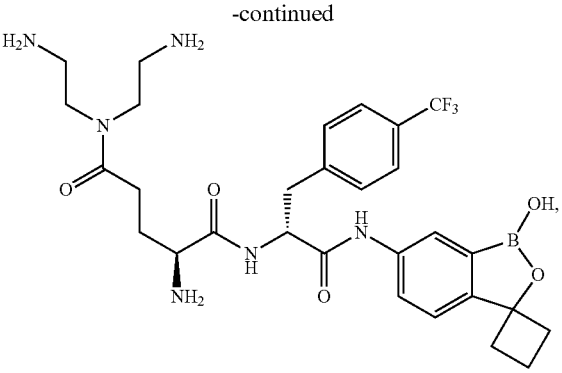
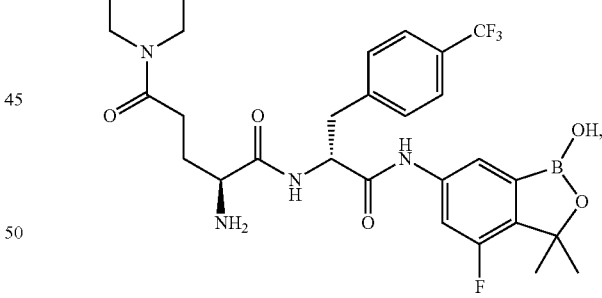
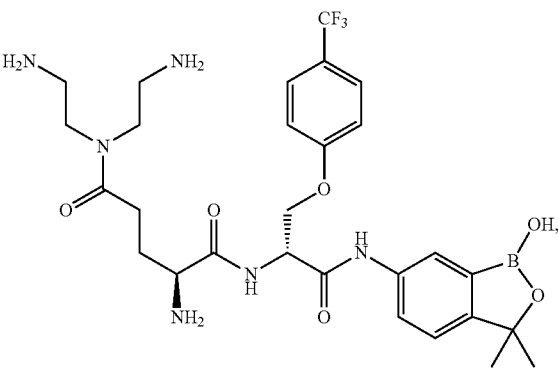

231
-continued
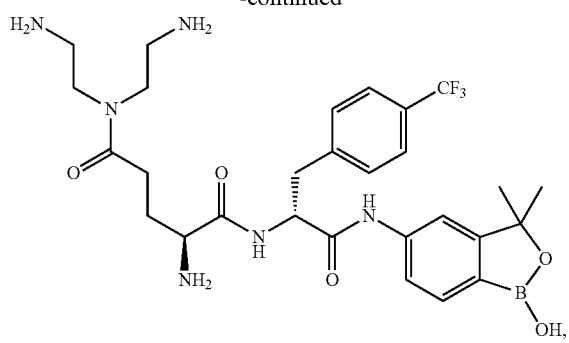
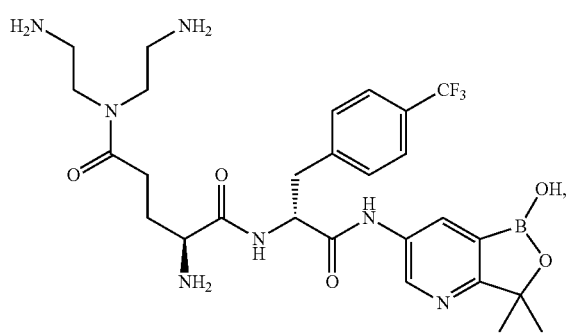
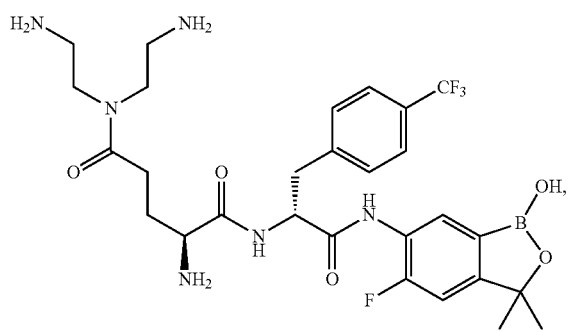
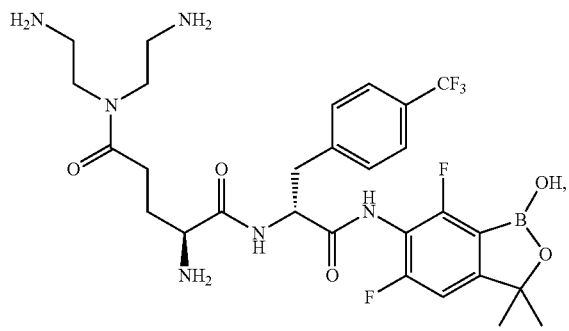
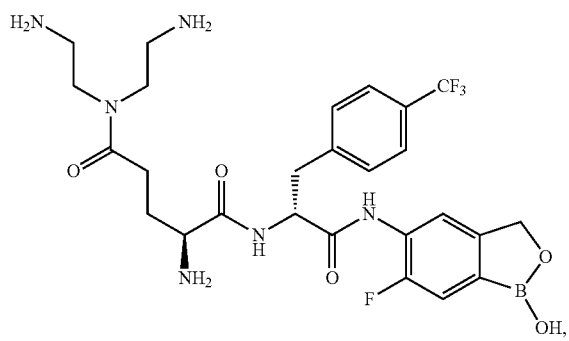
232
-continued
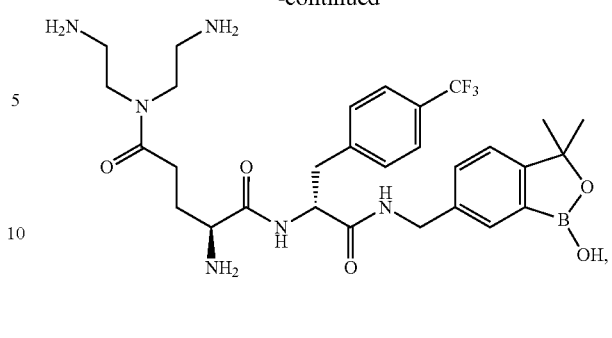
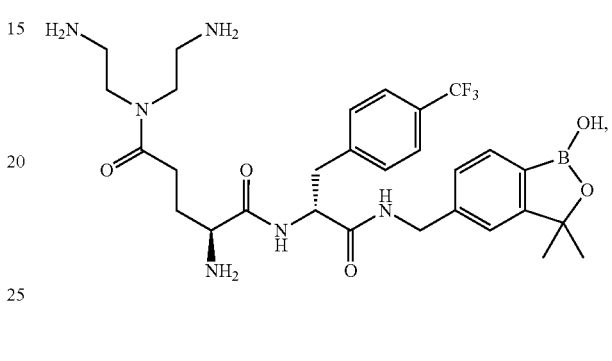
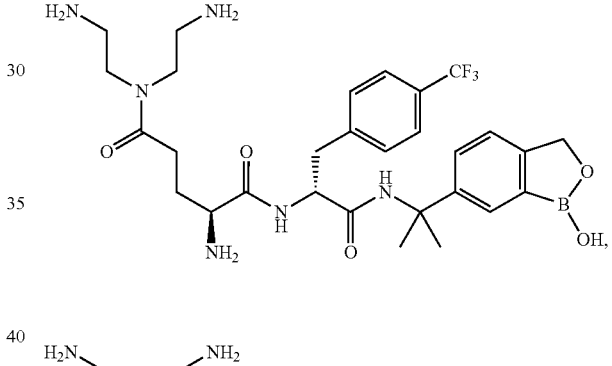
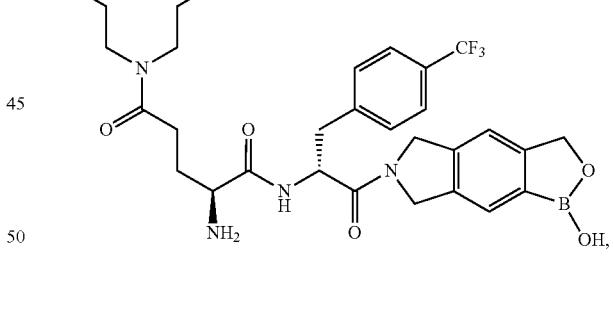
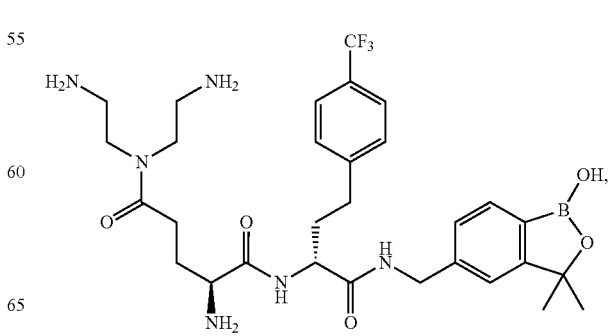

233
-continued
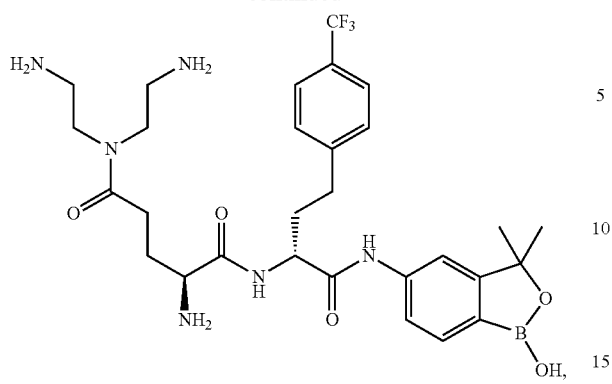
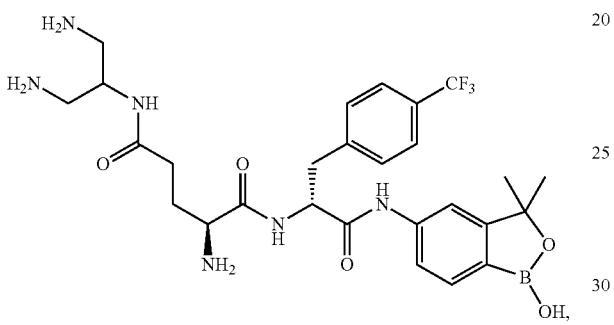
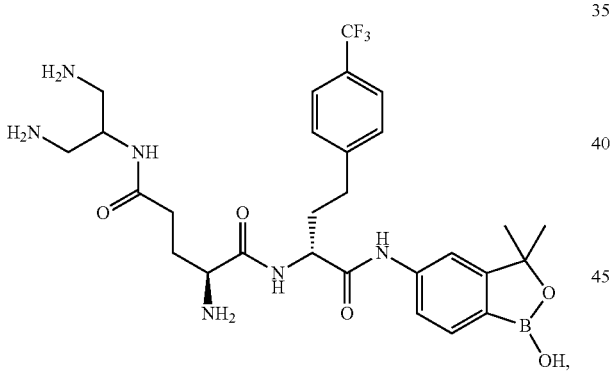
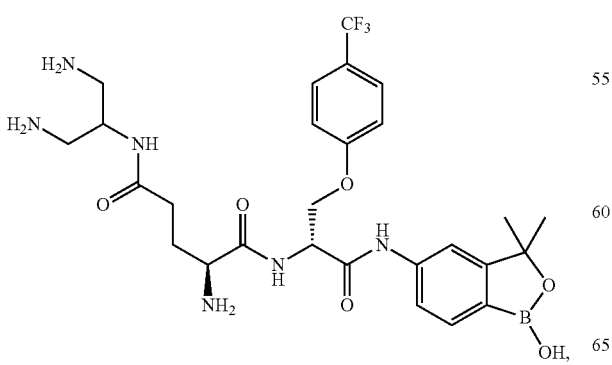
234
-continued
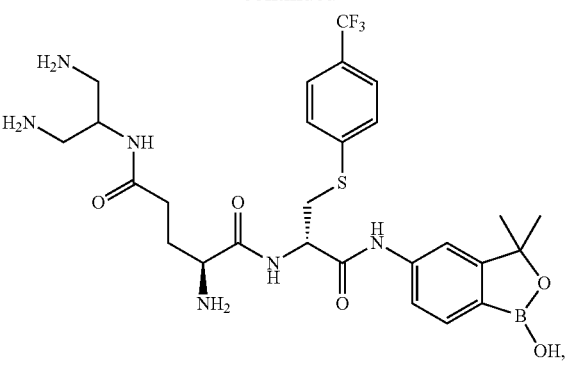
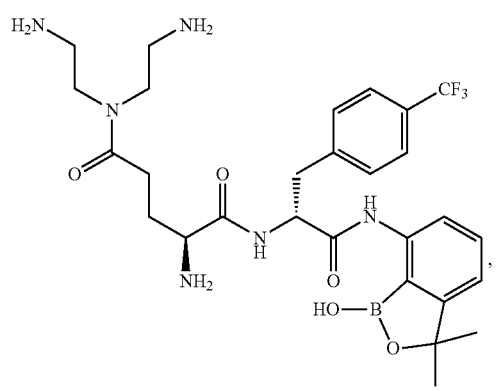
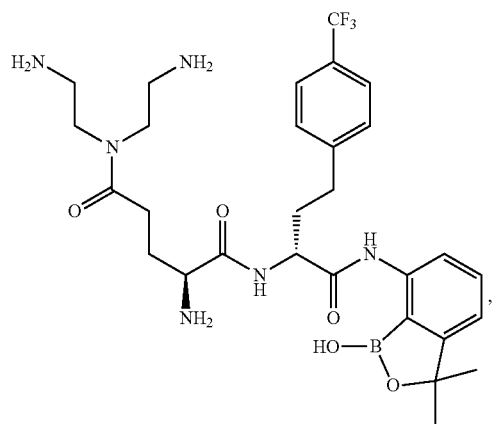
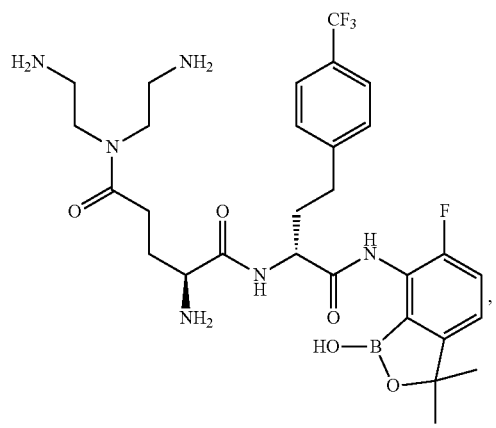

-continued

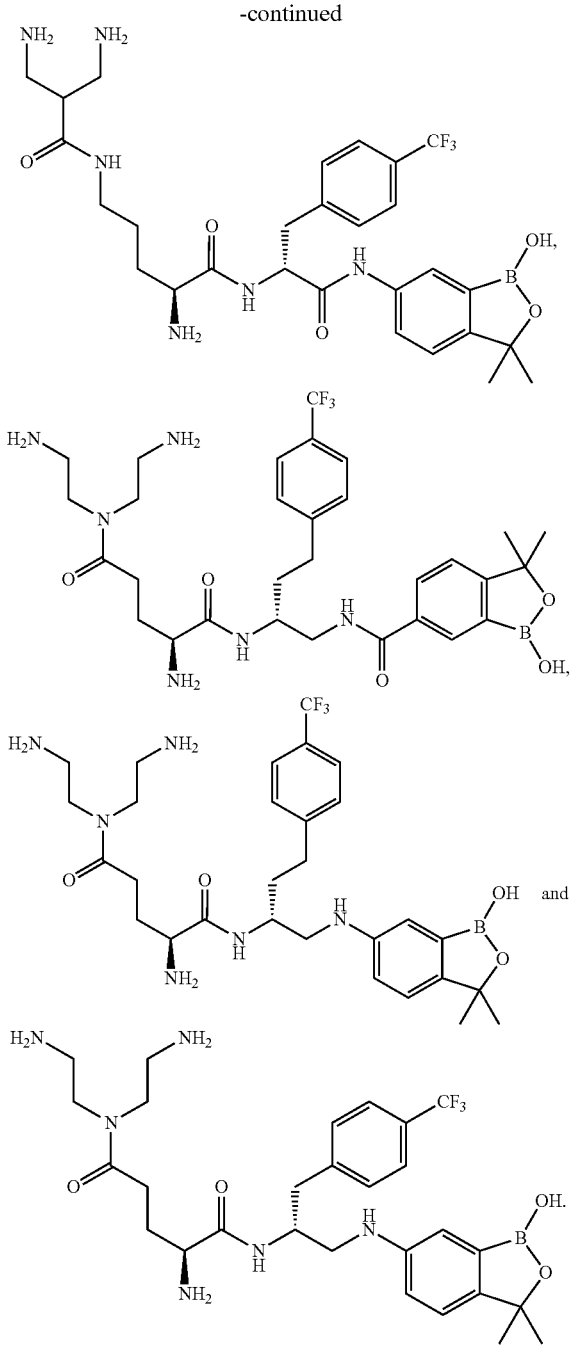

22. A method of inhibiting a bacterial efflux pump, comprising administering a compound according to claim 1 to a subject infected with a bacteria comprising said efflux pump.

23. A method of treating or preventing a bacterial infection, comprising co-administering a compound according to claim 1 and another anti-bacterial agent to a subject infected with a bacteria or susceptible to infection with a bacteria.

24. The method of claim 23, wherein the bacteria is selected from one or more of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtherias, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* and *Staphylococcus saccharolyticus.*

25. The method of claim 23, wherein the bacteria is selected from one or more of *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* and *Bacteroides splanchnicus.*

26. The method of claim 23, wherein the anti-bacterial agent is selected from one or more of quinolones, tetracyclines, glycopeptides, aminoglycosides, β-lactams, rifamycins, macrolides/ketolides, oxazolidinones, coumermycins, and chloramphenicol.

27. The method of claim 22, wherein the subject is a mammal.

28. The method of claim 27, wherein the mammal is a human.

29. A pharmaceutical composition, comprising a compound of claim 1 and a pharmaceutically acceptable carrier, diluent, or excipient.

* * * * *

UNITED STATES PATENT AND TRADEMARK OFFICE
CERTIFICATE OF CORRECTION

PATENT NO. : 8,933,018 B2
APPLICATION NO. : 13/983747
DATED : January 13, 2015
INVENTOR(S) : Tomasz Glinka et al.

It is certified that error appears in the above-identified patent and that said Letters Patent is hereby corrected as shown below:

In the specification,

In column 3 at line 66, Change "B(OH)OR$^{13}$);" to --B(OH)(OR$^{13}$);--.

In column 4 at lines 14-15, After "substituted" insert --with--.

In column 6 at line 28, Change "ovalus," to --ovatus,--.

In column 6 at lines 49-50, Change "parainjluenzae," to --parainfluenzae,--.

In column 6 at line 56, Change "ovalus," to --ovatus,--.

In column 7 at line 67, Change "S(O)$_2$NH—;" to --S(O)$_2$NH—.--.

In column 9 at line 4, After "substituted" insert --with--.

In column 11 at line 12, Change "NR$_2$;" to --NR$_2$.--.

In column 27 at line 6, Change "intrapulmonarilly," to --intrapulmonary,--.

In column 28 at line 65, Change "hydrotropies," to --hydrotropes,--.

In column 29 at line 35, Change "croscarmelose;" to --croscarmellose;--.

In column 31 at lines 47-48, Change "parainjluenzae," to --parainfluenzae,--.

In column 31 at line 58, Change "ovalus," to --ovatus,--.

In column 32 at lines 13-14, Change "parainjluenzae," to --parainfluenzae,--.

In column 32 at line 20, Change "ovalus," to --ovatus,--.

In column 32 at line 59, Change "cephaacetrile," to --cefacetrile,--.

In column 32 at line 60, Change "cefinetazole," to --cefmetazole,--.

In column 32 at line 61, Change "azthreonam," to --aztreonam,--.

In column 32 at line 62, Change "amidinocillin," to --amdinocillin,--.

In column 33 at line 2, Change "LY206763" to --LY206763.--.

In column 33 at line 9, Change "cethrimycin." to --cethromycin.--.

Signed and Sealed this
Twenty-fourth Day of November, 2015

Michelle K. Lee
*Director of the United States Patent and Trademark Office*

CERTIFICATE OF CORRECTION (continued)

In column 33 at lines 26-27, Change "linezolide, eperozolid and torezolide." to --linezolid, eperezolid and torezolid.--.

In column 35 at line 60, Change "dimethylforamide" to --dimethylformamide--.

In column 44 at line 51 (approx.), Change "nitrophenyl sulfonylazanediyl)" to --nitrophenylsulfonylazanediyl)--.

In column 44 at line 63 (approx.), Change "(br s," to --(brs,--.

In column 44 at line 63 (approx.), Change "(br s," to --(brs,--.

In column 50 at line 23, Change "(d. J=" to --(d, J=--.

In column 51 at line 22 (approx.), Change "dilluted" to --diluted--.

In column 53 at lines 62-63, Change "(Aspergilus" to --(Aspergillus--.

In column 58 at line 64 (approx.), Change "dihydro oxazole" to --dihydrooxazole--.

In column 59 at line 60 (approx.), Change "(M-H)" to --(M-H).--.

In column 63 at line 56, Change "ovenight." to --overnight.--.

In column 65 at line 46, Change "(dd J=" to --(dd, J=--.

In column 66 at line 44, Change "(d, J=8 Hz." to --(d, J=8 Hz,--.

In column 66 at line 67, Change "(d. J=" to --(d, J=--.

In column 73 at line 35, Change "oxaborole" to --oxaborol--.

In column 73 at lines 40-41, Change "oxaborole" to --oxaborol--.

In column 75 at line 32 (approx.), Change "diboran" to --diborane--.

In column 84 at line 45 (approx.), Change "dihydro benzo" to --dihydrobenzo--.

In column 85 at line 64, Change "J=13 Hz, J=13 Hz," to --J=13 Hz,--.

In column 86 at line 57, Change "J=13 Hz, J=13 Hz," to --J=13 Hz,--.

In column 87 at line 24, Change "dihydro benzo" to --dihydrobenzo--.

In column 107 at line 55, Change "N5,N5" to --$N^5,N^5$--.

In column 108 at line 65, Change "(d, J=8 Hz 2H)," to --(d, J=8 Hz, 2H),--.

In column 113 at line 52, Change "oxaborole" to --oxaborol--.

In column 120 at line 15, Change "((1s,3R,5S)" to --((1S,3R,5S)--.

In column 120 at lines 15-16, Change "diamino cyclohexyl)" to --diaminocyclohexyl)--.

In column 124 at lines 13-14, Change "amino cyclohexane" to --aminocyclohexane--.

In column 124 at line 24, Change "b is" to --bis--.

In column 124 at line 34, Change "((1r,3R,5S)" to --((1R,3R,5S)--.

In column 126 at line 64, Change "$2^{st}$" to --$2^{nd}$--.

In column 126 at line 65, Change "$2^{st}$" to --$2^{nd}$--.

In column 128 at line 56, Change "amino methyl" to --aminomethyl--.

In column 129 at line 35 (approx.), Change "$BP_3$" to --$BF_3$--.

CERTIFICATE OF CORRECTION (continued)
U.S. Pat. No. 8,933,018 B2

In column 131 at line 21 (approx.), Change "((1s,3R,5S)" to --((1S,3R,5S)--.

In column 132 at line 21 (approx.), Change "diamino piperidin" to --diaminopiperidin--.

In the claims,

In column 189 at line 13 (approx.), In Claim 1, after "substituted" insert --with--.

In column 195 at line 12, In Claim 16, change "of" to --of:--.

In column 206 at lines 55-56 (approx.), In Claim 20, change

"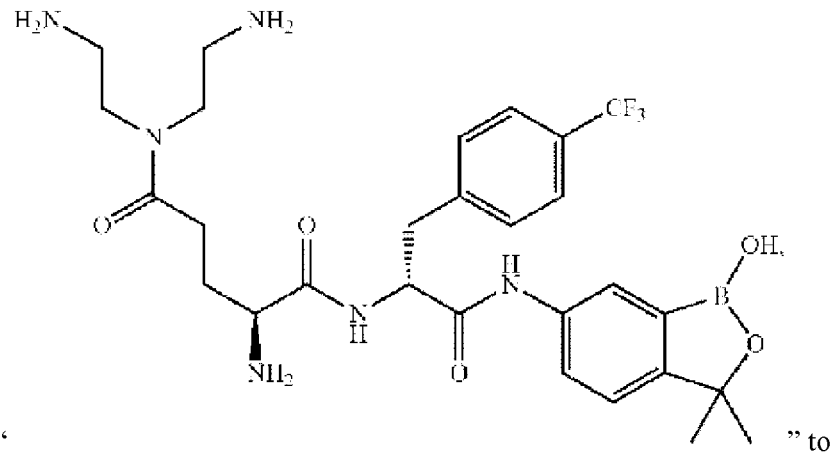" to

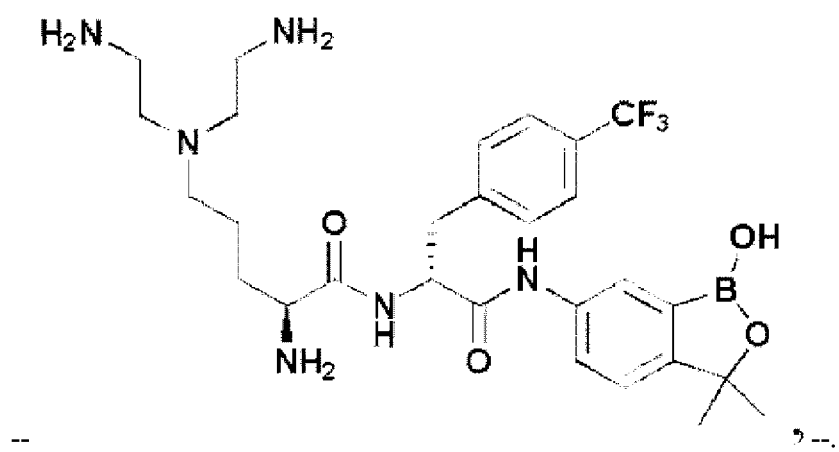

--.

In column 236 at line 21, In Claim 24, change "ovalus," to --ovatus,--.

In column 236 at line 26, In Claim 24, change "diphtherias," to --diphtheriae,--.

In column 236 at line 51, In Claim 25, change "ovalus," to --ovatus,--.